(12) United States Patent
Stockwell et al.

(10) Patent No.: US 10,259,775 B2
(45) Date of Patent: *Apr. 16, 2019

(54) COMPOUNDS, COMPOSITIONS, AND METHODS FOR MODULATING FERROPTOSIS AND TREATING EXCITOTOXIC DISORDERS

(71) Applicant: THE TRUSTEES OF COLUMBIA UNIVERSITY IN THE CITY OF NEW YORK, New York, NY (US)

(72) Inventors: Brent R. Stockwell, New York, NY (US); Rachid Skouta, New York, NY (US); Scott Dixon, New York, NY (US)

(73) Assignee: The Trustees of Columbia University in the City of New York, New York, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 15/100,967

(22) PCT Filed: Dec. 1, 2014

(86) PCT No.: PCT/US2014/067977
§ 371 (c)(1),
(2) Date: Jun. 1, 2016

(87) PCT Pub. No.: WO2015/084749
PCT Pub. Date: Jun. 11, 2015

(65) Prior Publication Data
US 2016/0297748 A1    Oct. 13, 2016

Related U.S. Application Data

(60) Provisional application No. 61/910,580, filed on Dec. 2, 2013, provisional application No. 61/948,242, filed on Mar. 5, 2014.

(51) Int. Cl.
| | |
|---|---|
| *C07C 229/56* | (2006.01) |
| *A61K 31/245* | (2006.01) |
| *A61K 45/06* | (2006.01) |
| *A61K 31/196* | (2006.01) |
| *A61K 31/505* | (2006.01) |
| *C07C 255/58* | (2006.01) |
| *C07C 271/24* | (2006.01) |

(Continued)

(52) U.S. Cl.
CPC ......... *C07C 229/56* (2013.01); *A61K 31/196* (2013.01); *A61K 31/245* (2013.01); *A61K 31/505* (2013.01); *A61K 45/06* (2013.01); *C07C 229/60* (2013.01); *C07C 255/58* (2013.01); *C07C 271/24* (2013.01); *C07D 213/38* (2013.01); *C07D 239/26* (2013.01); *C07D 401/12* (2013.01); *C07C 2601/02* (2017.05); *C07C 2601/04* (2017.05); *C07C 2601/08* (2017.05); *C07C 2601/14* (2017.05); *C07C 2601/18* (2017.05); *C07C 2601/20* (2017.05); *C07C 2603/72* (2017.05); *C07C 2603/74* (2017.05)

(58) Field of Classification Search
CPC .. A61K 31/196; A61K 31/245; A61K 31/505; A61K 45/06; C07C 229/56; C07C 229/60; C07C 255/58; C07C 271/24; C07C 2601/02; C07C 2601/04; C07C 2601/08; C07C 2601/14; C07C 2601/18; C07C 2601/20; C07D 213/38; C07D 239/26; C07D 401/12
See application file for complete search history.

(56) References Cited

U.S. PATENT DOCUMENTS 9,580,398 B2 * 2/2017 Stockwell ............ C07D 309/14
2007/0049565 A1    3/2007 Gwag et al.
(Continued)

FOREIGN PATENT DOCUMENTS

WO    WO/2008/008234 A1    1/2008
WO    WO/2013/152039 A1    10/2013

OTHER PUBLICATIONS

Ulrich, Crystallization, Kirk-Othmer Encyclopedia of Chemical Technology, pp. 1 -7, 2002.*
(Continued)

*Primary Examiner* — Deepak R Rao
(74) *Attorney, Agent, or Firm* — Bryan Cave Leighton Paisner LLP

(57) ABSTRACT

The present invention provides, inter alia, a compound having the structure of Formula (I). Also provided are compositions containing a pharmaceutically acceptable carrier and a compound according to the present invention. Further provided are methods for treating or ameliorating the effects of an excitotoxic disorder in a subject, methods of modulating ferroptosis in a subject, methods of reducing reactive oxygen species (ROS) in a cell, and methods for treating or ameliorating the effects of a neurodegenerative disease.

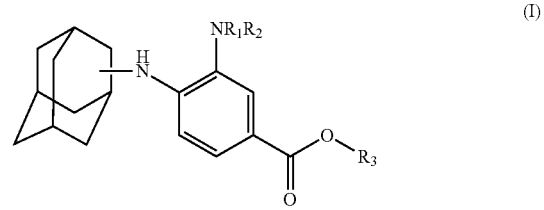

13 Claims, 69 Drawing Sheets
Specification includes a Sequence Listing.

(51) Int. Cl.
  C07C 229/60  (2006.01)
  C07D 401/12  (2006.01)
  C07D 239/26  (2006.01)
  C07D 213/38  (2006.01)

(56) References Cited

U.S. PATENT DOCUMENTS

2008/0194803 A1  8/2008  Sinclair et al.
2012/0022254 A1  1/2012  Nunes et al.

OTHER PUBLICATIONS

Vippagunta et al., Crystalline Solids, Advanced Drug Delivery Reviews 48 (2001), pp. 3-26.*
ChemCats (RN 1178119-09-9) Supplier: UkrOrgSynthesis, 2 pages, Aug. 2009.*
Abdel-Magid, A. F., et al. (1996) Reductive Amination of Aldehydes and Ketones with Sodium Triacetoxyborohydride. Studies on Direct and Indirect Reductive Amination Procedures[1]. J. Org. Chem. 61, 3849-3862.
Anitha, M., et al. (2011) Targeting glutamate mediated excitotoxicity in Huntington's disease: neural progenitors and partial glutamate antagonist--memantine. Med Hypotheses 76(1):138-40.
Banjac, A., et al. (2008) The cystine/cysteine cycle: a redox cycle regulating susceptibility versus resistance to cell death. Oncogene 27(11):1618-28.
Bartzokis, G., et al. (1999) Increased basal ganglia iron levels in Huntington disease. Arch Neurol 56(5):569-74.
Beaulieu, P. L., et al. (2003) A practical oxone®-Mediated, high-throughput, solution-phase synthesis of benzimidazoles from 1,2-phenylenediamines and aldehydes and its application to preparative scale synthesis. Synthesis 11:1683-1692.
Behl, C. (1999) Alzheimer's disease and oxidative stress: implications for novel therapeutic approaches. Prog Neurobiol 57(3):301-23.
Bergsbaken, T., et al. (2009) Pyroptosis: host cell death and inflammation. Nat Rev Microbiol 7(2):99-109.
Blois, M.S. (1958). Antioxidant determinations by the use of a stable free radical. Nature 181:1199-1200.
Cater, H.L., et al. (2007). Stretch-induced injury in organotypic hippocampal slice cultures reproduces in vivo post-traumatic neurodegeneration: role of glutamate receptors and voltage-dependent calcium channels. J Neurochem 101, 434-447.
Cha, J. H. et al. (1998). Altered brain neurotransmitter receptors in transgenic mice expressing a portion of an abnormal human huntington disease gene. Proc Natl Acad Sci USA 95, 6480-6485.
Cheah, J.H., et al. (2006). NMDA receptor-nitric oxide transmission mediates neuronal iron homeostasis via the GTPase Dexras1. Neuron 51, 431-440.
Chen, J. C. et al.(1993) MR of human postmortem brain tissue: correlative study between T2 and assays of iron and ferritin in Parkinson and Huntington disease. AJNR Am J Neuroradiol. 14(2):275-281.
Chen, J. et al. (2013) Iron accumulates in Huntington's disease neurons: protection by deferoxamine. PLoS One 8(10):e77023.
Choi, D.W. (1988) Glutamate neurotoxicity and diseases of the nervous system. Neuron 1, 623-634.
Christofferson, D.E., and Yuan, J. (2010) Necroptosis as an alternative form of programmed cell death. Current Opinion in Cell Biology 22, 263-268.
Chung, N. et al. (2008). Median absolute deviation to improve hit selection for genome-scale RNAi screens. J Biomol Screen 13, 149-158.
Cruz-Aguado, R., et al. (2000) Nerve growth factor and striatal glutathione metabolism in a rat model of Huntington's disease. Restor Neurol Neurosci 17(4):217-221.
Degterev A, et al. (2005) Chemical inhibitor of nonapoptotic cell death with therapeutic potential for ischemic brain injury. Nat Chem Biol 1 (2):112-119.

Desilva, T. M. et al. (2008) Glutamate transporter EAAT2 expression is up-regulated in reactive astrocytes in human periventricular leukomalacia. J Comp Neurol 508, 238- 248.
Dillon, C. P., et al. (2012) Survival function of the FADD-CASPASE-8-cFLIP(L) complex. Cell Reports 1(5):401-407.
Dillon, C. P., et al. (2014) RIPK1 blocks early postnatal lethality mediated by caspase-8 and RIPK3. Cell 157(5):1189-1202.
Dixon, D. J. et al., (2012) Ferroptosis: An Iron-Dependent Form of Nonapoptotic Cell Death. Cell, 149(5)1060-1072.
Dolma, S., et al. (2003). Identification of genotype-selective anti-tumor agents using synthetic lethal chemical screening in engineered human tumor cells. Cancer Cell 3, 285-296.
Dommergues, M. A., et al. (1998) Iron supplementation aggravates periventricular cystic white matter lesions in newborn mice. Eur J Paediatr Neurol 2(6):313-8.
Duce, J.A., et al. (2010). Iron-export ferroxidase activity of beta-amyloid precursor protein is inhibited by zinc in Alzheimer's disease. Cell 142, 857-867.
Estrada-Sanchez, A. M., et al. (2008) Excitotoxic neuronal death and the pathogenesis of Huntington's disease. Arch Med Res. 39(3):265-76.
Folkerth, R. D. (2006) Periventricular leukomalacia: overview and recent findings. Pediatr Dev Pathol. 9(1):3-13.
Follett, P. L., et al. (2004) Glutamate receptor-mediated oligodendrocyte toxicity in periventricular leukomalacia: a protective role for topiramate. J Neurosci 24(18):4412- 4420.
Fuchs, Y., and Steller, H. (2011) Programmed cell death in animal development and disease. Cell 147, 742-758.
Galluzzi L, et al. (2014) Molecular mechanisms of regulated necrosis. Semin Cell Dev Biol 35C:24-32.
Genna, D. T. & Posner, G. H. (2011) Cyanocuprates convert carboxylic acids directly into ketones. Org Lett 13, 5358-5361.
Gout, P.W., et al. (2001) Sulfasalazine, a potent suppressor of lymphoma growth by inhibition of the x(c)-cystine transporter: a new action for an old drug. Leukemia 15, 1633-1640.
Guo, W. et al. (2008) Identification of a small molecule with synthetic lethality for K-ras and protein kinase C iota. Cancer Res 68, 7403-7408.
Hamada, Y. & Kiso, Y. (2012) The application of bioisosteres in drug design for novel drug discovery: focusing on acid protease inhibitors. Expert Opin Drug Discov 7(10):903-22.
Haynes, R. L., et al. (2005) Oxidative and nitrative injury in periventricular leukomalacia: a review. Brain Pathol. 15(3): 225-233.
Haynes, R. L., et al. (2003) Nitrosative and oxidative injury to premyelinating oligodendrocytes in periventricular leukomalacia. J Neuropathol Exp Neurol. 62(5):441-50.
He, S., et al. (2009) Receptor interacting protein kinase-3 determines cellular necrotic response to TNF-alpha. Cell 137(6):1100-1111.
Hoffstrom, B. G., et al. (2010) Inhibitors of protein disulfide isomerase suppress apoptosis induced by misfolded proteins. Nat Chem Biol 6(12):900-906.
Huang, D., Ou, B. & Prior, R. L. (2005) The chemistry behind antioxidant capacity assays. J Agric Food Chem 53(6):1841 -1856.
International Search Report for PCT/US2014/067977, dated Mar. 3, 2015.
Ishida, T., et al.(2006) Benzimidazole inhibitors of hepatitis C virus NS5B polymerase: identification of 2-[(4-diarylmethoxy)phenyl]-benzimidazole. Bioorg Med Chem Lett 16, 1859-1863.
Ishii, T., Bannai, S., & Sugita, Y. (1981) Mechanism of growth stimulation of L1210 cells by 2-mercaptoethanol in vitro. Role of the mixed disulfide of 2- mercaptoethanol and cysteine. J Biol Chem. 10;256(23):12387-92.
Jacobson, M.D., & Raff, M.C. (1995) Programmed cell death and Bcl-2 protection in very low oxygen. Nature 374, 814-816.
Johri, A., & Beal, M. F. (2012) Antioxidants in Huntington's disease. Biochim Biophys Acta 1822, 664-674.
Kamata, T. (2009) Roles of Nox1 and other Nox isoforms in cancer development. Cancer Sci 100, 1382-1388.
Kanai, Y., and Endou, H. (2003) Functional properties of multispecific amino acid transporters and their implications to transporter-mediated toxicity. J Toxicol Sci 28, 1 -17.

(56) References Cited

OTHER PUBLICATIONS

Laleu, B. et al.(2010). First in class, potent, and orally bioavailable NADPH oxidase isoform 4 (Nox4) inhibitors for the treatment of idiopathic pulmonary fibrosis. Journal of medicinal chemistry 53, 7715-7730.

Lei, P., et al. (2012). Tau deficiency induces parkinsonism with dementia by impairing APP-mediated iron export. Nature medicine 18, 291 -295.

Li, Y., Maher, P., and Schubert, D. (1997) a role for 12-lipoxygenase in nerve cell death caused by glutathione depletion. Neuron 19, 453-463.

Linkermann, A., et al. (2012) Rip1 (receptor-interacting protein kinase 1) mediates necroptosis and contributes to renal ischemia/reperfusion injury. Kidney Int 81 (8):751-761.

Linkermann, A., et al. (2013A) The RIP1-kinase inhibitor necrostatin-1 prevents osmotic nephrosis and contrast-induced AKI in mice. J Am Soc Nephrol 24(10):1545-1557.

Linkermann, A., et al. (2013B) Two independent pathways of regulated necrosis mediate ischemia-reperfusion injury. Proc Natl Acad Sci USA 110(29):12024-12029.

Linkermann, A., Green DR (2014A) Necroptosis. N Engl J Med 370(5):455-465.

Linkermann, A., et al. (2014B) Regulated Cell Death in AKI. J Am Soc Nephrol 25(12):2689-701.

Lipinski, C.A., et al. (2001) Experimental and computational approaches to estimate solubility and permeability in drug discovery and development settings. Adv Drug Deliv Rev 46(1-3):3-26.

Lo, M., et al. (2008). The $x_c^-$ cystine/glutamate antiporter: a mediator of pancreatic cancer growth with a role in drug resistance. Br J Cancer 99(3):464-72.

Lossi, L., et al. (2009). Cell death and proliferation in acute slices and organotypic cultures of mammalian CNS. Prog Neurobiol 88, 221-245.

Luedde, M., et al. (2014) RIP3, a kinase promoting necroptotic cell death, mediates adverse remodelling after myocardial infarction. Cardiovasc Res 103(2):206-216.

Macarron, R., et al. (2011). Impact of high-throughput screening in biomedical research. Nat Rev Drug Discov 10(3):188-95.

Mason, R. P., et al. (2013) Glutathione peroxidase activity is neuroprotective in models of Huntington's disease. Nat Genet 45(10):1249-54.

Miller, B. R. & Bezprozvanny, I. (2010) Corticostriatal circuit dysfunction in Huntington's disease: intersection of glutamate, dopamine and calcium. Future Neurol 5(5):735-756.

Moffat, J., et al. (2006) A lentiviral RNAi library for human and mouse genes applied to an arrayed viral high-content screen. Cell 124, 1283-1298.

Morrison, P. J. & Nevin, N. C. (1994) Serum iron, total iron binding capacity and ferritin in early Huntington disease patients. Ir J Med Sci 163(5):236-7.

Morrison, B., 3rd, et al. (2002) L-arginyl-3,4-spermidine is neuroprotective in several in vitro models of neurodegeneration and in vivo ischaemia without suppressing synaptic transmission. Br J Pharmacol 137, 1255- 1268.

Mulay Sr, et al. (2013) Calcium oxalate crystals induce renal inflammation by NLRP3-mediated IL-1 β secretion. J Clin Invest 123(1 ):236-246.

Mullen, A.R., et al. (2011) Reductive carboxylation supports growth in tumour cells with defective mitochondria. Nature 481(7381):385-8.

Murphy, T.H., et al. (1989) Glutamate toxicity in a neuronal cell line involves inhibition of cystine transport leading to oxidative stress. Neuron 2, 1547-1558.

National Research Council (2011) Guide for the Care and Use of Laboratory Animals (National Academies Press, Washington, DC), 8th Ed.

Ni Chonghaile, T., et al. (2011) Pretreatment mitochondrial priming correlates with clinical response to cytotoxic chemotherapy. Science 334, 1129-1133.

Noraberg, J., et al. (2005) Organotypic hippocampal slice cultures for studies of brain damage, neuroprotection and neurorepair. Curr Drug Targets CNS Neurol Disord 4, 435-452.

Pagliarini, D.J., et al. (2008) A mitochondrial protein compendium elucidates complex I disease biology. Cell 134, 112-123.

Park, J. S., et al. (2011) Cyclophilin D and the mitochondrial permeability transition in kidney proximal tubules after hypoxic and ischemic injury. Am J Physiol Renal Physiol 301(1):F134-50.

Passaniti, P., et al. (2002) Synthesis, spectroscopic and electrochemical properties of mononuclear and dinuclear bis(bipy)ruthenium(II) complexes containing dimethoxyphenyl(pyridin-2-yl)-1 ,2,4-triazole ligands J. Chem. Soc., Dalton Transactions 8, 1740-1746.

Petr, G. T., et al. (2013) Glutamate transporter expression and function in a striatal neuronal model of Huntington's disease. Neurochem Int 62(7):973-81.

Pinnix, Z.K., et al. (2010). Ferroportin and iron regulation in breast cancer progression and prognosis. Sci Transl Med 2(43):43ra56.

Pipik, B., et al. (2004) A preferred synthesis of 1,2,4-oxadiazoles. Synthetic Communications 34, 1863-1870.

Raj, L., et al. (2011) Selective killing of cancer cells by a small molecule targeting the stress response to ROS. Nature 475, 231-234.

Ramana, K. V., et al. Lipid Peroxidation Products in Human Health and Disease. Oxid Med Cell Longev 2013:583438.

Ramanathan, A., & Schreiber, S.L. (2009) Direct control of mitochondrial function by mTOR. Proc Natl Acad Sci U S A 106, 22229-22232.

Ratan, R.R., Murphy, T.H., and Baraban, J.M. (1994) Oxidative stress induces apoptosis in embryonic cortical neurons. J Neurochem 62, 376-379.

Ribeiro, F. M., Pires, R. G. & Ferguson, S. S. (2011) Huntington's disease and Group I metabotropic glutamate receptors. Mol Neurobiol 43(1):1-11.

Ribeiro, M. et al. (2012) Glutathione redox cycle dysregulation in Huntington's disease knock-in striatal cells. Free Radic Biol Med 53, 1857-1867.

Saitoh, M. et al. (2009) Design, synthesis and structure-activity relationships of 1 ,3,4- oxadiazole derivatives as novel inhibitors of glycogen synthase kinase-3beta. Bioorg Med Chem 17, 2017-2029.

Salahudeen, A.A., et al. (2009) An E3 ligase possessing an iron-responsive hemerythrin domain is a regulator of iron homeostasis. Science 326, 722-726.

Sanchez, M., et al. (2011) Iron regulatory protein-1 and -2: transcriptome-wide definition of binding mRNAs and shaping of the cellular proteome by iron regulatory proteins. Blood 118, e168-179.

Sato, H., et al. (1999) Cloning and expression of a plasma membrane cystine/glutamate exchange transporter composed of two distinct proteins. J Biol Chem 274(17):11455-8.

Shaw, A.T., et al. (2011) Selective killing of K-ras mutant cancer cells by small molecule inducers of oxidative stress. Proc Natl Acad Sci U S A 108(21):8773-8.

Skouta R, et al. (2014) Ferrostatins inhibit oxidative lipid damage and cell death in diverse disease models. J Am Chem Soc 136(12):4551-4556.

Smith CC, et al. (2007) Necrostatin: A potentially novel cardioprotective agent? Cardiovasc Drugs Ther 21 (4):227-233.

Sogabe, K., et al. (1996) Differential cytoprotection by glycine against oxidant damage to proximal tubule cells. Kidney Int 50(3):845-54.

Sundstrom, L., et al. (2005) Organotypic cultures as tools for functional screening in the CNS. Drug Discov Today 10(14):993-1000.

Tan, S., et al. (1998) The regulation of reactive oxygen species production during programmed cell death. J Cell Biol 141(6):1423-32.

Thompson, C.B. (1995). Apoptosis in the pathogenesis and treatment of disease. Science 267, 1456-1462.

Trachootham, D., et al. (2006) Selective killing of oncogenically transformed cells through a ROS-mediated mechanism by beta-phenylethyl isothiocyanate. Cancer Cell 10, 241 -252.

Traykova-Brauch, M., et al. (2008) An efficient and versatile system for acute and chronic modulation of renal tubular function in transgenic mice. Nat Med 14(9): 979-984.

(56) References Cited

OTHER PUBLICATIONS

Turmaine, M., et al.(2000) Nonapoptotic neurodegeneration in a transgenic mouse model of Huntington's disease. Proc Natl Acad Sci U S A 97(14):8093-8097.

Varma, H., Lo, D. C. & Stockwell, B. R. (2011) "High-Throughput and High-Content Screening for Huntington's Disease Therapeutics," in Neurobiology of Huntington's Disease: Applications to Drug Discovery Frontiers in Neuroscience (eds D. C. Lo & R. E. Hughes).

Vashisht, A.A., et al. (2009) Control of iron homeostasis by an iron-regulated ubiquitin ligase. Science 326, 718-721.

Vigil, D., et al. (2010) Ras superfamily GEFs and GAPs: validated and tractable targets for cancer therapy? Nat Rev Cancer 10, 842-857.

Wang, Y., Dawson, V.L., and Dawson, T.M. (2009) Poly(ADP-ribose) signals to mitochondrial AIF: a key event in parthanatos. Exp Neurol 218, 193-202.

Watkins, P.A., et al. (2007) Evidence for 26 distinct acyl-coenzyme A synthetase genes in the human genome. J Lipid Res 48, 2736-2750.

Wise, D.R., et al. (2008) Myc regulates a transcriptional program that stimulates mitochondrial glutaminolysis and leads to glutamine addiction. Proc Natl Acad Sci U S A. 105(48):18782-7.

Wolpaw, A.J., et al. (2011) Modulatory profiling identifies mechanisms of small molecule-induced cell death. Proceedings of the National Academy of Sciences of the United States of America.

Written Opinion of the International Searching Authority for PCT/US2014/067977, dated Mar. 3, 2015.

Wu, C., et al. (2004) Discovery, modeling, and human pharmacokinetics of N-(2-acetyl-4,6-dimethylphenyl)-3-(3,4-dimethylisoxazol-5-ylsulfamoyl)thiophene-2-carboxamide (TBC3711), a second generation, ETA selective, and orally bioavailable endothelin antagonist. J Med Chem 47(8):1969-86.

Yagoda, N., et al. (2007) RAS-RAF-MEK-dependent oxidative cell death involving voltage-dependent anion channels. Nature 447(7146):864-8.

Yang, W.S., and Stockwell, B.R. (2008) Synthetic lethal screening identifies compounds activating iron-dependent, nonapoptotic cell death in oncogenic-RAS-harboring cancer cells. Chem Biol 15(3):234-45.

Yonezawa, M., et al. (1996) Cystine deprivation induces oligodendroglial death: rescue by free radical scavengers and by a diffusible glial factor. J Neurochem 67, 566-573.

Zeron, M. M. et al. (2002) Increased sensitivity to N-methyl-D-aspartate receptor-mediated excitotoxicity in a mouse model of Huntington's disease. Neuron 33, 849-860.

Zhang DW, et al. (2009) RIP3, an energy metabolism regulator that switches TNFinduced cell death from apoptosis to necrosis. Science 325(5938):332-336.

\* cited by examiner

Figure 1
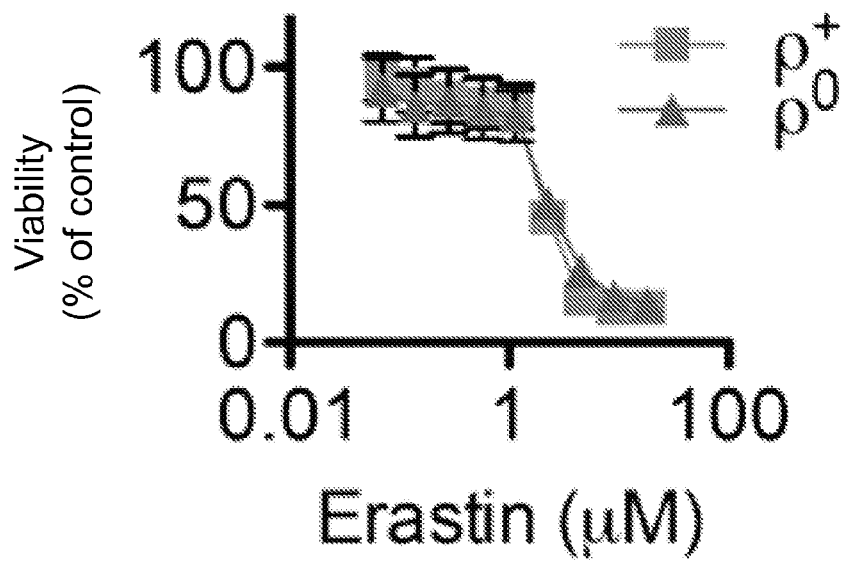
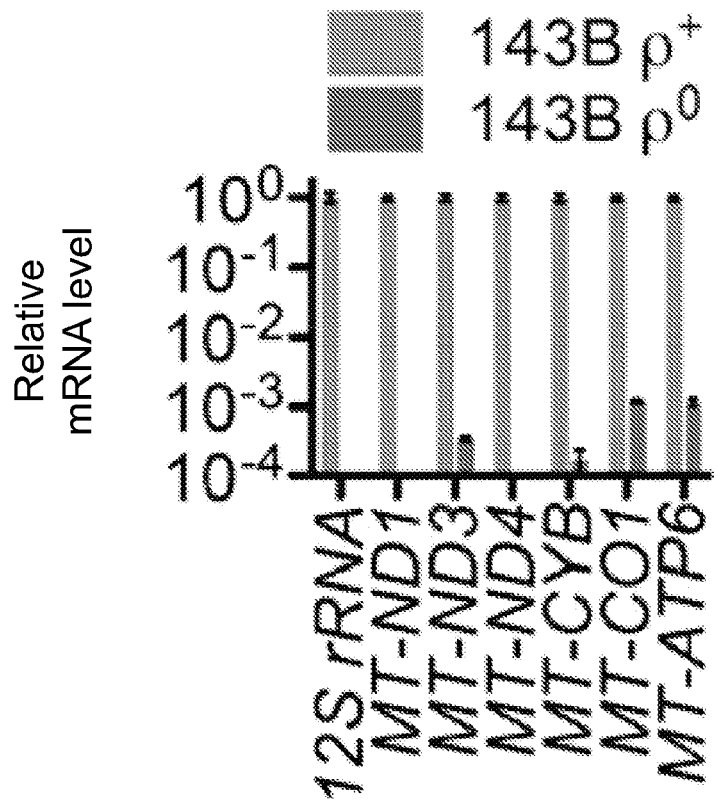

Figure 2
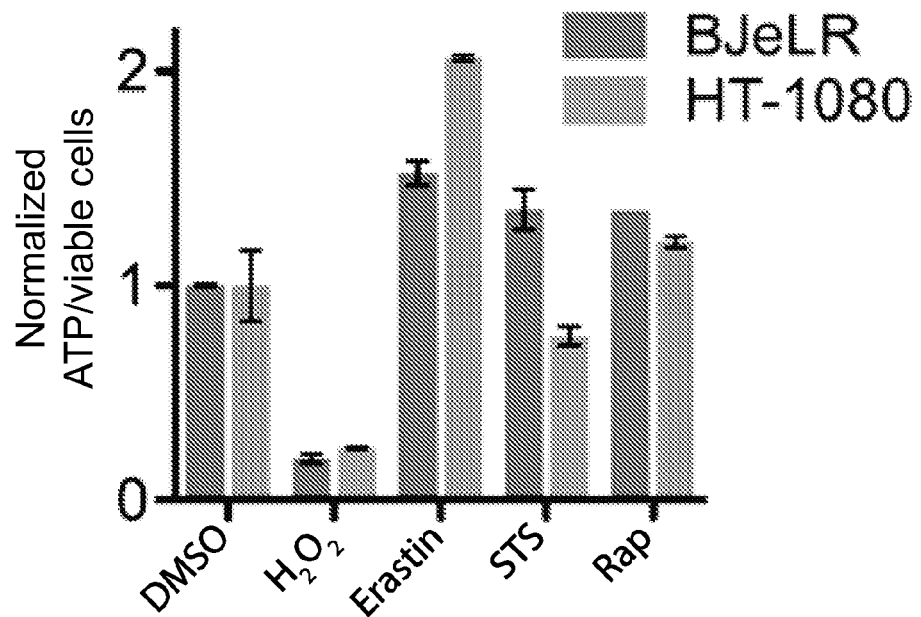
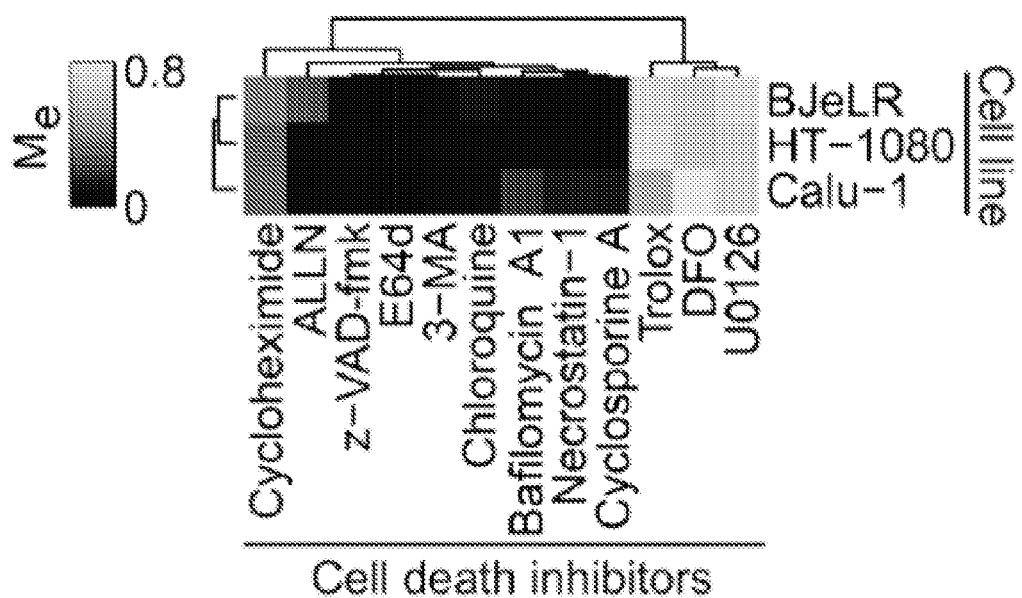

Figure 2
D
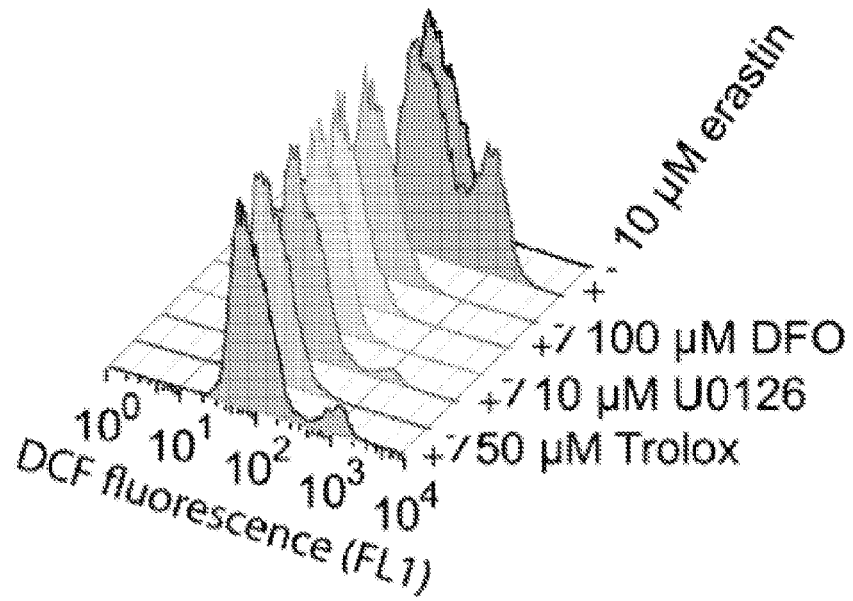
E
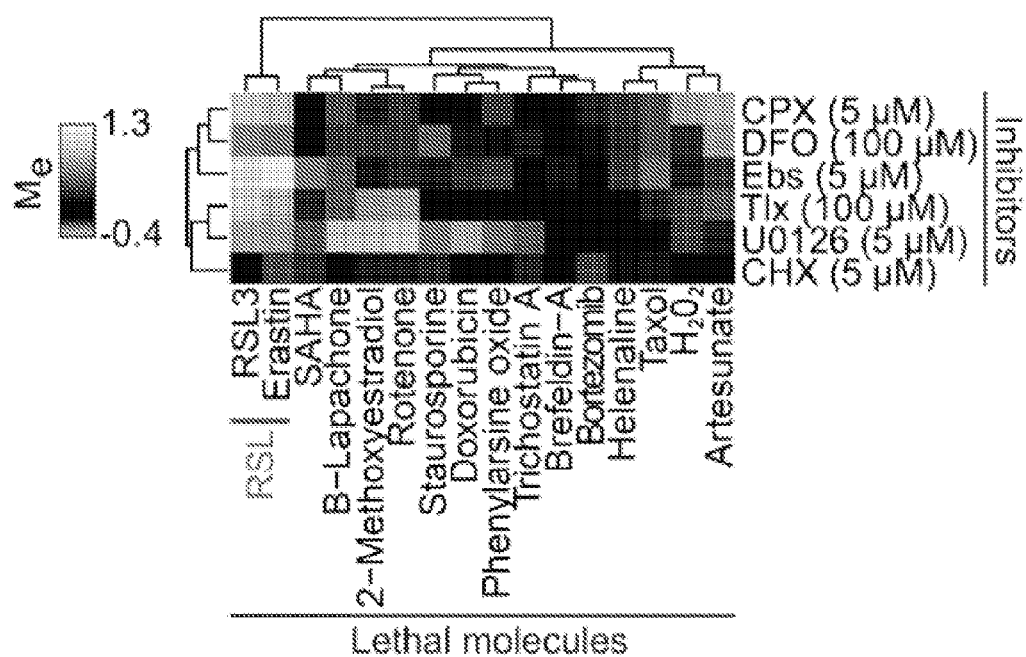

Figure 3 Continued
D
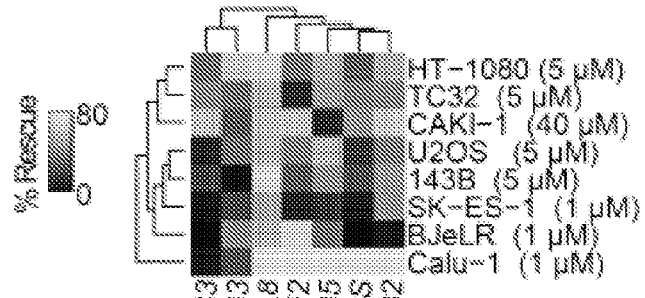
E
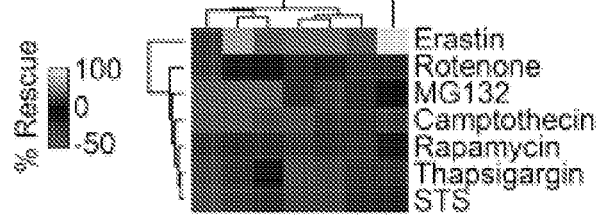
F
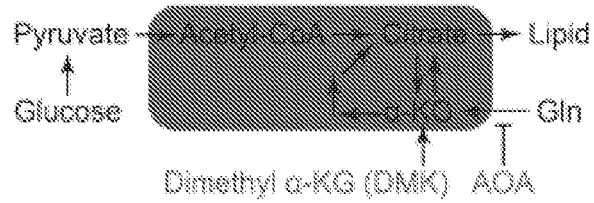
G
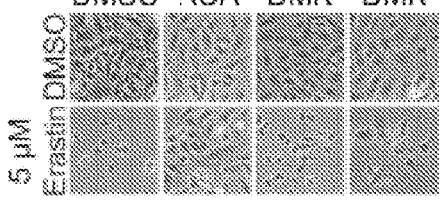

Figure 4
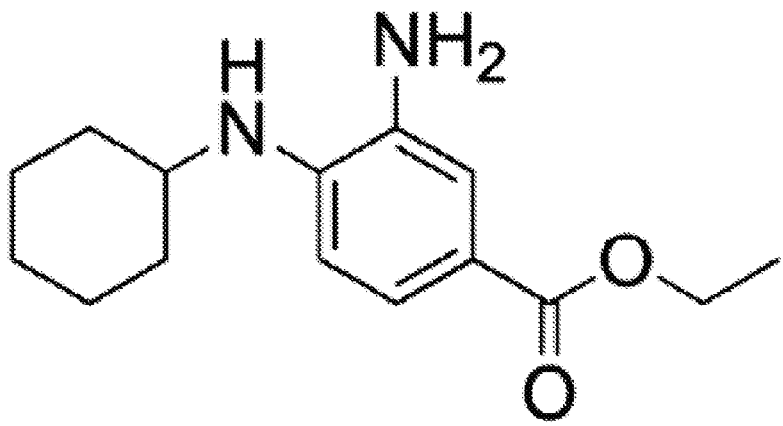
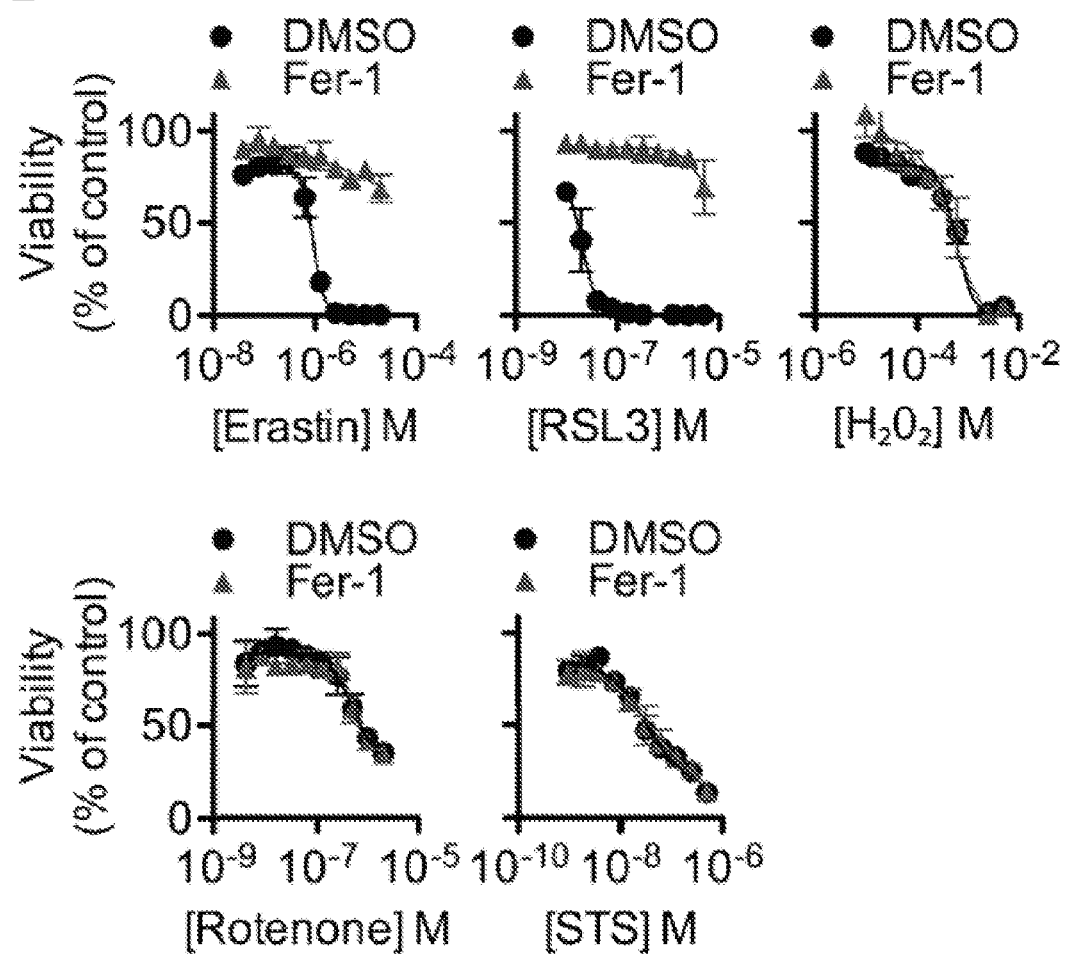

Figure 4
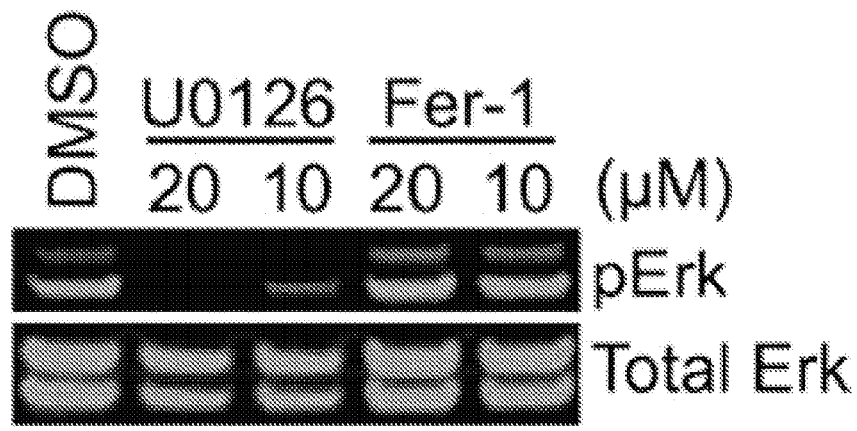
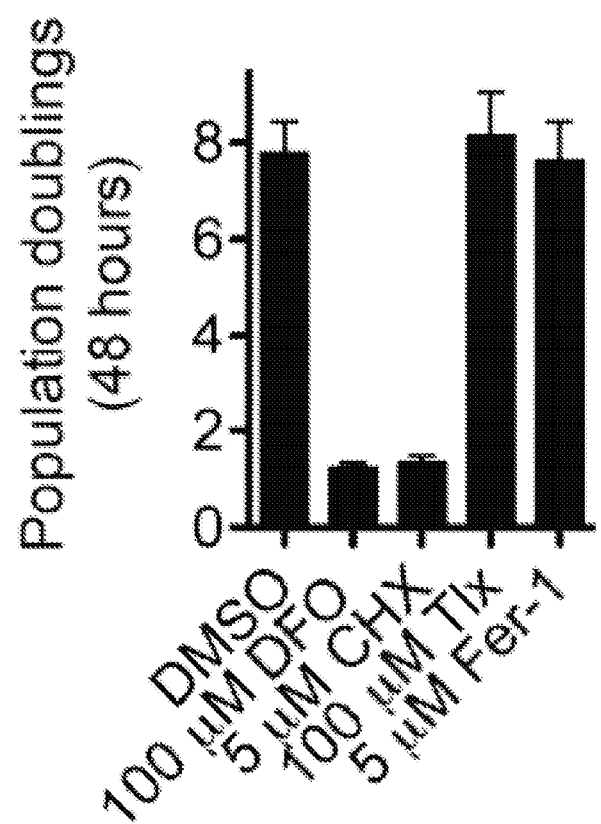

Figure 4
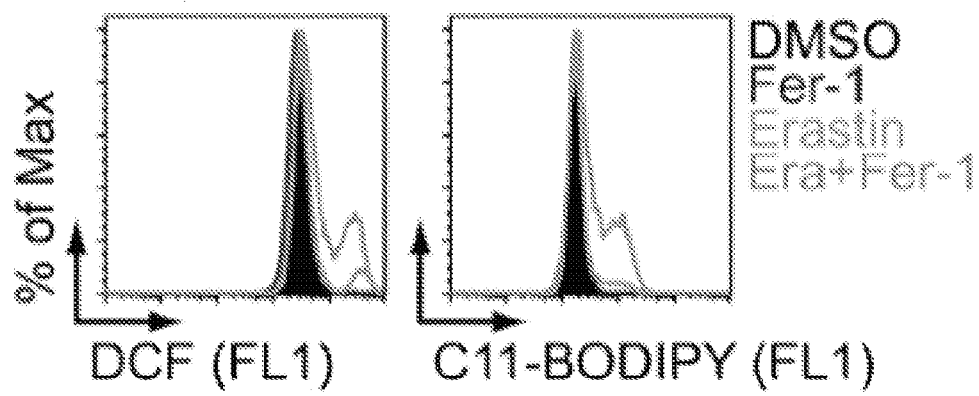
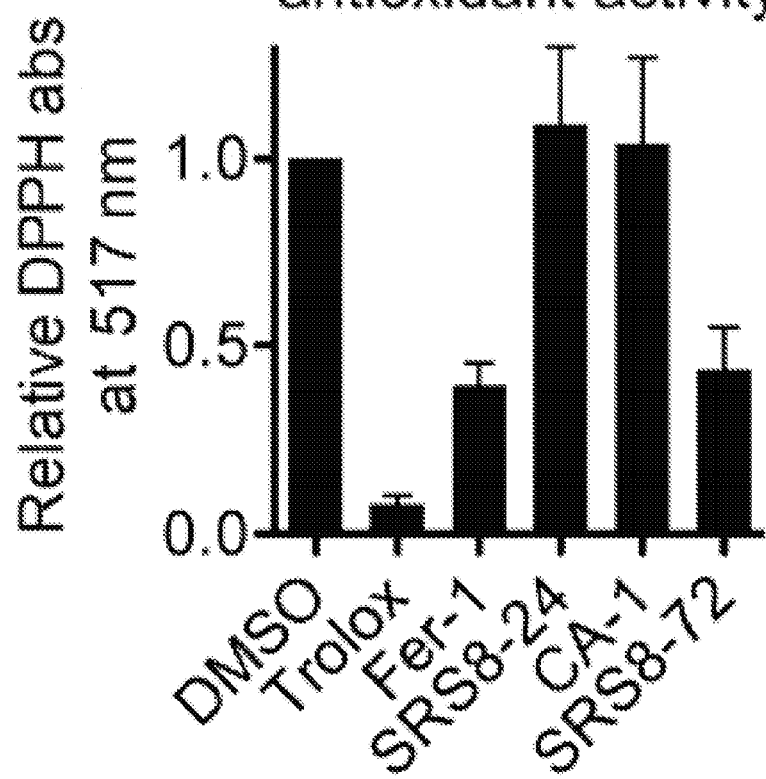

Figure 4
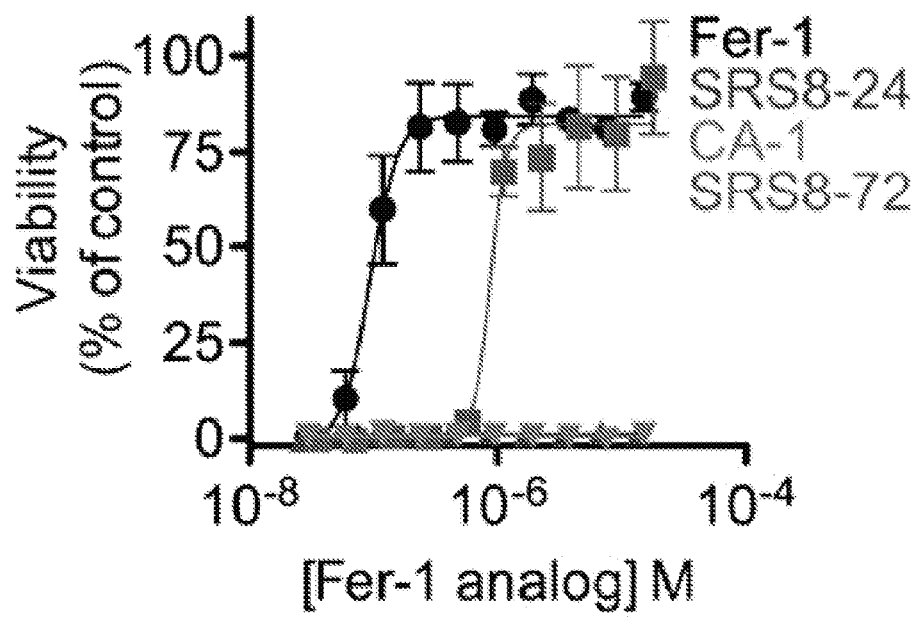
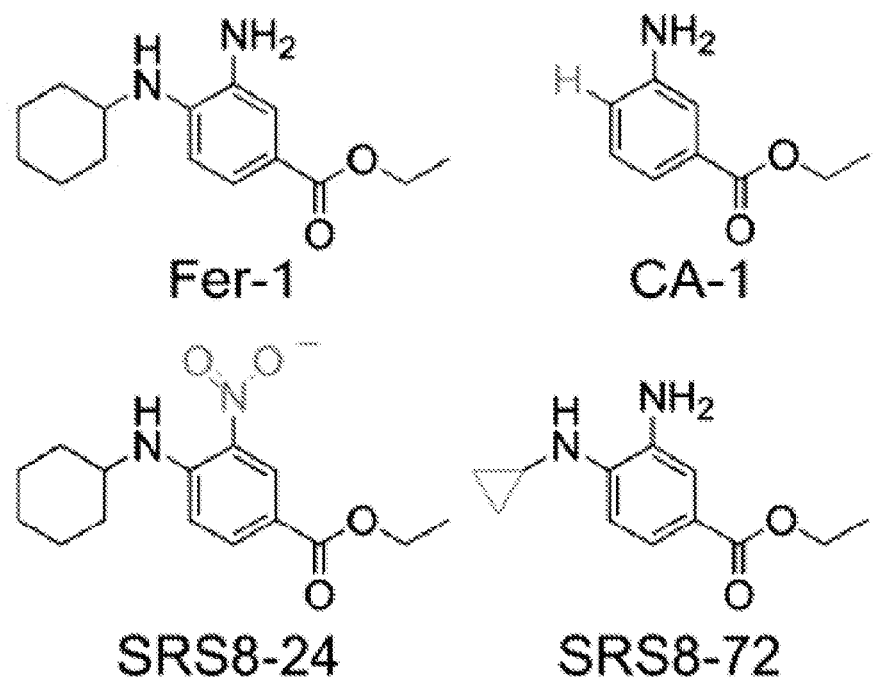

Figure 4
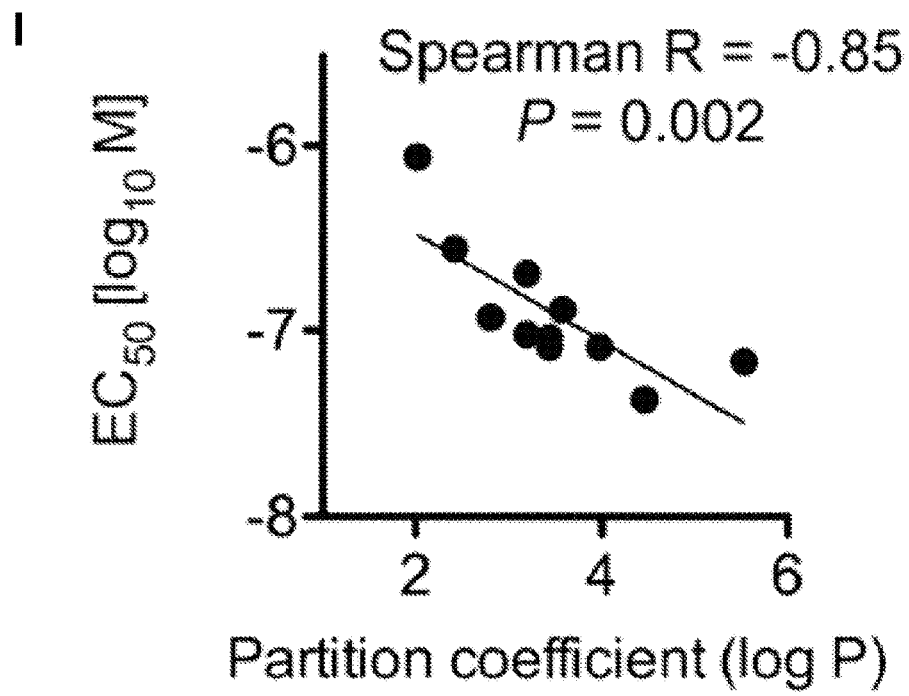
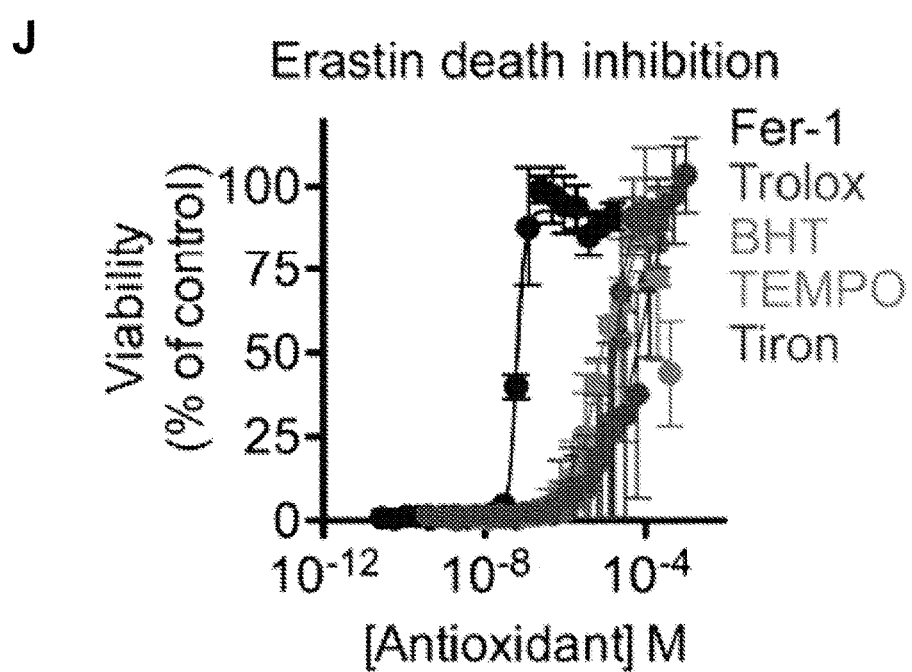

Figure 6
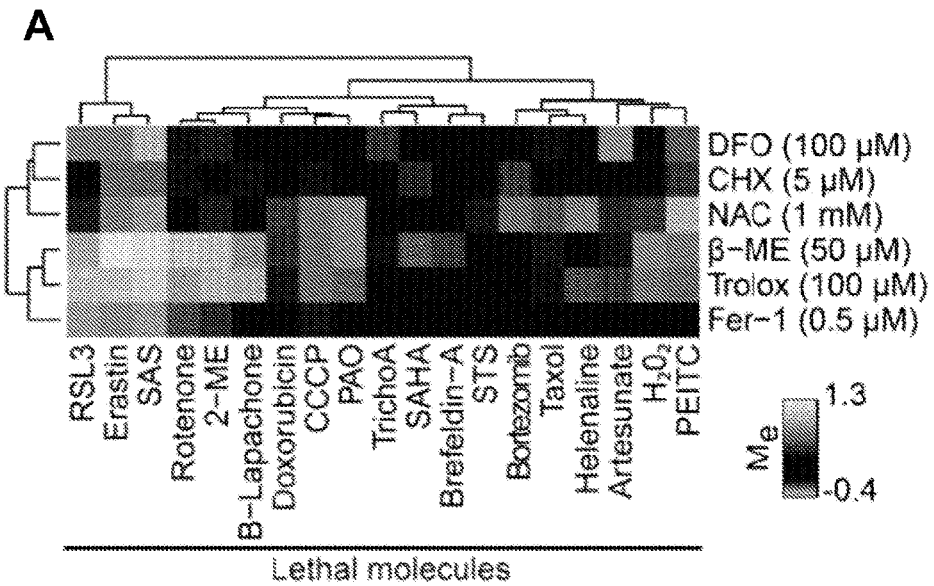
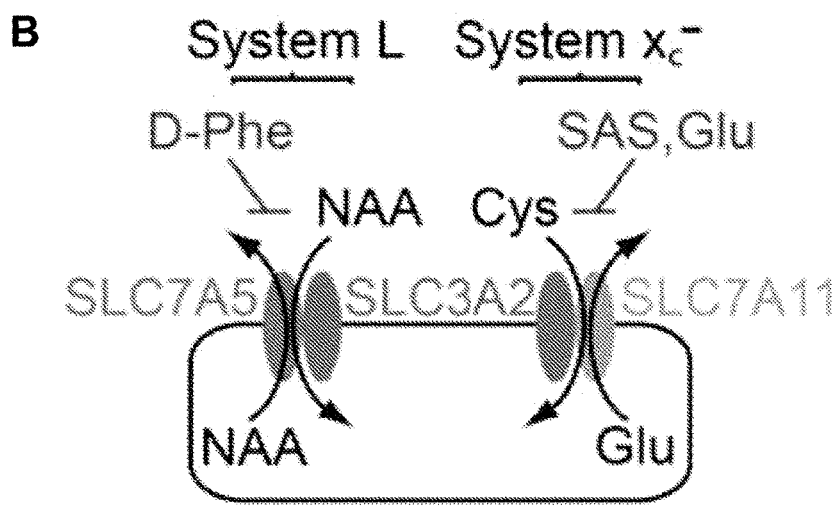

Figure 6
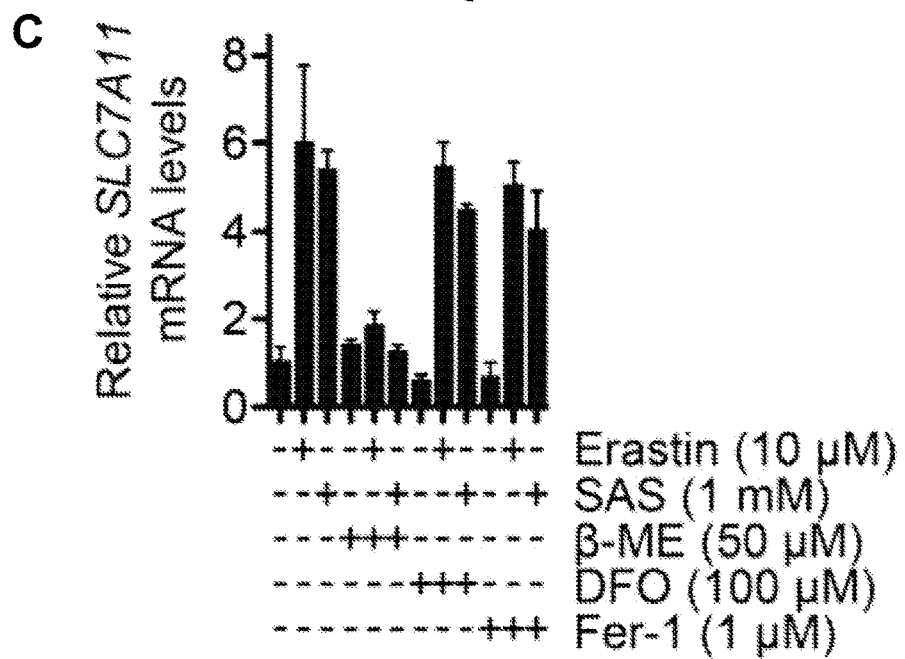
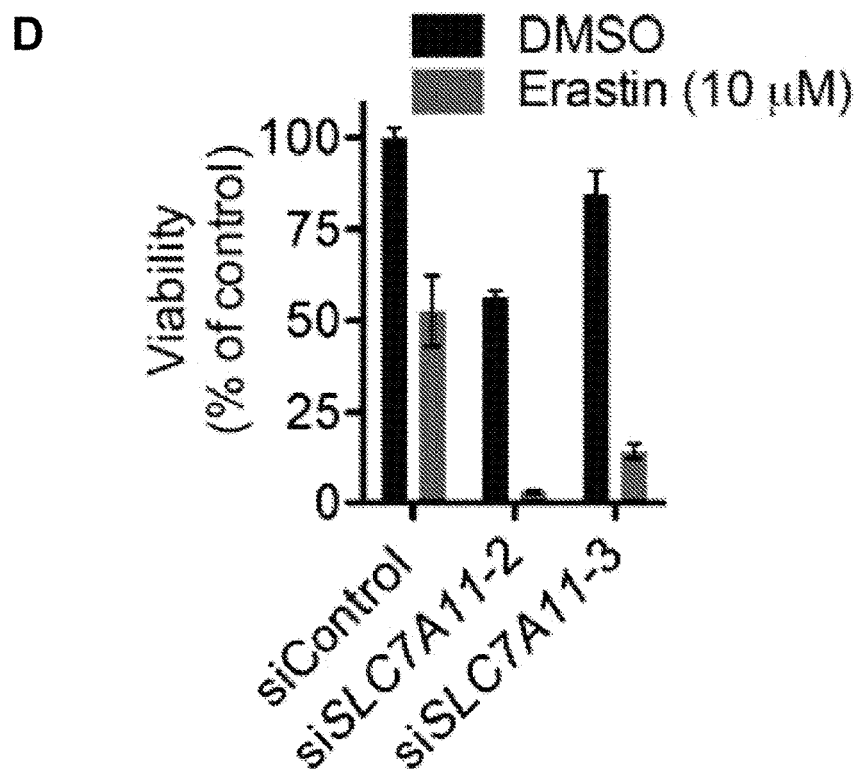

Figure 6
E
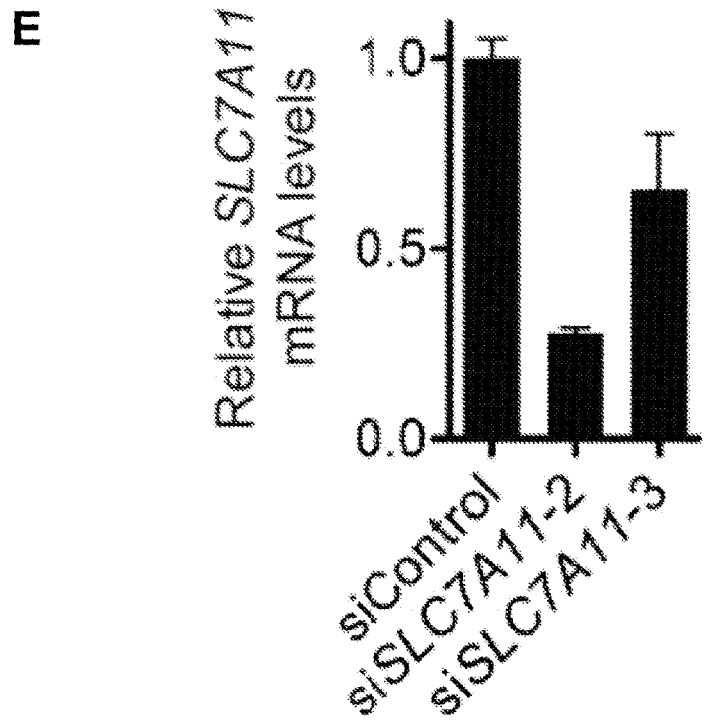
F
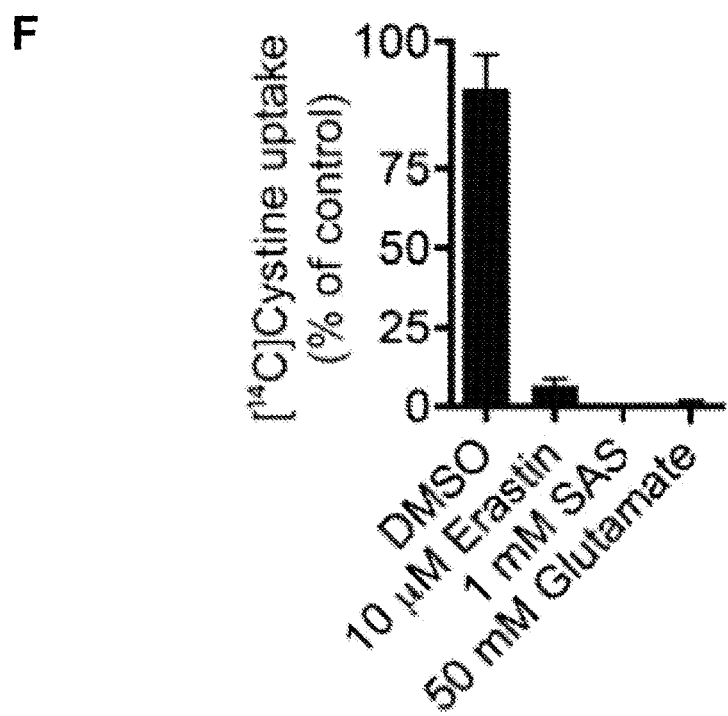

G

Erastin affinity purification
BJeH    BJeLR 4  1  10

↓

SLC7A5

H  Metabolic profile: Jurkat T cells
(1 µM erastin, 25 minutes)

*System L substrates:*

| AA | Fold-chng | P value | Rank |
|---|---|---|---|
| Tyr | 0.81 | 0.0005 | 1/123 |
| Trp | 0.77 | 0.001 | 2/123 |
| Phe | 0.82 | 0.002 | 6/123 |
| Met | 0.83 | 0.002 | 7/123 |
| Ile/Leu | 0.86 | 0.004 | 12/123 |
| His | 0.80 | 0.06 | 50/123 |

*Non-system L substrates:*

| AA | Fold-chng | P value | Rank |
|---|---|---|---|
| Ser | 1.44 | 0.1 | 57/123 |
| Thr | 1.36 | 0.03 | 35/123 |
| Asn | 1.23 | 0.13 | 67/123 |
| Ala | 1.3 | 0.15 | 68/123 |
| Arg | 1.07 | 0.21 | 87/123 |

A

B

A

Activity of Ferrostatins Analogs

| Entry | $R_1$ | $R_2$ | Name | EC50 (nM) for erastin lethality suppression | cLogP | In vitro reducing activity of DPPH radical (% DPPH inhibition ± stdev) |
|---|---|---|---|---|---|---|
| 1 | H | H | Fer-1 (SRS8-28) | 95 | 3.2 | 69 ± 5 |
| 2 | H | tert-butyl | SRS13-10F2 | 13 | 4.7 | 63 ± 6 |
| 3 | benzyl | H | SRS11-92 | 6 | 5.3 | 87 ± 5 |
| 4 | 4-picolyl | H | SRS12-45 | 25 | 4.0 | 84 ± 13 |
| 5 | pyrimidinylmethyl | H | SRS13-35 | 27 | 2.9 | 69 ± 6 |
| 6 | pyrimidinylmethyl | tert-butyl | SRS13-37 | 15 | 4.4 | 64 ± 6 |

B

Figure 23 continued
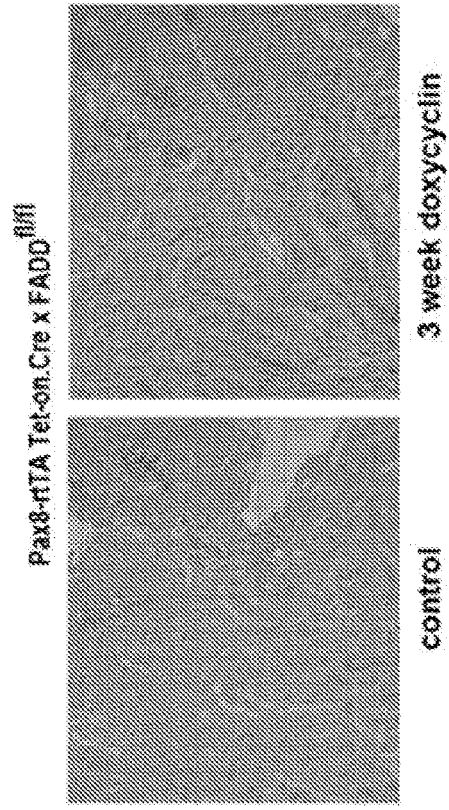
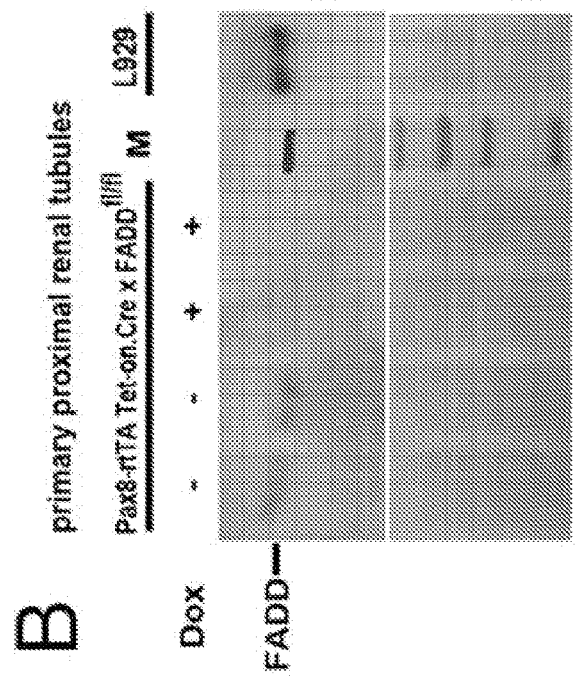

Figure 27 continued
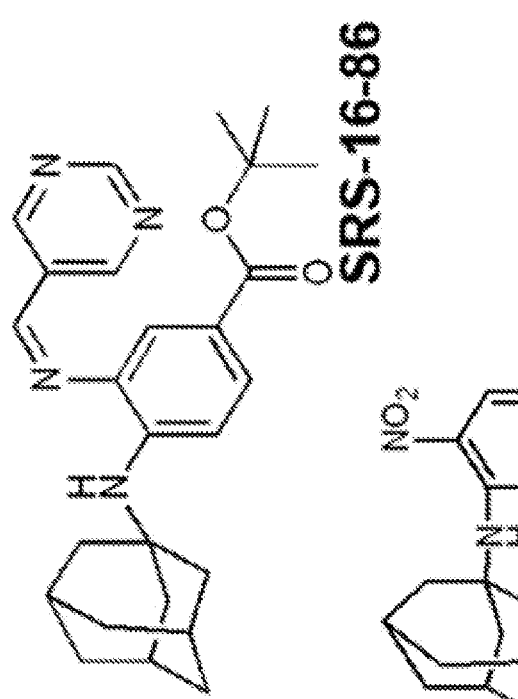
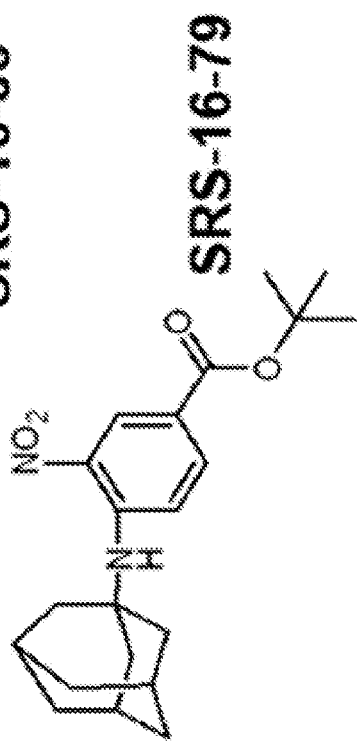

Figure 29
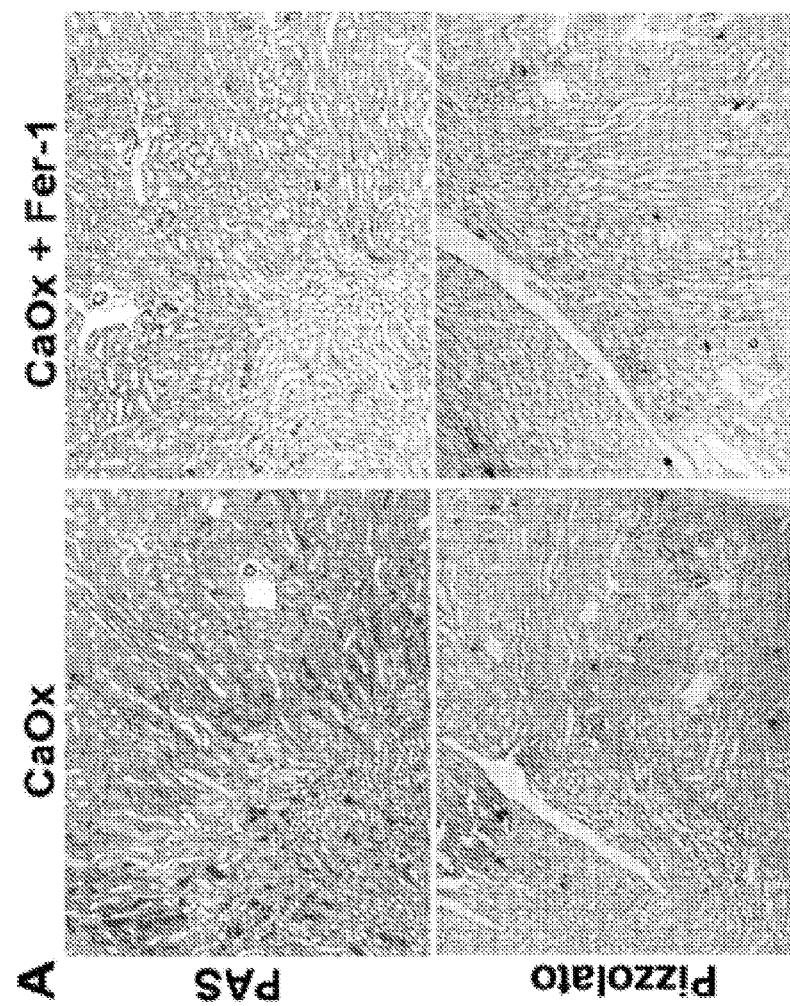
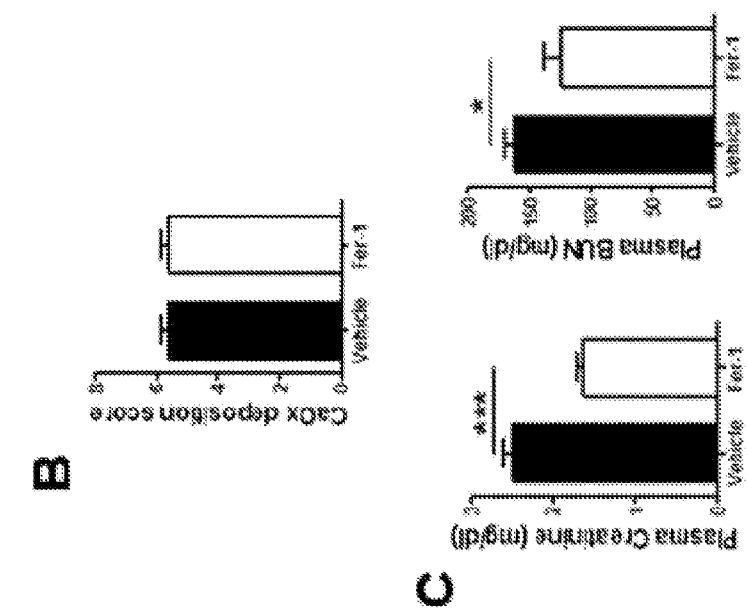

SEQUENCE LISTING

```
<160> NUMBER OF SEQ ID NOS: 24

<210> SEQ ID NO 1
<211> LENGTH: 21
<212> TYPE: DNA
<213> ORGANISM: Artificial Sequence
<220> FEATURE:
<223> OTHER INFORMATION: Synthetic construct

<400> SEQUENCE: 1
caggcaacct agaaaccaaa t                                                    21

<210> SEQ ID NO 2
<211> LENGTH: 21
<212> TYPE: DNA
<213> ORGANISM: Artificial Sequence
<220> FEATURE:
<223> OTHER INFORMATION: Synthetic construct

<400> SEQUENCE: 2
ccgaattgac aaacccatct t                                                    21

<210> SEQ ID NO 3
<211> LENGTH: 21
<212> TYPE: DNA
<213> ORGANISM: Artificial Sequence
<220> FEATURE:
<223> OTHER INFORMATION: Synthetic construct

<400> SEQUENCE: 3
cagtgcaatc agcagagaca t                                                    21

<210> SEQ ID NO 4
<211> LENGTH: 21
<212> TYPE: DNA
<213> ORGANISM: Artificial Sequence
<220> FEATURE:
<223> OTHER INFORMATION: Synthetic construct

<400> SEQUENCE: 4
gaacttattg gcctgtaact t                                                    21

<210> SEQ ID NO 5
<211> LENGTH: 21
<212> TYPE: DNA
<213> ORGANISM: Artificial Sequence
<220> FEATURE:
<223> OTHER INFORMATION: Synthetic construct

<400> SEQUENCE: 5
gcaggaagta tcgctaggaa t                                                    21

<210> SEQ ID NO 6
<211> LENGTH: 21
```

```
<212> TYPE: DNA
<213> ORGANISM: Artificial Sequence
<220> FEATURE:
<223> OTHER INFORMATION: Synthetic construct

<400> SEQUENCE: 6
gattccgaag tacatcgtgt t                                              21

<210> SEQ ID NO 7
<211> LENGTH: 21
<212> TYPE: DNA
<213> ORGANISM: Artificial Sequence
<220> FEATURE:
<223> OTHER INFORMATION: Synthetic construct

<400> SEQUENCE: 7
gcaggccaga attaagactt t                                              21

<210> SEQ ID NO 8
<211> LENGTH: 21
<212> TYPE: DNA
<213> ORGANISM: Artificial Sequence
<220> FEATURE:
<223> OTHER INFORMATION: Synthetic construct

<400> SEQUENCE: 8
ccatgtctag actggacaag a                                              21

<210> SEQ ID NO 9
<211> LENGTH: 21
<212> TYPE: DNA
<213> ORGANISM: Artificial Sequence
<220> FEATURE:
<223> OTHER INFORMATION: Synthetic construct

<400> SEQUENCE: 9
ctccaggcca catatgatta g                                              21

<210> SEQ ID NO 10
<211> LENGTH: 30
<212> TYPE: DNA
<213> ORGANISM: Artificial Sequence
<220> FEATURE:
<223> OTHER INFORMATION: Synthetic construct

<400> SEQUENCE: 10
gcattaccgg tcgatgcaac gagtgatgag                                     30

<210> SEQ ID NO 11
<211> LENGTH: 30
<212> TYPE: DNA
<213> ORGANISM: Artificial Sequence
<220> FEATURE:
<223> OTHER INFORMATION: Synthetic construct

<400> SEQUENCE: 11
gagtgaacga acctggtcga aatcagtgcg                                     30

<210> SEQ ID NO 12
<211> LENGTH: 24
<212> TYPE: DNA
<213> ORGANISM: Artificial Sequence
<220> FEATURE:
<223> OTHER INFORMATION: Synthetic construct

<400> SEQUENCE: 12
```
ataattcccc caaatcctcg catc                                              24

<210> SEQ ID NO 13
<211> LENGTH: 21
<212> TYPE: DNA
<213> ORGANISM: Artificial Sequence
<220> FEATURE:
<223> OTHER INFORMATION: Synthetic construct

<400> SEQUENCE: 13
ggctcactcc cagggcttcc t                                                 21

<210> SEQ ID NO 14
<211> LENGTH: 21
<212> TYPE: DNA
<213> ORGANISM: Artificial Sequence
<220> FEATURE:
<223> OTHER INFORMATION: Synthetic construct

<400> SEQUENCE: 14
tcaccgttgc tctttgtcta c                                                 21

<210> SEQ ID NO 15
<211> LENGTH: 21
<212> TYPE: DNA
<213> ORGANISM: Artificial Sequence
<220> FEATURE:
<223> OTHER INFORMATION: Synthetic construct

<400> SEQUENCE: 15
gtaatctctg tagggagccc t                                                 21

<210> SEQ ID NO 16
<211> LENGTH: 21
<212> TYPE: DNA
<213> ORGANISM: Artificial Sequence
<220> FEATURE:
<223> OTHER INFORMATION: Synthetic construct

<400> SEQUENCE: 16
ctagcgcata ggatgatcag a                                                 21

<210> SEQ ID NO 17
<211> LENGTH: 18
<212> TYPE: DNA
<213> ORGANISM: Artificial Sequence
<220> FEATURE:
<223> OTHER INFORMATION: Synthetic construct

<400> SEQUENCE: 17
tcagctcggg aatgcaca                                                     18

<210> SEQ ID NO 18
<211> LENGTH: 18
<212> TYPE: DNA
<213> ORGANISM: Artificial Sequence
<220> FEATURE:
<223> OTHER INFORMATION: Synthetic construct

<400> SEQUENCE: 18
tggttgcctt ccgtgtct                                                     18

<210> SEQ ID NO 19
<211> LENGTH: 20
<212> TYPE: DNA
<213> ORGANISM: Artificial Sequence

```
<220> FEATURE:
<223> OTHER INFORMATION: Synthetic construct

<400> SEQUENCE: 19
tgatgcactt gcagaaaaca                                          20

<210> SEQ ID NO 20
<211> LENGTH: 21
<212> TYPE: DNA
<213> ORGANISM: Artificial Sequence
<220> FEATURE:
<223> OTHER INFORMATION: Synthetic construct

<400> SEQUENCE: 20
accagaggaa attttcaata g                                        21

<210> SEQ ID NO 21
<211> LENGTH: 20
<212> TYPE: DNA
<213> ORGANISM: Artificial Sequence
<220> FEATURE:
<223> OTHER INFORMATION: Synthetic construct

<400> SEQUENCE: 21
tccaggtcag ttagccttgc                                          20

<210> SEQ ID NO 22
<211> LENGTH: 20
<212> TYPE: DNA
<213> ORGANISM: Artificial Sequence
<220> FEATURE:
<223> OTHER INFORMATION: Synthetic construct

<400> SEQUENCE: 22
cggtcaaaaa gtttgccttg                                          20

<210> SEQ ID NO 23
<211> LENGTH: 19
<212> TYPE: DNA
<213> ORGANISM: Artificial Sequence
<220> FEATURE:
<223> OTHER INFORMATION: Synthetic construct

<400> SEQUENCE: 23
cgcttctctt caatccggt                                           19

<210> SEQ ID NO 24
<211> LENGTH: 20
<212> TYPE: DNA
<213> ORGANISM: Artificial Sequence
<220> FEATURE:
<223> OTHER INFORMATION: Synthetic construct

<400> SEQUENCE: 24
gagtctccat gcagctacgg                                          20
```

COMPOUNDS, COMPOSITIONS, AND METHODS FOR MODULATING FERROPTOSIS AND TREATING EXCITOTOXIC DISORDERS

CROSS REFERENCE TO RELATED APPLICATIONS

This application is a U.S. National Stage Application of International Application No. PCT/US2014/067977, filed on Dec. 1, 2014, and which claims priority to U.S. Provisional Patent Application Nos. 61/910,580, filed on Dec. 2, 2013, and 61/948,242, filed on Mar. 5, 2014. The entire contents of the above applications are incorporated by reference as if recited in full herein.

FIELD OF INVENTION

The present invention provides, inter alia, compounds having the structure:

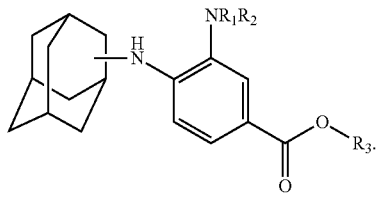

Also provided are pharmaceutical compositions containing the compounds of the present invention, as well as methods of using the compounds and compositions of the present invention.

INCORPORATION BY REFERENCE OF SEQUENCE LISTING

This application contains references to amino acids and/or nucleic acid sequences that have been filed concurrently herewith as sequence listing text file "0365713pct_ST25.txt", file size of 4.86 KB, created on Nov. 24, 2014. The aforementioned sequence listing is hereby incorporated by reference in its entirety pursuant to 37 C.F.R. § 1.52(e)(5).

BACKGROUND OF THE INVENTION

Cell death is crucial for normal development, homeostasis and the prevention of hyper-proliferative diseases such as cancer (Fuchs and Steller, 2011; Thompson, 1995). It was once thought that almost all regulated cell death in mammalian cells resulted from the activation of caspase-dependent apoptosis (Fuchs and Steller, 2011; Thompson, 1995). More recently this view has been challenged by the discovery of several regulated non-apoptotic cell death pathways activated in specific disease states, including poly(ADP-ribose) polymerase-1 (PARP-1) and apoptosis inducing factor 1 (AIF1)-dependent parthanatos, caspase-1-dependent pyroptosis and receptor interacting protein kinase 1 (RIPK1)-dependent necroptosis (Bergsbaken et al., 2009; Christofferson and Yuan, 2010; Wang et al., 2009). It is believed that additional regulated forms of non-apoptotic cell death likely remain to be discovered that mediate cell death in other developmental or pathological circumstances.

The RAS family of small GTPases (HRAS, NRAS and KRAS) are mutated in about 30% of all cancers (Vigil et al., 2010). Finding compounds that are selectively lethal to RAS-mutant tumor cells is, therefore, a high priority. Two structurally unrelated small molecules, named erastin and RSL3, were previously identified. These molecules were selectively lethal to oncogenic RAS-mutant cell lines, and together, they were referred to as RAS-selective lethal (RSL) compounds (Dolma et al., 2003; Yang and Stockwell, 2008). Using affinity purification, voltage dependent anion channels 2 and 3 (VDAC2/3) were identified as direct targets of erastin (Yagoda et al., 2007), but not RSL3. ShRNA and cDNA overexpression studies demonstrated that VDAC2 and VDAC3 are necessary, but not sufficient, for erastin-induced death (Yagoda et al., 2007), indicating that additional unknown targets are required for this process.

The type of cell death activated by the RSLs has been enigmatic. Classic features of apoptosis, such as mitochondrial cytochrome c release, caspase activation and chromatin fragmentation, are not observed in RSL-treated cells (Dolma et al., 2003; Yagoda et al., 2007; Yang and Stockwell, 2008). RSL-induced death is, however, associated with increased levels of intracellular reactive oxygen species (ROS) and is prevented by iron chelation or genetic inhibition of cellular iron uptake (Yagoda et al., 2007; Yang and Stockwell, 2008). In a recent systematic study of various mechanistically unique lethal compounds, the prevention of cell death by iron chelation was a rare phenomenon (Wolpaw et al., 2011), suggesting that few triggers can access iron-dependent lethal mechanisms.

Accordingly, there is a need for the exploration of various pathways of regulated cell death, as well as for compositions and methods for preventing the occurrence of regulated cell death. This invention is directed to meeting these and other needs.

SUMMARY OF THE INVENTION

Without being bound to a particular theory, the inventors hypothesized that RSLs, such as erastin, activate a lethal pathway that is different from apoptosis, necrosis and other well-characterized types of regulated cell death. It was found that erastin-induced death involves a unique constellation of morphological, biochemical and genetic features, which led to the name "ferroptosis" as a description for this phenotype. Small molecule inhibitors of ferroptosis that prevent ferroptosis in cancer cells, as well as glutamate-induced cell death in postnatal rat brain slices have been identified and disclosed herein. The inventors have found an underlying similarity between diverse forms of iron-dependent, non-apoptotic death and that the manipulation of ferroptosis may be exploited to selectively destroy RAS-mutant tumor cells or to preserve neuronal cells exposed to specific oxidative conditions.

Accordingly, one embodiment of the present invention is a compound according to formula (I):

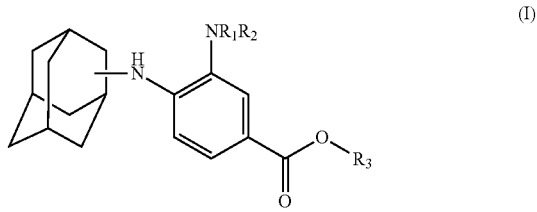

wherein:

R$_1$ and R$_2$, are independently selected from the group consisting of no atom, H, D, O, halo, C$_{1-6}$alkyl, C$_{1-6}$alkyl-aryl, C$_{1-6}$alkyl-heteroaryl, C$_{1-6}$alkenyl, C$_{1-6}$alkenyl-aryl, and C$_{1-6}$alkenyl-heteroaryl, wherein the C$_{1-6}$alkyl, C$_{1-6}$alkyl-aryl, C$_{1-6}$alkyl-heteroaryl, C$_{1-6}$alkenyl, C$_{1-6}$alkenyl-aryl, and C$_{1-6}$alkenyl-heteroaryl may be optionally substituted with an atom or a group selected from the group consisting of halo, deuterium, C$_{1-4}$alkyl, CF$_3$, and combinations thereof; and R$_3$ is independently selected from the group consisting of H, C$_{1-12}$aliphatic, C$_{1-6}$-alkyl-aryl and C$_{1-6}$-alkyl-heteroaryl;

or an N-oxide, crystalline form, hydrate, or pharmaceutically acceptable salt thereof, with the proviso that:

when R$_3$ is ethyl, R$_1$ and R$_2$ cannot be both H, O, or

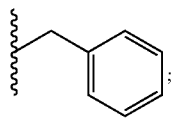

and when R$_3$ is ethyl and at least one of R$_1$ or R$_2$ is H, R$_1$ or R$_2$ cannot be

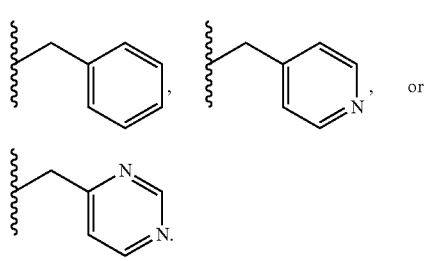

Another embodiment of the present invention is a compound having the formula:

SRS16-86

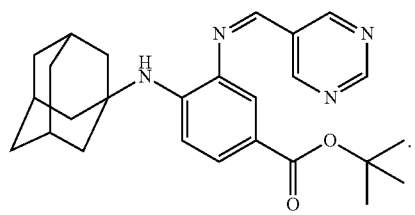

Another embodiment of the present invention is a pharmaceutical composition. This pharmaceutical composition comprises a pharmaceutically acceptable carrier or diluent and a compound according to formula (I):

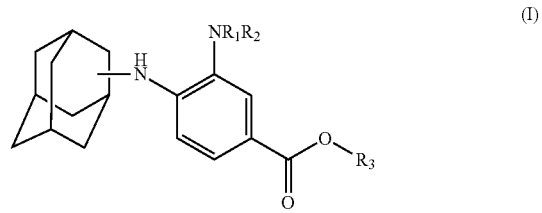

(I)

wherein:

R$_1$ and R$_2$, are independently selected from the group consisting of no atom, H, D, O, halo, C$_{1-6}$alkyl, C$_{1-6}$alkyl-aryl, C$_{1-6}$alkyl-heteroaryl, C$_{1-6}$alkenyl, C$_{1-6}$alkenyl-aryl, and C$_{1-6}$alkenyl-heteroaryl, wherein the C$_{1-6}$alkyl, C$_{1-6}$alkyl-aryl, C$_{1-6}$alkyl-heteroaryl, C$_{1-6}$alkenyl, C$_{1-6}$alkenyl-aryl, and C$_{1-6}$alkenyl-heteroaryl may be optionally substituted with an atom or a group selected from the group consisting of halo, deuterium, C$_{1-4}$alkyl, CF$_3$, and combinations thereof; and R$_3$ is independently selected from the group consisting of H, C$_{1-12}$aliphatic, C$_{1-6}$-alkyl-aryl and C$_{1-6}$-alkyl-heteroaryl;

or an N-oxide, crystalline form, hydrate, or pharmaceutically acceptable salt thereof, with the proviso that:

when R$_3$ is ethyl, R$_1$ and R$_2$ cannot be both H, O, or

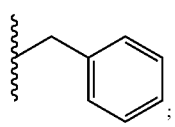 [SMILES: *Cc1ccccc1]

and when R$_3$ is ethyl and at least one of R$_1$ or R$_2$ is H, R$_1$ or R$_2$ cannot be

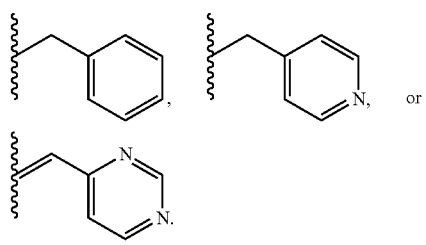

A further embodiment of the present invention is a kit. This kit comprises a compound or a pharmaceutical composition according to the present invention with instructions for the use of the compound or the pharmaceutical composition, respectively.

Another embodiment of the present invention is a method for treating or ameliorating the effects of a disorder in a subject in need thereof. This method comprises administering to the subject an effective amount of a compound having the structure of formula (I):

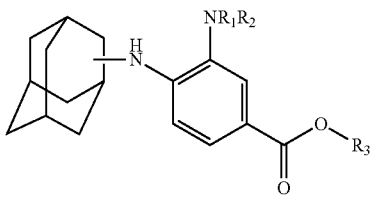

(I)

wherein:
R₁ and R₂, are independently selected from the group consisting of no atom, H, D, O, halo, $C_{1-6}$alkyl, $C_{1-6}$alkyl-aryl, $C_{1-6}$alkyl-heteroaryl, $C_{1-6}$alkenyl, $C_{1-6}$alkenyl-aryl, and $C_{1-6}$alkenyl-heteroaryl, wherein the $C_{1-6}$alkyl, $C_{1-6}$alkyl-aryl, $C_{1-6}$alkyl-heteroaryl, $C_{1-6}$alkenyl, $C_{1-6}$alkenyl-aryl, and $C_{1-6}$alkenyl-heteroaryl may be optionally substituted with an atom or a group selected from the group consisting of halo, deuterium, $C_{1-4}$alkyl, $CF_3$, and combinations thereof; and R₃ is independently selected from the group consisting of H, $C_{1-12}$aliphatic, $C_{1-6}$-alkyl-aryl and $C_{1-6}$-alkyl-heteroaryl;

or an N-oxide, crystalline form, hydrate, or pharmaceutically acceptable salt thereof, with the proviso that:
when R₃ is ethyl, R₁ and R₂ cannot be both H, O, or

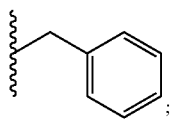 [SMILES: *Cc1ccccc1]

;

and when R₃ is ethyl and at least one of R₁ or R₂ is H, R₁ or R₂ cannot be

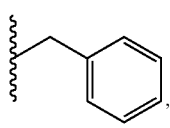

,

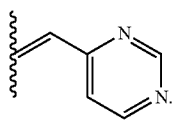

, or

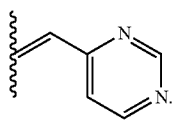

.

An additional embodiment of the present invention is a method for treating or ameliorating the effects of a disorder in a subject in need thereof. This method comprises administering to the subject an effective amount of a pharmaceutical composition comprising a pharmaceutically acceptable carrier or diluent and a compound having the structure of formula (I):

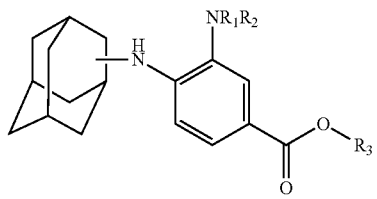

(I)

wherein:
R₁ and R₂, are independently selected from the group consisting of no atom, H, D, O, halo, $C_{1-6}$alkyl, $C_{1-6}$alkyl-aryl, $C_{1-6}$alkyl-heteroaryl, $C_{1-6}$alkenyl, $C_{1-6}$alkenyl-aryl, and $C_{1-6}$alkenyl-heteroaryl, wherein the $C_{1-6}$alkyl, $C_{1-6}$alkyl-aryl, $C_{1-6}$alkyl-heteroaryl, $C_{1-6}$alkenyl, $C_{1-6}$alkenyl-aryl, and $C_{1-6}$alkenyl-heteroaryl may be optionally substituted with an atom or a group selected from the group consisting of halo, deuterium, $C_{1-4}$alkyl, $CF_3$, and combinations thereof; and R₃ is independently selected from the group consisting of H, $C_{1-12}$aliphatic, $C_{1-6}$-alkyl-aryl and $C_{1-6}$-alkyl-heteroaryl;

or an N-oxide, crystalline form, hydrate, or pharmaceutically acceptable salt thereof, with the proviso that:
when R₃ is ethyl, R₁ and R₂ cannot be both H, O, or

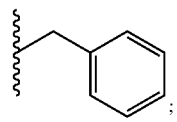 [SMILES: *Cc1ccccc1]

;

and when R₃ is ethyl and at least one of R₁ or R₂ is H, R₁ or R₂ cannot be

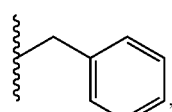 , 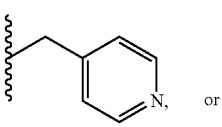 or

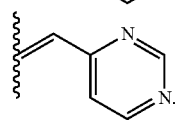

.

Another embodiment of the present invention is a method of modulating ferroptosis in a subject in need thereof. This method comprises administering to the subject an effective amount of a ferroptosis inhibitor, which comprises a compound having the structure of formula (I):

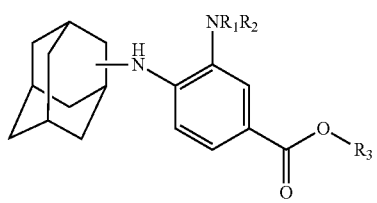

(I)

wherein:
R₁ and R₂, are independently selected from the group consisting of no atom, H, D, O, halo, $C_{1-6}$alkyl, $C_{1-6}$alkyl-aryl, $C_{1-6}$alkyl-heteroaryl, $C_{1-6}$alkenyl, $C_{1-6}$alkenyl-aryl, and $C_{1-6}$alkenyl-heteroaryl, wherein the $C_{1-6}$alkyl, $C_{1-6}$alkyl-aryl, $C_{1-6}$alkyl-heteroaryl, $C_{1-6}$alkenyl, $C_{1-6}$alkenyl-aryl, and $C_{1-6}$alkenyl-heteroaryl may be optionally substituted with an atom or a group selected from the group consisting of halo, deuterium, $C_{1-4}$alkyl, $CF_3$, and combinations thereof; and R₃ is independently selected from the group consisting of H, $C_{1-12}$aliphatic, $C_{1-6}$-alkyl-aryl and $C_{1-6}$-alkyl-heteroaryl;

or an N-oxide, crystalline form, hydrate, or pharmaceutically acceptable salt thereof,
with the proviso that:
when R₃ is ethyl, R₁ and R₂ cannot be both H, O, or

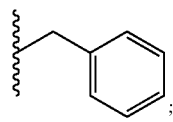 [SMILES: *Cc1ccccc1];

and
when R₃ is ethyl and at least one of R₁ or R₂ is H, R₁ or R₂ cannot be

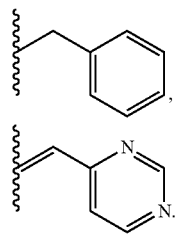

A further embodiment of the present invention is a method of reducing reactive oxygen species (ROS) in a cell. This method comprises contacting a cell with a ferroptosis modulator, which comprises a compound having the structure of formula (I):

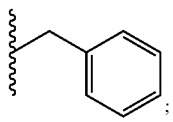 (I)

wherein:
R₁ and R₂, are independently selected from the group consisting of no atom, H, D, O, halo, $C_{1-6}$alkyl, $C_{1-6}$alkyl-aryl, $C_{1-6}$alkyl-heteroaryl, $C_{1-6}$alkenyl, $C_{1-6}$alkenyl-aryl, and $C_{1-6}$alkenyl-heteroaryl, wherein the $C_{1-6}$alkyl, $C_{1-6}$alkyl-aryl, $C_{1-6}$alkyl-heteroaryl, $C_{1-6}$alkenyl, $C_{1-6}$alkenyl-aryl, and $C_{1-6}$alkenyl-heteroaryl may be optionally substituted with an atom or a group selected from the group consisting of halo, deuterium, $C_{1-4}$alkyl, $CF_3$, and combinations thereof; and R₃ is independently selected from the group consisting of H, $C_{1-12}$aliphatic, $C_{1-6}$-alkyl-aryl and $C_{1-6}$-alkyl-heteroaryl;

or an N-oxide, crystalline form, hydrate, or pharmaceutically acceptable salt thereof,
with the proviso that:
when R₃ is ethyl, R₁ and R₂ cannot be both H, O, or

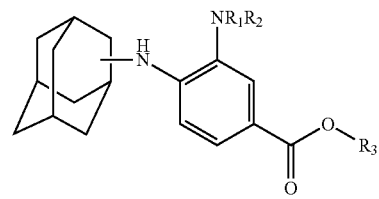

and
when R₃ is ethyl and at least one of R₁ or R₂ is H, R₁ or R₂ cannot be

An additional embodiment of the present invention is a method for treating or ameliorating the effects of a neurodegenerative disease in a subject in need thereof. This method comprises administering to the subject an effective amount of a compound selected from the group consisting of

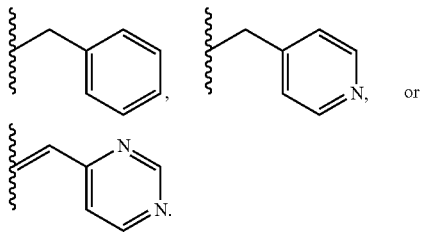 SRS15-72

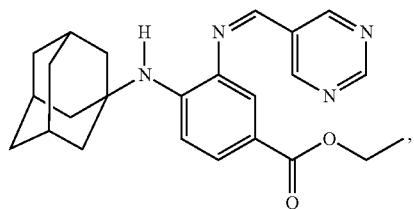 SRS16-80

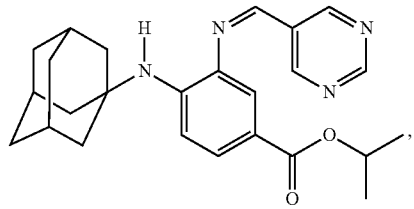 SRS16-86

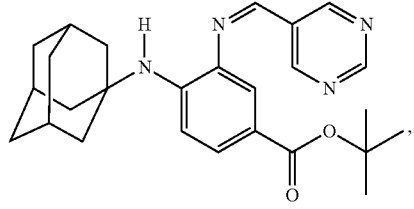

and combinations thereof, or an N-oxide, crystalline form, hydrate, or pharmaceutically acceptable salt thereof.

Another embodiment of the present invention is a compound according to formula (IV):

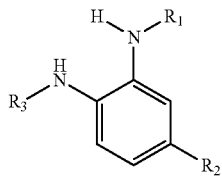

(IV)

wherein:
R$_1$ is selected from the group consisting of aryl, C$_{1-6}$alkylaryl, and C$_{3-10}$carbocycle, wherein the aryl, C$_{1-6}$alkylaryl, and C$_{3-10}$carbocycle may be optionally substituted with an atom or a group selected from the group consisting of halo, deuterium, C$_{1-6}$alkyl, CF$_3$, and combinations thereof;
R$_2$ is a triazole, an oxazole, an oxadiazole, or a ketone; and
R$_3$ is a C$_{3-12}$carbocycle, optionally substituted with C$_{1-10}$ alkyl or halo;
or an N-oxide, crystalline form, hydrate, or pharmaceutically acceptable salt thereof.

A further embodiment of the present invention is a pharmaceutical composition. This pharmaceutical composition comprises a pharmaceutically acceptable carrier or diluent and a compound according to formula (IV):

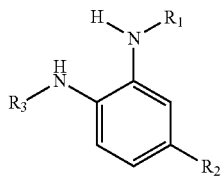

(IV)

wherein:
R$_1$ is selected from the group consisting of aryl, C$_{1-6}$alkylaryl, and C$_{3-10}$carbocycle, wherein the aryl, C$_{1-6}$alkylaryl, and C$_{3-10}$carbocycle may be optionally substituted with an atom or a group selected from the group consisting of halo, deuterium, C$_{1-6}$alkyl, CF$_3$, and combinations thereof;
R$_2$ is a triazole, an oxazole, an oxadiazole, or a ketone; and
R$_3$ is a C$_{3-12}$carbocycle, optionally substituted with C$_{1-10}$ alkyl or halo;
or an N-oxide, crystalline form, hydrate, or pharmaceutically acceptable salt thereof.

An additional embodiment of the present invention is a kit. This kit comprises a compound or a pharmaceutical composition according to any compound of the present invention together with instructions for the use of the compound.

Another embodiment of the present invention is a method for treating or ameliorating the effects of a disorder in a subject in need thereof. This method comprises administering to the subject an effective amount of a compound having the structure of formula (IV):

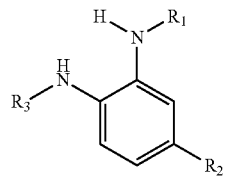

(IV)

wherein:
R$_1$ is selected from the group consisting of aryl, C$_{1-6}$alkylaryl, and C$_{3-10}$carbocycle, wherein the aryl, C$_{1-6}$alkylaryl, and C$_{3-10}$carbocycle may be optionally substituted with an atom or a group selected from the group consisting of halo, deuterium, C$_{1-6}$alkyl, CF$_3$, and combinations thereof;
R$_2$ is a triazole, an oxazole, an oxadiazole, or a ketone; and
R$_3$ is a C$_{3-12}$carbocycle, optionally substituted with C$_{1-10}$ alkyl or halo;
or an N-oxide, crystalline form, hydrate, or pharmaceutically acceptable salt thereof.

A further embodiment of the present invention is a method for treating or ameliorating the effects of a disorder in a subject in need thereof. This method comprises administering to the subject an effective amount of a pharmaceutical composition comprising a pharmaceutically acceptable carrier or diluent and a compound having the structure of formula (IV):

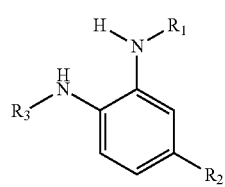

(IV)

wherein:
R$_1$ is selected from the group consisting of aryl, C$_{1-6}$alkylaryl, and C$_{3-10}$carbocycle, wherein the aryl, C$_{1-6}$alkylaryl, and C$_{3-10}$carbocycle may be optionally substituted with an atom or a group selected from the group consisting of halo, deuterium, C$_{1-6}$alkyl, CF$_3$, and combinations thereof;
R$_2$ is a triazole, an oxazole, an oxadiazole, or a ketone; and
R$_3$ is a C$_{3-12}$carbocycle, optionally substituted with C$_{1-10}$ alkyl or halo;
or an N-oxide, crystalline form, hydrate, or pharmaceutically acceptable salt thereof.

Another embodiment of the present invention is a method of modulating ferroptosis in a subject in need thereof. This method comprises administering to the subject an effective amount of a ferroptosis inhibitor, which comprises a compound having the structure of formula (IV):

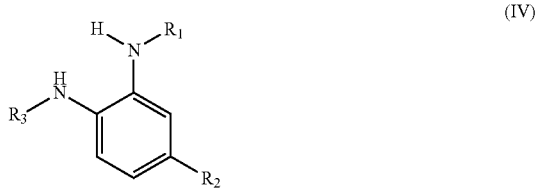

(IV)

wherein:
R₁ is selected from the group consisting of aryl, $C_{1-6}$alkyl-aryl, and $C_{3-10}$carbocycle, wherein the aryl, $C_{1-6}$alkyl-aryl, and $C_{3-10}$carbocycle may be optionally substituted with an atom or a group selected from the group consisting of halo, deuterium, $C_{1-6}$alkyl, $CF_3$, and combinations thereof;
R₂ is a triazole, an oxazole, an oxadiazole, or a ketone; and
R₃ is a $C_{3-12}$carbocycle, optionally substituted with $C_{1-10}$ alkyl or halo;
or an N-oxide, crystalline form, hydrate, or pharmaceutically acceptable salt thereof.

An additional embodiment of the present invention is a method of reducing reactive oxygen species (ROS) in a cell. This method comprises contacting a cell with a ferroptosis modulator, which comprises a compound having the structure of formula (IV):

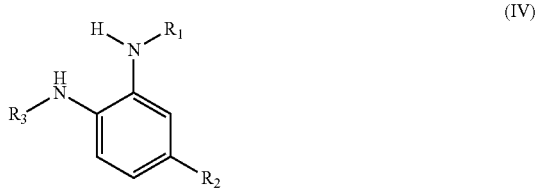

(IV)

wherein:
R₁ is selected from the group consisting of aryl, $C_{1-6}$alkyl-aryl, and $C_{3-10}$carbocycle, wherein the aryl, $C_{1-6}$alkyl-aryl, and $C_{3-10}$carbocycle may be optionally substituted with an atom or a group selected from the group consisting of halo, deuterium, $C_{1-6}$alkyl, $CF_3$, and combinations thereof;
R₂ is a triazole, an oxazole, an oxadiazole, or a ketone; and
R₃ is a $C_{3-12}$carbocycle, optionally substituted with $C_{1-10}$ alkyl or halo;
or an N-oxide, crystalline form, hydrate, or pharmaceutically acceptable salt thereof.

Another embodiment of the present invention is a compound having the formula:

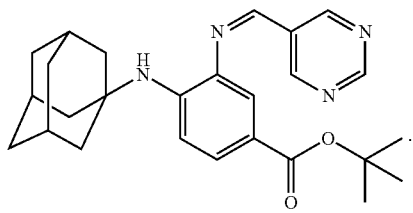

SRS16-86

BRIEF DESCRIPTION OF THE DRAWINGS

FIG. 1A shows representative microscopy images of HT-1080 cell viability over time +/−erastin (Era, 10 μM) and deferoxamine (DFO, 100 μM). FIGS. 1B and 1C show cytosolic and lipid ROS production assessed over time (2, 4 and 6 hours) by flow cytometry using H₂DCFDA and C11-BODIPY. FIG. 1D shows mitochondrial ROS assessed in HT-1080 cells treated for 6 hours with erastin +/−DFO, as above, or with rotenone (250 nM)+/−DFO. In FIGS. 1A-D, representative data from one of four experiments are shown. FIG. 1E shows erastin-induced death in 143B ρ⁰ and ρ⁺ cells. FIG. 1F shows mtDNA-encoded transcript levels in ρ⁰ and ρ⁺ cells. Results in FIGS. 1E and 1F are mean±SD from one of three representative experiments.

FIG. 2A shows a transmission electron microscopy image of BJeLR cells treated with DMSO (10 hours), erastin (37 μM, 10 hours), staurosporine (STS, 0.75 μM, 8 hours), H₂O₂ (16 mM, 1 hour) and rapamycin (Rap, 100 nM, 24 hours). Single white arrowheads show shrunken mitochondria, paired white arrowheads show chromatin condensation, black arrowheads show cytoplasmic and organelle swelling, plasma membrane rupture, and black arrow shows formation of double-membrane vesicles. A minimum of 10 cells per treatment condition were examined. FIG. 2B shows normalized ATP levels in HT-1080 and BJeLR cells treated as in FIG. 2A with the indicated compounds. Representative data (mean±SD) from one of three independent experiments are shown. FIG. 2C shows modulatory profiling of known small molecule cell death inhibitors in HT-1080, BJ-eLR and Calu-1 cells treated with erastin (10 μM, 24 hours). FIG. 2D shows the effect of inhibitors on H₂DCFDA-sensitive ROS production in HT-1080 cells treated for 4 hours. FIG. 2E shows modulatory profiling of ciclopirox olamine (CPX), DFO, ebselen (Ebs), trolox (Tlx), U0126 and CHX on oxidative and non-oxidative lethal agents.

FIG. 3A shows an outline of the MitoCarta shRNA screen and confirmation pipeline. FIGS. 3B and 3C show six high confidence genes required for erastin-induced ferroptosis. FIG. 3B shows the viability of HT-1080 cells infected with shRNAs for 72 hours and treated with erastin (10 μM, 24 hours). FIG. 3C shows the mRNA levels for hairpins shown in FIG. 3B determined using RT-qPCR. Data in FIGS. 3B and 3C are mean±SD from one of three experiments. The sequences of various clones of shRNA listed in FIGS. 3B and 3C are as follows: the sequence for sh263-VDAC3 is shown in SEQ ID NO:1, the sequence for sh548-RPL8 is shown in SEQ ID NO:2, the sequence for sh440-ATP5G3 is shown in SEQ ID NO:3, the sequence for sh978-TTC35 is shown in SEQ ID NO:4, the sequence for sh2326-IREB2 is shown in SEQ ID NO:5, the sequence for sh1776-ACSF2 is shown in SEQ ID NO:6, and the sequence for sh332-CS is shown in SEQ ID NO:7. FIGS. 3D and 3E show the effect of shRNA-mediated silencing of high-confidence genes using the best hairpin identified by mRNA silencing efficiency in FIG. 3C on cell viability. FIG. 3D shows the viability of various cell lines treated with a lethal dose of erastin (indicated in parentheses) for 24 hours. FIG. 3E shows the viability of HT-1080 cells treated with various death-inducing or cytostatic compounds. For FIGS. 3D and 3E, % rescue was computed relative to each shRNA alone+DMSO. FIG. 3F is a cartoon outline of glutamine (Gln) metabolism. Shaded box indicates mitochondria. FIG. 3G shows images of HT-1080 cells treated with aminooxyacetic acid (AOA)+/−dimethyl alphaketoglutarate (DMK)+/−erastin.

FIG. 4A shows the structure of ferrostatin-1 (Fer-1). FIG. 4B shows the effect of resynthesized Fer-1 (0.5 μM) on the lethality of various compounds in HT-1080 cells. FIG. 4C shows the effect of Fer-1 and U0126 on ERK phosphorylation in HT-1080 cells. FIG. 4D shows the effect of DFO, CHX, trolox (Tlx) and Fer-1 on HT-1080 cell proliferation over 48 hours as assessed by Vi-Cell. FIG. 4E shows the effect of Fer-1 (0.5 μM) on erastin (10 μM)-induced ROS production in HT-1080 cells (4 hour treatment). FIG. 4F shows cell-free antioxidant potential monitored by changes in the absorbance at 517 nm of the stable radical DPPH. FIG. 4G shows the dose-response relationship for inhibition of erastin (10 μM, 24 hours)-induced death in HT-1080 cells by Fer-1 and analogs. FIG. 4H shows the structure of various compounds listed in FIG. 4G. FIG. 4I shows the correlation between predicted partition coefficient (log P) and the ability of various Fer-1 analogs to prevent erastin-induced death. FIG. 4J shows the dose-response relationship for inhibition of erastin (10 μM, 24 hours)-induced death by various antioxidants. FIG. 4K shows a plot of predicted partition coefficient (log P) and ability of various antioxidants to prevent erastin-induced death. Data in FIGS. 4B, 4D, 4F, 4G, and 4J represent mean±SD from one of three representative experiments.

FIG. 5A is a cartoon outline of the hippocampal slice procedure used herein. FIG. 5B shows bright-field and fluorescent images of propidium iodide (PI) staining of treated hippocampal slices. Slices were treated with glutamate (5 mM, 3 hours)+/−Fer-1 (2 μM), CPX (5 μM) or MK-801 (10 μM). Representative images from 1 one 6 slices per condition are shown. FIGS. 5C-E show quantification of the effects depicted in FIG. 5B. Data were analyzed using a two-way ANOVA (brain region× drug treatment) followed by Bonferroni post-tests. *: P<0.05, : P<0.01, *: P<0.001.

FIG. 6A shows the modulatory profile of HT-1080 cells treated with different lethal compounds and inhibitors. FIG. 6B is a cartoon depicting the composition and function of system L and system $x_c^-$. Cys: cystine, NAA: neutral amino acids. FIG. 6C shows SLC7A11 mRNA levels in compound (6 hours)-treated HT-1080 cells determined by RT-qPCR. FIGS. 6D and 6E show the effect of silencing SLC7A11 using siRNA on erastin (10 μM, 8 hours)-induced death (FIG. 6D) and mRNA levels (FIG. 6E) in HT-1080 cells. FIG. 6F shows $Na^+$-independent [$^{14}C$] cystine uptake by HT-1080 cells in response to various drugs. FIG. 6G shows identification of SLC7A5 as the lone target identified by erastin affinity purification in both BJeH and BJeLR cells. FIG. 6H shows the metabolic profiling of system L and non-system L substrate amino acid levels in erastin-treated Jurkat cells. FIG. 6I shows the effect of L-glutamic acid (L-Glu, 12.5 mM) and D-phenylalanine (D-Phe, 12.5 mM) on erastin-induced death in HT-1080 cells.

FIG. 7A shows the outline of the NOX (NADPH oxidase) pathway. Inhibitors are shown in gray. FIG. 7B shows the effect of NOX pathway inhibitors on erastin-induced death in Calu-1 and HT-1080 cells. GKT: GKT137831. FIGS. 7C and 7D show the effect of shRNA silencing of the PPP enzymes glucose-6-phosphate dehydrogenase (G6PD) and phosphogluconate dehydrogenase (PGD) on viability of erastin (2.5 μM)-treated Calu-1 cells. Infection with shRNA targeting VDAC2 was used as a positive control. Relative mRNA levels in (FIG. 7D) were assessed by qPCR following shRNA knockdown. Data in FIGS. 7B, 7C, and 7D represents mean±SD. FIG. 7E shows a model of ferroptosis pathway. The core ferroptotic lethal mechanism is in the shaded portion.

FIG. 8A shows the viability of HT-1080 cells treated with erastin +/−ferric ammonium citrate (FAC) as assessed in triplicate by Vi-Cell. FIG. 8B shows the viability of HT-1080 cells treated with DMSO or erastin +/−FAC, ferric citrate (FC), iron chloride hexahydrate (IHC), manganese chloride (Mn), nickel sulfate hexahydrate (Ni), cobalt chloride hexahydrate (Co) or copper sulfate (Cu). FAC was used at 10 μg/mL, all other metals were used at 25 μM. Cell viability was assessed by Trypan Blue exclusion (Vi-Cell) in triplicate and the effects of the erastin+metal combination were expressed as a percentage of the DMSO+metal viability alone. FIGS. 8C and 8D show mitochondrial superoxide levels in 143B cells assessed by flow cytometry using MitoSOX. Treatments used: 250 nM rotenone (Rote), 100 μM DFO alone or in combination, as indicated. FIG. 8E shows the viability of 143B $\rho^+$ and $\rho^0$ cells treated for 24 hours with RSL3 and assessed by Alamar Blue. All experiments were repeated two to four times with similar results, and representative data from one experiment are shown. Data in FIGS. 8A, 8B and 8E represent mean±SD from multiple replicates within one experiment.

FIG. 9A shows the viability of SV40-transformed MEFs (control and Bax/Bak double knockout, DKO) that were treated with erastin +/−DFO, Trolox, U0126 or cycloheximide (CHX) for 24 hours as indicated. FIG. 9B shows the viability of wild-type and DKO MEFs that were treated with staurosporine (STS) for 24 hours at the indicated concentrations to induce apoptosis. Bax/Bak double knockout MEFs are more resistant to STS, as expected. In FIGS. 9A and 9B, cell viability was assessed by Alamar Blue. Experiments were repeated twice with similar results and representative data from one experiment are shown. All values are mean±SD from multiple replicates within each experiment. FIG. 9C shows microscopy images of cells that were treated +/−erastin and co-treated with the indicated inhibitors. Inhibitors were added either at the same time as erastin (0 hours) or 2-6 hours later (+2, +4, +6 hours). 2,2-bipyridyl (2,2-BP) is a membrane permeable iron chelator. All cells were photographed 24 hours after the start of the experiment. This experiment was repeated three times with similar results, and representative data from one experiment is shown.

In FIGS. 10A-10C, HT-1080 cells were infected with shRNAs targeting IREB2 and FBXL5 for 3 days and then examined for gene expression or drug sensitivity. FIGS. 10A and 10B show reciprocal transcriptional regulation of iron-regulated genes induced by silencing of IREB2 and FBXL5 as assessed by RT-qPCR. DFO treatment (48 hours) was used as a control for changes in gene expression. ISCU, FTH1, FTL and TFRC are known iron-regulated genes (Sanchez et al., 2011). FIG. 10C shows silencing of FBXL5 sensitizes cells to erastin-induced death.

FIG. 10D shows that aminooxyacetic acid (AOA), but not dichloroacetic acid (DCA), inhibits erastin-induced death in HT-1080 and BJeLR cells. All data are mean±SD from multiple replicates within one experiment. All experiments were performed 2-4 times with similar results. Representative data from one experiment are shown.

FIG. 11A shows that the re-testing in 10-point, 2-fold dilution series of the top four compounds from a LOC (Lead Optimized Compound) library screen validated to suppress erastin-induced death in HT-1080 cells. FIG. 11B shows the structure of these top 4 compounds.

FIG. 12A shows the viability of HT-1080 cells treated for 24 hours with erastin +/−DMSO, the calcium chelators BAPTA-AM or Fura-2, or, as a positive control for death rescue, the iron chelator ciclopirox olamine (CPX), at the indicated concentration. FIG. 12B shows the viability of HT-1080 cells treated for 24 hours with erastin, monosodium L-glutamic acid or RSL3+/−inhibitors using Alamar Blue. FIG. 12C shows that sulfasalazine, like erastin, displays RAS-selective lethal properties in the BJ cell series assay. For FIGS. 12A-12C, values represent mean±SD from multiple replicates within one experiment. The entire experiment was repeated twice and representative data from one experiment are shown. FIG. 12D shows microscopy images of HT-1080 cells that were transfected for 48 hours with either a control plasmid (pMaxGFP) or pCMV6-SLC7A11-DDK then treated with DMSO, erastin or SAS, as indicated, and photographed. FIG. 12E shows [$^{14}$C]-cystine uptake into HT-1080 cells measured under Na$^+$-free conditions in response to DMSO, erastin and RSL3. Data represents mean±SD, n=3.

FIG. 13A shows relative expression of NOX family catalytic subunit mRNAs in Calu-1 cells assessed by RT-qPCR. FIG. 13B shows the viability of Calu-1 and BJeLR cells in response to erastin (10 μM)+/−the PPP inhibitor 6-aminonicotinamde (6-AN, 200 μM) after 24 hours by Vi-Cell. Data in FIGS. 13A and 13B represent mean±SD of replicates from one experiment.

FIG. 15A shows the effect of ferrostatins on cell survival in an HD brain-slice model. YFP=yellow fluorescent protein transfection control. httN90Q73 is mutant huntingtin (N-terminal 90aa with a Q73 repeat). KW+SP is a combination used as a positive control for protection. FIG. 15B shows a dose-response test of the effect of ferrostatins in a model of PVL. Cys=Cystine supplementation, a positive control for cell death rescue. FIG. 15C shows the effect of ferrostatins, at various concentrations, in a primary kidney renal tubule damage model.

FIG. 16A shows mitochondrial ROS production in response to rotenone (Rot, 250 nM, 3 hr)+/−Fer-1 (1 μM) was detected using MitoSOX. FIG. 16B shows cardiolipin peroxidation in response to staurosporine (STS, 100 nM, 3 hr) detected using 10-nonyl acridine orange (NAO). Data in FIGS. 16A-B were analyzed by one-way ANOVA *** P<0.001, ns=not significant. FIG. 16C shows lysosomal membrane permeabilization detected in response to H$_2$O$_2$ using acridine orange (AO) re-localization. An iron chelator, ciclopirox olamine (CPX), protects from lysosomal rupture.

FIG. 18A shows EC50, cLogP, and % DPPH inhibition of selected potent ferrostatins. DPPH: 2,2-diphenyl-1-picrylhydrazyl radical. FIG. 18B shows an X-ray structure of the most potent Fer-1 analog (SRS11-92).

DETAILED DESCRIPTION OF THE INVENTION

Figure 1:
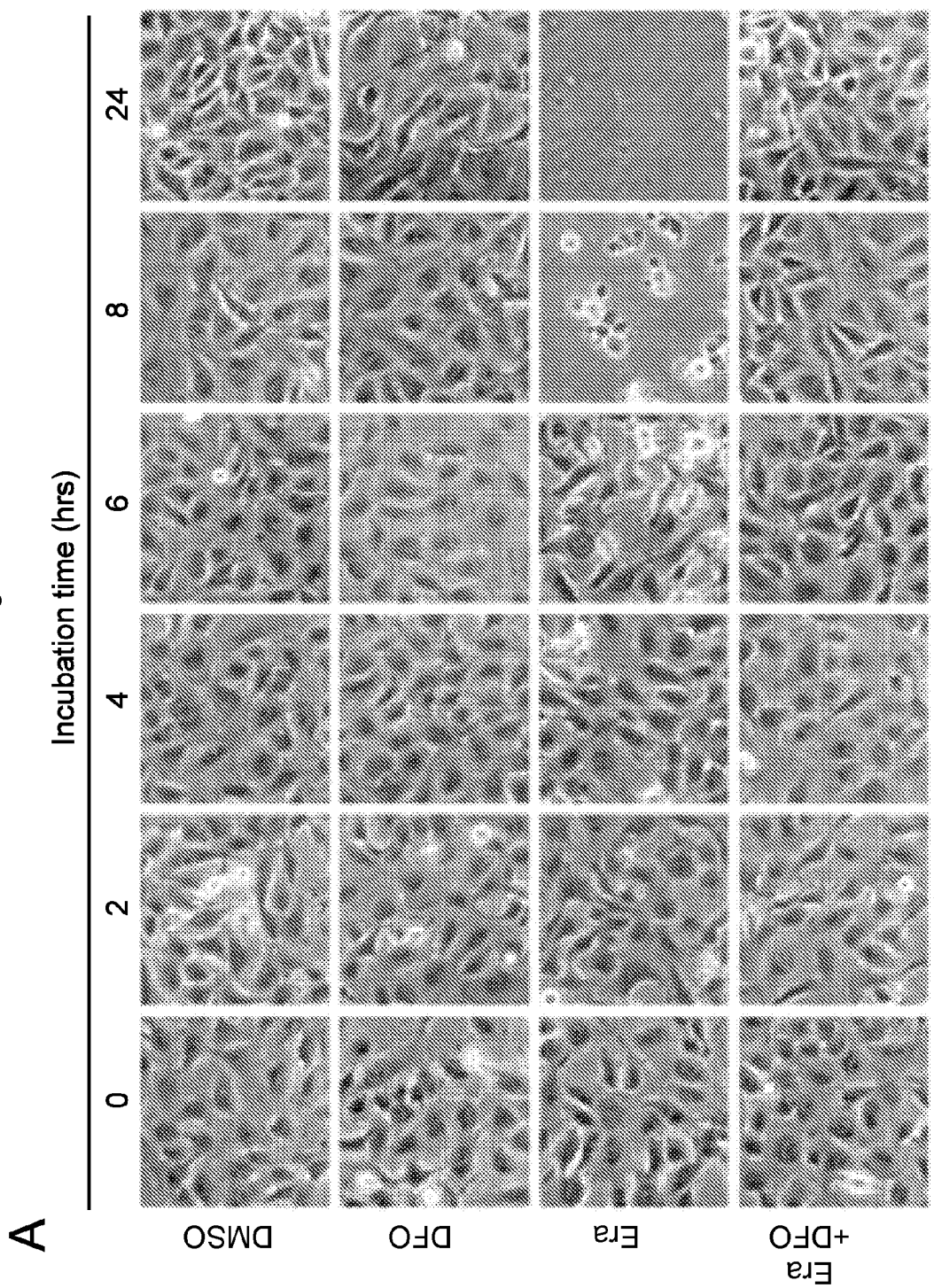
FIGS. 1A-1F show that erastin-induced death triggers the accumulation of cytosolic ROS whose production can be inhibited by the iron chelator deferoxamine (DFO).
Figure 1:
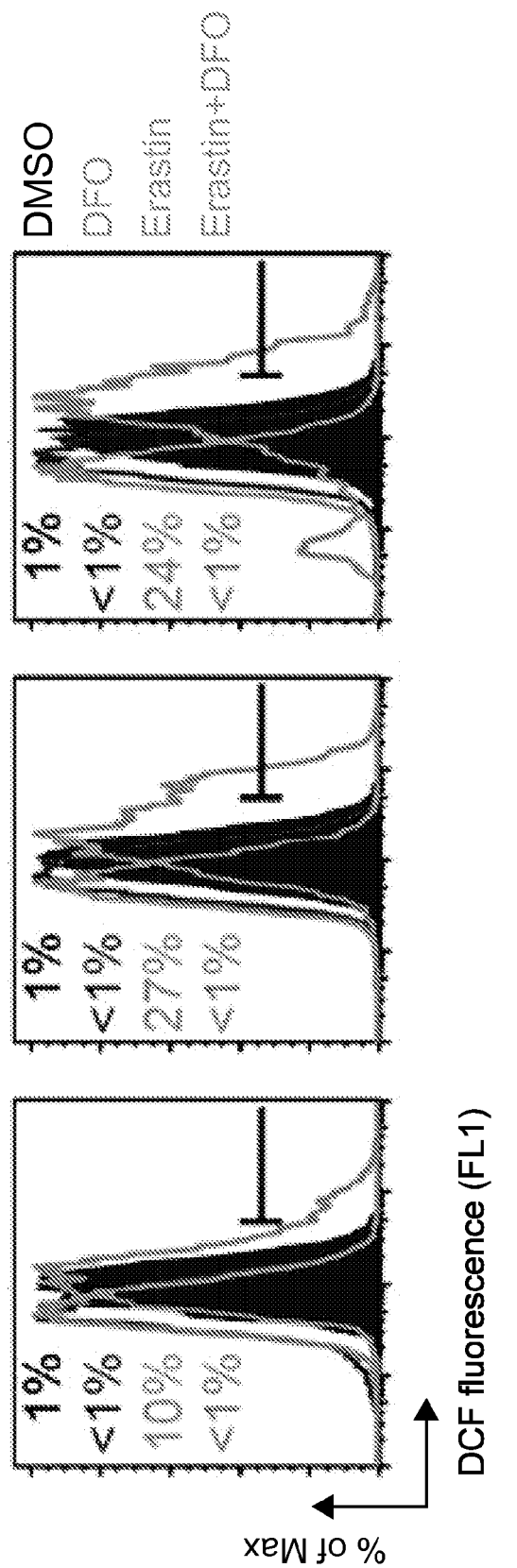
Figure 1:
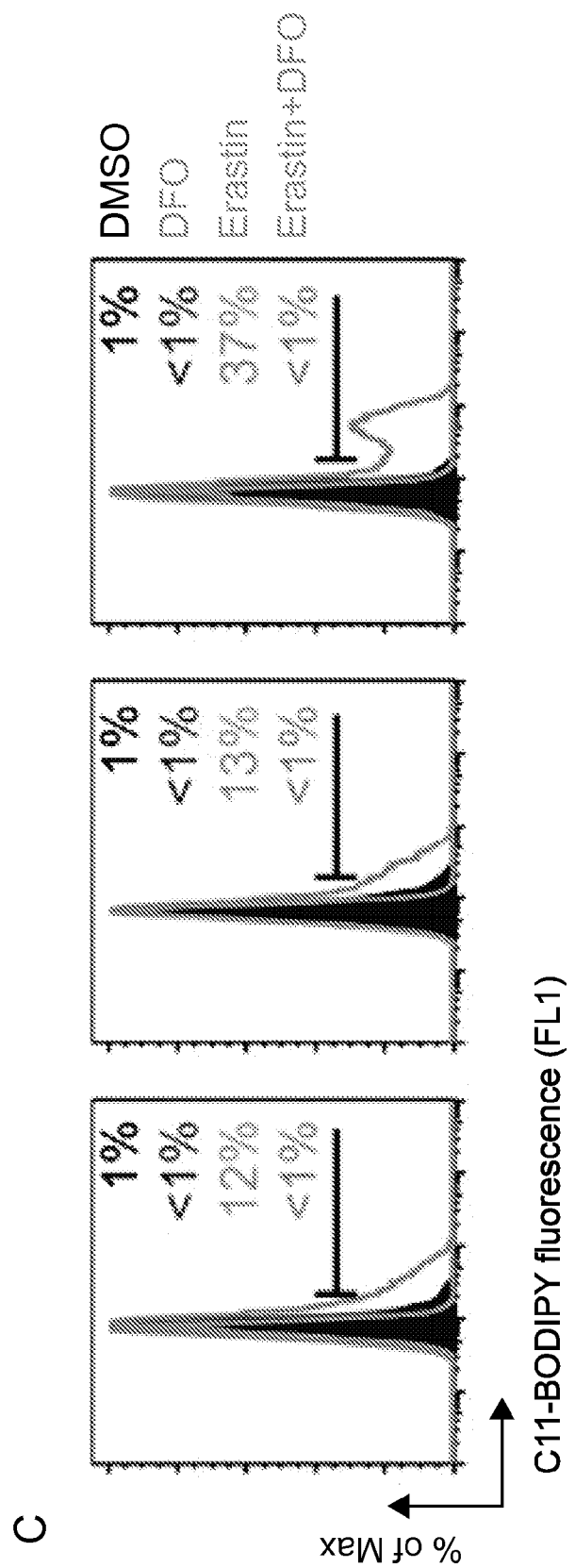
Figure 1:
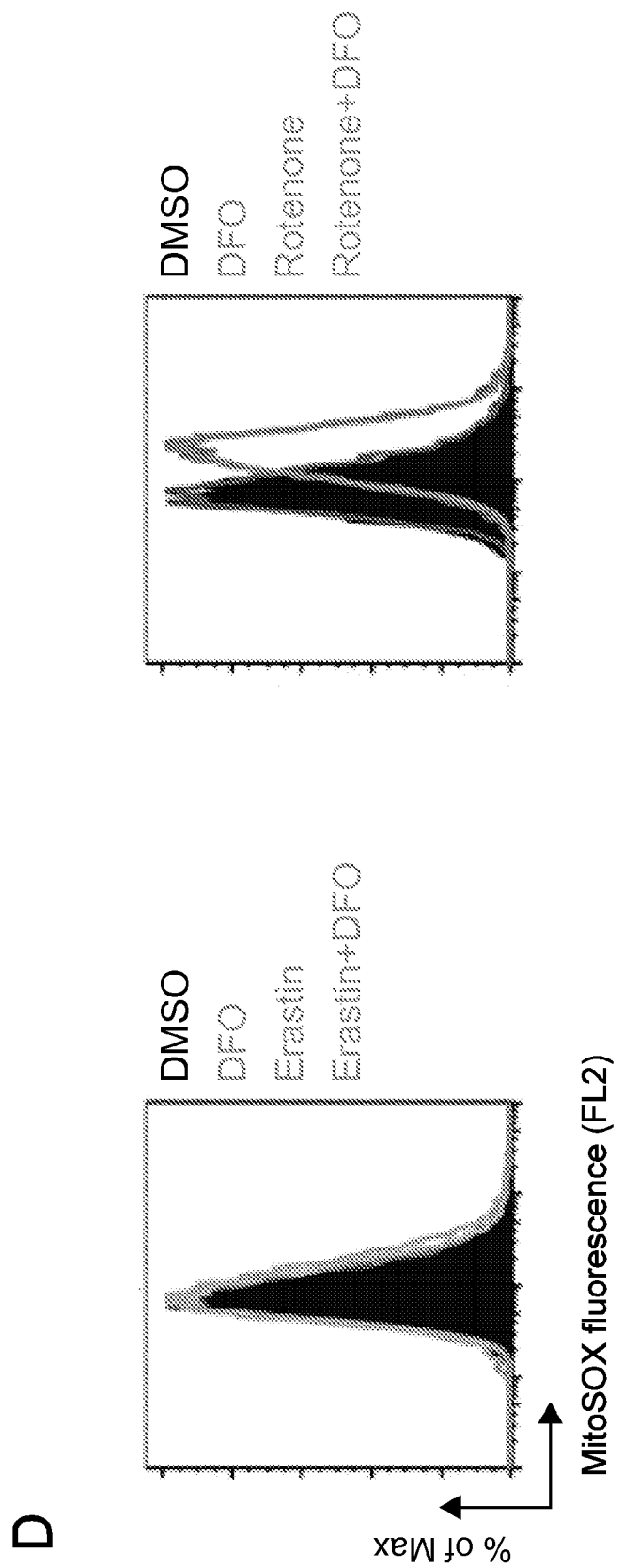

In the present invention, new analogs of Fer-1 are provided. Certain of the analogs have improved microsomal stability and solubility while still maintaining good inhibition potency of ferroptosis. Accordingly, one embodiment of the present invention is a compound according to formula (I):

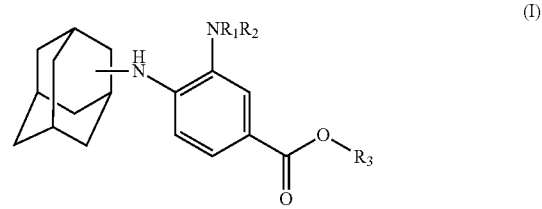

wherein:

$R_1$ and $R_2$, are independently selected from the group consisting of no atom, H, D, O, halo, $C_{1-6}$alkyl, $C_{1-6}$alkyl-aryl, $C_{1-6}$alkyl-heteroaryl, $C_{1-6}$alkenyl, $C_{1-6}$alkenyl-aryl, and $C_{1-6}$alkenyl-heteroaryl, wherein the $C_{1-6}$alkyl, $C_{1-6}$alkyl-aryl, $C_{1-6}$alkyl-heteroaryl, $C_{1-6}$alkenyl, $C_{1-6}$alkenyl-aryl, and $C_{1-6}$alkenyl-heteroaryl may be optionally substituted with an atom or a group selected from the group consisting of halo, deuterium, $C_{1-4}$alkyl, $CF_3$, and combinations thereof; and $R_3$ is independently selected from the group consisting of H, $C_{1-12}$aliphatic, $C_{1-6}$-alkyl-aryl and $C_{1-6}$-alkyl-heteroaryl;

or an N-oxide, crystalline form, hydrate, or pharmaceutically acceptable salt thereof, with the proviso that:

when $R_3$ is ethyl, $R_1$ and $R_2$ cannot be both H, O, or

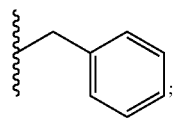 [SMILES: *Cc1ccccc1]

and when $R_3$ is ethyl and at least one of $R_1$ or $R_2$ is H, $R_1$ or $R_2$ cannot be

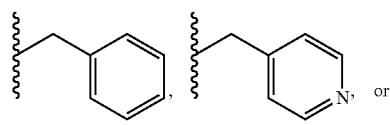

In one aspect of this embodiment, the compound has the structure of formula (II):

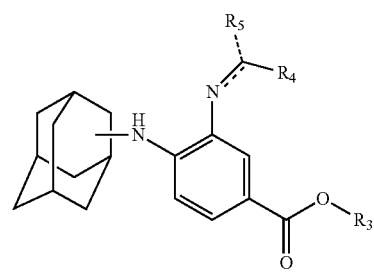

(II)

wherein:

$R_3$ is independently selected from the group consisting of H, $C_{1-12}$aliphatic, $C_{1-6}$-alkyl-aryl and $C_{1-6}$-alkyl-heteroaryl;

$R_4$ and $R_5$ are independently selected from the group consisting of no atom, H, D, O, halo, aryl, heteroaryl, $C_{1-6}$alkyl, $C_{1-6}$alkyl-aryl, and $C_{1-6}$alkyl-heteroaryl; and --- is an optional bond, or an N-oxide, crystalline form, hydrate, or pharmaceutically acceptable salt thereof.

In another aspect of this embodiment, the compound has the structure of formula (III):

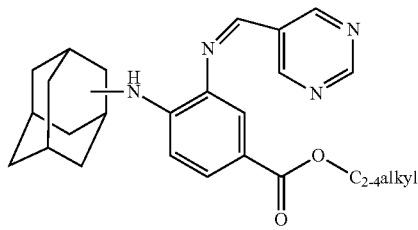

(III)

wherein the $C_{2-4}$ alkyl is selected from the group consisting of ethyl, isopropyl, n-propyl, butyl, and t-butyl, or an N-oxide, crystalline form, hydrate, or pharmaceutically acceptable salt thereof.

In another aspect of this embodiment, the compound is selected from the group consisting of:

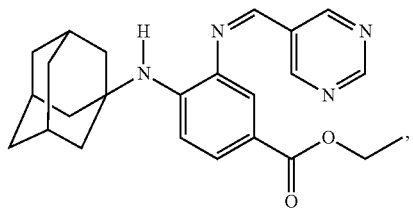

SRS15-72

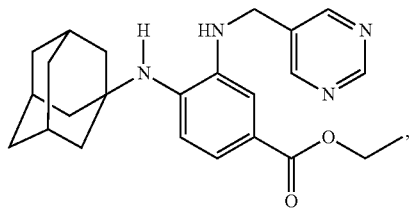

SRS16-41

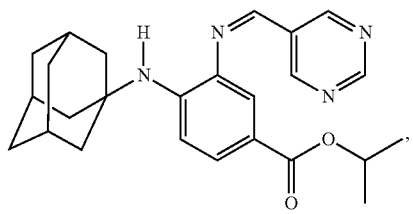

SRS16-80

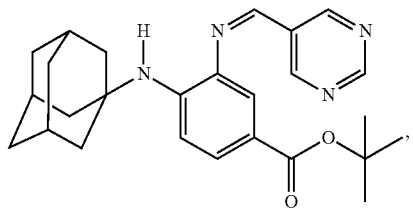

SRS16-86

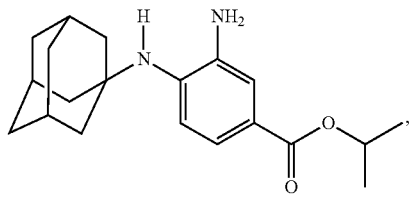

SRS16-78

SRS16-82
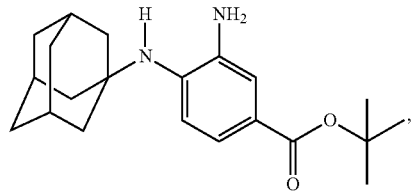
Fer2_SRS01
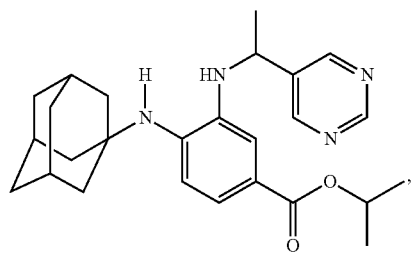
Fer2_SRS02
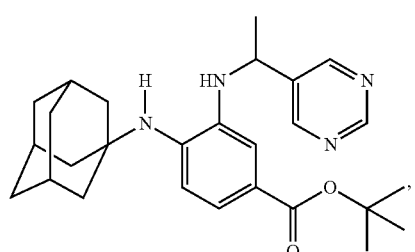
Fer_SRS03
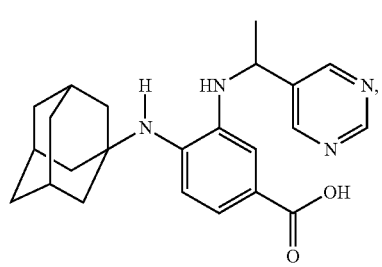
Fer2_SRS04
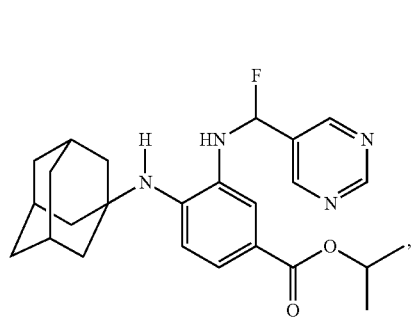
Fer2_SRS05
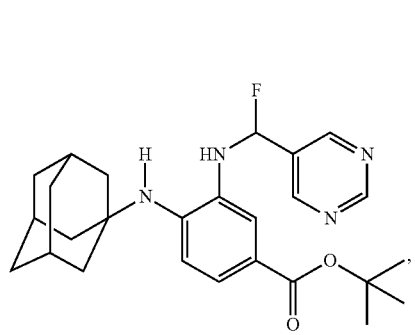
Fer2_SRS06
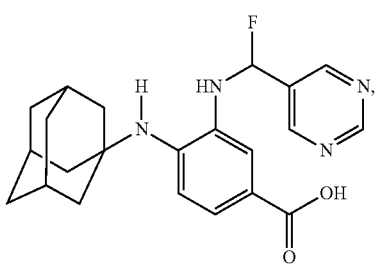
Fer2_SRS07
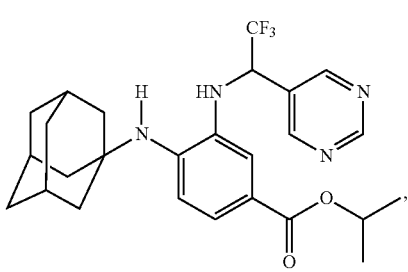
Fer2_SRS08
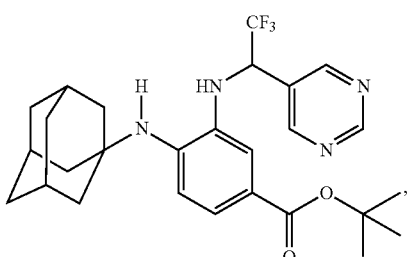
Fer2_SRS09
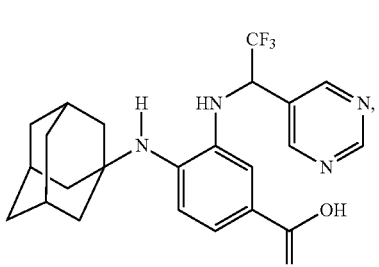
Fer2_SRS10
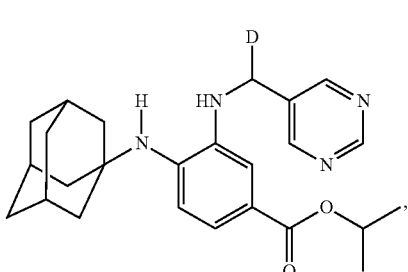
Fer2_SRS11
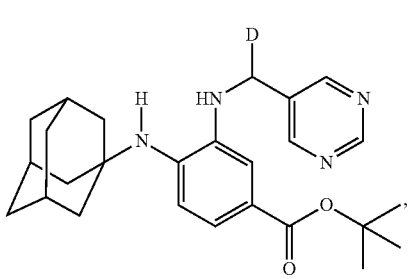

-continued

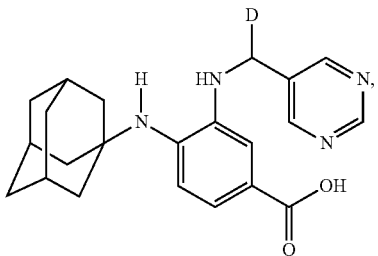
Fer2_SRS12 or an N-oxide, crystalline form, hydrate, or pharmaceutically acceptable salt thereof.

Preferably, the compound is selected from the group consisting of:

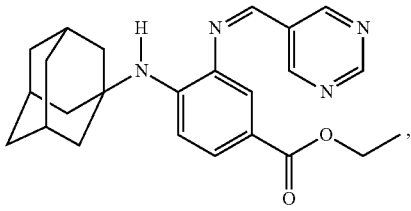
SRS15-72

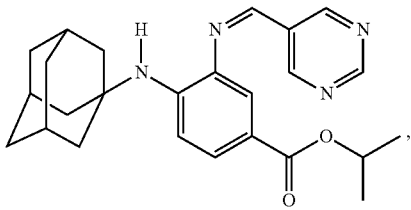
SRS16-80

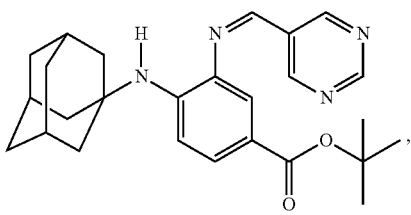
SRS16-86 and combinations thereof, or an N-oxide, crystalline form, hydrate, or pharmaceutically acceptable salt thereof.

Another embodiment of the present invention is a compound having the formula:

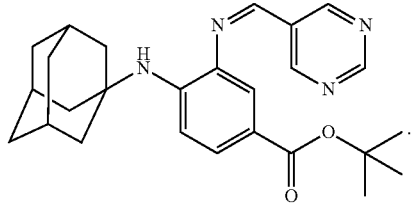
SRS16-86

Another embodiment of the present invention is a pharmaceutical composition. This pharmaceutical composition comprises a pharmaceutically acceptable carrier or diluent and a compound according to formula (I):

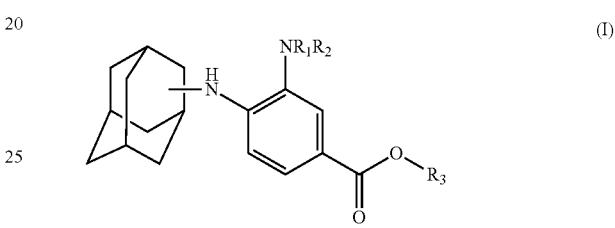
(I)

wherein:
R$_1$ and R$_2$, are independently selected from the group consisting of no atom, H, D, O, halo, C$_{1-6}$alkyl, C$_{1-6}$alkyl-aryl, C$_{1-6}$alkyl-heteroaryl, C$_{1-6}$alkenyl, C$_{1-6}$alkenyl-aryl, and C$_{1-6}$alkenyl-heteroaryl, wherein the C$_{1-6}$alkyl, C$_{1-6}$alkyl-aryl, C$_{1-6}$alkyl-heteroaryl, C$_{1-6}$alkenyl, C$_{1-6}$alkenyl-aryl, and C$_{1-6}$alkenyl-heteroaryl may be optionally substituted with an atom or a group selected from the group consisting of halo, deuterium, C$_{1-4}$alkyl, CF$_3$, and combinations thereof; and R$_3$ is independently selected from the group consisting of H, C$_{1-12}$aliphatic, C$_{1-6}$-alkyl-aryl and C$_{1-6}$-alkyl-heteroaryl;

or an N-oxide, crystalline form, hydrate, or pharmaceutically acceptable salt thereof, with the proviso that:
when R$_3$ is ethyl, R$_1$ and R$_2$ cannot be both H, O, or

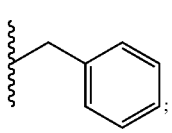 [SMILES: *Cc1ccccc1]
;

and
when R$_3$ is ethyl and at least one of R$_1$ or R$_2$ is H, R$_1$ or R$_2$ cannot be

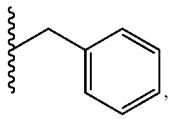 [SMILES: *Cc1ccccc1], 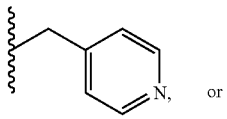 or

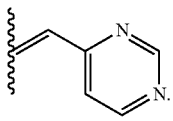

Suitable and preferred compounds that are used in the pharmaceutical compositions of the present invention are disclosed above in formulas (I)-(III), including the particular SRS compounds also identified above.

A further embodiment of the present invention is a kit. This kit comprises a compound or a pharmaceutical composition disclosed herein with instructions for the use of the compound or the pharmaceutical composition, respectively.

The kits may also include suitable storage containers, e.g., ampules, vials, tubes, etc., for each compound of the present invention (which, e.g., may be in the form of pharmaceutical compositions) and other reagents, e.g., buffers, balanced salt solutions, etc., for use in administering the active agents to subjects. The compounds and/or pharmaceutical compositions of the invention and other reagents may be present in the kits in any convenient form, such as, e.g., in a solution or in a powder form. The kits may further include a packaging container, optionally having one or more partitions for housing the compounds and/or pharmaceutical compositions and other optional reagents.

Another embodiment of the present invention is a method for treating or ameliorating the effects of a disorder in a subject in need thereof. This method comprises administering to the subject an effective amount of a compound having the structure of formula (I):

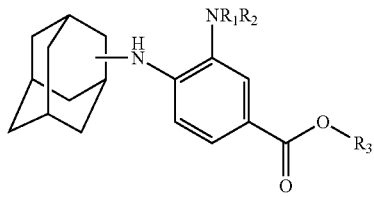

wherein:

$R_1$ and $R_2$, are independently selected from the group consisting of no atom, H, D, O, halo, $C_{1-6}$alkyl, $C_{1-6}$alkyl-aryl, $C_{1-6}$alkyl-heteroaryl, $C_{1-6}$alkenyl, $C_{1-6}$alkenyl-aryl, and $C_{1-6}$alkenyl-heteroaryl, wherein the $C_{1-6}$alkyl, $C_{1-6}$alkyl-aryl, $C_{1-6}$alkyl-heteroaryl, $C_{1-6}$alkenyl, $C_{1-6}$alkenyl-aryl, and $C_{1-6}$alkenyl-heteroaryl may be optionally substituted with an atom or a group selected from the group consisting of halo, deuterium, $C_{1-4}$alkyl, $CF_3$, and combinations thereof; and $R_3$ is independently selected from the group consisting of H, $C_{1-12}$aliphatic, $C_{1-6}$-alkyl-aryl and $C_{1-6}$-alkyl-heteroaryl;

or an N-oxide, crystalline form, hydrate, or pharmaceutically acceptable salt thereof, with the proviso that:

when $R_3$ is ethyl, $R_1$ and $R_2$ cannot be both H, O, or

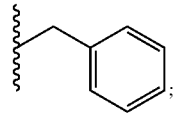 [SMILES: *Cc1ccccc1]

and when $R_3$ is ethyl and at least one of $R_1$ or $R_2$ is H, $R_1$ or $R_2$ cannot be

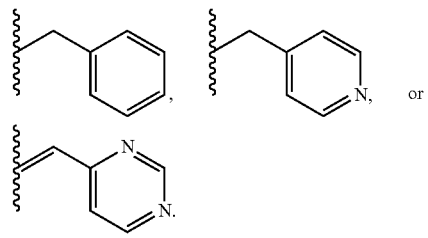

As used herein, the terms "treat," "treating," "treatment" and grammatical variations thereof mean subjecting an individual subject to a protocol, regimen, process or remedy, in which it is desired to obtain a physiologic response or outcome in that subject, e.g., a patient. In particular, the methods and compositions of the present invention may be used to slow the development of disease symptoms or delay the onset of the disease or condition, or halt the progression of disease development. However, because every treated subject may not respond to a particular treatment protocol, regimen, process or remedy, treating does not require that the desired physiologic response or outcome be achieved in each and every subject or subject population, e.g., patient population. Accordingly, a given subject or subject population, e.g., patient population, may fail to respond or respond inadequately to treatment.

As used herein, the terms "ameliorate", "ameliorating" and grammatical variations thereof mean to decrease the severity of the symptoms of a disease in a subject.

As used herein, a "subject" is a mammal, preferably, a human. In addition to humans, categories of mammals within the scope of the present invention include, for example, agricultural animals, veterinary animals, laboratory animals, etc. Some examples of agricultural animals include cows, pigs, horses, goats, etc. Some examples of veterinary animals include dogs, cats, etc. Some examples of laboratory animals include primates, rats, mice, rabbits, guinea pigs, etc.

Suitable and preferred compounds and pharmaceutical compositions for use in this method are as disclosed above in formulas (I)-(III), including the particular SRS compounds.

In one aspect of this embodiment, the disorder is a degenerative disease that involves lipid peroxidation. As used herein, "lipid peroxidation" means the oxidative degradation of fats, oils, waxes, sterols, triglycerides, and the like. Lipid peroxidation has been linked with many degenerative diseases, such as atherosclerosis, ischemia-reperfusion, heart failure, Alzheimer's disease, rheumatic arthritis, cancer, and other immunological disorders. (Ramana et al., 2013).

In another aspect of this embodiment, the disorder is an excitotoxic disease involving oxidative cell death. As used herein, an "excitotoxic disorder" means a disease related to the death of central neurons that are mediated by excitatory amino acids (such as glutamate). Excitotoxic disorders within the scope of the present invention include diseases involving oxidative cell death. As used herein, "oxidative" cell death means cell death associated with increased levels of intracellular reactive oxygen species (ROS). In the present invention, "reactive oxygen species" means chemically reactive molecules, such as free radicals, containing oxygen. Non-limiting examples of ROS include oxygen ions and peroxides.

Non-limiting examples of disorders according to the present invention include epilepsy, kidney disease, stroke, myocardial infarction, type I diabetes, traumatic brain injury (TBI), periventricular leukomalacia (PVL), and neurodegenerative disease. Non-limiting examples of neurodegenerative diseases according to the present invention include Alzheimer's, Parkinson's, Amyotrophic lateral sclerosis, Friedreich's ataxia, Multiple sclerosis, Huntington's Disease, Transmissible spongiform encephalopathy, Charcot-Marie-Tooth disease, Dementia with Lewy bodies, Corticobasal degeneration, Progressive supranuclear palsy, and Hereditary spastic paraparesis.

In another aspect of this embodiment, the method further comprises co-administering, together with one or more compounds or pharmaceutical compositions of the present invention, to the subject an effective amount of one or more of additional therapeutic agents such as 5-hydroxytryptophan, Activase, AFQ056 (Novartis Corp., New York, N.Y.), Aggrastat, Albendazole, alpha-lipoic acid/L-acetyl carnitine, Alteplase, Amantadine (Symmetrel), amlodipine, Ancrod, Apomorphine (Apokyn), Arimoclomol, Arixtra, Armodafinil, Ascorbic acid, Ascriptin, Aspirin, atenolol, Avonex, baclofen (Lioresal), Banzel, Benztropine (Cogentin), Betaseron, BGG492 (Novartis Corp., New York, N.Y.), Botulinum toxin, Bufferin, Carbatrol®, Carbidopa/levodopa immediate-release (Sinemet), Carbidopa/levodopa oral disintegrating (Parcopa), Carbidopa/levodopa/Entacapone (Stalevo), CERE-110: Adeno-Associated Virus Delivery of NGF (Ceregene, San Diego, Calif.), cerebrolysin, CinnoVex, citalopram, citicoline, Clobazam, Clonazepam, Clopidogrel, clozapine (Clozaril), Coenzyme Q, Creatine, dabigatran, dalteparin, Dapsone, Davunetide, Deferiprone, Depakene®, Depakote ER®, Depakote®, Desmoteplase, Diastat, Diazepam, Digoxin, Dilantin®, Dimebon, dipyridamole, divalproex (Depakote), Donepezil (Aricept), EGb 761, Eldepryl, ELND002 (Elan Pharmaceuticals, Dublin, Ireland), Enalapril, enoxaparin, Entacapone (Comtan), epoetin alfa, Eptifibatide, Erythropoietin, Escitalopram, Eslicarbazepine acetate, Esmolol, Ethosuximide, Ethyl-EPA (Miraxion™), Exenatide, Extavia, Ezogabine, Felbamate, Felbatol®, Fingolimod (Gilenya), fluoxetine (Prozac), fondaparinux, Fragmin, Frisium, Gabapentin, Gabitril®, Galantamine, Glatiramer (Copaxone), haloperidol (Haldol), Heparin, human chorionic gonadotropin (hCG), Idebenone, Inovelon®, insulin, Interferon beta 1a, Interferon beta 1b, ioflupane 123I (DATSCAN®), IPX066 (Impax Laboratories Inc., Hayward, Calif.), JNJ-26489112 (Johnson and Johnson, New Brunswick, N.J.), Keppra®, Klonopin, Lacosamide, L-Alpha glycerylphosphorylcholine, Lamictal®, Lamotrigine, Levetiracetam, liraglutide, Lisinopril, Lithium carbonate, Lopressor, Lorazepam, losartan, Lovenox, Lu AA24493, Luminal, LY450139 (Eli Lilly, Indianapolis, Ind.), Lyrica, Masitinib, Mecobalamin, Memantine, methylprednisolone, metoprolol tartrate, Minitran, Minocycline, mirtazapine, Mitoxantrone (Novantrone), Mysoline®, Natalizumab (Tysabri), Neurontin®, Niacinamide, Nitro-Bid, Nitro-Dur, nitroglycerin, Nitrolingual, Nitromist, Nitrostat, Nitro-Time, Norepinephrine (NOR), Carbamazepine, octreotide, Onfi®, Oxcarbazepine, Oxybutinin chloride, PF-04360365 (Pfizer, New York, N.Y.), Phenobarbital, Phenytek®, Phenytoin, piclozotan, Pioglitazone, Plavix, Potiga, Pramipexole (Mirapex), pramlintide, Prednisone, Primidone, Prinivil, probenecid, Propranolol, PRX-00023 (EPIX Pharmaceuticals Inc.), PXT3003, Quinacrine, Ramelteon, Rasagiline (Azilect), Rebif, ReciGen, remacemide, Resveratrol, Retavase, reteplase, riluzole (Rilutek), Rivastigmine (Exelon), Ropinirole (Requip), Rotigotine (Neupro), Rufinamide, Sabril, safinamide (EMD Serono, Rockland, Mass.), Salagen, Sarafem, Selegiline (1-deprenyl, Eldepryl), SEN0014196 (Siena Biotech, Siena, Italy), sertraline (Zoloft), Simvastatin, Sodium Nitroprussiate (NPS), sodium phenylbutyrate, Stanback Headache Powder, Tacrine (Cognex), Tamoxifen, tauroursodeoxycholic acid (TUDCA), Tegretol®, Tenecteplase, Tenormin, Tetrabenazine (Xenazine), THR-18 (Thrombotech Ltd.), Tiagabine, Tideglusib, tirofiban, tissue plasminogen activator (tPA), tizanidine (Zanaflex), TNKase, Tolcapone (Tasmar), Tolterodine, Topamax®, Topiramate, Trihexyphenidyl (formerly Artane), Trileptal®, ursodiol, Valproic Acid, valsartan, Varenicline (Pfizer), Vimpat, Vitamin E, Warfarin, Zarontin®, Zestril, Zonegran®, Zonisamide, Zydis selegiline HCL Oral disintegrating (Zelapar), and combinations thereof.

For example, to treat or ameliorate the effects of epilepsy, a subject may be administered an effective amount of one or more compounds or pharmaceutical compositions of the present invention and, e.g., one or more of the following: Albendazole, Banzel, BGG492 (Novartis Corp., New York, N.Y.) Carbamazepine, Carbatrol®, Clobazam, Clonazepam, Depakene®, Depakote®, Depakote ER®, Diastat, Diazepam, Dilantin®, Eslicarbazepine acetate, Ethosuximide, Ezogabine, Felbatol®, Felbamate, Frisium, Gabapentin, Gabitril®, Inovelon®, JNJ-26489112 (Johnson and Johnson, New Brunswick, N.J.) Keppra®, Keppra XR™, Klonopin, Lacosamide, Lamictal®, Lamotrigine, Levetiracetam, Lorazepam, Luminal, Lyrica, Mysoline®, Memantine, Neurontin®, Onfi®, Oxcarbazepine, Phenobarbital, Phenytek®, Phenytoin, Potiga, Primidone, probenecid, PRX-00023 (EPIX Pharmaceuticals Inc, Lexington, Mass.), Rufinamide, Sabril, Tegretol®, Tegretol XR®, Tiagabine, Topamax®, Topiramate, Trileptal®, Valproic Acid, Vimpat, Zarontin®, Zonegran®, and Zonisamide.

To treat or ameliorate the effects of stroke, a subject may be administered an effective amount of one or more compounds or pharmaceutical compositions of the present invention and, e.g., one or more of the following: Aspirin, dipyridamole, Clopidogrel, tissue plasminogen activator (tPA), Warfarin, dabigatran, Heparin, Lovenox, citicoline, L-Alpha glycerylphosphorylcholine, cerebrolysin, Eptifibatide, Escitalopram, Tenecteplase, Alteplase, Minocycline, Esmolol, Sodium Nitroprussiate (NPS), Norepinephrine (NOR), Dapsone, valsartan, Simvastatin, piclozotan, Desmoteplase, losartan, amlodipine, Ancrod, human chorionic gonadotropin (hCG), epoetin alfa (EPO), Galantamine, and THR-18 (Thrombotech Ltd., Ness Ziona, Israel).

To treat or ameliorate the effects of myocardial infarction, a subject may be administered an effective amount of one or more compounds or pharmaceutical compositions of the present invention and, e.g., one or more of the following: lisinopril, atenolol, Plavix, metoprolol tartrate, Lovenox, Lopressor, Zestril, Tenormin, Prinivil, aspirin, Arixtra, clopidogrel, Salagen, nitroglycerin, metoprolol tartrate, heparin, Nitrostat, Nitro-Bid, Stanback Headache Powder, nitroglycerin, Activase, Nitrolingual, nitroglycerin, fondaparinux, Lopressor, heparin, nitroglycerin TL, Nitro-Time, Nitromist, Ascriptin, alteplase, Retavase, TNKase, Bufferin, Nitro-Dur, Minitran, reteplase, tenecteplase, clopidogrel, Fragmin, enoxaparin, dalteparin, tirofiban, and Aggrastat.

To treat or ameliorate the effects of type I diabetes, a subject may be administered an effective amount of one or more compounds or pharmaceutical compositions of the present invention and, e.g., one or more of the following: insulin, such as regular insulin (Humulin R, Novolin R, others), insulin isophane (Humulin N, Novolin N), insulin lispro (Humalog), insulin aspart (NovoLog), insulin glargine (Lantus) and insulin detemir (Levemir), octreotide, pramlintide, and liraglutide.

To treat or ameliorate the effects of Alzheimer's disease, a subject may be administered an effective amount of one or more compounds or pharmaceutical compositions of the present invention and, e.g., one or more of the following: Donepezil (Aricept), Rivastigmine (Exelon), Galantamine (Razadyne), Tacrine (Cognex), Memantine (Namenda), Vitamin E, CERE-110: Adeno-Associated Virus Delivery of NGF (Ceregene), LY450139 (Eli Lilly), Exenatide, Varenicline (Pfizer), PF-04360365 (Pfizer), Resveratrol, and Donepezil (Eisai Korea).

To treat or ameliorate the effects of Parkinson's disease, a subject may be administered an effective amount of one or more compounds or pharmaceutical compositions of the present invention and, e.g., one or more of the following: Carbidopa/levodopa immediate-release (Sinemet), Carbidopa/levodopa oral disintegrating (Parcopa), Carbidopa/levodopa/Entacapone (Stalevo), Ropinirole (Requip), Pramipexole (Mirapex), Rotigotine (Neupro), Apomorphine (Apokyn), Selegiline (1-deprenyl, Eldepryl), Rasagiline (Azilect), Zydis selegiline HCL Oral disintegrating (Zelapar), Entacapone (Comtan), Tolcapone (Tasmar), Amantadine (Symmetrel), Trihexyphenidyl (formerly Artane), Benztropine (Cogentin), IPX066 (Impax Laboratories Inc.), Rasagiline (Teva Neuroscience, Inc.), ioflupane 123I (DATSCAN®), safinamide (EMD Serono), and Pioglitazone.

To treat or ameliorate the effects of amyotrophic lateral sclerosis, a subject may be administered an effective amount of one or more compounds or pharmaceutical compositions of the present invention and, e.g., one or more of the following: riluzole (Rilutek), Lithium carbonate, Arimoclomol, Creatine, Tamoxifen, Mecobalamin, Memantine (Ebixa), and tauroursodeoxycholic acid (TUDCA).

To treat or ameliorate the effects of Friedreich's ataxia, a subject may be administered an effective amount of one or more compounds or pharmaceutical compositions of the present invention and, e.g., one or more of the following: Idebenone, Coenzyme Q, 5-hydroxytryptophan, Propranolol, Enalapril, Lisinopril, Digoxin, Erythropoietin, Lu AA24493, Deferiprone, Varenicline, IVIG, Pioglitazone, and EGb 761.

To treat or ameliorate the effects of multiple sclerosis, a subject may be administered an effective amount of one or more compounds or pharmaceutical compositions of the present invention and, e.g., one or more of the following: Avonex, Betaseron, Extavia, Rebif, Glatiramer (Copaxone), Fingolimod (Gilenya), Natalizumab (Tysabri), Mitoxantrone (Novantrone), baclofen (Lioresal), tizanidine (Zanaflex), methylprednisolone, CinnoVex, ReciGen, Masitinib, Prednisone, Interferon beta 1a, Interferon beta 1b, and ELND002 (Elan Pharmaceuticals).

To treat or ameliorate the effects of Huntington's disease, a subject may be administered an effective amount of one or more compounds or pharmaceutical compositions of the present invention and, e.g., one or more of the following: Tetrabenazine (Xenazine), haloperidol (Haldol), clozapine (Clozaril), clonazepam (Klonopin), diazepam (Valium), escitalopram (Lexapro), fluoxetine (Prozac, Sarafem), sertraline (Zoloft), valproic acid (Depakene), divalproex (Depakote), lamotrigine (Lamictal), Dimebon, AFQ056 (Novartis), Ethyl-EPA (Miraxion™), SEN0014196 (Siena Biotech), sodium phenylbutyrate, citalopram, ursodiol, minocycline, remacemide, and mirtazapine.

To treat or ameliorate the effects of transmissible spongiform encephalopathy, a subject may be administered an effective amount of one or more compounds or pharmaceutical compositions of the present invention and e.g., Quinacrine.

To treat or ameliorate the effects of Charcot-Marie-Tooth disease, a subject may be administered an effective amount of one or more compounds or pharmaceutical compositions of the present invention and, e.g., one or more of the following: ascorbic acid and PXT3003.

To treat or ameliorate the effects of dementia with Lewy bodies, a subject may be administered an effective amount of one or more compounds or pharmaceutical compositions of the present invention and, e.g., one or more of the following: Aricept, Galantamine, Memantine, Armodafinil, Donepezil, and Ramelteon.

To treat or ameliorate the effects of corticobasal degeneration, a subject may be administered an effective amount of one or more compounds or pharmaceutical compositions of the present invention and, e.g., one or more of the following: Davunetide and Coenzyme Q10.

To treat or ameliorate the effects of progressive supranuclear palsy, a subject may be administered an effective amount of one or more compounds or pharmaceutical compositions of the present invention and, e.g., one or more of the following: Tideglusib, Rasagiline, alpha-lipoic acid/L-acetyl carnitine, Riluzole, Niacinamide, and Rivastigmine.

To treat or ameliorate the effects of hereditary spastic paraparesis, a subject may be administered an effective amount of one or more compounds or pharmaceutical compositions of the present invention and, e.g., one or more of the following: Baclofen, Tizanidine, Oxybutinin chloride, Tolterodine, and Botulinum toxin.

In the present invention, one or more compounds or pharmaceutical compositions may be co-administered to a subject in need thereof together in the same composition, simultaneously in separate compositions, or as separate compositions administered at different times, as deemed most appropriate by a physician.

An additional embodiment of the present invention is a method for treating or ameliorating the effects of a disorder in a subject in need thereof. This method comprises administering to the subject an effective amount of a pharmaceutical composition comprising a pharmaceutically acceptable carrier or diluent and a compound having the structure of formula (I):

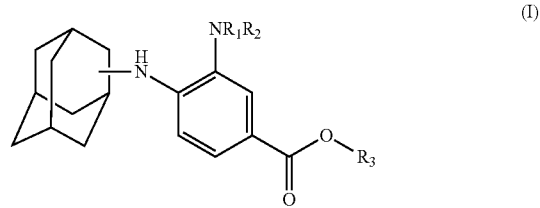

wherein:

R₁ and R₂, are independently selected from the group consisting of no atom, H, D, O, halo, $C_{1-6}$alkyl, $C_{1-6}$alkyl-aryl, $C_{1-6}$alkyl-heteroaryl, $C_{1-6}$alkenyl, $C_{1-6}$alkenyl-aryl, and $C_{1-6}$alkenyl-heteroaryl, wherein the $C_{1-6}$alkyl, $C_{1-6}$alkyl-aryl, $C_{1-6}$alkyl-heteroaryl, $C_{1-6}$alkenyl, $C_{1-6}$alkenyl-aryl, and $C_{1-6}$alkenyl-heteroaryl may be optionally substituted with an atom or a group selected from the group consisting of halo, deuterium, $C_{1-4}$alkyl, $CF_3$, and combinations thereof; and R₃ is independently selected from the group consisting of H, $C_{1-12}$aliphatic, $C_{1-6}$-alkyl-aryl and $C_{1-6}$-alkyl-heteroaryl;

or an N-oxide, crystalline form, hydrate, or pharmaceutically acceptable salt thereof, with the proviso that:

when R₃ is ethyl, R₁ and R₂ cannot be both H, O, or

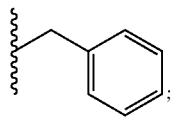

and when R₃ is ethyl and at least one of R₁ or R₂ is H, R₁ or R₂ cannot be

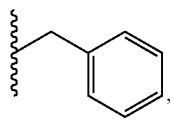, 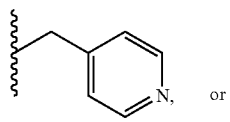 or

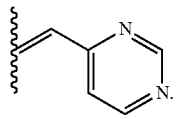

Suitable and preferred pharmaceutical compositions for use in this method are as disclosed above in formulas (I)-(III), including pharmaceutical compositions containing the particular SRS compounds. Suitable and preferred subjects who may be treated in accordance with this method are as disclosed above. In this embodiment, the methods may be used to treat disorders set forth above, including degenerative diseases that involve lipid peroxidation and excitotoxic diseases that involve oxidative cell death.

In another aspect of this embodiment, the method further comprises co-administering to the subject an effective amount of one or more additional therapeutic agents disclosed herein.

Another embodiment of the present invention is a method of modulating ferroptosis in a subject in need thereof. This method comprises administering to the subject an effective amount of a ferroptosis inhibitor, which comprises a compound having the structure of formula (I):

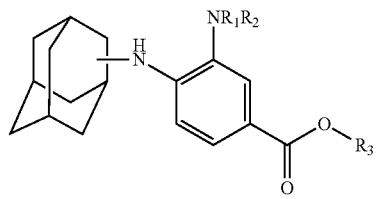

wherein:

R₁ and R₂, are independently selected from the group consisting of no atom, H, D, O, halo, $C_{1-6}$alkyl, $C_{1-6}$alkyl-aryl, $C_{1-6}$alkyl-heteroaryl, $C_{1-6}$alkenyl, $C_{1-6}$alkenyl-aryl, and $C_{1-6}$alkenyl-heteroaryl, wherein the $C_{1-6}$alkyl, $C_{1-6}$alkyl-aryl, $C_{1-6}$alkyl-heteroaryl, $C_{1-6}$alkenyl, $C_{1-6}$alkenyl-aryl, and $C_{1-6}$alkenyl-heteroaryl may be optionally substituted with an atom or a group selected from the group consisting of halo, deuterium, $C_{1-4}$alkyl, $CF_3$, and combinations thereof; and R₃ is independently selected from the group consisting of H, $C_{1-12}$aliphatic, $C_{1-6}$-alkyl-aryl and $C_{1-6}$-alkyl-heteroaryl;

or an N-oxide, crystalline form, hydrate, or pharmaceutically acceptable salt thereof, with the proviso that:

when R₃ is ethyl, R₁ and R₂ cannot be both H, O, or

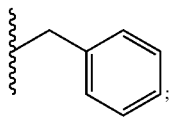 [SMILES: *Cc1ccccc1]

and when R₃ is ethyl and at least one of R₁ or R₂ is H, R₁ or R₂ cannot be

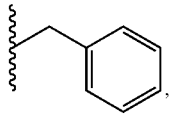 [SMILES: *Cc1ccccc1], 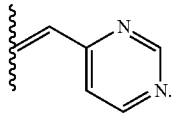 or

As used herein, "ferroptosis" means regulated cell death that is iron-dependent. Ferroptosis is characterized by the overwhelming, iron-dependent accumulation of lethal lipid reactive oxygen species. (Dixon et al., 2012) Ferroptosis is distinct from apoptosis, necrosis, and autophagy. (Id.) Assays for ferroptosis are as disclosed herein, for instance, in the Examples section.

Suitable and preferred compounds for use in this method are as disclosed above in formulas (I)-(III), including the particular SRS compounds. Suitable and preferred subjects who may be treated in accordance with this method are as disclosed above. In this embodiment, the methods may be used to treat the disorders set forth above, including degenerative diseases that involve lipid peroxidation and excitotoxic diseases that involve oxidative cell death.

In another aspect of this embodiment, the method further comprises co-administering to the subject an effective amount of one or more additional therapeutic agents disclosed herein.

A further embodiment of the present invention is a method of reducing reactive oxygen species (ROS) in a cell. This method comprises contacting a cell with a ferroptosis modulator, which comprises a compound having the structure of formula (I):

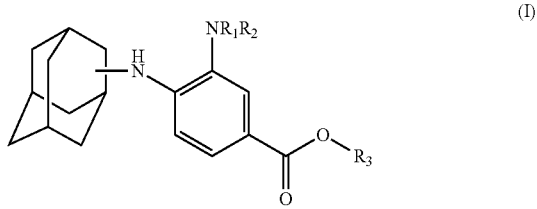

wherein:
- $R_1$ and $R_2$, are independently selected from the group consisting of no atom, H, D, O, halo, $C_{1-6}$alkyl, $C_{1-6}$alkyl-aryl, $C_{1-6}$alkyl-heteroaryl, $C_{1-6}$alkenyl, $C_{1-6}$alkenyl-aryl, and $C_{1-6}$alkenyl-heteroaryl, wherein the $C_{1-6}$alkyl, $C_{1-6}$alkyl-aryl, $C_{1-6}$alkyl-heteroaryl, $C_{1-6}$alkenyl, $C_{1-6}$alkenyl-aryl, and $C_{1-6}$alkenyl-heteroaryl may be optionally substituted with an atom or a group selected from the group consisting of halo, deuterium, $C_{1-4}$alkyl, $CF_3$, and combinations thereof; and
- $R_3$ is independently selected from the group consisting of H, $C_{1-12}$aliphatic, $C_{1-6}$-alkyl-aryl and $C_{1-6}$-alkyl-heteroaryl;

or an N-oxide, crystalline form, hydrate, or pharmaceutically acceptable salt thereof,
with the proviso that:
when $R_3$ is ethyl, $R_1$ and $R_2$ cannot be both H, O, or

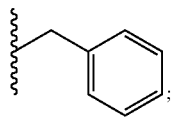;

and
when $R_3$ is ethyl and at least one of $R_1$ or $R_2$ is H, $R_1$ or $R_2$ cannot be

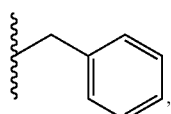, 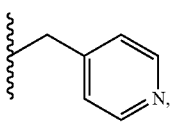, or

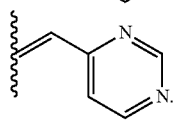.

As used herein, the terms "modulate", "modulating", "modulator" and grammatical variations thereof mean to change, such as decreasing or reducing the occurrence of ferroptosis. In this embodiment, "contacting" means bringing the compound and optionally one or more additional therapeutic agents into close proximity to the cells in need of such modulation. This may be accomplished using conventional techniques of drug delivery to the subject or in the in vitro situation by, e.g., providing the compound and optionally other therapeutic agents to a culture media in which the cells are located.

Suitable and preferred compounds for use in this method are as disclosed above in formulas (I)-(III), including the particular SRS compounds. In this embodiment, reducing ROS may be accomplished in cells obtained from a subject having a disorder as disclosed herein. Suitable and preferred subjects of this embodiment are as disclosed above.

In one aspect of this embodiment, the cell is a mammalian cell. Preferably, the mammalian cell is obtained from a mammal selected from the group consisting of humans, primates, farm animals, and domestic animals. More preferably, the mammalian cell is a human cancer cell.

In another aspect of this embodiment, the method further comprises contacting the cell with at least one additional therapeutic agent as disclosed herein.

An additional embodiment of the present invention is a method for treating or ameliorating the effects of a neurodegenerative disease in a subject in need thereof. This method comprises administering to the subject an effective amount of a compound selected from the group consisting of

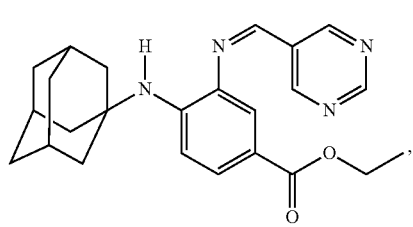

SRS15-72

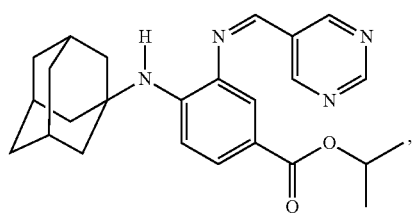

SRS16-80

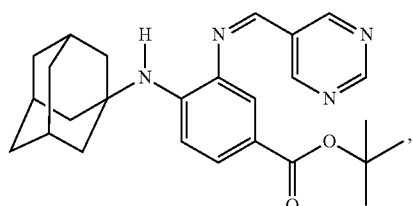

SRS16-86 and combinations thereof, or an N-oxide, crystalline form, hydrate, or pharmaceutically acceptable salt thereof.

Suitable and preferred subjects are as disclosed herein. In this embodiment, the methods may be used to treat the neurodegenerative disorders set forth above.

In one aspect of this embodiment, the method further comprises co-administering to the subject an effective amount of one or more therapeutic agents disclosed herein.

Another embodiment of the present invention is a compound according to formula (IV):

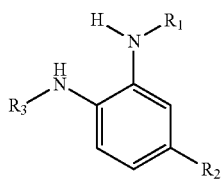

(IV)

wherein:
- $R_1$ is selected from the group consisting of aryl, $C_{1-6}$alkyl-aryl, and $C_{3-10}$carbocycle, wherein the aryl, $C_{1-6}$alkyl-aryl, and $C_{3-10}$carbocycle may be optionally substituted with an atom or a group selected from the group consisting of halo, deuterium, $C_{1-6}$alkyl, $CF_3$, and combinations thereof;
- $R_2$ is a triazole, an oxazole, an oxadiazole, or a ketone; and
- $R_3$ is a $C_{3-12}$carbocycle, optionally substituted with $C_{1-10}$ alkyl or halo;

or an N-oxide, crystalline form, hydrate, or pharmaceutically acceptable salt thereof.

In one aspect of this embodiment, the compound has the structure of formula (V):

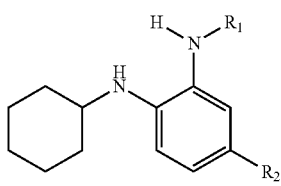

(V)

wherein:
- $R_1$ is selected from the group consisting of aryl, $C_{1-6}$alkyl-aryl, and $C_{3-10}$carbocycle, wherein the aryl, $C_{1-6}$alkyl-aryl, and $C_{3-10}$carbocycle may be optionally substituted with an atom or a group selected from the group consisting of halo, deuterium, $C_{1-6}$alkyl, $CF_3$, and combinations thereof; and
- $R_2$ is selected from the group consisting of

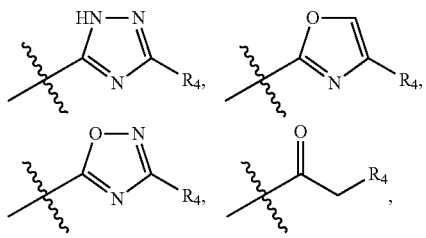

wherein $R_4$ is selected from the group consisting of H, $C_{1-12}$alkyl, $C_{3-12}$carbocycle, and aryl, or an N-oxide, crystalline form, hydrate, or pharmaceutically acceptable salt thereof.

In another aspect of this embodiment, R1 is selected from the group consisting of:

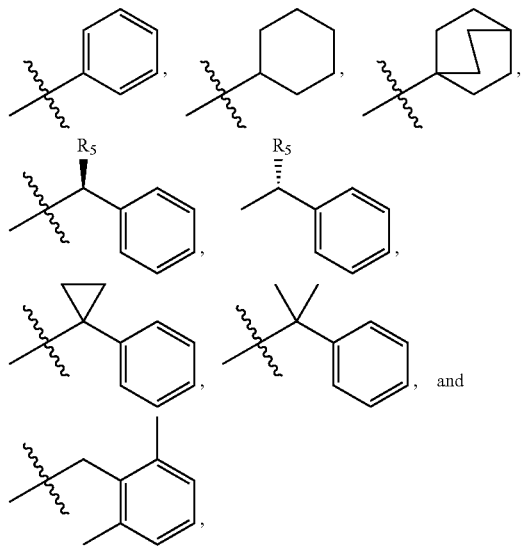

wherein $R_5$ is selected from the group consisting of $CF_3$, $CH_3$, $CH_2CH_3$, $CH(CH_3)_2$, $C(CH_3)_3$;

or an N-oxide, crystalline form, hydrate, or pharmaceutically acceptable salt thereof.

In a further aspect of this embodiment, the compound has the structure of:

SRS13-10F2

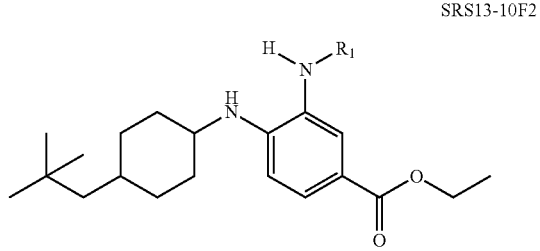

or an N-oxide, crystalline form, hydrate, or pharmaceutically acceptable salt thereof.

A further embodiment of the present invention is a pharmaceutical composition. This pharmaceutical composition comprises a pharmaceutically acceptable carrier or diluent and a compound according to formula (IV):

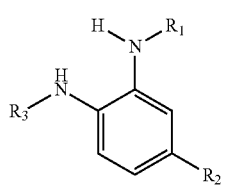

(IV)

wherein:
- $R_1$ is selected from the group consisting of aryl, $C_{1-6}$alkyl-aryl, and $C_{3-10}$carbocycle, wherein the aryl, $C_{1-6}$alkyl-aryl, and $C_{3-10}$carbocycle may be optionally substituted with an atom or a group selected from the group consisting of halo, deuterium, $C_{1-6}$alkyl, $CF_3$, and combinations thereof;
- $R_2$ is a triazole, an oxazole, an oxadiazole, or a ketone; and R$_3$ is a C$_{3-12}$carbocycle, optionally substituted with C$_{1-10}$ alkyl or halo;

or an N-oxide, crystalline form, hydrate, or pharmaceutically acceptable salt thereof.

Suitable and preferred compounds, including preferred R1 groups, compounds of formula (V), and SRS13-10F2, are as set forth above.

An additional embodiment of the present invention is a kit. This kit comprises a compound or a pharmaceutical composition according to any compound of the present invention together with instructions for the use of the compound.

Suitable and preferred compounds, including preferred R$_1$ groups, compounds of formula (V), and SRS13-10F2, are as set forth above.

Another embodiment of the present invention is a method for treating or ameliorating the effects of a disorder in a subject in need thereof. This method comprises administering to the subject an effective amount of a compound having the structure of formula (IV):

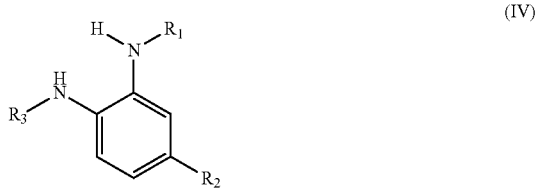

(IV)

wherein:
- R$_1$ is selected from the group consisting of aryl, C$_{1-6}$alkyl-aryl, and C$_{3-10}$carbocycle, wherein the aryl, C$_{1-6}$alkyl-aryl, and C$_{3-10}$carbocycle may be optionally substituted with an atom or a group selected from the group consisting of halo, deuterium, C$_{1-6}$alkyl, CF$_3$, and combinations thereof;
- R$_2$ is a triazole, an oxazole, an oxadiazole, or a ketone; and
- R$_3$ is a C$_{3-12}$carbocycle, optionally substituted with C$_{1-10}$ alkyl or halo;

or an N-oxide, crystalline form, hydrate, or pharmaceutically acceptable salt thereof.

Suitable and preferred compounds, including preferred R$_1$ groups, compounds of formula (V), and SRS13-10F2, are as set forth above. Suitable and preferred subjects are also as set forth above.

In one aspect of this embodiment, the disorder is a degenerative disease that involves lipid peroxidation. In another aspect of this embodiment, the disorder is an excitotoxic disease involving oxidative cell death. The disorder may also be selected from the group consisting of epilepsy, kidney disease, stroke, myocardial infarction, type I diabetes, TBI, PVL, and neurodegenerative disease. Suitable and preferred neurodegenerative diseases are as set forth above.

In a further aspect of this embodiment, the method further comprises co-administering to the subject an effective amount of one or more additional therapeutic agents as disclosed herein.

A further embodiment of the present invention is a method for treating or ameliorating the effects of a disorder in a subject in need thereof. This method comprises administering to the subject an effective amount of a pharmaceutical composition comprising a pharmaceutically acceptable carrier or diluent and a compound having the structure of formula (IV):

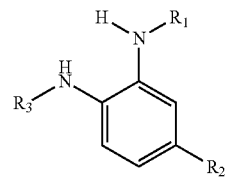

(IV)

wherein:
- R$_1$ is selected from the group consisting of aryl, C$_{1-6}$alkyl-aryl, and C$_{3-10}$carbocycle, wherein the aryl, C$_{1-6}$alkyl-aryl, and C$_{3-10}$carbocycle may be optionally substituted with an atom or a group selected from the group consisting of halo, deuterium, C$_{1-6}$alkyl, CF$_3$, and combinations thereof;
- R$_2$ is a triazole, an oxazole, an oxadiazole, or a ketone; and
- R$_3$ is a C$_{3-12}$carbocycle, optionally substituted with C$_{1-10}$ alkyl or halo;

or an N-oxide, crystalline form, hydrate, or pharmaceutically acceptable salt thereof.

Suitable and preferred compounds, including preferred R$_1$ groups, compounds of formula (V), and SRS13-10F2, are as set forth above. Suitable and preferred subjects are also as set forth above.

In one aspect of this embodiment, the disorder is a degenerative disease that involves lipid peroxidation. In another aspect of this embodiment, the disorder is an excitotoxic disease involving oxidative cell death. The disorder may also be selected from the group consisting of epilepsy, kidney disease, stroke, myocardial infarction, type I diabetes, TBI, PVL, and neurodegenerative disease. Suitable and preferred neurodegenerative diseases are as set forth above.

Another embodiment of the present invention is a method of modulating ferroptosis in a subject in need thereof. This method comprises administering to the subject an effective amount of a ferroptosis inhibitor, which comprises a compound having the structure of formula (IV):

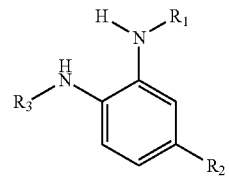

(IV)

wherein:
- R$_1$ is selected from the group consisting of aryl, C$_{1-6}$alkyl-aryl, and C$_{3-10}$carbocycle, wherein the aryl, C$_{1-6}$alkyl-aryl, and C$_{3-10}$carbocycle may be optionally substituted with an atom or a group selected from the group consisting of halo, deuterium, C$_{1-6}$alkyl, CF$_3$, and combinations thereof;
- R$_2$ is a triazole, an oxazole, an oxadiazole, or a ketone; and
- R$_3$ is a C$_{3-12}$carbocycle, optionally substituted with C$_{1-10}$ alkyl or halo;

or an N-oxide, crystalline form, hydrate, or pharmaceutically acceptable salt thereof.

Suitable and preferred compounds, including preferred R$_1$ groups, compounds of formula (V), and SRS13-10F2, are as set forth above. Suitable and preferred subjects are also as set forth above.

An additional embodiment of the present invention is a method of reducing reactive oxygen species (ROS) in a cell. This method comprises contacting a cell with a ferroptosis modulator, which comprises a compound having the structure of formula (IV):

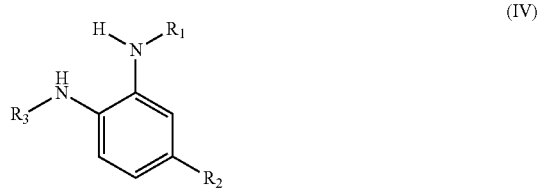

wherein:
- $R_1$ is selected from the group consisting of aryl, $C_{1-6}$alkyl-aryl, and $C_{3-10}$carbocycle, wherein the aryl, $C_{1-6}$alkyl-aryl, and $C_{3-10}$carbocycle may be optionally substituted with an atom or a group selected from the group consisting of halo, deuterium, $C_{1-6}$alkyl, $CF_3$, and combinations thereof;
- $R_2$ is a triazole, an oxazole, an oxadiazole, or a ketone; and
- $R_3$ is a $C_{3-12}$carbocycle, optionally substituted with $C_{1-10}$ alkyl or halo;

or an N-oxide, crystalline form, hydrate, or pharmaceutically acceptable salt thereof.

Suitable and preferred compounds, including preferred $R_1$ groups, compounds of formula (V), and SRS13-10F2, are as set forth above.

In one aspect of this embodiment, the cell may be accomplished in cells obtained from a subject having a disease that involves lipid peroxidation. Suitable and preferred subjects are as set forth above. Preferably, the disorder is an excitotoxic disease involving oxidative cell death. The disorder may also be selected from the group consisting of epilepsy, kidney disease, stroke, myocardial infarction, type I diabetes, TBI, PVL, and neurodegenerative disease. Suitable and preferred neurodegenerative diseases are as set forth above.

In one aspect of this embodiment, the cell is a mammalian cell. Preferably, the mammalian cell is obtained from a mammal selected from the group consisting of humans, primates, farm animals, and domestic animals. More preferably, the mammalian cell is a human cancer cell.

As used herein, a "pharmaceutically acceptable salt" means a salt of the compounds of the present invention which are pharmaceutically acceptable, as defined herein, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as acetic acid, propionic acid, hexanoic acid, heptanoic acid, cyclopentanepropionic acid, glycolic acid, pyruvic acid, lactic acid, malonic acid, succinic acid, malic acid, maleic acid, fumaric acid, tartaric acid, citric acid, benzoic acid, o-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, p-chlorobenzenesulfonic acid, 2-naphthalenesulfonic acid, p-toluenesulfonic acid, camphorsulfonic acid, 4-methylbicyclo[2.2.2]oct-2-ene-1-carboxylic acid, glucoheptonic acid, 4,4'-methylenebis(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like.

In the present invention, an "effective amount" or "therapeutically effective amount" of a compound or pharmaceutical composition, is an amount of such a compound or composition that is sufficient to effect beneficial or desired results as described herein when administered to a subject. Effective dosage forms, modes of administration, and dosage amounts may be determined empirically, and making such determinations is within the skill of the art. It is understood by those skilled in the art that the dosage amount will vary with the route of administration, the rate of excretion, the duration of the treatment, the identity of any other drugs being administered, the age, size, and species of the subject, and like factors well known in the arts of, e.g., medicine and veterinary medicine. In general, a suitable dose of a compound or pharmaceutical composition according to the invention will be that amount of the compound or composition, which is the lowest dose effective to produce the desired effect with no or minimal side effects. The effective dose of a compound or pharmaceutical composition according to the present invention may be administered as two, three, four, five, six or more sub-doses, administered separately at appropriate intervals throughout the day.

A suitable, non-limiting example of a dosage of a compound or pharmaceutical composition according to the present invention or a composition comprising such a compound, is from about 1 ng/kg to about 1000 mg/kg, such as from about 1 mg/kg to about 100 mg/kg, including from about 5 mg/kg to about 50 mg/kg. Other representative dosages of a compound or a pharmaceutical composition of the present invention include about 1 mg/kg, 5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 60 mg/kg, 70 mg/kg, 80 mg/kg, 90 mg/kg, 100 mg/kg, 125 mg/kg, 150 mg/kg, 175 mg/kg, 200 mg/kg, 250 mg/kg, 300 mg/kg, 400 mg/kg, 500 mg/kg, 600 mg/kg, 700 mg/kg, 800 mg/kg, 900 mg/kg, or 1000 mg/kg.

A compound or pharmaceutical composition of the present invention may be administered in any desired and effective manner: for oral ingestion, or as an ointment or drop for local administration to the eyes, or for parenteral or other administration in any appropriate manner such as intraperitoneal, subcutaneous, topical, intradermal, inhalation, intrapulmonary, rectal, vaginal, sublingual, intramuscular, intravenous, intraarterial, intrathecal, or intralymphatic. Further, a compound or pharmaceutical composition of the present invention may be administered in conjunction with other treatments. A compound or pharmaceutical composition of the present invention may be encapsulated or otherwise protected against gastric or other secretions, if desired.

The pharmaceutical compositions of the invention are pharmaceutically acceptable and comprise one or more active ingredients in admixture with one or more pharmaceutically-acceptable carriers or diluents and, optionally, one or more other compounds, drugs, ingredients and/or materials. Regardless of the route of administration selected, the compounds/pharmaceutical compositions of the present invention are formulated into pharmaceutically-acceptable dosage forms by conventional methods known to those of skill in the art. See, e.g., Remington, The Science and Practice of Pharmacy (21$^{st}$ Edition, Lippincott Williams and Wilkins, Philadelphia, Pa.). More generally, "pharmaceutically acceptable" means that which is useful in preparing a composition that is generally safe, non-toxic, and neither biologically nor otherwise undesirable and includes that which is acceptable for veterinary use as well as human pharmaceutical use.

Pharmaceutically acceptable carriers and diluents are well known in the art (see, e.g., Remington, The Science and Practice of Pharmacy (21$^{st}$ Edition, Lippincott Williams and Wilkins, Philadelphia, Pa.) and The National Formulary (American Pharmaceutical Association, Washington, D.C.)) and include sugars (e.g., lactose, sucrose, mannitol, and sorbitol), starches, cellulose preparations, calcium phosphates (e.g., dicalcium phosphate, tricalcium phosphate and calcium hydrogen phosphate), sodium citrate, water, aqueous solutions (e.g., saline, sodium chloride injection, Ringer's injection, dextrose injection, dextrose and sodium chloride injection, lactated Ringer's injection), alcohols (e.g., ethyl alcohol, propyl alcohol, and benzyl alcohol), polyols (e.g., glycerol, propylene glycol, and polyethylene glycol), organic esters (e.g., ethyl oleate and tryglycerides), biodegradable polymers (e.g., polylactide-polyglycolide, poly(orthoesters), and poly(anhydrides)), elastomeric matrices, liposomes, microspheres, oils (e.g., corn, germ, olive, castor, sesame, cottonseed, and groundnut), cocoa butter, waxes (e.g., suppository waxes), paraffins, silicones, talc, silicylate, etc. Each pharmaceutically acceptable carrier or diluent used in a composition of the invention must be "acceptable" in the sense of being compatible with the other ingredients of the formulation and not injurious to the subject. Carriers or diluents suitable for a selected dosage form and intended route of administration are well known in the art, and acceptable carriers or diluents for a chosen dosage form and method of administration can be determined using ordinary skill in the art.

The pharmaceutical compositions of the invention may, optionally, contain additional ingredients and/or materials commonly used in such compositions. These ingredients and materials are well known in the art and include (1) fillers or extenders, such as starches, lactose, sucrose, glucose, mannitol, and silicic acid; (2) binders, such as carboxymethylcellulose, alginates, gelatin, polyvinyl pyrrolidone, hydroxypropylmethyl cellulose, sucrose and acacia; (3) humectants, such as glycerol; (4) disintegrating agents, such as agar-agar, calcium carbonate, potato or tapioca starch, alginic acid, certain silicates, sodium starch glycolate, cross-linked sodium carboxymethyl cellulose and sodium carbonate; (5) solution retarding agents, such as paraffin; (6) absorption accelerators, such as quaternary ammonium compounds; (7) wetting agents, such as cetyl alcohol and glycerol monostearate; (8) absorbents, such as kaolin and bentonite clay; (9) lubricants, such as talc, calcium stearate, magnesium stearate, solid polyethylene glycols, and sodium lauryl sulfate; (10) suspending agents, such as ethoxylated isostearyl alcohols, polyoxyethylene sorbitol and sorbitan esters, microcrystalline cellulose, aluminum metahydroxide, bentonite, agar-agar and tragacanth; (11) buffering agents; (12) excipients, such as lactose, milk sugars, polyethylene glycols, animal and vegetable fats, oils, waxes, paraffins, cocoa butter, starches, tragacanth, cellulose derivatives, polyethylene glycol, silicones, bentonites, silicic acid, talc, salicylate, zinc oxide, aluminum hydroxide, calcium silicates, and polyamide powder; (13) inert diluents, such as water or other solvents; (14) preservatives; (15) surface-active agents; (16) dispersing agents; (17) control-release or absorption-delaying agents, such as hydroxypropylmethyl cellulose, other polymer matrices, biodegradable polymers, liposomes, microspheres, aluminum monosterate, gelatin, and waxes; (18) opacifying agents; (19) adjuvants; (20) wetting agents; (21) emulsifying and suspending agents; (22), solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan; (23) propellants, such as chlorofluorohydrocarbons and volatile unsubstituted hydrocarbons, such as butane and propane; (24) antioxidants; (25) agents which render the formulation isotonic with the blood of the intended recipient, such as sugars and sodium chloride; (26) thickening agents; (27) coating materials, such as lecithin; and (28) sweetening, flavoring, coloring, perfuming and preservative agents. Each such ingredient or material must be "acceptable" in the sense of being compatible with the other ingredients of the formulation and not injurious to the subject. Ingredients and materials suitable for a selected dosage form and intended route of administration are well known in the art, and acceptable ingredients and materials for a chosen dosage form and method of administration may be determined using ordinary skill in the art.

Compounds or pharmaceutical compositions suitable for oral administration may be in the form of capsules, cachets, pills, tablets, powders, granules, a solution or a suspension in an aqueous or non-aqueous liquid, an oil-in-water or water-in-oil liquid emulsion, an elixir or syrup, a pastille, a bolus, an electuary or a paste. These formulations may be prepared by methods known in the art, e.g., by means of conventional pan-coating, mixing, granulation or lyophilization processes.

Solid dosage forms for oral administration (capsules, tablets, pills, dragees, powders, granules and the like) may be prepared, e.g., by mixing the active ingredient(s) with one or more pharmaceutically-acceptable carriers or diluents and, optionally, one or more fillers, extenders, binders, humectants, disintegrating agents, solution retarding agents, absorption accelerators, wetting agents, absorbents, lubricants, and/or coloring agents. Solid compositions of a similar type may be employed as fillers in soft and hard-filled gelatin capsules using a suitable excipient. A tablet may be made by compression or molding, optionally with one or more accessory ingredients. Compressed tablets may be prepared using a suitable binder, lubricant, inert diluent, preservative, disintegrant, surface-active or dispersing agent. Molded tablets may be made by molding in a suitable machine. The tablets, and other solid dosage forms, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein. They may be sterilized by, for example, filtration through a bacteria-retaining filter. These compositions may also optionally contain opacifying agents and may be of a composition such that they release the active ingredient only, or preferentially, in a certain portion of the gastrointestinal tract, optionally, in a delayed manner. The active ingredient can also be in microencapsulated form.

Liquid dosage forms for oral administration include pharmaceutically-acceptable emulsions, microemulsions, solutions, suspensions, syrups and elixirs. The liquid dosage forms may contain suitable inert diluents commonly used in the art. Besides inert diluents, the oral compositions may also include adjuvants, such as wetting agents, emulsifying and suspending agents, sweetening, flavoring, coloring, perfuming and preservative agents. Suspensions may contain suspending agents.

Compositions for rectal or vaginal administration may be presented as a suppository, which may be prepared by mixing one or more active ingredient(s) with one or more suitable nonirritating carriers which are solid at room temperature, but liquid at body temperature and, therefore, will melt in the rectum or vaginal cavity and release the active compound. Compositions which are suitable for vaginal administration also include pessaries, tampons, creams, gels, pastes, foams or spray formulations containing such pharmaceutically-acceptable carriers as are known in the art to be appropriate.

Dosage forms for the topical or transdermal administration include powders, sprays, ointments, pastes, creams, lotions, gels, solutions, patches, drops and inhalants. The active agent(s)/compound(s) may be mixed under sterile conditions with a suitable pharmaceutically-acceptable carrier or diluent. The ointments, pastes, creams and gels may contain excipients. Powders and sprays may contain excipients and propellants.

Compositions suitable for parenteral administrations comprise one or more agent(s)/compound(s) in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain suitable antioxidants, buffers, solutes which render the formulation isotonic with the blood of the intended recipient, or suspending or thickening agents. Proper fluidity can be maintained, for example, by the use of coating materials, by the maintenance of the required particle size in the case of dispersions, and by the use of surfactants. These compositions may also contain suitable adjuvants, such as wetting agents, emulsifying agents and dispersing agents. It may also be desirable to include isotonic agents. In addition, prolonged absorption of the injectable pharmaceutical form may be brought about by the inclusion of agents which delay absorption.

In some cases, in order to prolong the effect of a drug (e.g., pharmaceutical formulation), it is desirable to slow its absorption from subcutaneous or intramuscular injection. This may be accomplished by the use of a liquid suspension of crystalline or amorphous material having poor water solubility.

The rate of absorption of the active agent/drug then depends upon its rate of dissolution which, in turn, may depend upon crystal size and crystalline form. Alternatively, delayed absorption of a parenterally-administered agent/drug may be accomplished by dissolving or suspending the active agent/drug in an oil vehicle. Injectable depot forms may be made by forming microencapsule matrices of the active ingredient in biodegradable polymers. Depending on the ratio of the active ingredient to polymer, and the nature of the particular polymer employed, the rate of active ingredient release can be controlled. Depot injectable formulations are also prepared by entrapping the drug in liposomes or microemulsions which are compatible with body tissue. The injectable materials can be sterilized for example, by filtration through a bacterial-retaining filter.

The formulations may be presented in unit-dose or multidose sealed containers, for example, ampules and vials, and may be stored in a lyophilized condition requiring only the addition of the sterile liquid carrier or diluent, for example water for injection, immediately prior to use. Extemporaneous injection solutions and suspensions may be prepared from sterile powders, granules and tablets of the type described above.

In the foregoing embodiments, the following definitions apply.

The term "aliphatic", as used herein, refers to a group composed of carbon and hydrogen that do not contain aromatic rings. Accordingly, aliphatic groups include alkyl, alkenyl, alkynyl, and carbocyclyl groups. Additionally, unless otherwise indicated, the term "aliphatic" is intended to include both "unsubstituted aliphatics" and "substituted aliphatics", the latter of which refers to aliphatic moieties having substituents replacing a hydrogen on one or more carbons of the aliphatic group. Such substituents can include, for example, a halogen, a deuterium, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, an aromatic, or heteroaromatic moiety.

The term "alkyl" refers to the radical of saturated aliphatic groups that does not have a ring structure, including straight-chain alkyl groups, and branched-chain alkyl groups. In certain embodiments, a straight chain or branched chain alkyl has 6 or fewer carbon atoms in its backbone (e.g., $C_1$-$C_6$ for straight chains, $C_3$-$C_6$ for branched chains). Such substituents include all those contemplated for aliphatic groups, as discussed below, except where stability is prohibitive.

The term "alkenyl", as used herein, refers to an aliphatic group containing at least one double bond and unless otherwise indicated, is intended to include both "unsubstituted alkenyls" and "substituted alkenyls", the latter of which refers to alkenyl moieties having substituents replacing a hydrogen on one or more carbons of the alkenyl group. Such substituents include all those contemplated for aliphatic groups, as discussed below, except where stability is prohibitive. For example, substitution of alkenyl groups by one or more alkyl, carbocyclyl, aryl, heterocyclyl, or heteroaryl groups is contemplated.

Moreover, unless otherwise indicated, the term "alkyl" as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Indeed, unless otherwise indicated, all groups recited herein are intended to include both substituted and unsubstituted options.

The term "$C_{x-y}$" when used in conjunction with a chemical moiety, such as, alkyl and cycloalkyl, is meant to include groups that contain from x to y carbons in the chain. For example, the term "$C_{x-y}$alkyl" refers to substituted or unsubstituted saturated hydrocarbon groups, including straight-chain alkyl and branched-chain alkyl groups that contain from x to y carbons in the chain, including haloalkyl groups such as trifluoromethyl and 2,2,2-tirfluoroethyl, etc.

The term "aryl" as used herein includes substituted or unsubstituted single-ring aromatic groups in which each atom of the ring is carbon. Preferably the ring is a 3- to 8-membered ring, more preferably a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The term "alkyl-aryl" refers to an alkyl group substituted with at least one aryl group.

The term "alkyl-heteroaryl" refers to an alkyl group substituted with at least one heteroaryl group.

The term "alkenyl-aryl" refers to an alkenyl group substituted with at least one aryl group.

The term "alkenyl-heteroaryl" refers to an alkenyl group substituted with at least one heteroaryl group.

The terms "carbocycle", "carbocyclyl", and "carbocyclic", as used herein, refer to a non-aromatic saturated or unsaturated ring in which each atom of the ring is carbon. Preferably a carbocycle ring contains from 3 to 10 atoms, more preferably from 3 to 8 atoms, including 5 to 7 atoms, such as for example, 6 atoms.

The terms "halo" and "halogen" are used interchangeably herein and mean halogen and include chloro, fluoro, bromo, and iodo.

The term "heteroaryl" includes substituted or unsubstituted aromatic single ring structures, preferably 3- to 8-membered rings, more preferably 5- to 7-membered rings, even more preferably 5- to 6-membered rings, whose ring structures include at least one heteroatom, preferably one to four heteroatoms, more preferably one or two heteroatoms. The term "heteroaryl" also includes polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, and pyrimidine, and the like.

The term "heteroatom" as used herein means an atom of any element other than carbon or hydrogen. Preferred heteroatoms are nitrogen, oxygen, and sulfur; more preferably, nitrogen and oxygen.

The term "ketone" means an organic compound with the structure RC(=O)R', wherein neither R and R' can be hydrogen atoms.

The term "substituted" refers to moieties having substituents replacing a hydrogen on one or more carbons of the backbone. It will be understood that "substitution" or "substituted with" includes the implicit proviso that such substitution is in accordance with the permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate.

As set forth previously, unless specifically stated as "unsubstituted," references to chemical moieties herein are understood to include substituted variants. For example, reference to an "aryl" group or moiety implicitly includes both substituted and unsubstituted variants.

As used herein, the term "oxadiazole" means any compound or chemical group containing the following structure:

As used herein, the term "oxazole" means any compound or chemical group containing the following structure:

As used herein, the term "triazole" means any compound or chemical group containing the following structure:

It is understood that the disclosure of a compound herein encompasses all stereoisomers of that compound. As used herein, the term "stereoisomer" refers to a compound made up of the same atoms bonded by the same bonds but having different three-dimensional structures which are not interchangeable. The three-dimensional structures are called configurations. Stereoisomers include enantiomers and diastereomers.

The terms "racemate" or "racemic mixture" refer to a mixture of equal parts of enantiomers. The term "chiral center" refers to a carbon atom to which four different groups are attached. The term "enantiomeric enrichment" as used herein refers to the increase in the amount of one enantiomer as compared to the other.

It is appreciated that to the extent compounds of the present invention have a chiral center, they may exist in and be isolated in optically active and racemic forms. Some compounds may exhibit polymorphism. It is to be understood that the present invention encompasses any racemic, optically-active, diastereomeric, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase).

Examples of methods to obtain optically active materials are known in the art, and include at least the following:
  i) physical separation of crystals—a technique whereby macroscopic crystals of the individual enantiomers are manually separated. This technique can be used if crystals of the separate enantiomers exist, i.e., the material is a conglomerate, and the crystals are visually distinct;
  ii) simultaneous crystallization—a technique whereby the individual enantiomers are separately crystallized from a solution of the racemate, possible only if the latter is a conglomerate in the solid state;
  iii) enzymatic resolutions—a technique whereby partial or complete separation of a racemate by virtue of differing rates of reaction for the enantiomers with an enzyme;
  iv) enzymatic asymmetric synthesis—a synthetic technique whereby at least one step of the synthesis uses an enzymatic reaction to obtain an enantiomerically pure or enriched synthetic precursor of the desired enantiomer;
  v) chemical asymmetric synthesis—a synthetic technique whereby the desired enantiomer is synthesized from an achiral precursor under conditions that produce asymmetry (i.e., chirality) in the product, which may be achieved using chiral catalysts as disclosed in more detail herein or chiral auxiliaries;
  vi) diastereomer separations—a technique whereby a racemic compound is reacted with an enantiomerically pure reagent (the chiral auxiliary) that converts the individual enantiomers to diastereomers. The resulting diastereomers are then separated by chromatography or crystallization by virtue of their now more distinct structural differences and the chiral auxiliary later removed to obtain the desired enantiomer;
  vii) first- and second-order asymmetric transformations—a technique whereby diastereomers from the racemate equilibrate to yield a preponderance in solution of the diastereomer from the desired enantiomer or where preferential crystallization of the diastereomer from the desired enantiomer perturbs the equilibrium such that eventually in principle all the material is converted to the crystalline diastereomer from the desired enantiomer. The desired enantiomer is then released from the diastereomer;
  viii) kinetic resolutions—this technique refers to the achievement of partial or complete resolution of a racemate (or of a further resolution of a partially resolved compound) by virtue of unequal reaction rates of the enantiomers with a chiral, non-racemic reagent or catalyst under kinetic conditions;
  ix) enantiospecific synthesis from non-racemic precursors—a synthetic technique whereby the desired enantiomer is obtained from non-chiral starting materials and where the stereochemical integrity is not or is only minimally compromised over the course of the synthesis;
  x) chiral liquid chromatography—a technique whereby the enantiomers of a racemate are separated in a liquid mobile phase by virtue of their differing interactions with a stationary phase. The stationary phase can be made of chiral material or the mobile phase can contain an additional chiral material to provoke the differing interactions;
  xi) chiral gas chromatography—a technique whereby the racemate is volatilized and enantiomers are separated by virtue of their differing interactions in the gaseous mobile phase with a column containing a fixed non-racemic chiral adsorbent phase;
  xii) extraction with chiral solvents—a technique whereby the enantiomers are separated by virtue of preferential dissolution of one enantiomer into a particular chiral solvent;
  xiii) transport across chiral membranes—a technique whereby a racemate is placed in contact with a thin membrane barrier. The barrier typically separates two miscible fluids, one containing the racemate, and a driving force such as concentration or pressure differential causes preferential transport across the membrane barrier. Separation occurs as a result of the non-racemic chiral nature of the membrane which allows only one enantiomer of the racemate to pass through.

The stereoisomers may also be separated by usual techniques known to those skilled in the art including fractional crystallization of the bases or their salts or chromatographic techniques such as LC or flash chromatography. The (+) enantiomer can be separated from the (−) enantiomer using techniques and procedures well known in the art, such as that described by J. Jacques, et al., Enantiomers, Racemates, and Resolutions", John Wiley and Sons, Inc., 1981. For example, chiral chromatography with a suitable organic solvent, such as ethanol/acetonitrile and Chiralpak AD packing, 20 micron can also be utilized to effect separation of the enantiomers.

The following examples are provided to further illustrate the methods of the present invention. These examples are illustrative only and are not intended to limit the scope of the invention in any way.

EXAMPLES

Example 1

Experimental Procedures

Flow Cytometry Experiments 200,000 HT-1080 cells were seeded into 6-well dishes (Corning). The next day, cells were treated with +/−rotenone +/−ferrostatin-1 for 3 hours (for MitoSOX experiments) or +/−STS +/−ferrostatin-1 for 4 hours (for 10-N-nonylacridine orange [NAO] experiments), harvested by trypsinization and analyzed as follows. For the analysis of mitochondrial ROS, cells were incubated with 5 μM MitoSOX (Molecular Probes/Invitrogen) in HBSS for 10 minutes in the dark at 37° C. For the analysis of mitochondrial cardiolipin peroxidation, cells were incubated with NAO dissolved to a final concentration of 25 ng/mL in HBSS for 10 minutes in the dark at 37° C. Cells were then washed once in HBSS and measurements were subsequently acquired using an flow cytometer (BD/Accuri C6) equipped with a 488 nm laser for excitation of fluorophores. MitoSOX data were collected in the FL2 channel and NAO data was collected in the FL1 channel. Data are from three independent biological replicates of each experiment. Data were analyzed by one-way ANOVA with Bonferroni's post-hoc test.

Analysis of Acridine Orange (AO) Relocalization 200,000 HT-1080 cells were seeded into 6-well dishes (Corning). The next day, cells were incubated with 25 ng/mL of AO for 15 minutes, then medium was removed and cells were incubated in growth medium for 15 minutes. The medium was then removed again and replaced with medium containing DMSO or erastin +/−ciclipirox olamine (CPX, an iron chelator) or ferrostatin-1 (Fer-1). Relocalization of AO from lysosomes (discrete red puncta) to the cytosol (diffuse green color) was determined using an EVOS fl digital inverted fluorescent microscope (Advanced Microscopy Group) equipped with GFP (ex/em 470/525) and RFP (ex/em 531/593) light cubes.

Analysis of Reactive Oxygen Species Production

The day before the experiment, 200,000 cells/well were seeded in 6-well dishes (Corning Inc., Corning, N.Y.). The day of the experiment, cells were treated with test compounds for the indicated times, then harvested by trypsinization, resuspended in 500 µL Hanks Balanced Salt Solution (HBSS, Gibco, Invitrogen Corp., Carlsbad, Calif.) containing either $H_2DCFDA$ (25 µM), C11-BODIPY(581/591) (2 µM) or MitoSOX (5 µM) (all from Molecular Probes, Invitrogen) and incubated for 10 minutes at 37° C. in a tissue culture incubator. Cells were then resuspended in 500 µL of fresh HBSS, strained through a 40 µM cell strainer (BD Falcon, BD Biosciences, San Jose, Calif.), and analyzed using a flow cytometer (FACSCalibur or Accuri C6, BD Biosciences), which was equipped with 488-nm laser for excitation. Data was collected from the FL1 ($H_2DCFDA$, C11-BODIPY) or FL2 channel (MitoSOX). A minimum of 10,000 cells were analyzed per condition.

Cancer Cell Viability Measurements

Cell viability was typically assessed in 384-well format by Alamar Blue (Invitrogen) fluorescence (ex/em 530/590) measured on a Victor3 platereader (Perkin Elmer, Waltham, Mass.). In some experiments, Trypan Blue dye exclusion counting was performed using an automated cell counter (ViCell, Beckman-Coulter Inc., Brea, Calif.). Cell viability in test conditions is reported as a percentage relative to the negative control treatment.

shRNA Screening

An arrayed collection of 6,528 shRNA hairpins derived from The RNAi Consortium (TRC) collection targeting 1,087 genes, kindly provided by Vamsi Mootha and Joshua Baughman (MIT), was screened in 384-well plate format (Corning) using both Calu-1 and HT-1080 cells. ShRNAs targeting GFP and RFP, randomly distributed through each plate, served as negative controls. 400 cells per well were infected in duplicate for 48 hours with 2 µL shRNA-containing viral supernatant, selected for 24 hours in puromycin (1.5 µg/mL), then treated with DMSO, erastin (7.3 µM) or staurosporine (STS) (1 µM) for 24 hours. Cell viability was determined using Alamar Blue. For each hairpin within each treatment condition, a cell death rescue score was computed as the ratio of the average viability of the two replicates to the average viability of the within-plate negative controls. These scores were used to compare the effects between compounds. To identify genes required for ferroptosis, individual hairpins were scored as hits if they displayed an average death suppression ≥3 median average deviations from the median within-plate or screen-wide negative control values. 51 candidate genes were identified with the same two (or more) unique hairpins per gene called as hits in both the Calu-1 and HT-1080 screens. For each candidate gene, confirmation studies using RT-qPCR analysis of mRNA silencing was performed in HT-1080 cells using freshly prepared virus as described in more detail below.

[$^{14}C$]Cystine Uptake Assay 200,000 HT-1080 cells/well were seeded overnight in 6-well dishes (Corning). The next day, cells were washed twice in pre-warmed $Na^+$-free uptake buffer (137 mM choline chloride, 3 mM KCl, 1 mM $CaCl_2$, 1 mM $MgCl_2$, 5 mM D-glucose, 0.7 mM $K_2HPO_4$, 10 mM HEPES, pH 7.4), then incubated for 10 minutes at 37° C. in 1 mL of uptake buffer, to deplete cellular amino acids. At this point, in each well the buffer was replaced with 600 µL uptake buffer containing compound and 0.12 µCi (80-110 mCi/mmol) of L-[3,3'-$^{14}C$]-cystine (Perkin Elmer) and incubated for 3 minutes at 37° C. Cells were then washed three times with ice-cold uptake buffer and lysed in 500 µL 0.1 M NaOH. To this lysate was added 15 mL of scintillation fluid and radioactive counts per minute were obtained using a scintillation counter. All measurements were performed in triplicate for each condition.

Statistical Analyses

All statistical analyses were performed using Prism 5.0c (GraphPad Software Inc., La Jolla, Calif.).

Chemicals

Erastin was synthesized as described (Yagoda et al., 2007). RSL3 was obtained from Leadgen Laboratories (Orange, Conn.). Rapamycin was obtained from Cell Signaling Technologies (Danvers, Mass.), z-VAD-fmk was from BioMol (Enzo Life Sciences, Inc., Farmingdale, N.Y.), ALLN and E64D were from CalBiochem (Merck KGaA, Darmstadt, Germany), bafilomycin A1 and U0126 were from LC Laboratories (Woburn, Mass.), BAPTA-AM and Fura-2 were from Invitrogen. GKT137831 was the generous gift of GenKyoTex S.A. (Geneva, Switzerland). Unless otherwise indicated, all other compounds were from Sigma (St. Louis, Mo.).

Cell Lines and Media

The following engineered human foreskin fibroblasts were obtained from Robert Weinberg (Whitehead Institute): BJeH, BJeHLT, BJeLR, DRD. BJeH cells express human telomerase (hTERT), BJeHLT express hTERT plus the large and small T oncoproteins (LT, ST), BJeLR express hTERT, LT, ST and an oncogenic HRAS allele ($HRAS^{V12}$), DRD cells express an alternative suite of oncoproteins: hTERT, ST, dominant-negative p53, cyclin D1, and a mutant form of CDK4, along with $HRAS^{V12}$. MEFs ($Bax^{-/-}Bak^{-/-}$ and wild-type) were obtained from Craig Thompson (Sloan Kettering), 143B.TK-mtDNA-depleted rho zero ($\rho^0$) and matching parental $\rho^+$ cells were obtained from Eric Schon (Columbia University), TC32 and SK-ES-1 were obtained from Stephen Lessnick (Huntsman Cancer Institute, Salt Lake City). HT-1080, Calu-1, U2OS and 293-T cells were obtained from American Type Culture Collection.

BJ series cell lines were grown in DMEM High-Glucose media (Gibco, Invitrogen Corp., Carlsbad, Calif.) plus 20% M199 (Sigma) and 15% heat-inactivated fetal bovine serum (FBS). HT-1080 cells were grown in DMEM High-Glucose media (Gibco) supplemented with 10% FBS and 1% non-essential amino acids (Gibco). Calu-1 and U2OS cells were grown in McCoy's 5A media (Gibco) supplemented with 10% fetal bovine serum. SK-ES-1 cells were grown in McCoy's 5A supplemented with 1.5 mM L-glutamine+15% FBS. 293-T and TC32 cells were grown in DMEM High-Glucose supplemented with 10% FBS. When used for transfections to generate virus, 293-T cells were seeded in the above media lacking antibiotics. 293-T viral collection media contained 30% HyClone FBS. MEFs were grown in DMEM supplemented with 10% fetal calf serum. 143B cells were grown in DMEM High-Glucose supplemented with 10% FBS. 143B $\rho^0$ cells were grown in the above media supplemented with 100 µg/mL uridine. The rho zero status of the 143B $\rho^0$ cell lines was confirmed using RT-qPCR by showing little or no mRNA expression for 7 mtDNA-encoded transcripts in the $\rho^0$ cell lines. All cell lines were grown in humidified tissue culture incubators (Thermo Scientific) at 37° C. with 5% $CO_2$. Except where indicated, all medias were supplemented with penicillin and streptomycin (Gibco).

Light Microscopy

Phase contrast images were acquired using an AMG EVOS FL (Advanced Microscopy Group) microscope equipped with a 10× phase-contrast objective. Three independent fields were acquired for each experimental condition. Representative samples from one field of view are shown.

Transmission Electron Microscopy

BJeLR cells were plated at 100,000 cells/dish in 35 mm tissue culture dishes. After 12 hours, cells were treated with vehicle (DMSO; 10 hours), erastin (37 µM; 10 hours), staurosporine (750 nM; 8 hours), hydrogen peroxide (16 mM; 1 hour) or rapamycin (100 nM; 24 hours). Cells were fixed with 2.5% glutaraldehyde in 0.1 M Sorenson's buffer (0.1 M $H_2PO_4$, 0.1 M $HPO_4$ (pH 7.2)) for at least 1 hour, and then treated with 1% $0SO_4$ in 0.1 M Sorenson's buffer for 1 hour. Enblock staining used 1% tannic acid. After dehydration through an ethanol series, cells were embedded in Lx-112 (Ladd Research Industries, Williston, Vt.) and Embed-812 (Electron Microscopy Sciences, Hatfield, Pa.). Thin sections were cut on an MT-7000 ultramicrotome, stained with 1% uranyl acetate and 0.4% lead citrate, and examined under a Jeol JEM-1200 EXII electron microscope. Pictures were taken on an ORCA-HR digital camera (Hamamatsu Corp., Bridgewater, N.J.) at 5,000-50,000-fold magnification, and measurements were made using the AMT Image Capture Engine.

Measurement of ATP Levels

ATP levels were evaluated using the ApoSENSOR ATP Assay Kit (Biovision Inc., Milpitas, Calif.) according to the manufacturer's instructions. 2000 HT-1080 or BJeLR cells were seeded in 96-well white bottom plates (Falcon). Cells were treated 12 hours later with compound as above for the TEM. Prior to luminescence measurement, medium was removed and cells were lysed and incubated with ATP Monitoring Enzyme. Luminescence was measured using a Victor3 platereader equipped with an infrared emission filter every 30 seconds for 10 minutes. Typically the first reading was used for data analysis. Parallel cell culture treatments were performed in 96-well clear bottom plates and cell viability was determined using Alamar Blue. These values were used to normalize ATP levels to cell viability.

Modulatory Profiling of Small Molecule Inhibitors

The following small molecule inhibitors were tested in a ten-point, four-fold dilution series for their ability to prevent erastin-induced death in HT-1080, Calu-1 and BJ-eLR cells (high dose of dilution series in brackets): carbobenzyloxy-valyl-alanyl-aspartyl-[O-methyl]-fluoromethylketone (z-VAD-fmk, 184 µM), necrostatin-1 (Nec-1, 19.3 µM), cyclosporine A (CspA, 33.2 µM), N-Acetyl-Leu-Leu-Nle-CHO (ALLN, 40 µM), (2S,3S)-trans-epoxysuccinyl-L-leucylamido-3-methylbutane ethyl ester (E64d, 400 µM), bafilomycin A1 (Baf A1, 4 µM), 3-methyladenine (3-MA, 6.25 mM), chloroquine (Chq, 250 µM), deferoxamine (DFO, 400), 6-hydroxy-2,5,7,8-tetramethylchroman-2-carboxylic acid (trolox, 320 µM), 1,4-diamino-2,3-dicyano-1,4-bis (2-aminophenylthio)butadiene (U0126, 52.4 µM) and cycloheximide (5.6 µM). The day before the experiment, cells were seeded in black, 384-well clear bottom plates (Corning) at a density of 1,000 cells/well using a Beckman Biomek FX Workstation. All compounds (except 3-methyladenine and chloroquine, which were diluted in water) were diluted in DMSO at 250 times the final highest test concentration, and aliquoted across a 384-well plate (Greiner, Monroe, N.C.). A ten-point, 4-fold dilution series of each inhibitor in DMSO was made using a multichannel pipette. Replicates of this mother plate were stored at −20° C. On the day of the experiment, a fresh inhibitor plate was thawed and diluted 25-fold into DMEM in a 384 deep well 'daughter' plate (Greiner), using a Biomek FX. Medium was removed from cells and replaced with 36 µL medium containing DMSO (0.1%) or erastin (10 µM final concentration). Using the Biomek FX, 4 µL were then transferred from each inhibitor daughter plate into the DMSO-containing or erastin-containing assay plates. For 3-methyladenine and chloroquine, inhibitors were prepared fresh in media at 10-fold the final concentration in the presence of DMSO or 10 µM erastin. These solutions were manually pipetted onto cells in 384-well format. Assay plates were incubated at 37° C. for 24 hours. Viability was assessed using Alamar Blue.

Computation of Modulatory Effects

The modulatory effect ($M_e$) for drug-drug interactions was computed as follows. First, plate-based background correction was performed using Alamar Blue values from empty (cell-free) wells included on each plate. Next, within each experiment, 100% viability is determined as the average Alamar Blue score for cells treated with modulator=DMSO and lethal=DMSO, and all Alamar Blue values were scaled from 0 to 1 with the DMSO×DMSO condition=1. The individual effects of each modulator and lethal (e.g. in the presence of DMSO) at all tested doses were then ascertained. Using these data, the "expected" effect on viability ($B_{Exp}$) for each modulator (M)×lethal (L) combination were modeled using the Bliss formula for drug interactions (M+L−M*L). Next, $B_{Exp}$ was compared to the actual observed viability. For each informative drug-drug interaction (i.e. modulator="DFO", modulator concentration=100 µM, lethal=Erastin) the modulatory effect ($M_e$) was equivalent to the maximum observed deviation, positive or negative, from $B_{Exp}$. By default, $M_e$ in DMSO-treated cells is equal to 0. This formula was empirically determined to provide a useful measure of modulation that is robust to differences in the shapes of individual dose-response curves for different inhibitors and lethal molecules. $M_e$ values for each inhibitor-lethal drug combination were hierarchically clustered and plotted as a heatmap using the heatmaps.2 function of the gplots library in R.

Modulatory Profile of Lethal Small Molecules

The following lethal molecules were compared in a ten-point, two-fold dilution series modulatory profiling assay (high dose of dilution series in brackets): erastin (20 µM), RSL3 (5 µM), hydrogen peroxide ($H_2O_2$, 5 mM), artesunate (200 µM), phenylarsine oxide (PAO, 1 µM), taxol (0.5 µM), suberoylanilide hydroxamic acid (SAHA, 50 µM), trichostatin A (2.5 µM), doxorubicin (2 µM), fenretinide (50 µM), staurosporine (STS, 0.5 µM), brefeldin A (10 µM), β-lapachone (25 µM), bortezomib (5 µM), carbonyl cyanide m-chlorophenyl hydrazine (CCCP, 50 µM), 2-methoxyestradiol (2-ME, 50 µM), rotenone (2 µM), helenaline (50 µM), sulfasalazine (SAS, 1 mM) and phenethyl isothiocyanate (PEITC, 50 µM).

The comparative analysis of the lethal effects of various molecules was conducted as above for the inhibitors experiment with the following modifications. All lethal molecules were tested in a ten point, two-fold dilution series. Inhibitors were made in media at 1× final concentration. The growth media was removed from the plates, and 36 µL media+inhibitor (or DMSO) was added back to the plate+4 µL from the 10× lethal stock plate. Cell viability and modulatory effects ($M_e$) were computed as above, to obtain the maximum deviation from $B_{Exp}$ produced by each modulator across the different lethal small molecule concentrations.

Arrayed shRNA Screen: Data Analysis and Hit Selection.

ShRNA screening and follow-up studies identified 51 initial candidate suppressor genes, each represented by 2 hairpins common to both cell lines. These candidates were re-tested. For 50 of these genes, fresh virus (see below) was prepared for the top two scoring shRNA hairpins. The resistance in HT-1080 cells infected with these hairpins in response to up to 10 µM erastin was re-tested. In parallel, target knockdown was validated for each shRNA hairpin by RT-qPCR. From the initial set of suppressor genes, high confidence genes were selected using the following criteria: (1) the degree of death suppression was consistent across two independent replicates in the re-testing phase; (2) the level of death suppression was at least 50% of that observed in the sh263-VDAC3 positive control at the highest dose of erastin (10 µM); (3) at least one of two shRNA hairpins must reduce the level of mRNA<50% of control, and (4) an inverse correlation must exist between erastin resistance and mRNA levels (providing a strong measure of confidence in the on-target nature of the shRNAs used). Finally, whether each hairpin had been reported as independently validated was determined on The RNAi Consortium/Sigma website. By intersecting the results of these confirmatory analyses, a final set of six high confidence genes was determined.

Arrayed shRNA Screen: shRNA Confirmation

For all candidate suppressors, individual "hit" shRNA hairpin sequences were non-overlapping (e.g. targeting unique sequences within the mRNA) and were confirmed using the siRNA-Check tool available from In Silico Solutions (Fairfax, Va.). Individual shRNAs are identified by the 3 or 4 number Clone ID suffixes assigned to each mRNA target sequences by TRC.

New virus were produced to validate erastin resistance and perform downstream analyses of target knockdown and functional effects in a 6-well format as follows. On Day 1, 170,000 293-T cells were seeded in antibiotic-free media into each well of a 6-well dish. On Day 2, these cells were transfected (Fugene, Roche) with 450 ng of shRNA plasmid DNA, 400 ng of pDelta8.9 helper plasmid and 45 ng of pVSVg helper plasmid. On Day 3, the media was switched to viral collection media. Virus was harvested the following morning and evening of Day 4 and then a final time the next morning of Day 5. The collected media was pooled, spun at 2,000 rpm for 5 minutes and the virus-containing supernatant aliquoted and stored at −80° C. This protocol was used for the production of virus in all other small-scale shRNA experiments as well (i.e. FIGS. 7C and 7D).

Six-well dish infections were performed as follows. On Day 1, 30,000 HT-1080 cells were seeded per well. On day 2, cells were infected with 150 µL of viral supernatant and spin infected as for 384-well plates.

Genetic Screening Follow-up Experiments: Cell Line and Lethal Compound Specificity Analysis These experiments were performed for all cell lines. Lethal compound experiments were performed in parallel by first re-arraying by hand virus prepared as described above for all suppressor hairpins in a single 384 deep well viral "mother plate" (Corning), including 3 independent copies of the negative control and positive controls (sh-Control and sh263-VDAC3). Each hairpin was arrayed in a block of 6 wells (2 across×3 down). For each experiment, cells were seeded at a standard density of 400 cells/well on Day 1. On Day 2, the media was removed either by flicking, (for HT-1080 cells in the lethal compound analysis) or using a BioMek FX (for the cell line analysis), and then replaced with 38 µl media containing 1× polybrene (8 µg/ml) using the BioMek. 2 µl viral soup was then transferred from each well of the viral mother plate to each well of the assay plate and a spin infection was performed as described above. On Day 3 (for the analysis of cell lines) or Day 4 (for the analysis of lethal compounds), the media+virus was removed using the BioMek and replaced with media+1.5 µg/ml puromycin. Next, for both experiments, on Day 5, the media was again removed using the BioMek and replaced with media+lethal compound. On Day 6, Alamar Blue was added as described above and the signal was measured 6 hours later. This experiment was repeated twice with similar results and representative data from one experiment is shown. Data for the best hairpin as defined by mRNA silencing levels in HT-1080 cells is disclosed herein. Similar results were obtained with the second best hairpins.

Reverse Transcription-quantitative Polymerase Chain Reaction (RT-qPCR)

RNA was extracted using the Qiashredder and Qiagen RNeasy Mini kits (Qiagen) according to the manufacturer's protocol. 2 µg total RNA for each sample was used as input for each reverse transcription reaction, performed using the TaqMan RT kit (Applied Biosystems, Life Technologies Corp., Carlsbad, Calif.). Primer pairs were designed for target transcripts using Primer Express 2.0 (Applied Biosystems). Quantitative PCR reactions were performed using the Power SYBR Green PCR Master Mix (Applied Biosystems). Triplicate samples per condition were analyzed on an Applied Biosystems 7300 qPCR instrument using absolute quantification settings. Differences in mRNA levels compared to HPRT1 or ACTB internal reference control were computed between control and experimental conditions using the ΔΔCt method.

LOC Library Construction

The LOC (Lead Optimized Compound) library is composed of 9,517 compounds selected from a starting pool of 3,372,615 compounds available through a variety of commercial libraries (Asinex, Moscow, Russia; Life Chemicals, Burlington, ON, Canada; Enamine Ltd., Kiev, Ukraine; TimTec, Newark, Del.; InterBioScreen Ltd., Moscow, Russia; Chembridge Corp., San Diego, Calif.). The starting pool was generated in silico by downloading structure files for available compounds from all vendors. From this pool, the application of Lipinski's rules (Lipinski et al., 2001) and other relevant physicochemical descriptors consistent with drug-like candidates (molecular weight>235, number of rotatable bonds<5, topological polar surface area<70 Å$^2$, aqueous solubility>0.5 mM) reduced the total number of compounds to 58,786. The total number of compounds was further reduced to 45,395 by filtering out compounds containing nitro and nitroso groups, reactive moieties, ketones and aldehydes, imines, scaffolds unsuitable for further modification, organometallic compounds and thiols. From this set, the final collection was derived by eliminating multiple copies of highly similar compounds (Tanimoto coefficient). All computational analyses were performed using MOE2008.10 (Chemical Computing Group, Montreal, Canada) on a MacPro with 2×2.93 GHz Quad-Core Intel Xeon CPUs. At this point, 5 mg of each compound was obtained from their respective suppliers and dissolved in DMSO at a standard concentration of 4 mg/mL. Aliquots of each compound were then arrayed into individual wells of several 384 shallow well "mother" plates (Grenier) using a BioMek liquid handling robot and frozen at −80° C. until use.

LOC Library Screening

The LOC library was screened over the course of several days. 384-well glass bottom assay plates (Corning) were seeded with 1,000 HT-1080 cells/well the day before the experiment. The day of the experiment, LOC mother plates were thawed at room temperature for 1 hour and spun at 1000 rpm for 1 minute prior to use. Using a BioMek liquid handing robot, 2 μL of compound solution from each LOC library mother plate was transferred to a 384 deep well "daughter" plate (Grenier) containing 148 μL of cell culture media. The cell culture media in each assay plate was then removed by flicking and, using a BioMek FX, replaced with 36 μL of growth media containing erastin (5 μM final). To this was added 4 μL of the drug solution from the daughter plate, for a final screening concentration of 5.3 μg/mL for each LOC library compound. 4 wells containing DMSO alone (no erastin), 4 wells containing 100 μM DFO alone (no erastin), 4 wells containing erastin plus DMSO, and 4 wells containing erastin plus 100 μM DFO (positive control) were included as controls on each plate. Each drug daughter plate was aliquoted separately to duplicate assay plates. Plates were then spun briefly (1000 rpm, 5 seconds) and returned to the 37° C. tissue culture incubator. 24 hours later, cell viability was assessed by Alamar Blue as described above.

LOC Library Screen Hit Identification and Confirmation

Candidate hits from the LOC library screen were identified. First, values for each duplicate screening plate were averaged. Next, a growth rescue score consisting of the ratio of the viability of each LOC compound+erastin versus the DMSO+erastin treatment within each plate was computed. These plate-based growth rescue scores were rank ordered from highest to lowest. The top 336 ranked compounds, derived from the same LOC library plates used for screening, were then re-tested in HT-1080 cells in a 10-point, 2-fold dilution series against erastin (5 μM) as described above for the modulatory profiling experiments. For the top 50 most potent compound inhibitors of erastin-induced death identified in this experiment, fresh compound in powder form was re-ordered from the respective vendors, the powder was re-dissolved in DMSO as above, and the 10-point, 2-fold dilution series experiment in HT-1080 cells repeated. Fer-1 proved to be the most potent of the re-tested compounds in this experiment and was selected for more detailed study.

Western Blotting

Cells were trypsinized, pelleted, and washed once in PBS. Cells were lysed for 20 minutes in buffer containing: 50 mM HEPES pH 7.4, 40 mM NaCl, 2 mM EDTA, 0.5% Triton X-100, 1.5 mM sodium orthovanadate, 50 mM NaF, 10 mM sodium pyrophosphate, 10 mM sodium β-glycerophosphate, and protease inhibitor tablet (Roche, Nutley, N.J.). Unlysed cells and debris were pelleted for 10 minutes at 10,000 rpm in a benchtop microcentrifuge at 4° C., and the supernatant was removed and mixed with 5×SDS loading buffer. Samples were separated by SDS-polyacrylamide gel electrophoresis. Western transfer was performed using the iBlot system (Invitrogen). Membrane was blocked for 1 hour in Licor Odyssey Blocking Buffer (LI-COR) and incubated in primary antibody overnight at 4° C. Following three 5-minute washes in Tris-buffered saline (pH 7.4) with 1% Tween-20 (TBS-T), membrane was incubated with secondary antibodies for 45 minutes in the dark. The membrane was washed again in TBST for three 5-minute washes with protection from light and scanned using the Odyssey Imaging System (LI-COR). Antibodies used were as follows: rabbit anti-phospho p42/44 MAPK (Cell Signaling Technology, #9101) and rabbit anti-p42/44 MAPK (Cell Signaling Technology, #9102). The secondary antibody was IR dye 800CW goat anti-rabbit IgG (LI-COR).

2,2-diphenyl-1-picrylhydrazyl (DPPH) Assay

The stable radical DPPH (Blois, 1958) was dissolved in methanol to a final working concentration of 0.05 mM. This was prepared as follows. First, a 100× stock concentration (5 mM) was prepared by dissolving 3.9 mg DPPH in 2 mL methanol. Then, for 25 mL of 0.05 mM final working solution, 250 μL of the 5 mM solution was added to 24.75 mL of methanol. 1 mL of DPPH solution was added to a small volume (<5 μL) each test compound dissolved in DMSO. The final concentration of each test compound was 0.05 mM. Samples were inverted several times and allowed to incubate at room temperature for 30 minutes. Samples were then aliquoted to white 96-well solid-bottom dishes (Corning) and absorbance at 517 nm was recorded using a TECAN M200 plate reader. All values were normalized to background (methanol only). The experiment was repeated three times and the data was averaged.

Analysis of Cell Death in Rat Brain Slices: Organotypic Hippocampal Slice Cultures (OHSCs)

OHSCs were cultured as previously described (Morrison et al., 2002) with approval from Columbia University's Institutional Animal Care and Use Committee (IACUC). Briefly, Sprague Dawley rat pups (P8-P10) were rapidly decapitated, and the hippocampus placed in ice-cold Gey's balanced salt solution (Sigma). 400 μm thick sections were cut using a McIlwain tissue chopper and immediately plated on Millicell cell culture inserts (Millipore, Billerica, Mass.) in Neurobasal (Invitrogen) media supplemented with B27 (1×, Invitrogen), GlutaMAX (1 mM, Invitrogen), and D-glucose (4.5 mg/mL, Sigma) at 37° C. and 5% $CO_2$. After 2 days in vitro (DIV), the media was changed to medium containing serum comprised of 50% DMEM (Sigma), 25% heat-inactivated horse serum (Sigma), 25% Hank's balanced salt solution (Sigma), GlutaMAX (1 mM, Invitrogen), and D-glucose (4.5 mg/mL, Sigma). Medium was changed every 2-3 days.

Analysis of Cell Death in Rat Brain Slices: Excitotoxic Injury

After 10-14 DIV, OBSCs were exposed to an excitotoxic injury consisting of a 3 hour exposure to 5 mM L-glutamate in SFM (Morrison et al., 2002). Only healthy OHSCs defined as those with less than 5% cell death in all regions of the hippocampus (DG, CA3, CA1) pre-injury were used for experiments. After the 3 hour exposure, the cultures were placed in fresh serum free media (SFM) containing 75% DMEM, 25% Hank's balanced salt solution, GlutaMAX (1 mM), D-glucose (4.5 mg/mL) until cell death was quantified at 24 hours. If drugs were added, they were added at the same time as glutamate.

Analysis of Cell Death in Rat Brain Slices: Cell Death Assessment

Quantification of cell death has been described previously (Cater et al., 2007; Morrison et al., 2002). Brightfield images of the hippocampal cultures were taken before injury for identification of regions of interest (ROI) including the dentate gyrus (DG), CA3 and CA1. Propidium iodide (PI, Invitrogen) was used as a fluorescent signal for cell death, and images were taken before the induction of injury and 24 hours following injury. For PI imaging, the cultures were transferred to SFM supplemented with 5 μg/mL PI. After a 30 minute incubation, brightfield and PI images were acquired. All images were captured on an Olympus IX-80 fluorescent microscope fitted with a 175 W Xenon Arc lamp (Perkin Elmer), CoolSNAP ES camera (Photometrics, Tucson, Ariz.), and standard rhodamine optics (excitation 556-

580 nm; emission 590-630 nm; PI exposure 2 seconds, brightfield exposure 3 milliseconds). Metamorph image analysis software was used to determine the ROI in the brightfield image, and this ROI was transferred to the PI image taken before and 24 hours after injury. Percentage cell death was expressed as the number of pixels in the ROI above a threshold in the PI fluorescent image divided by the total number of pixels in the ROI.

Brain Slice Assay for HD

250 μm corticostriatal brain slices were prepared from postnatal day 10 CD Sprague-Dawley rat pups (Charles River) as previously described (Hoffstrom et al., 2010). Brain slice explants were placed in interface culture in 6-well plates using culture medium containing 15% heat-inactivated horse serum, 10 mM KCl, 10 mM HEPES, 100 U/ml penicillin/streptomycin, 1 mM MEM sodium pyruvate, and 1 mM L-glutamine in Neurobasal A (Invitrogen) and maintained in humidified incubators under 5% $CO_2$ at 32 deg. C. A custom-modified biolistic device (Helios Gene Gun; Bio-Rad) was used to transfect the brain slices with a human htt exon-1 expression construct containing a 73 CAG repeat ("HttN90Q73") in the gWiz backbone (Genlantis) together with a YFP expression construct to visualize transfected neurons. Control brain slices were transfected with gWiz blank vector and YFP at the equivalent DNA amounts. After 4 days of incubation, MSNs were identified by their location within the striatum and by their characteristic dendritic morphology and scored as healthy if expressing bright and continuous YFP labeling throughout, normal-sized cell bodies, and >2 primary dendrites >2 cell bodies long, as previously described[21]. Data were expressed as mean numbers of healthy MSNs per striatal region in each brain slice, with statistical significance tested by ANOVA followed by Dunnett's post hoc comparison test at the 0.05 confidence level. Fer-1 was added to the culture medium at the time of brain slice preparation; positive control brain slices were treated with a combination of the adenosine receptor 2A modulator KW-6002 (50 μM) and the JNK inhibitor SP600125 (30 μM). Final DMSO concentration of 0.1% for all conditions.

Brain Slice Assay for HD Fer-1 Analogs Protected Developing Oligodendrocytes from Cystine Deprivation Induced Cell Death Primary pre-oligodendrocytes cultures were prepared from the forebrains of P2 Sprague Dawley (Charles River Laboratory) rat pups using a differential detachment method. Forebrains free of meninges were dissociated with Hanks' Balanced Salt Solution containing 0.01% trypsin and 10 μg/ml DNase, and triturated with DMEM containing 10% heat-inactivated fetal bovine serum and 100 U/ml penicillin and 100 μg/ml streptomycin. Dissociated cells were plated onto poly-D-lysine-coated 75 cm² flasks and fed cells every other day for 10-17 days. On day 10 or 17, following 1 hour pre-shake at 200 rpm 37° C. to remove microglia, the flasks were shaken overnight to separate pre-oligodendrocytes from astrocyte layer. The cell suspension was passed through a 20 μm filter and plated onto uncoated (bacteriological) petri dishes for 1 hour in incubator to remove residual microglia/astrocytes. Cell suspension was plated onto poly-D,L-ornithine-coated plates with DMEM, 1×ITS (Life Technologies), 2 mM L-glutamine, 1 mM sodium pyruvate, 0.5% FBS and 0.05% gentamicin (Sigma), 10 ng/ml PDGF and 10 ng/ml FGF (Peprotech), with full medium change the next day and half medium change every other day. At day 8, cells were washed twice with cystine deprivation medium, treated with Fer-1 and analogs (stock 1 mM in DMSO) in cystine deprivation medium plus PDGF and FGF (treatment medium) for 24 hrs. Cells were treated with treatment medium plus 100 μM cystine as positive control; and cells were treated with treatment medium as negative control. Cells in each well, received same amount of DMSO as a vehicle. After 24 hours, cells were assayed with Alamar Blue (Treck Diagnostics) by full medium change with 1×AlamarBlue in Earle's Balance Salt Solution for 2 hours at 37° C. and 5% $CO_2$. Fluorescence was assayed in each well using FluoroCount Plate Reader (Packard), with Packard Plate Reader Version 3.0, and 530 nm excitation, and 590 nm emission filters.

Studies of Isolated Mouse Proximal Tubules

Tubule preparation: 8-12 week old C57/BL6 female mice were euthanized with isoflurane. Kidneys were removed and immediately injected intraparenchymally with a cold 95% $O_2$/5% $CO_2$-gassed solution consisting of 115 mM NaCl, 2.1 mM KCl, 25 mM $NaHCO_3$, 1.2 mM $KH_2PO_4$, 2.5 mM $CaCl_2$, 1.2 mM $MgCl_2$, 1.2 mM $MgSO_4$, 25 mM mannitol, 2.5 mg/ml fatty acid free bovine serum albumin, 5 mM glucose, 4 mM sodium lactate, 1 mM alanine, and 1 mM sodium butyrate (Solution A) with the addition of 1 mg/ml collagenase (Type I, Worthington Biochemical Corp., Freehold). The cortices were then dissected and minced on an ice cold tile, then resuspended in additional Solution A for 8-10 min. of digestion at 37° C. followed by enrichment of proximal tubules using centrifugation on self-forming Percoll gradients as previously described for rabbit tubules.

Experimental procedures for isolated tubules: Tubules were suspended at 1.5-2.0 mg tubule protein/ml in a 95% air/5% $CO_2$-gassed medium containing (in mM) 110 NaCl, 2.6 KCl, 25 $NaHCO_3$, 2.4 $KH_2PO_4$, 1.25 $CaCl_2$, 1.2 $MgCl_2$, 1.2 $MgSO_4$, 5 glucose, 4 sodium lactate, 0.3 alanine, 5 sodium butyrate, 2 glycine, and 1.0 mg/ml bovine gelatin (75 bloom) (Solution B). After precincubation for 15 min. at 37° C., then were then resuspended in fresh Solution B containing 2 mM heptanoic acid instead of sodium butyrate along with experimental compounds.

Oncogenic-RAS-selective Lethal Assay

Analysis of oncogenic-RAS-selective lethality in BJeH, BJeHLT, BJeLR and DRD cells was performed as described previously (Yang and Stockwell, 2008).

siRNA Gene Silencing

All siRNAs were obtained from Qiagen. 50,000 HT-1080 cells were seeded in antibiotic-free HT-1080 media into each well of a 6-well tissue culture dish (Corning) the day before the start of the experiment. The next day, cells were transfected with 2 nM of siRNAs (final concentration/well) using Lipofectamine RNAiMAX (Invitrogen) according to the manufacturer's protocols. The media was replaced with fresh antibiotic-containing HT-1080 media the following day. Parallel cultures were assayed for gene expression after 48 hours using RT-qPCR and for cell viability in response to drug treatment at 72 hours post-transfection.

Plasmids and Transfection pMaxGFP plasmid was from Amaxa (Lonza Group Ltd., Basel, Switzerland). pCMV6-SLC7A11-DDK was from Origene Technologies (Rockville, Md.). 50,000 HT-1080 cells were seeded in 6-well dishes (Corning) the day before the experiment in regular HT-1080 media. The next day, cells were transfected with 0.5 μg plasmid DNA/well using Lipofectamine LTX (Invitrogen) according to the manufacturer's protocol. 72 hours post-transfection, cell viability was assessed by microscopy in response to erastin and sulfasalazine.

Identification of SLC7A5 as an Erastin Target in BJeH and BJeLR Cells

Affinity chromatography and mass spectrometry were used to identify proteins that bound an active (lethal) erastin analog (erastin-A6) and an inactive control (erastin-B2) in lysates from oncogenic HRAS-mutant BJeLR cells and HRAS-wild-type BJeH cells (2 independent experimental replicates for each cell line) (Yagoda et al., 2007). Previously, the analyses on targets bound by active erastin-A6 were done in BJeLR versus BJeH cells, on the assumption that such targets were most likely to mediate oncogenic-RAS-selective lethality (Yagoda et al., 2007). However, given that erastin was lethal to various cells, including some that lack mutant HRAS, the data were re-analyzed in order to look for targets bound by active erastin-A6 (but not inactive erastin-B2) in both cells types, as follows. First the two experimental replicates were merged on the basis of protein reference IDs to identify high confidence targets for each erastin analog in both cell lines. Any proteins also bound by inactive erastin-B2 (i.e. non-specific interactions) were then eliminated from the erastin-A6 target lists. Next, the lists of proteins uniquely bound by active erastin-A6 in BJeH cells (gi|4506675 [RPN1], gi|4505773 [PHB], gi|1174469 [STT3A], gi|14017819 [LRRIQ1], gi|12643412 [SLC7A5]) and BJeLR cells (gi|1172554 [VDAC2], gi|19923753 [SLC16A1], gi|11281610 [TECR], gi|23308572 [MBOAT7], gi|4759086 [SEC22B], gi|7448310 [TSPO], gi|4507943 [XPO1], gi|21361181 [ATP1A1], gi|29029559 [CSEL1], gi|23308577 [PHGDH], gi|1362789 [PRKDC], gi|12643412 [SLC7A5]) were compared. This new analysis identified SLC7A5 as the lone protein bound by active erastin-A6 in both cell types. Of note, VDAC2 was identified in both experimental replicates for erastin-A6-treated BJeLR cells, but annotated with two different identifiers (gi|4507881 and gi|1172554). Also of note, SLC3A2 was identified in one replicate of erastin-A6-treated BJeLR cells.

Analysis of Metabolic Profiling Data for Erastin-treated Jurkat Cells

Figure 6:
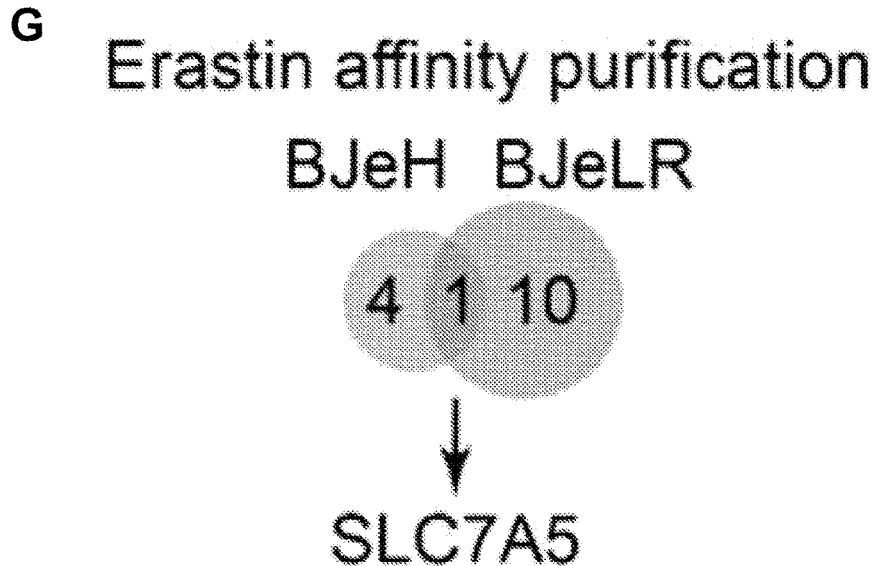
FIGS. 6A-6I show that erastin inhibits the activity of system $x_c^-$.
Figure 6:
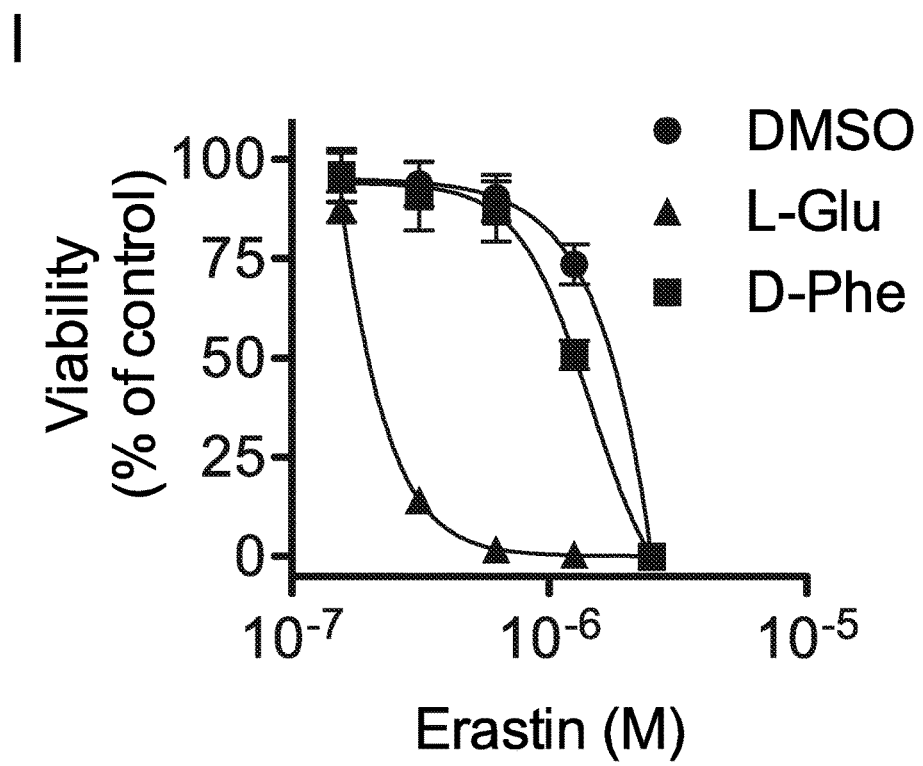

Ramanathan and Schreiber isolated a total of 123 metabolites from Jurkat T cells treated with erastin (1 µM, 25 minutes) or vehicle control (Ramanathan and Schreiber, 2009). These authors previously reported on a subset (11/123) of the metabolites that are specifically related to mitochondrial metabolism and glycolytic pathway function (FIG. 6, (Ramanathan and Schreiber, 2009)). The complete (123 metabolite) normalized dataset was obtained, and the data were ranked by the observed significance (P values) of the change in abundance between erastin-treated and control samples. The substrate specificity of system L has previously been established (Kanai and Endou, 2003).

Software

Flow cytometry data was analyzed using FloJo (9.3.2, Tree Star, Inc., Ashland, Oreg.). Chemical structures were drawn using ChemDraw Ultra (Cambridgesoft, Cambridge, Mass.). Computational determination of log P (S log P function) was performed using MOE 2010.10 (Chemical Computing Group, Montreal, Calif.). Viability data was analyzed using Excel (Microsoft Corp., Seattle, Oreg.). Summary data and heatmaps were generated using R. Dose response curves were computed by 4-parameter logistic regression in Prism 5.0c (GraphPad Software). Images were manipulated using Photoshop CS4 and Illustrator CS4 (Adobe, San Jose, Calif.).

Example 2

Synthesis of Ferrostatin-1 Analogs

Chemicals:

Solvents, inorganic salts, and organic reagents were purchased from commercial sources such as Sigma and Fisher and used without further purification unless otherwise noted. Erastin was dissolved in DMSO to a final concentration of 73.1 mM and stored in aliquots at −20° C.

Chromatography:

Merck pre-coated 0.25 mm silica plates containing a 254 nm fluorescence indicator were used for analytical thin-layer chromatography. Flash chromatography was performed on 230-400 mesh silica (SiliaFlash® P60) from Silicycle.

Spectroscopy:

$^1$H, $^{13}$C and $^{19}$F NMR spectra were obtained on a Bruker DPX 400 MHz spectrometer. HRMS spectra were taken on double focusing sector type mass spectrometer HX-110A. Maker JEOL Ltd. Tokyo Japan (resolution of 10,000 and 10 KV accel. Volt. Ionization method; FAB (Fast Atom Bombardment) used Xe 3Kv energy. Used Matrix, NBA (m-Nitro benzyl alcohol)).

General Procedure A (ArS$_N$2 Reaction) (Beaulieu et al. 2003)

To ethyl 4-chloro-3-nitrobenzoate (1 equiv., 300 mg, 1.3 mmol) in dry DMSO (5 mL) was added K$_2$CO$_3$ (2 equiv., 360 mg, 1.739 mmol) and 1-adamantylamine (1.2 equiv., 238 mg, 1.572 mmol). The mixture was stirred for 17 hours at 60° C. The solution was poured into water and the organic layer was extracted three times with ethyl acetate. After drying with anhydrous magnesium sulfate the solvents were removed under vacuum. The residue was purified by flash-column chromatography on silica gel to provide the desired ethyl 4-(adamanthyl-amino)-3-nitrobenzoate derivatives (Scheme 3; Scheme 4, SRS-16-79, R$_a$=tert-butyl, MW=372).

General Procedure B (Hydrogenolysis)

The ethyl 4-(adamanthyl-amino)-3-nitrobenzoates (130 mg, 0.445 mmol) were dissolved in MeOH (10 mL) and hydrogenated (H$_2$ gas) over 10% Pd(OH)$_2$ on charcoal (90 mg) for 17 hours at room temperature. The solution was filtered through a pad of celite and volatiles were removed under vacuum. The residue was purified by flash-column chromatography on silica gel to provide the desired Ferrostatin-1 analogs.

General Procedure C (Reductive Amination Reaction) (Abdel-Magid et al., 1996)

Method I: ethyl 3-amino-4-(cyclohexylamino)benzoate (Fer-1) (100 mg, 0.382 mmol, 1 equiv) and benzaldehyde (39 µL, 0.382 mmol, 1 equiv) were heated in DCE for 1 hour at 80° C. in the presence of molecular sieve (4 Å) then the mixture was cooled down to room temperature before addition of the NaBH(OAc)$_3$ in small portions over 3 hours. The reaction mixture was stirred at room temperature under a nitrogen atmosphere for 17 hours. The reaction mixture was quenched with aqueous saturated NaHCO$_3$, and the product was extracted with EtOAc. The EtOAc extract was dried (MgSO$_4$), and the solvent was evaporated. The residue was purified by flash-column chromatography on silica gel to provide the desired ethyl 3-(benzylamino)-4-(cyclohexylamino)benzoate (SRS15-23, Scheme 3).

Method II: To ethyl 3-amino-4-(cyclohexylamino)benzoate (Fer-1) (100 mg, 0.382 mmol, 1 equiv) and benzaldehyde (39 µL, 0.382 mmol, 1 equiv) in DCE was added NaBH(OAc)$_3$ (129.5 mg, 0.611 mmol, 1.6 equiv). The reaction mixture was treated in the same way as in method I.

General Procedure D (Alkylation Reaction)

A representative example is the methylation of the SRS15-24 using 4-(bromomethyl)pyridine (Scheme 1). To the ethyl 3-amino-4-(cyclooctylamino)benzoate (SRS15-18; 30 mg, 0.095 mmol) in THF (1 mL), 4-(bromomethyl) pyridine hydrogen bromide salt (24 mg, 0.095 mmol) and DIPEA (50 μL, 0.285 mmol) were added. The mixture was stirred at 40° C. for 17 hours then poured in water. The organic layer was extracted with EtOAc then dried under $MgSO_4$, and the solvent was evaporated. The residue was purified by flash-column chromatography on silica gel to provide the desired ethyl 4-(adamanthylamino)-3-(pyridin-4-ylmethylamino)benzoate (SRS15-24).

General Procedure E (Imine Formation)

A representative example is the condensation reaction between SRS15-67 and pyrimidine-5-carbaldehyde in ethanol in the presence of a catalytic amount of HCl (Scheme 3). To the ethyl 3-amino-4-(adamantylamino)benzoate (SRS15-67; 100 mg, 0.318 mmol) in ethanol (4 mL), drops of HCl (10 μL) were added. The mixture was stirred at 80° C. for 4 hours. The solvent was evaporated. The residue was purified by flash-column chromatography on silica gel to provide the desired (Z)-ethyl 4-(adamantylamino)-3-(pyrimidin-5-ylm-ethyleneamino)benzoate (SRS15-72).

General Procedure F (Ester Formation)

A representative example is the esterification of 4-chloro-3-nitrobenzoic acid using isopropanol or tert-butanol in dichloromethane in the presence of N,N'-Dicyclohexylcarbodiimide (DCC) and 4-dimethylaminopyridine (DMAP) (Scheme 4). To the 4-chloro-3-nitrobenzoic acid in dichloromethane was added 4-dimethylaminopyridine and isopropanol. The N,N'-Dicyclohexylcarbodiimide (DCC) was added, at 0° C., and the mixture was stirred for 17 hours at room temperature. The precipitate was filtered out under celite and the organic layer was concentrated under vacuum. The residue was purified by flash-column chromatography on silica gel to provide the desired ester (Scheme 4).

Scheme 1. Synthesis of Ferrostation analogs SRS15-18, SRS15-23, SRS15-24, SRS15-25.

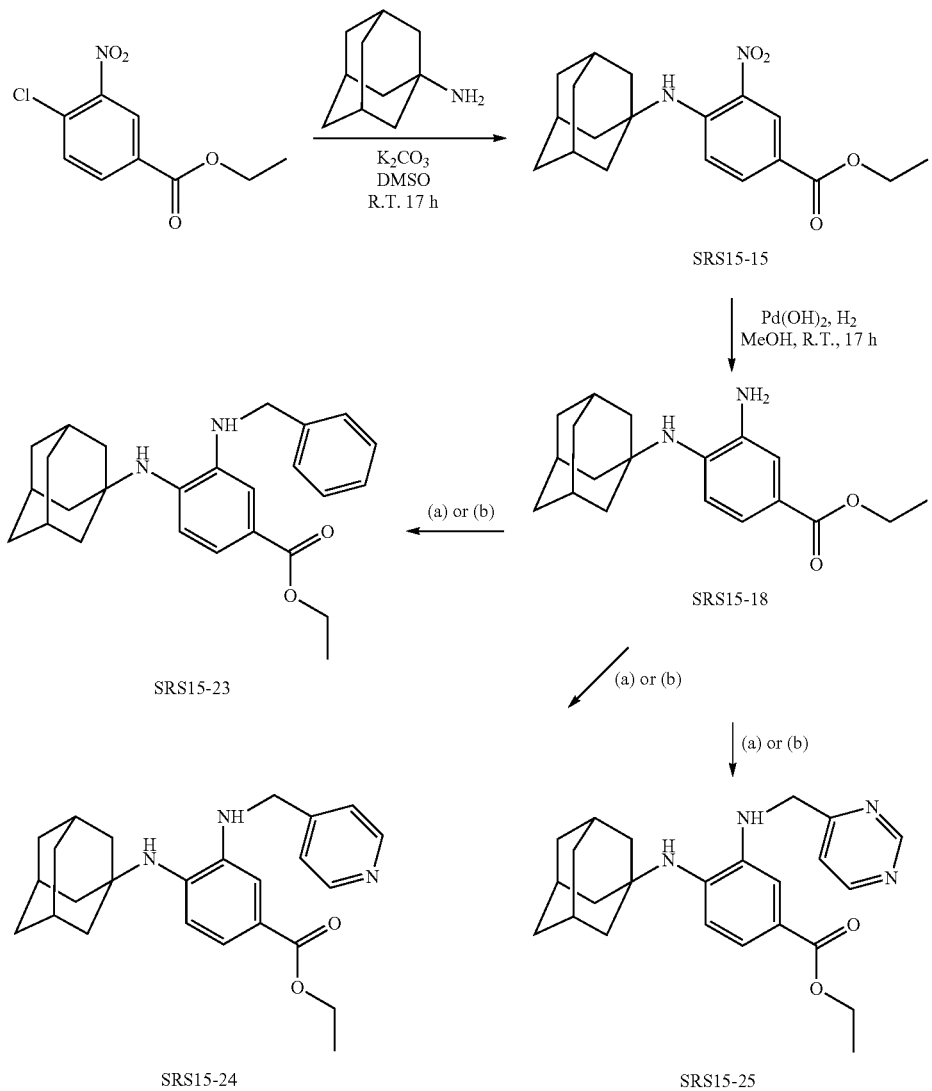

(a) alkylation reaction: arylhalide, DIPEA, THF, 60° C., 17 h. (b) reductive amination reaction: aryhaldehyde, NaBH(OAc)₃, molecular sieve (4), DCE, R.T. to 80° C., 17 h.

Synthesis of ethyl 3-amino-4-(1-adamantylamino)benzoate (SRS15-18. Scheme 1)

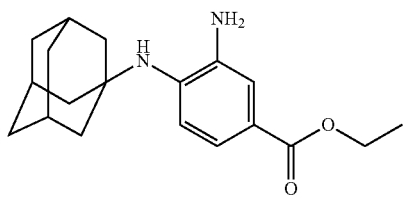
SRS15-18

Following the above general procedure A and B and starting from the commercially available ethyl 4-chloro-3-nitrobenzoate, the crude reaction mixture was purified by column chromatography (dichloromethane: methanol=40:1) to provide the desired ethyl 3-amino-4-(1-adamantylamino)-benzoate (SRS15-18, Scheme 1) (649 mg, 2.067 mmol, 95% (2 steps)). $^1$H NMR (500 MHz, CDCl$_3$) δ 7.52 (d, J=8.1 Hz, 1H), 7.43 (s, 1H), 6.93 (d, J=8.1 Hz, 1H), 4.34-4.27 (m, 2H), 2.15-1.72 (m, 15H), 1.36 (t, J=6.6 Hz, 3H); LC/MS (APCI+, M+1) 315.36.

Synthesis of ethyl 3-(benzylamino)-4-(1-adamantylamino)benzoate (SRS15-23. Scheme 1)

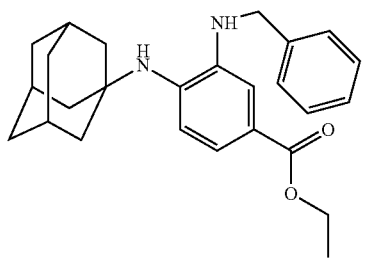
SRS15-23

Following the above general procedure C or D the crude reaction mixture was purified by column chromatography (dichloromethane: methanol=100:1) to provide the desired ethyl 3-(benzylamino)-4-(1-adamantylamino)benzoate (SRS15-23, Scheme 1) (26 mg, 0.064 mmol, 68%). $^1$H NMR (400 MHz, CDCl$_3$) δ 7.54 (dd, J=8.1, 1.5 Hz, 1H), 7.49-7.27 (m, 7H), 6.98 (dd, J=11.3, 4.7 Hz, 1H), 4.37-4.28 (m, 4H), 3.69 (s, 1H), 2.16 (s, 3H), 1.98 (s, 6H), 1.72 (s, 6H), 1.38 (ddd, J=7.1, 5.8, 1.6 Hz, 3H); LC/MS (APCI+, M+1) 405.36.

Synthesis of ethyl 4-(1-adamantylamino)-3-((pyridin-4-ylmethyl)amino)-benzoate (SRS15-24. Scheme 1)

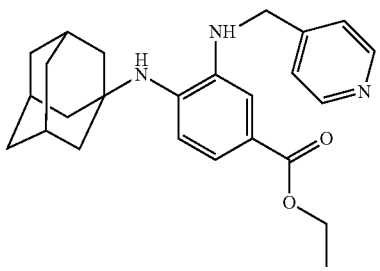
SRS15-24

Following the above general procedure C or D the crude reaction mixture was purified by column chromatography (dichloromethane: methanol=40:1) to provide the desired ethyl 4-(1-adamantylamino)-3-((pyridin-4-ylmethyl)amino)-benzoate (SRS15-24, Scheme 1) (27 mg, 0.066 mmol, 70%). $^1$H NMR (400 MHz, CDCl$_3$) δ 8.61 (s, 2H), 7.53 (d, J=8.2 Hz, 1H), 7.38-7.26 (m, 4H), 6.99 (d, J=8.3 Hz, 1H), 4.34 (dd, J=15.7, 8.6 Hz, 4H), 3.89 (s, 1H), 2.17-1.38 (m, 15H), 1.36 (t, J=7.1 Hz, 4H); LC/MS (APCI+, M+1) 406.36.

Synthesis of ethyl 4-(1-adamantylamino)-3-(pyrimidin-5-ylmethylamino)-benzoate (SRS15-25. Scheme 1)

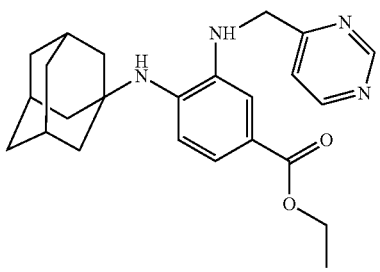
SRS15-25

Following the above general procedure C or D the crude reaction mixture was purified by column chromatography (dichloromethane: methanol=40:1) to provide the desired ethyl 4-(1-adamantylamino)-3-(pyrimidin-5-ylmethylamino)-benzoate (SRS15-25, Scheme 1) (23 mg, 0.056 mmol, 54%). $^1$H NMR (400 MHz, CDCl$_3$) δ 9.24 (s, 1H), 8.71 (t, J=5.0 Hz, 1H), 7.53 (d, J=8.3 Hz, 1H), 7.37 (d, J=4.9 Hz, 1H), 7.31 (s, 1H), 7.00 (d, J=8.4 Hz, 1H), 4.47 (s, 2H), 4.33 (dd, J=9.6, 4.5 Hz, 2H), 2.17-1.40 (m, 15H), 1.36 (t, J=7.1 Hz, 3H); LC/MS (APCI+, M+1) 406.36.

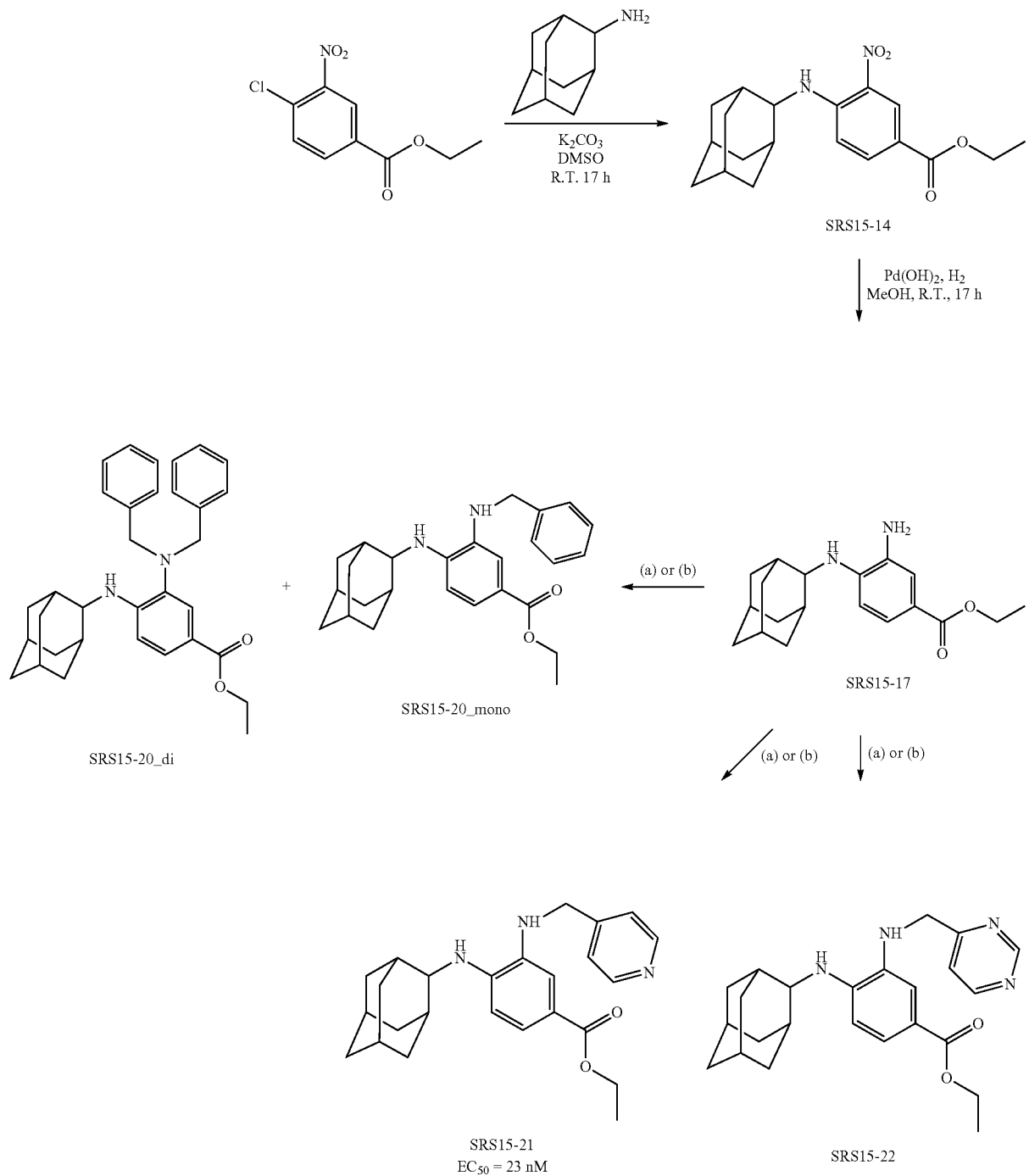
Scheme 2. Synthesis of Ferrostation analogs SRS15-17, SRS15-20, SRS15-21, SRS15-22.
(a) alkylation reaction: arylhalide, DIPEA, THF, 60° C., 17 hours. (b) reductive amination reaction: aryhaldehyde, NaBH(OAc)₃, molecular sieve (4Å), DCE, room temperature to 80° C., 17 hours.

Synthesis of ethyl 3-amino-4-(2-adamantylamino)benzoate (SRS15-17. Scheme 2)

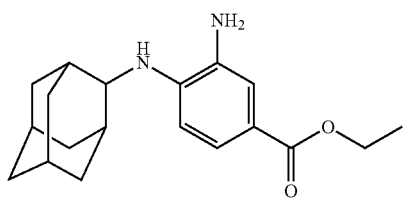

SRS15-17

Following the above general procedure A and B and starting from the commercially available ethyl 4-chloro-3-nitrobenzoate (Scheme 2), the crude reaction mixture was purified by column chromatography (dichloromethane:methanol=40:1) to provide the desired ethyl 3-amino-4-(2-adamantylamino)-benzoate (SRS15-17, Scheme 2) (624 mg, 1.98 mmol, 91% (2 steps)). $^1$H NMR (500 MHz, CDCl$_3$) δ 7.60 (s, 1H), 7.45 (s, 1H), 6.57 (s, 1H), 4.86 (s, 1H), 4.34 (d, J=5.4 Hz, 2H), 3.83 (s, 1H), 3.65 (s, 1H), 3.29 (s, 1H), 2.04-1.60 (m, 14H), 1.38 (d, J=3.8 Hz, 3H); LC/MS (APCI+, M+1) 315.36.

Synthesis of ethyl 3-(benzylamino)-4-(2-adamantylamino)benzoate (SRS15-20 mono. Scheme 2)

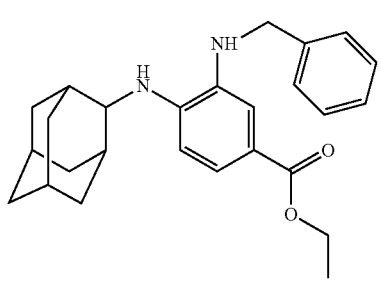

SRS15-20_mono

Following the above general alkylation reaction (procedure C) the crude reaction mixture was purified by column chromatography (dichloromethane: methanol=100:1) to provide the desired ethyl 3-(benzylamino)-4-(2 adamantylamino)-benzoate (SRS15-20_mono, Scheme 2) (19 mg, 0.047 mmol, 50%) and the dialkylation compound, the ethyl 3-(dibenzylamino)-4-(2-adamantylamino)-benzoate, (SRS15-20_di, Scheme 2) (9 mg, 0.018 mmol, 19%). $^1$H NMR (400 MHz, CDCl$_3$) δ 7.68-7.61 (m, 1H), 7.52 (d, J=1.7 Hz, 1H), 7.49-7.25 (m, 5H), 6.69-6.52 (m, 1H), 4.53 (s, 1H), 4.40-4.29 (m, 4H), 3.67 (s, 1H), 3.23 (s, 1H), 2.09 (s, 2H), 1.99-1.86 (m, 8H), 1.80 (s, 2H), 1.66-1.58 (m, 2H), 1.41-1.36 (m, 3H); LC/MS (APCI+, M+1) 405.36.

Synthesis of ethyl 3-(dibenzylamino)-4-(2-adamantylamino)benzoate (SRS15-20 di. Scheme 2)

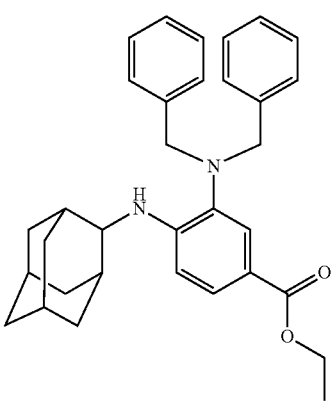

SRS15-20_di $^1$H NMR (400 MHz, CDCl$_3$) δ 7.80 (s, 1H), 7.72 (d, J=8.5 Hz, 1H), 7.28 (dd, J=9.0, 1.4 Hz, 10H), 6.46 (d, J=8.6 Hz, 1H), 5.99 (d, J=7.0 Hz, 1H), 4.38-4.28 (m, 2H), 4.06 (s, 4H), 3.54 (s, 1H), 2.00-1.50 (m, 14H), 1.39 (t, J=7.1 Hz, 3H); LC/MS (APCI+, M+1) 495.36.

Synthesis of ethyl 4-(2-adamantylamino)-3-((pyridin-4-ylmethyl)amino)-benzoate (SRS15-21. Scheme 2)

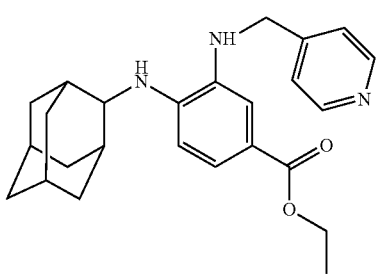

SRS15-21

Following the above general procedure C or D the crude reaction mixture was purified by column chromatography (dichloromethane: methanol=40:1) to provide the desired ethyl 4-(2-adamantylamino)-3-((pyridin-4-ylmethyl) amino)-benzoate (SRS15-21, Scheme 2) (25 mg, 0.061 mmol, 65%). $^1$H NMR (400 MHz, CDCl$_3$) δ 8.62 (s, 2H), 7.64 (d, J=8.2 Hz, 1H), 7.46-7.31 (m, 3H), 6.63 (d, J=8.4 Hz, 1H), 4.41 (s, 2H), 4.35-4.25 (m, 2H), 3.68 (s, 1H), 2.09 (s, 2H), 1.94 (d, J=15.1 Hz, 8H), 1.81 (s, 2H), 1.72-1.64 (m, 2H), 1.36 (t, J=7.1 Hz, 3H); LC/MS (APCI+, M+1) 406.26.

Synthesis of ethyl 4-(2-adamantylamino)-3-(pyrimidin-5-ylmethylamino)-benzoate (SRS15-22. Scheme 2)

Synthesis of ethyl 4-(adamantylamino)-3-(pyrimidin-5-ylmethyleneamino)benzoate (SRS15-72, Scheme 2)

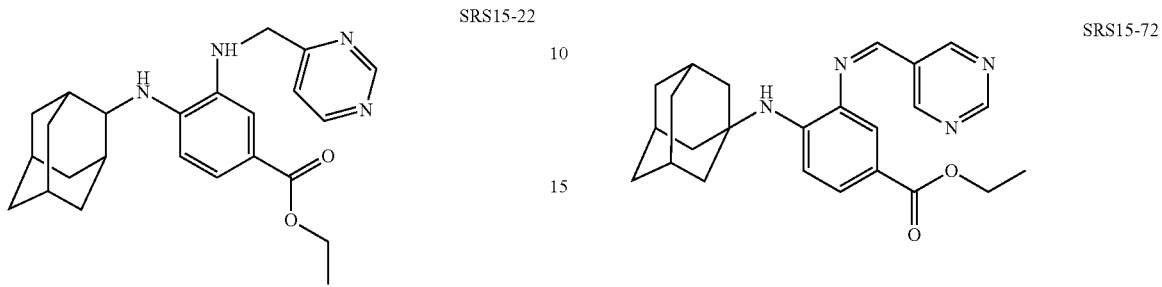

Following the above general procedure C or D the crude reaction mixture was purified by column chromatography (dichloromethane: methanol=40:1) to provide the desired ethyl 4-(2-adamantylamino)-3-(pyrimidin-5-ylmethylamino)-benzoate (SRS15-22, Scheme 2) (26 mg, 0.064 mmol, 60%). $^1$H NMR (400 MHz, CDCl$_3$) δ 9.24 (s, 1H), 8.71 (d, J=5.1 Hz, 1H), 7.69-7.59 (m, 1H), 7.38 (d, J=2.0 Hz, 2H), 6.63 (d, J=8.4 Hz, 1H), 4.47 (d, J=21.3 Hz, 2H), 4.32 (dd, J=14.2, 7.1 Hz, 2H), 4.15 (s, 1H), 3.69 (s, 1H), 2.04-1.60 (m, 14H), 1.36 (d, J=7.1 Hz, 3H); LC/MS (APCI+, M+1) 407.46.

Following the above general procedure E, the reaction was purified by flash-column chromatography on silica gel to provide the desired ethyl 4-(adamantylamino)-3-(pyrimidin-5-ylmethyleneamino)benzoate (SRS15-72, Scheme 3) (99 mg, 0.245 mmol, 77%). $^1$H NMR (400 MHz, CDCl$_3$) δ 9.31 (s, 1H), 9.22 (s, 2H), 8.68 (s, 1H), 7.89-7.78 (m, 2H), 7.00 (d, J=8.7 Hz, 1H), 5.62 (s, 1H), 4.37 (q, J=7.1 Hz, 2H), 2.20 (s, 3H), 2.09 (d, J=2.5 Hz, 6H), 1.77 (s, 6H), 1.40 (t, J=7.1 Hz, 3H); $^{13}$C NMR (101 MHz, CDCl$_3$) δ 166.72, 159.78, 156.48, 150.74, 146.56, 134.47, 130.69, 129.70, 117.92, 117.03, 112.46, 60.38, 51.89, 42.52, 36.38, 29.60, 14.49; LC/MS (APCI+, M+1) 405.57.

Scheme 3. Synthesis of ferrostatin analogs SRS15-72 and SRS16-41.

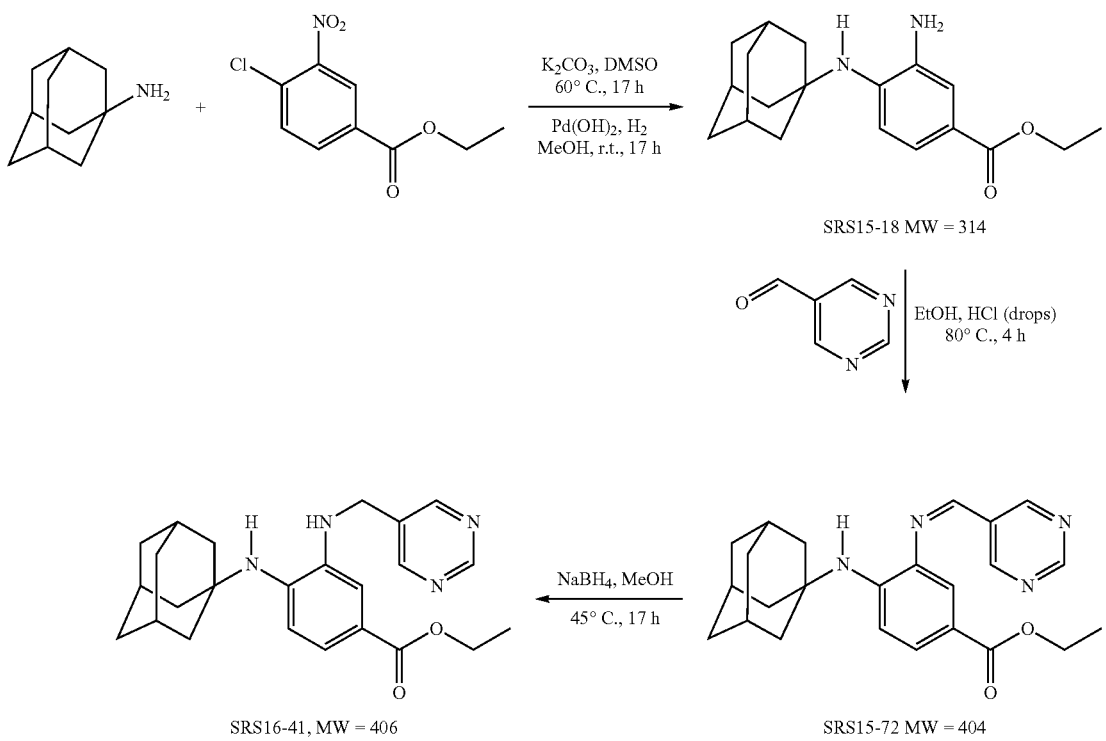

Synthesis of ethyl 4-(adamantylamino)-3-(pyrimidin-5-ylmethylamino)benzoate (SRS16-41, Scheme 2)

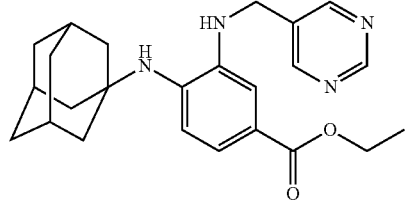
SRS16-41

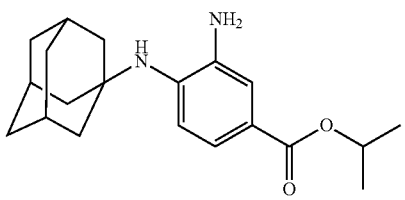
SRS16-78

Following the above general procedure C, the reaction was purified by flash-column chromatography on silica gel to provide the desired ethyl 4-(adamantylamino)-3-(pyrimidin-5-ylmethylamino)benzoate (SRS16-41, Scheme 3) (80 mg, 0.197 mmol, 80%). $^1$H NMR (400 MHz, CDCl$_3$) δ $^1$H NMR (400 MHz, CDCl$_3$) δ 9.17 (s, 1H), 8.77 (s, 2H), 7.55 (d, J=8.3 Hz, 1H), 7.40 (s, 1H), 6.96 (d, J=8.3 Hz, 1H), 4.37-4.29 (m, 4H), 3.76 (s, 1H), 2.14 (s, 3H), 1.94 (s, 6H), 1.72 (d, J=12.3 Hz, 6H), 1.35 (dd, J=9.3, 4.9 Hz, 3H); $^{13}$C NMR (101 MHz, CDCl$_3$) δ 166.93, 157.98, 156.52, 140.64, 136.71, 132.54, 123.24, 120.65, 116.53, 115.76, 60.37, 52.51, 44.83, 42.88, 36.40, 29.63, 14.43; LC/MS (APCI+, M+1) 407.27.

Following the above general procedure F, A and B respectively and starting from the commercially available 4-chloro-3-nitrobenzoic acid (Scheme 4), the crude reaction mixture was purified by column chromatography (dichloromethane: methanol=40:1) to provide the desired isopropyl 3-amino-4-(2-adamantylamino)-benzoate (SRS16-78, Scheme 4) (600 mg, 1.83 mmol, 95% (3 steps). $^1$H NMR (400 MHz, CDCl$_3$) δ 7.50 (d, J=6.4 Hz, 1H), 7.41 (s, 1H), 6.92 (d, J=7.2 Hz, 1H), 5.19 (s, 1H), 3.36 (s, 2H), 2.12 (s, 3H), 1.96 (s, 6H), 1.70 (s, 6H), 1.33 (s, 6H); LC/MS (APCI+, M+1) 329.06.

Scheme 4. Synthesis of novel ferrostatin analogs with various esters.

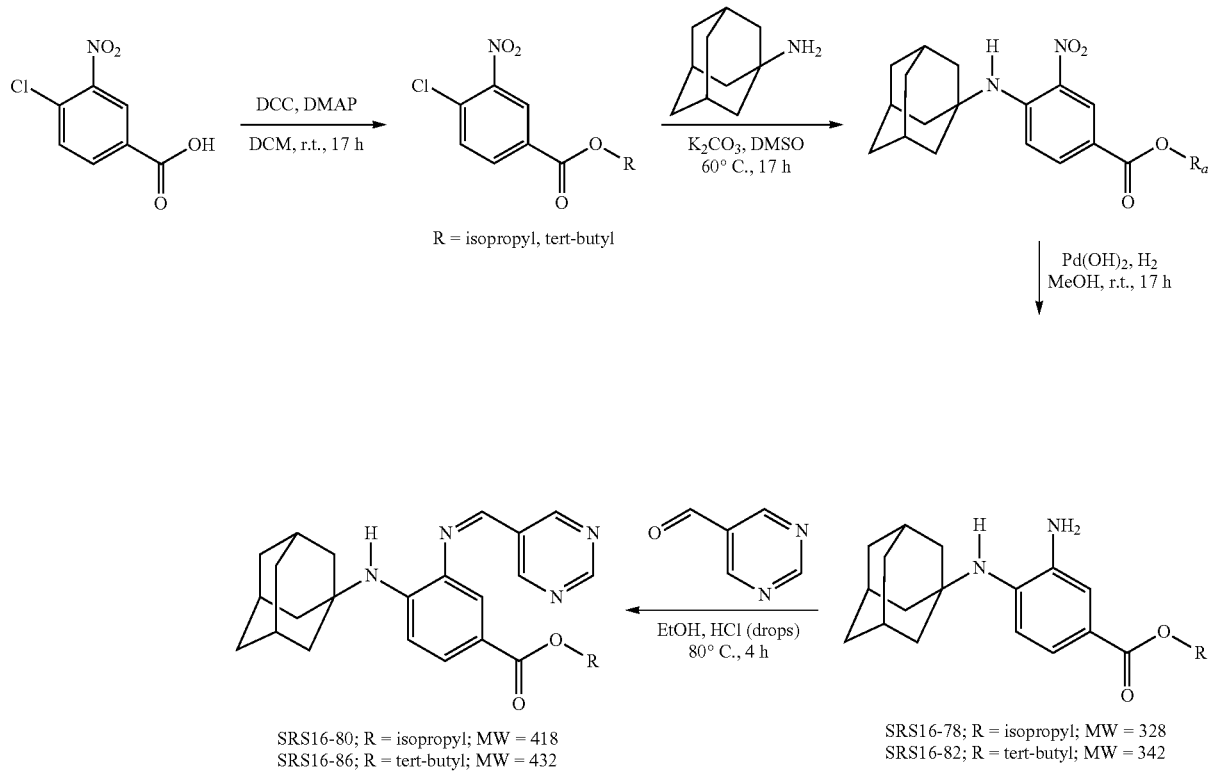

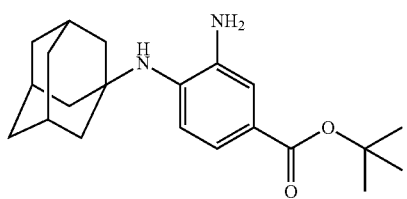

SRS16-82

Following the above general procedure F, A and B respectively and starting from the commercially available 4-chloro-3-nitrobenzoic acid (Scheme 4), the crude reaction mixture was purified by column chromatography (dichloromethane: methanol=40:1) to provide the desired tert-butyl 3-amino-4-(2-adamantylamino)-benzoate (SRS16-82, Scheme 4) (700 mg, 2.046 mmol, 88% (3 steps). $^1$H NMR (400 MHz, CDCl$_3$) δ 7.47 (dd, J=8.4, 1.9 Hz, 1H), 7.38 (d, J=1.8 Hz, 1H), 6.93 (d, J=8.4 Hz, 1H), 3.33 (s, 2H), 2.15 (s, 3H), 1.99 (s, 6H), 1.72 (s, 6H), 1.57 (s, 9H); LC/MS (APCI+, M+1) 343.09.

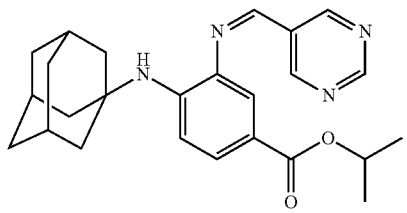

SRS16-80

Following the above general procedure E, the reaction was purified by flash-column chromatography on silica gel to provide the desired isopropyl 4-(adamantylamino)-3-(pyrimidin-5-ylmethyleneamino)benzoate (SRS15-80, Scheme 4) (90 mg, 0.215 mmol, 77%). $^1$H NMR (400 MHz, CDCl$_3$) δ 9.40-9.03 (m, 3H), 8.68 (d, J=5.8 Hz, 1H), 7.81 (dd, J=21.3, 5.2 Hz, 2H), 7.29 (d, J=5.7 Hz, 1H), 7.00 (d, J=8.7 Hz, 1H), 5.61 (s, 1H), 5.25 (dd, J=12.5, 6.3 Hz, 1H), 2.19 (s, 3H), 2.08 (s, 6H), 1.76 (s, 6H), 1.37 (d, J=6.2 Hz, 6H); LRMS (FAB+, M+) 419.3; HRMS (FAB+) calculated for C$_{16}$H$_{24}$N$_2$O$_2$, 418.2369; found: 418.2365.

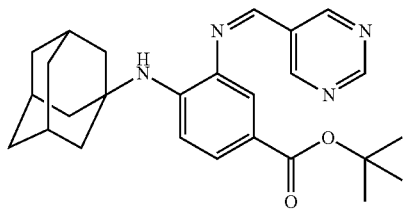

SRS16-86

Following the above general procedure E, the reaction was purified by flash-column chromatography on silica gel to provide the desired tert-butyl 4-(adamantylamino)-3-(pyrimidin-5-ylmethyleneamino)benzoate (SRS15-86, Scheme 4) (200 mg, 0.462 mmol, 89%). $^1$H NMR (400 MHz, CDCl$_3$) δ 9.30 (s, 10H), 9.29-9.15 (m, 33H), 8.66 (d, J=4.1 Hz, 14H), 7.99-7.70 (m, 28H), 7.19-6.92 (m, 14H), 5.58 (s, 13H), 2.13 (d, J=46.0 Hz, 117H), 2.00 (s, 21H), 1.75 (s, 106H), 1.71-1.54 (m, 140H); LRMS (FAB+, M+) 432.1; HRMS (FAB+) calculated for C$_{16}$H$_{24}$N$_2$O$_2$, 432.2525; found: 432.2541.

Additional Ferrostatin-1 Analogs

The following Ferrostatin-1 analogs may be made according to the general procedures set forth above:

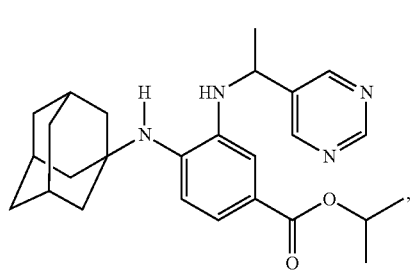

Fer2_SRS01

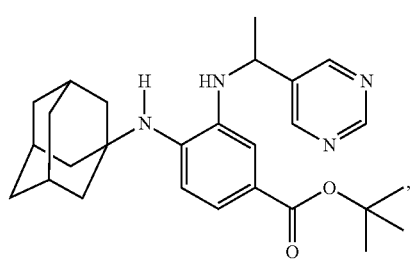

Fer2_SRS02

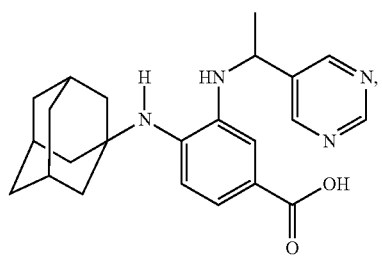

Fer_SRS03

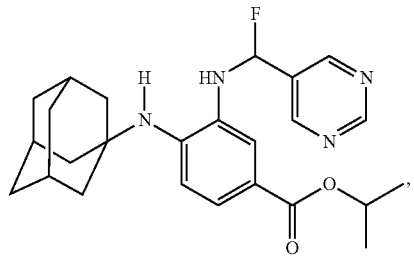

Fer2_SRS04

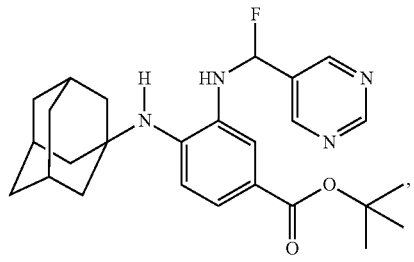

Fer2_SRS05

Fer2_SRS06
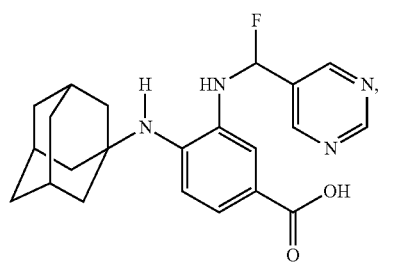

Fer2_SRS07
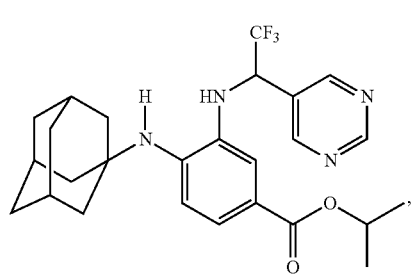

Fer2_SRS08
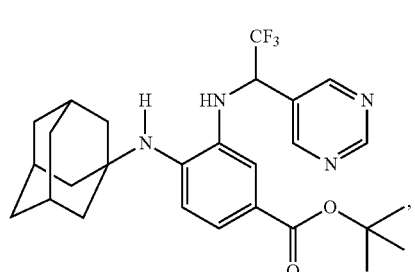

Fer2_SRS09
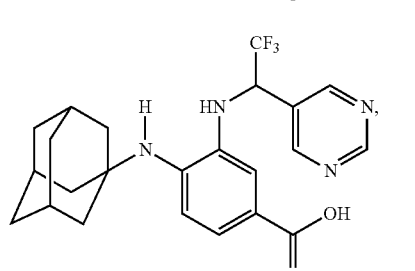

Fer2_SRS10
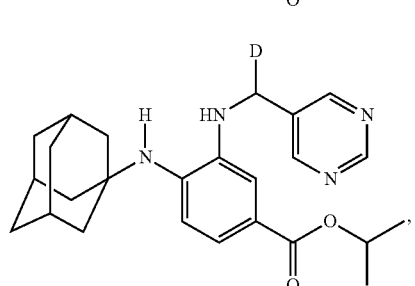

Fer2_SRS11
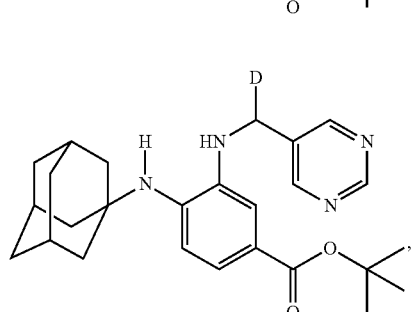, and

Fer2_SRS12
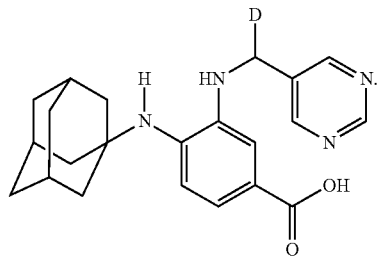

Example 3

Erastin Triggers Oxidative, Iron-Dependent Cell Death

Figure 8:
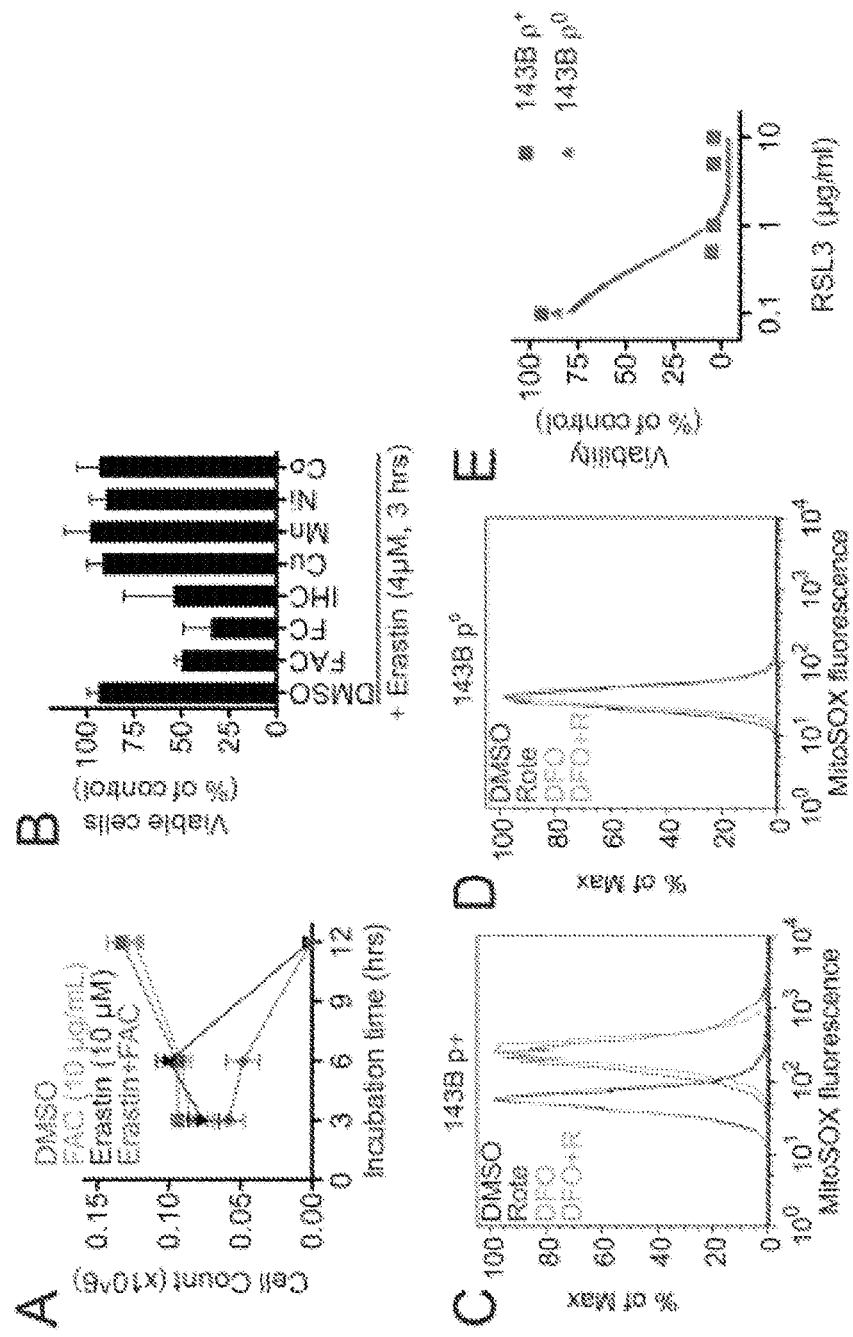
FIGS. 8A-8E show that RSLs trigger iron-dependent cell death independent of the mitochondrial electron transport chain.

RSL-induced cell death is a poorly characterized process involving the accumulation of ROS derived from an unknown source and the inhibition of cell death by iron chelation (Yagoda et al., 2007; Yang and Stockwell, 2008). It was observed that these two processes were linked. Treatment of NRAS-mutant HT-1080 fibrosarcoma cells with the RSL molecule erastin (10 μM) resulted in a time-dependent increase in cytosolic and lipid ROS beginning at 2 hours, as assayed by flow cytometry using the fluorescent probes $H_2DCFDA$ and C11-BODIPY, respectively (FIGS. 1B and 1C). This increase in ROS preceded cell detachment and overt death, which began at 6 hours (FIG. 1A). ROS accumulation and cell death were suppressed by co-treatment with the iron chelator deferoxamine (DFO, 100 μM) (FIGS. 1A-C), while incubation with three different exogenous sources of iron, but not by other divalent transition metal ions ($Cu^{2+}$, $Mn^{2+}$, $Ni^{2+}$, $Co^{2+}$), potentiated erastin-induced death (FIGS. 8A and 8B). Because cell death occurred in erastin-treated cells following a prolonged period of ROS accumulation and was suppressed by anti-oxidants (see below), the data suggest that the overwhelming, iron-dependent accumulation of ROS is what kills these cells.

Because two erastin targets, VDAC2 and VDAC3, reside in the mitochondria, it was hypothesized that erastin-induced death involved aberrant ROS production by the mitochondrial electron transport chain (ETC). However, in erastin-treated (10 μM, 6 hours) HT-1080 cells, no increase in MitoSOX-sensitive mitochondrial ROS production was observed (FIG. 1D, left). The ETC complex I inhibitor rotenone (250 nM, 6 hours) enhanced MitoSOX-sensitive ROS production, but in a manner that was insensitive to DFO (FIG. 1D, right). Furthermore, KRAS-mutant 143B osteosarcoma cells incapable of ETC-dependent ROS formation, due to the depletion of mitochondrial DNA (mtDNA)-encoded transcripts ($\rho^0$ cells), were as sensitive to erastin and RSL3 as matched mtDNA-wild-type ($\rho^+$) cells (FIGS. 1E, 1F, and 8C-E). Thus, erastin-induced cell death in human cancer cells involves DFO-sensitive ROS accumulation and can occur in cells lacking a functional ETC. This iron-dependent death phenotype was named ferroptosis.

Example 4

Ferroptosis is Distinct from Known Forms of Cell Death

Whether ferroptosis shared morphological, bioenergetic or other similarities with apoptotic or necrotic death, or with autophagy was examined. Using transmission electron microscopy, it was observed that HRAS-mutant BJeLR engineered tumor cells treated with erastin exhibited none of the characteristic morphologic features associated with staurosporine (STS)-induced apoptosis (e.g. chromatin condensation and margination), hydrogen peroxide ($H_2O_2$)-induced necrosis (e.g. cytoplasmic and organelle swelling, plasma membrane rupture) or rapamycin-induced autophagy (e.g. formation of double-membrane enclosed vesicles) (FIG. 2A). The lone distinctive morphological feature of erastin-treated cells were mitochondria that appeared smaller than normal, with increased membrane density, consistent with the previous report (Yagoda et al., 2007) (FIG. 2A). With respect to bioenergetics, substantial depletion of intracellular ATP in BJeLR and HT-1080 cells treated with $H_2O_2$, but not erastin, STS or rapamycin, was observed (FIG. 2B), thus distinguishing ferroptosis from various forms of necrosis that involve bioenergetic failure.

Using a variation of the modulatory profiling strategy (Wolpaw et al., 2011), the ability of twelve established small molecule cell death inhibitors to prevent ferroptosis in HT-1080, BJeLR and KRAS-mutant Calu-1 non-small cell lung cancer cells was tested. The modulatory effect ($M_e$) for each inhibitor (tested in a 10-point, 4-fold dilution series) on the normalized viability of cells treated with a lethal dose of erastin ($M_e<0$: death sensitization; $M_e=0$: no effect; $M_e>0$: death rescue) was computed. The resultant values were clustered hierarchically in an unsupervised fashion and displayed as a heatmap. Using this approach, it was observed that erastin-induced death was not consistently modulated by inhibitors of caspase, cathepsin or calpain proteases (z-VAD-fmk, E64d or ALLN), RIPK1 (necrostatin-1), cyclophilin D (cyclosporin A) or lysosomal function/autophagy (bafilomycin A1, 3-methyladenine, chloroquine), compounds known to inhibit various forms of apoptosis, necrosis and autophagic cell death (FIG. 2C).

Figure 9:
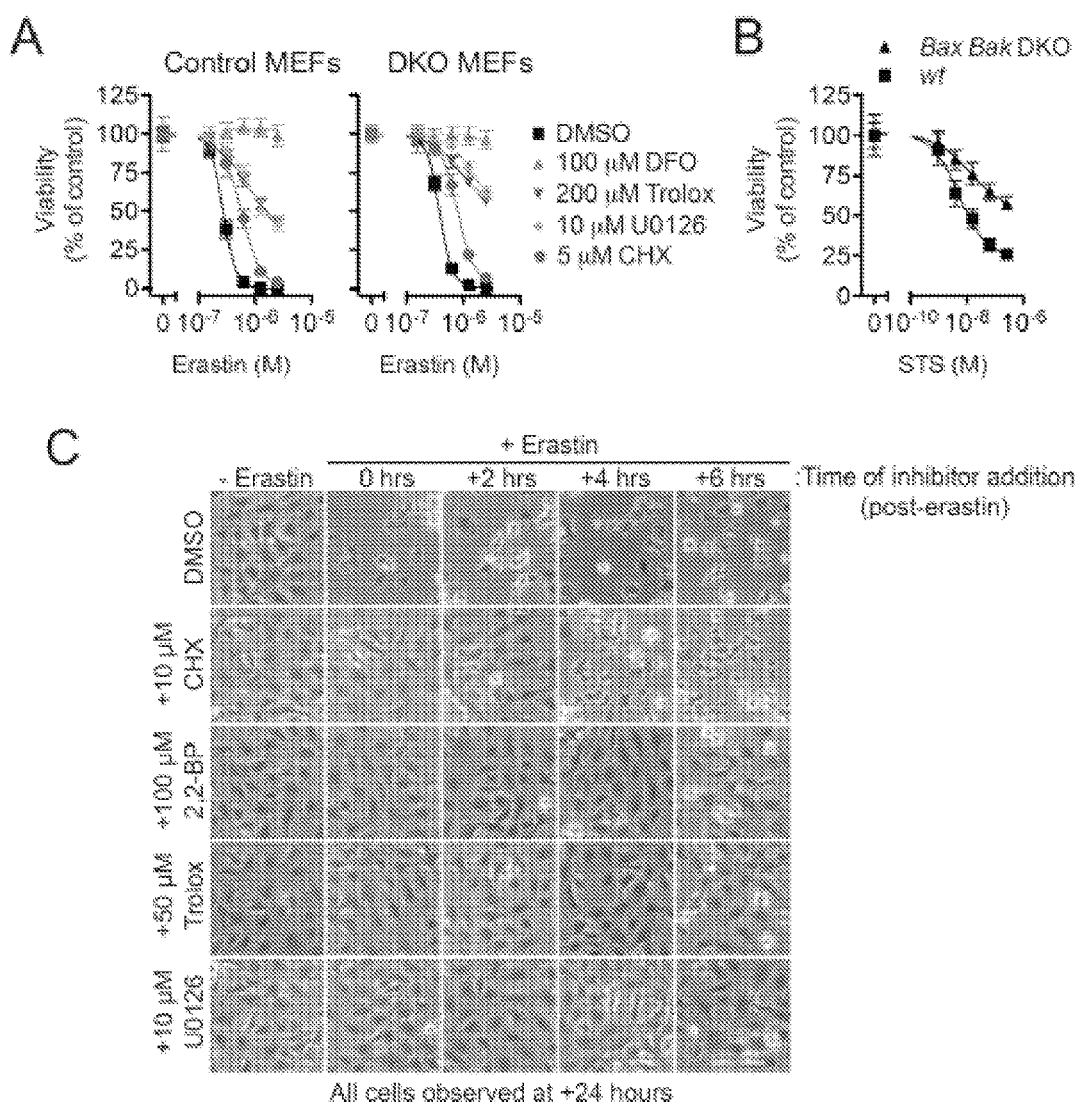
FIGS. 9A-9C show that ferroptosis occurs in mouse embryonic fibroblasts (MEFs), independent of Bax and Bak, and can be attenuated by the late addition of inhibitors.

DFO, the anti-oxidant trolox, the MEK inhibitor U0126 and, to a weaker extent, the protein synthesis inhibitor cycloheximide (CHX), all rescued from erastin-induced death in HT-1080, BJeLR and Calu-1 cells (FIG. 2C) (Yagoda et al., 2007). These inhibitors were also effective at preventing erastin-induced ferroptosis in both wild-type and apoptosis-deficient Bax/Bak double knockout (DKO) mouse embryonic fibroblasts (FIGS. 9A and 9B), indicating that ferroptosis can be activated in human- and mouse-derived cells and is independent of the core apoptotic machinery regulated by Bax and Bak. DFO, trolox and U0126 all prevented the accumulation of $H_2DCFDA$-sensitive ROS in erastin-treated HT-1080 cells (FIG. 2D), demonstrating that these inhibitors act to prevent death upstream or at the level of ROS production. Because trolox, U0126 and the membrane permeable iron chelator 2,2-bipyridyl could be added to HT-1080 cells up to 6 hours after erastin and still confer substantial protection from death (FIG. 9C), ferroptosis likely requires continuous iron-dependent ROS formation over an extended period of time to trigger death.

Finally, in a modulatory profiling experiment that tested the ability of DFO, trolox, U0126, CHX, the membrane permeable iron chelator ciclopirox olamine (CPX) and the glutathione peroxidase mimetic ebselen (Ebs) to modulate the lethality of erastin, RSL3 or sixteen other mechanistically distinct lethal compounds thought to kill cells through various ROS-dependent and -independent mechanisms, it was observed that erastin and RSL3 formed a distinct cluster, separate from all other inducers of cell death (FIG. 2E). Together, these data support the hypothesis that RSL-induced ferroptosis is a novel death phenotype distinct from apoptosis, various forms of necrosis and autophagy.

Example 5

Ferroptosis is Regulated by a Distinct Set of Genes

Figure 2:
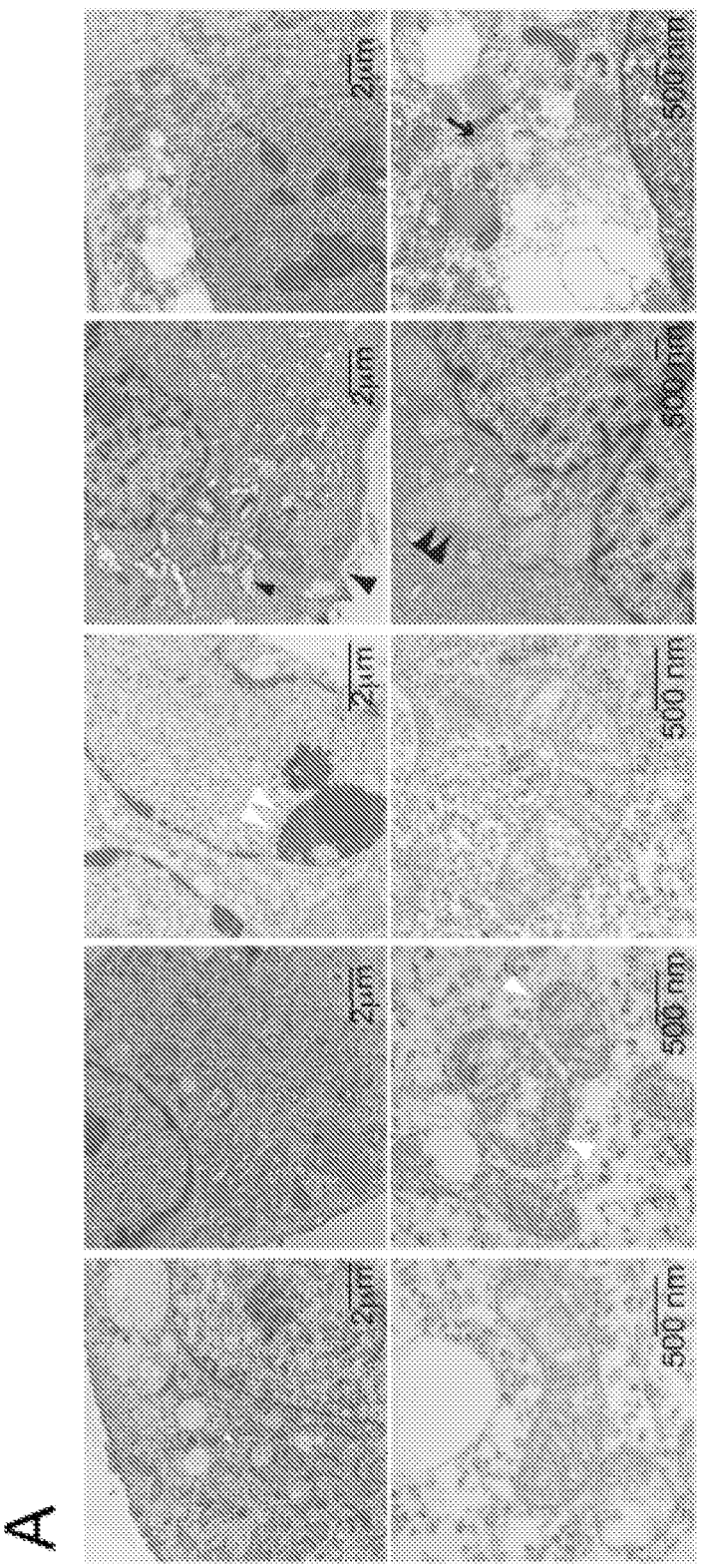
FIGS. 2A-2E show that erastin-induced oxidative death is iron-dependent.
Figure 3:
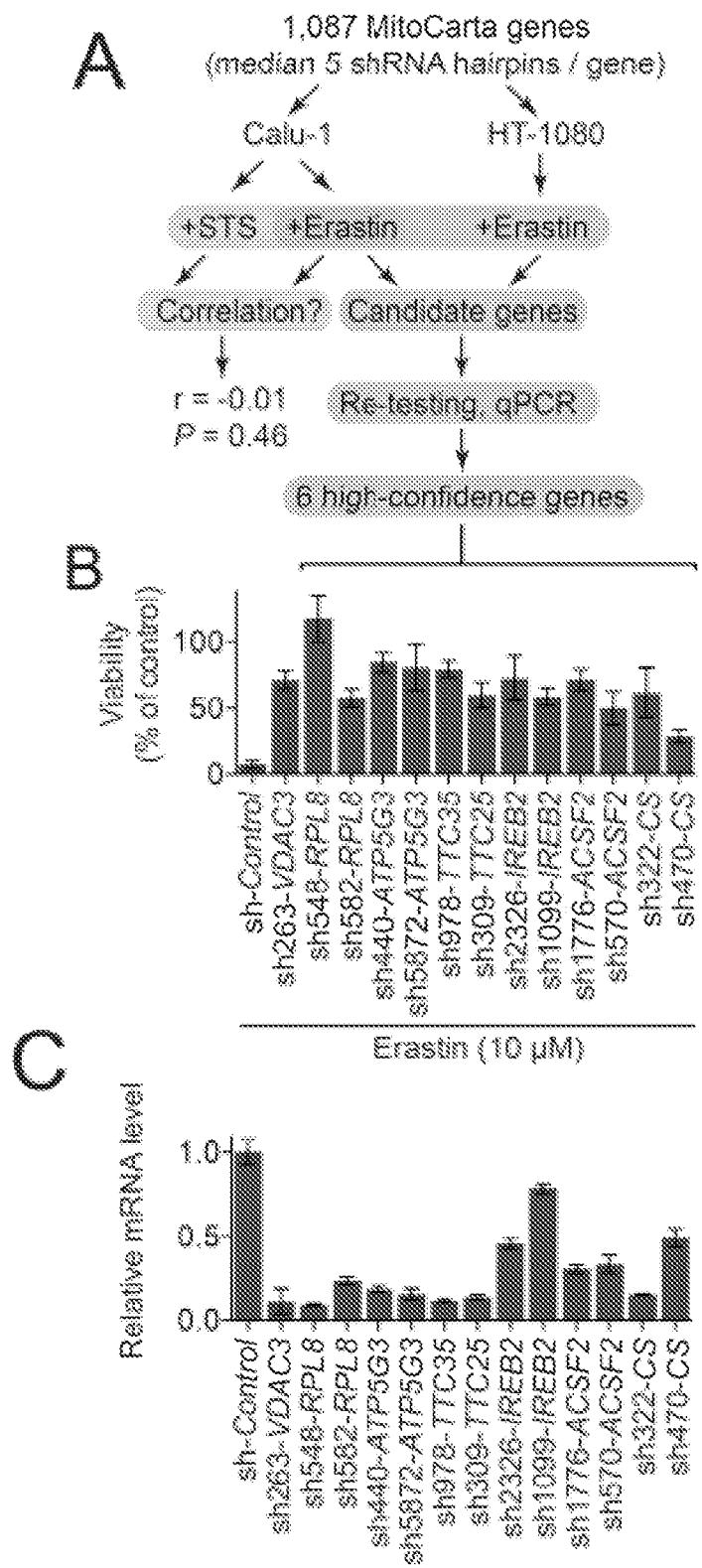
FIGS. 3A-3G show that erastin-induced ferroptosis exhibits a unique genetic profile.

To explore the genetic basis of ferroptosis, genes uniquely required for this process were identify. The potential role of the mitochondria were focused on, because this organelle displayed an aberrant morphology in erastin-treated cells (FIG. 2A). Mitochondrial gene function was perturbed using a custom arrayed shRNA library targeting 1,087 genes (median 5 hairpins/gene), most of which (901, 88%) encode predicted mitochondrial proteins (Pagliarini et al., 2008) (FIG. 3A). Using this library, the genetic suppressibility of erastin (7.3 μM)-induced ferroptosis and STS (1 μM)-induced apoptosis in Calu-1 cells was compared (FIG. 3A). Across all 5,817 informative hairpins, no significant correlation between those shRNAs that rescued from erastin-induced ferroptosis and from STS-induced apoptosis (Spearman rank sum test, r=−0.01, P=0.46) was observed, thus confirming that distinct genetic networks govern erastin-induced ferroptosis and STS-induced apoptosis.

Figure 10:
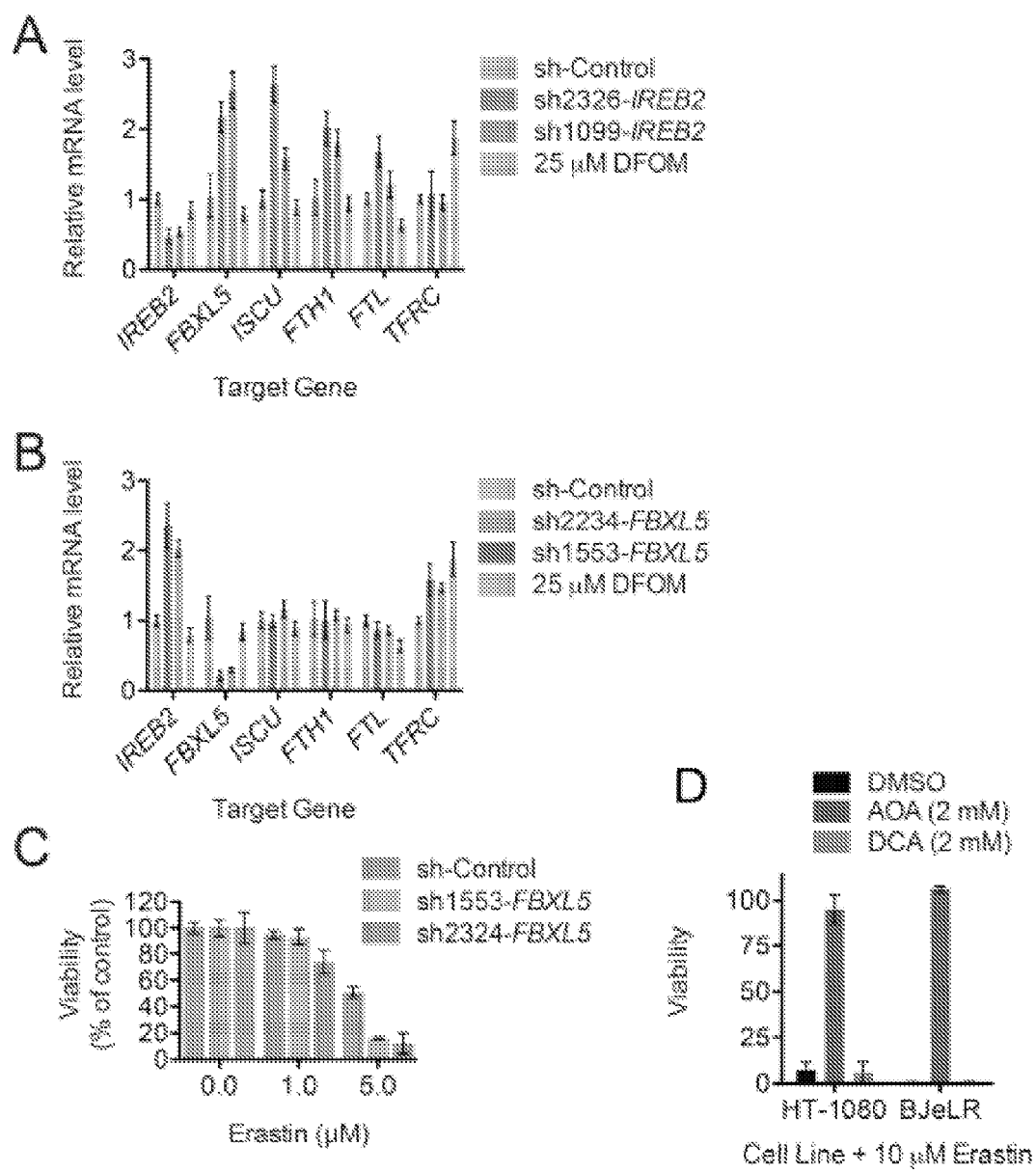
FIGS. 10A-10D show various methods of validating the role of IREB2 in ferroptosis.

Next, a second erastin resistance screen in HT-1080 cells was performed and, using a rigorous confirmation pipeline, six high-confidence genes were identified. These six high-confidence genes were supported by at least two independent shRNAs per gene that are required for erastin-induced ferroptosis in both HT-1080 and Calu-1 cells—RPL8 (ribosomal protein L8), IREB2 (iron response element binding protein 2), ATP5G3 (ATP synthase $F_0$ complex subunit C3), CS (citrate synthase), TTC35 (tetratricopeptide repeat domain 35) and ACSF2 (acyl-CoA synthetase family member 2) (FIGS. 3B and 3C). Consistent with the established CHX- and DFO-sensitive nature of erastin-induced ferroptosis, RPL8 encodes a component of the 60S ribosomal subunit presumably required for translation and IREB2 encodes a master regulator of iron metabolism. These results were further validated. It was found that shRNA-mediated silencing of IREB2 and the IREB2 negative regulator FBXL5 (Salahudeen et al., 2009; Vashisht et al., 2009) resulted in reciprocal changes in the expression of the known iron uptake, metabolism and storage genes TFRC, ISCU, FTH1, FTL and in erastin sensitivity (FIG. 10A-C). These results provide confidence in the quality of the screening and confirmation procedures.

To establish the generalizability of the results obtained in HT-1080 and Calu-1 cells, the effects of silencing these genes in HT-1080, Calu-1 and six additional cell lines treated with erastin were tested. Silencing of these six high confidence genes using the most effective hairpin for each gene, defined by mRNA silencing levels in HT-1080 cells (FIG. 3C), conferred ≥20% rescue in 79% (38/48) of shRNA-cell line combinations (FIG. 3D). Thus, these genes appear to be broadly required for erastin-induced ferroptosis. Next, whether silencing of these genes specifically attenuated erastin-induced ferroptosis, or more broadly modulated a variety of lethal effects was tested. Silencing of these six genes conferred protection against erastin-induced ferroptosis (≥40% rescue for 6/6 hairpins), but not cell death/cytostasis induced by STS, rotenone, rapamycin, the proteasome inhibitor MG132, the DNA-damaging agent camptothecin or the $Ca^{2+}$-dependent ATPase inhibitor thapsigargin (≥40% rescue for 0/6 hairpins) (FIG. 3E). Together, these data support the hypothesis that a unique genetic network governs erastin-induced ferroptosis compared to other forms of cell death.

Both ACSF2 and CS are implicated in the regulation of mitochondrial fatty acid metabolism (Mullen et al., 2011; Watkins et al., 2007). Whether this process could contribute to ferroptosis was examined. In cancer cells, fatty acid synthesis is in part dependent upon the metabolism of glutamine (Gln) to alphaketoglutarate, a process that can be inhibited by the small molecule transaminase inhibitor aminooxyacetic acid (AOA) (Wise et al., 2008) (FIG. 3F). In cell culture media containing both glucose and Gln, AOA (2 mM) rescued both HT-1080 and BJeLR cells from erastin-induced ferroptosis (FIGS. 3F, 10D), mimicking the effects of silencing CS and ACSF2. In AOA-treated HT-1080 cells, the lethality of erastin was restored by co-incubation with dimethyl alpha ketoglutarate (DMK), which provides the downstream metabolite whose production from Gln is blocked by AOA (Wise et al., 2008) (FIGS. 3F and 3G). An unrelated modulator of mitochondrial function not predicted to directly affect Gln metabolism, dichloroacetic acid (DCA), had no effect on erastin-induced ferroptosis (FIG. 10D). These results suggest that a Gln-CS- and ACSF2-dependent lipid synthesis pathway could supply a specific lipid precursor required for ferroptosis.

Example 6

Identification of Ferrostatin-1 as a Small Molecule Inhibitor of Ferroptosis

Figure 4:
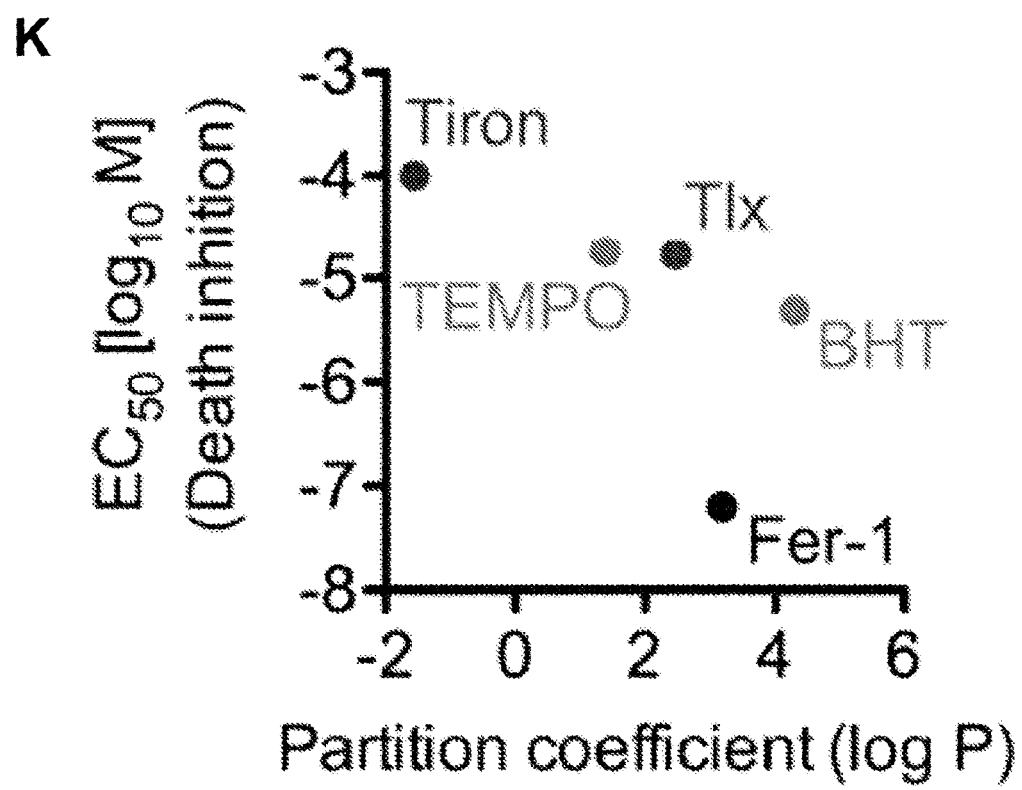
FIGS. 4A-4K show the identification and characterization of Ferrostatin-1.

One ultimate aim is to investigate the potential role of ferroptosis in vivo. Therefore, a potent and specific drug-like small molecule inhibitor of this process was identified. As set forth above, to overcome the inherent limitations of many individual small molecule collections (Macarron et al., 2011), a custom screening library of 9,517 small molecules derived from a starting pool of 3,372,615 commercially available compounds that were filtered in silico on the basis of drug-likeness, solubility, scaffold diversity and other parameters was assembled. Screening of this lead-optimized compound' (LOC) library and subsequent confirmation studies identified a compound, which the inventors named ferrostatin-1 (Fer-1), as the most potent inhibitor of erastin-induced ferroptosis in HT-1080 cells ($EC_{50}$=60 nM) (FIGS. 4A, 10A, and 10B). To the inventors' knowledge, the activity for Fer-1 has not previously been reported in any biological system. A total synthesis of Fer-1 was performed as set forth above, and this material was used to confirm the activity of Fer-1 and to demonstrate that it specifically inhibited RSL-induced death, but not cell death induced by other oxidative lethal compounds and apoptosis-inducing agents (FIGS. 4B, 6A).

The Fer-1 mechanism of action was examined. Fer-1 did not inhibit ERK phosphorylation or arrest the proliferation of HT-1080 cells, suggesting that it does not inhibit the MEK/ERK pathway, chelate iron or inhibit protein synthesis (FIGS. 4C and 4D). Fer-1 did, however, prevent erastin-induced accumulation of cytosolic and lipid ROS (FIG. 4E). Moreover, similar to the positive control antioxidant trolox, Fer-1 readily oxidized the stable radical 2,2-diphenyl-1-picrylhydrazyl (DPPH) under cell free conditions, a test of intrinsic antioxidant potential (FIG. 4F). Substitution of the primary aromatic amine for a nitro group (SRS8-24), or elimination of the N-cyclohexyl moiety (CA-1), destroyed the antioxidant capability of Fer-1, as well as its ability to prevent erastin (10 µM)-induced death in HT-1080 cells (FIGS. 4F-H). Thus, both aromatic amines are required for Fer-1 to prevent RSL-induced death, a function plausibly linked to its ability to scavenge free radicals.

Figure 11:
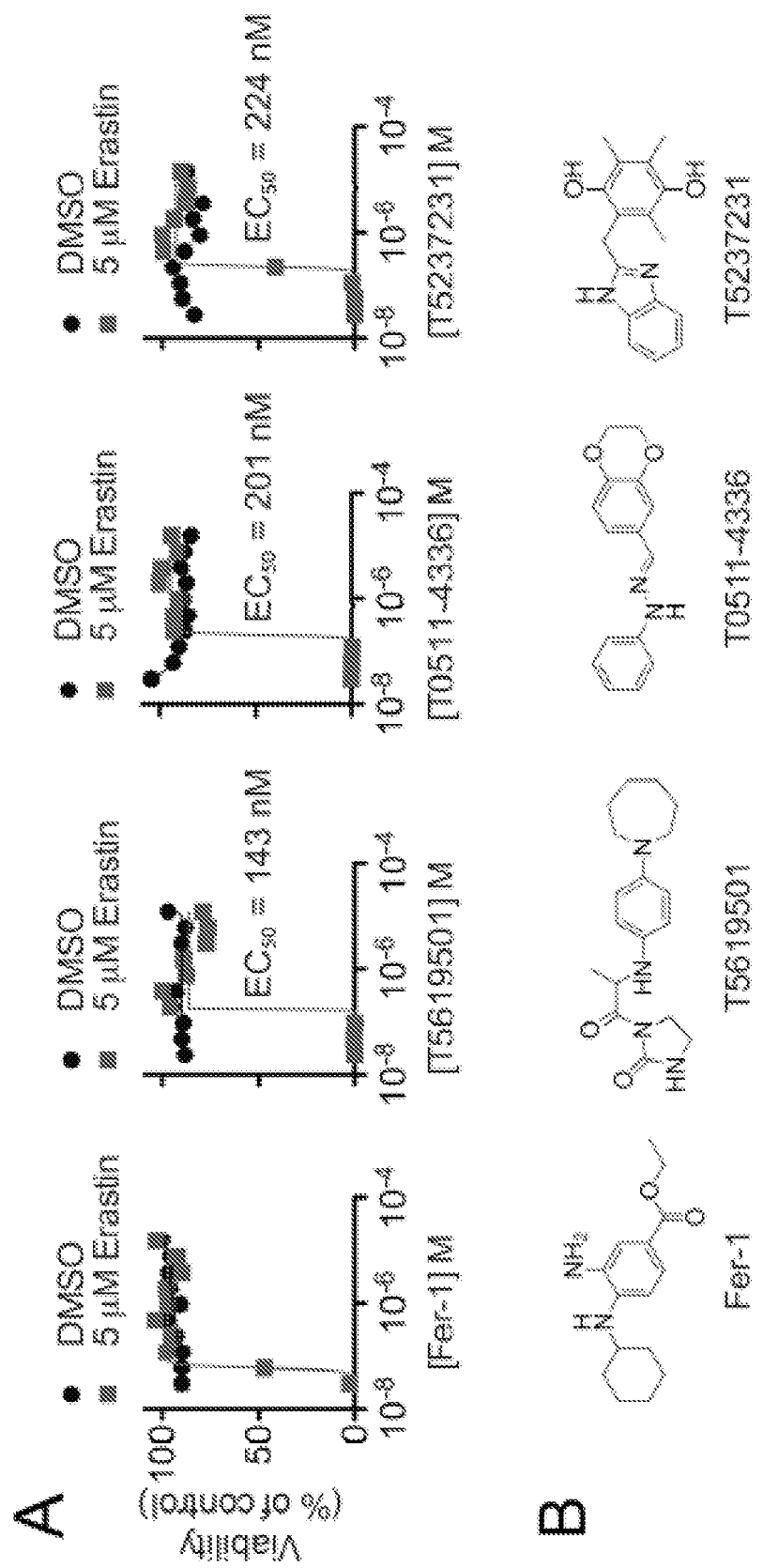
FIGS. 11A-11B show Fer-1, and a Fer-1 structure-activity relationship (SAR) analysis.

The results suggested that lipid ROS were crucial for erastin-induced death. The inventors therefore hypothesized that Fer-1 was a lipid ROS scavenger, with the N-cyclohexyl moiety serving as a lipophilic anchor within biological membranes. Consistent with this hypothesis, in a series of ten Fer-1 analogs, where the number of carbons in the N-substituted cyclic moiety was systematically varied, a significant correlation between the predicted lipophilicity (octanol-water partition coefficient, log P) and the erastin-death-suppressing ability of each molecule (Spearman $R=-0.85$, $P=0.002$) was observed (FIGS. 4I and 11C). Of note, SRS8-72, a Fer-1 analog with N-cyclopropyl in place of N-cyclohexyl, which was an order of magnitude less potent than Fer-1 at preventing death, nonetheless retained equivalent intrinsic antioxidant capability in the cell-free DPPH assay (FIGS. 4F-H and 10C). Thus, the N-cyclohexyl moiety likely enables Fer-1 to prevent ferroptosis by promoting the tethering of Fer-1 within lipid membranes, as opposed to influencing the intrinsic antioxidant potential of this molecule.

Intriguingly, lipid partitioning alone does not appear to be sufficient to account for the potency of Fer-1. Fer-1 has similar predicted lipophilicity, but much greater erastin-suppressing potency than two canonical lipophilic antioxidants (trolox and butylated hydroxyltoluene [BHT]), while being both considerably more lipophilic and more potent than two representative soluble antioxidants (Tiron, TEMPO) (FIGS. 4J and 4K). Both trolox and BHT are phenolic antioxidants, while Fer-1 contains an aromatic amine. It was hypothesized that this difference may confer a unique profile of radical reactivity upon Fer-1 that is better tuned to the RSL mechanism.

Example 7

Fer-1 Prevents Glutamate-Induced Neurotoxicity

Excitotoxic cell death that occurs in the nervous system in epilepsy, stroke and other trauma situations has also been described as an oxidative, iron-dependent process (Cheah et al., 2006; Choi, 1988; Murphy et al., 1989). It was hypothesized that excitotoxic death could be related to erastin-induced ferroptosis. This hypothesis was tested using a rat organotypic hippocampal slice culture (OHSC) model that closely resembles the hippocampus in vivo by preserving the integrity of neuronal connections, both inhibitory and excitatory, and their supporting cells, including astrocytes and microglia (Lossi et al., 2009). OHSCs have proven to be ideal complex preparations for lead-compound identification and validation (Noraberg et al., 2005; Sundstrom et al., 2005), capable of predicting in vivo efficacy (Cater et al., 2007; Morrison et al., 2002).

Figure 5:
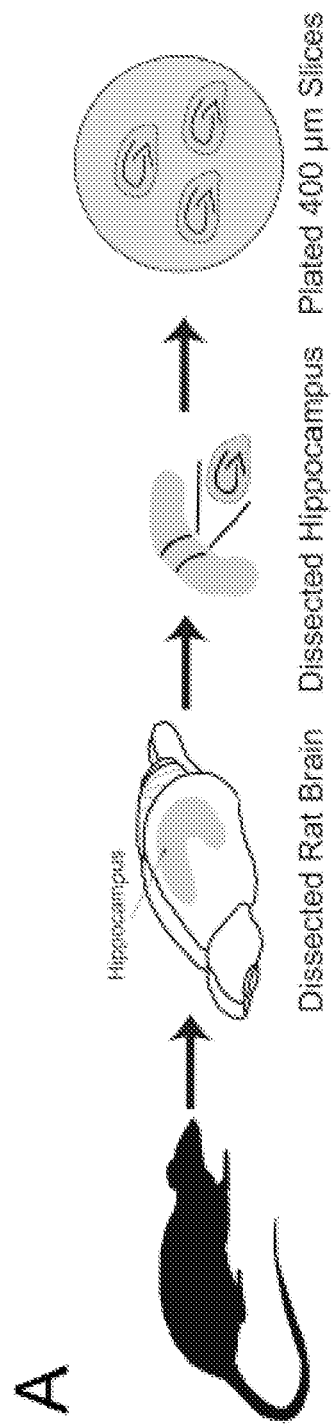
FIGS. 5A-5E show the effects of Fer-1 on excitotoxic cell death in organotypic hippocampal slice cultures.
Figure 5:
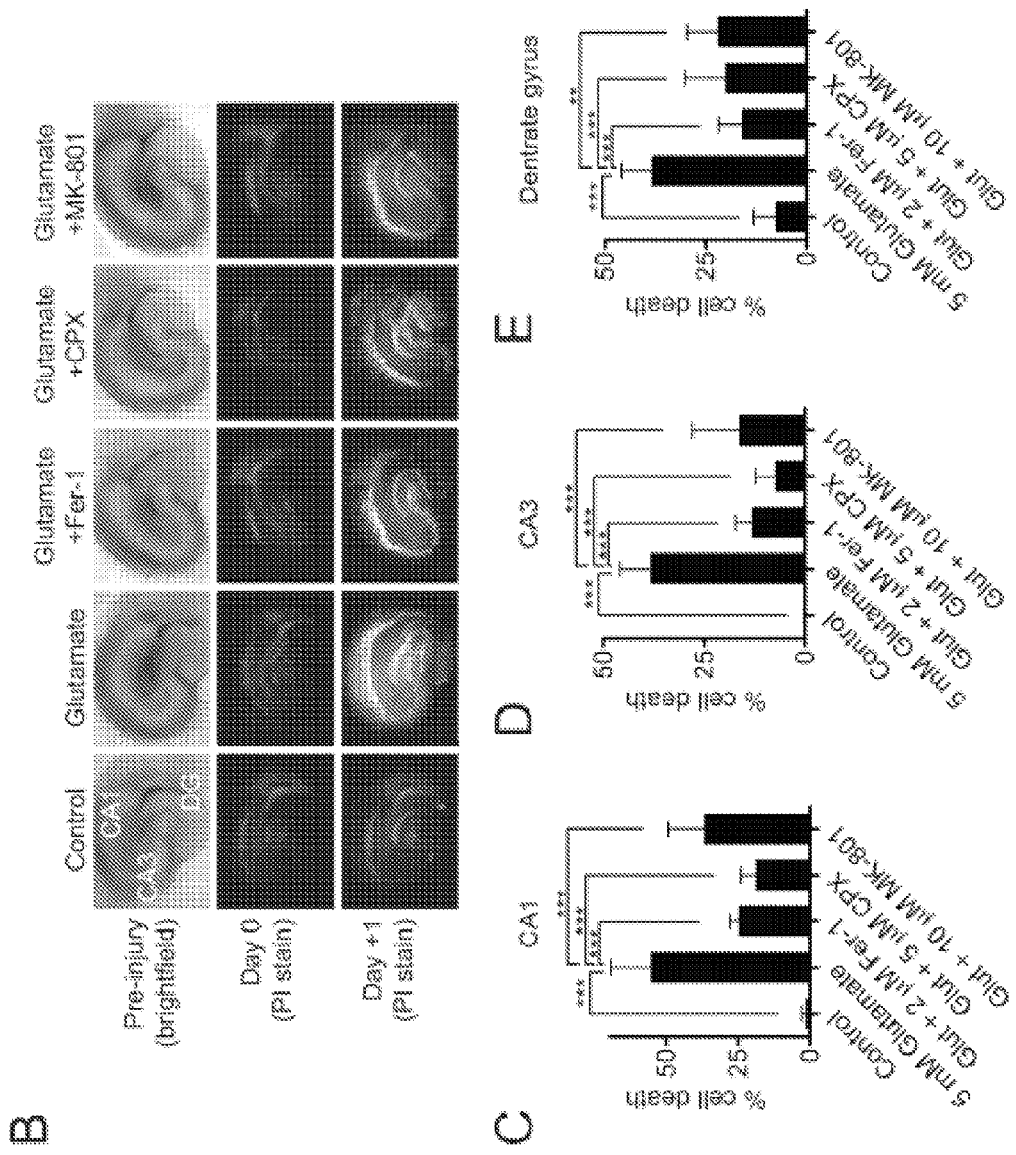

OHSCs were treated with a lethal excitotoxic stimulus (5 mM L-glutamate, 3 hours) that mimics the consequences of stroke and neurodegenerative disease (Morrison et al., 2002; Sundstrom et al., 2005) (FIG. 5A). These slices were co-incubated with glutamate and vehicle alone or with glutamate plus Fer-1 (2 µM), the iron chelator CPX (5 µM) or, as a positive control, the NMDA receptor antagonist MK-801 (10 µM). The effects of these compound treatments on propidium iodide (PI) uptake were analyzed, as an indicator of cell death, 24 hours following the end of glutamate treatment, in 3 defined regions of the OHSCs: the dentate gyrus (DG), the CA1 and the CA3 fields of the hippocampus. A two-way analysis of variance (ANOVA) suggested significant differences for both brain region ($F_{2,75}=19.23$, P<0.0001) and compound treatment ($F_{4,75}=67.8$, P<0.0001) factors. Focusing on the compound treatment effect, Bonferroni post-tests indicated that glutamate induced significant cell death in all three regions of the brain, and that this death was attenuated significantly and to an almost identical extent by co-treatment with Fer-1, CPX or MK-801 (P<0.001 for all interactions except glutamate+MK-801 within the DG, P<0.01) (FIG. 5B-E). These results suggest that glutamate-induced death in OHSCs and erastin-induced death in cancer cells share in common a core lethal mechanism that can be inhibited by iron chelation or Fer-1.

Example 8

Erastin Inhibits System $x_c^-$

CPX and Fer-1 suppressed erastin-induced death in cancer cells and glutamate-induced toxicity in OHSCs, consistent with a common iron- and ROS-dependent death execution mechanism. Whether any death-initiating mechanisms could also be shared between these two processes was investigated.

Figure 12:
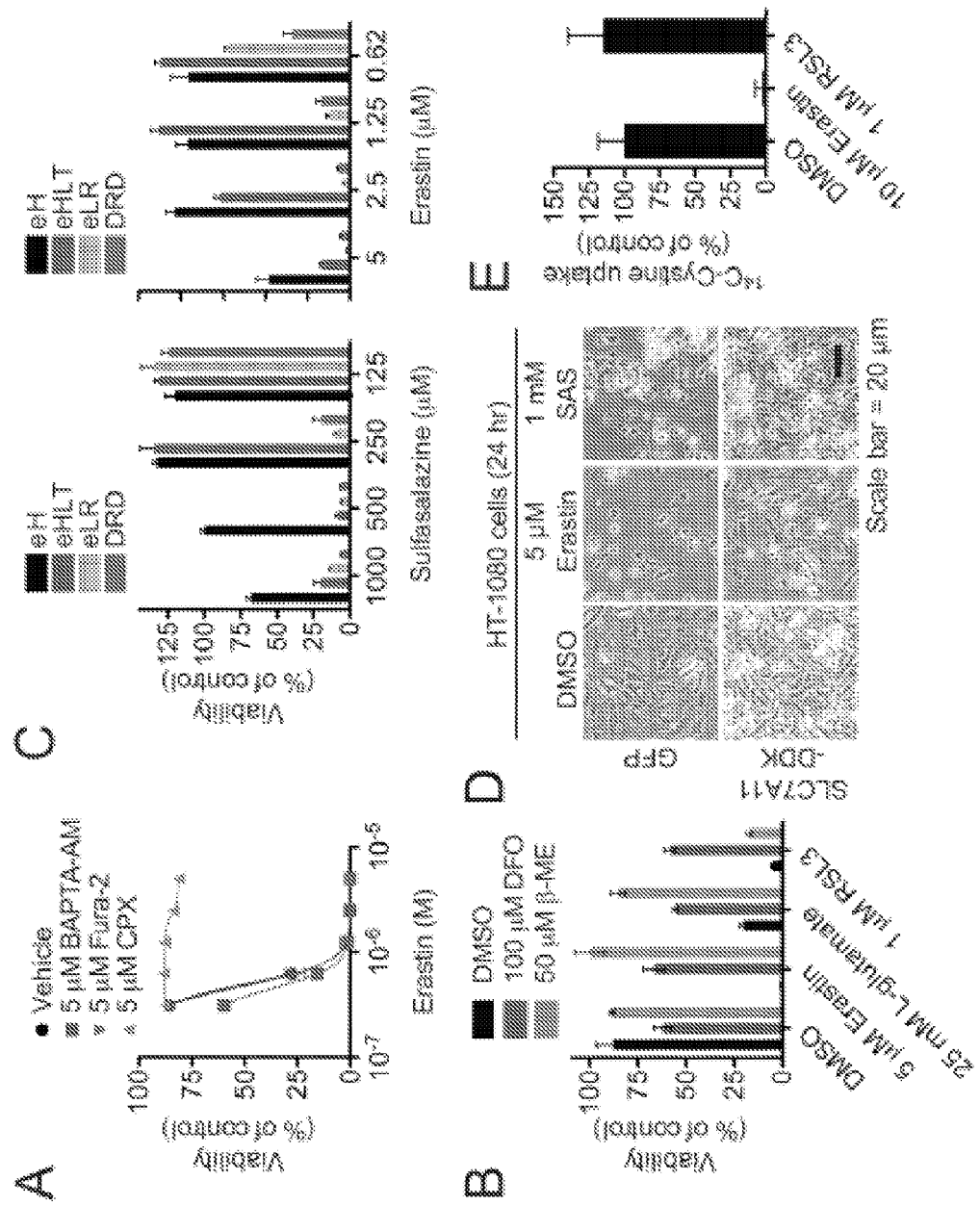
FIGS. 12A-12E show the analysis of the role of calcium and system $x_c^-$ in ferroptosis.

Glutamate-induced death in brain cells can be initiated by calcium influx through ionotropic glutamate receptors and through competitive inhibition of cystine uptake by the Na$^+$-independent cystine/glutamate antiporter, system $x_c^-$ (Choi, 1988; Murphy et al., 1989). The calcium chelators BAPTA-AM, Fura-2 and EGTA had no effect on erastin-induced death (FIG. 12A) (Wolpaw et al., 2011), arguing against a role for Ca$^{2+}$ influx in this process. However, striking clustering of erastin and sulfasalazine (SAS), a specific inhibitor of system $x_c^-$ (Gout et al., 2001), was observed in a modulatory profile of 19 oxidative and non-oxidative lethal molecules generated in HT-1080 cells (FIG. 6A). If blockade of system $x_c^-$-mediated cystine import can trigger ferroptosis, then providing this metabolite to cells through an alternative means should rescue from death. Indeed, β-mercaptoethanol (β-ME), which can circumvent the inhibition of system $x_c^-$ by promoting cystine uptake through an alternative pathway (Ishii et al., 1981), strongly inhibited cell death in HT-1080 cells induced by erastin, SAS and glutamate (FIGS. 6A and 12B). As predicted by these results, SAS, like erastin, behaved as an oncogenic RAS-selective lethal (RSL) compound, albeit with considerably lower potency than erastin (FIG. 12C). This is nonetheless noteworthy, as SAS is an FDA-approved drug not previously shown to demonstrate such activity.

System $x_c^-$ is a disulfide-linked heterodimer composed of SLC7A11 (xCT) and SLC3A2 (4F2hc, CD98hc) (Sato et al., 1999) (FIG. 6B). Inhibition of system $x_c^-$ can lead to a compensatory transcriptional up-regulation of SLC7A11 (Lo et al., 2008). Consistent with this, substantial upregulation of SLC7A11 in HT-1080 cells treated with erastin or SAS was observed. This effect was suppressed by β-ME, but not DFO or Fer-1 (FIG. 6C). Further confirming the relevance of system $x_c^-$ to erastin-induced ferroptosis, siRNA-mediated silencing of SLC7A11 with two independent siRNAs sensitized HT-1080 cells to erastin-induced death (FIGS. 6D and 6E), while transfection of HT-1080 cells with a plasmid encoding DDK-tagged SLC7A11 conferred protection from erastin- and SAS-induced death (FIG. 12D). Given these results, the uptake of [$^{14}$C]cystine in HT-1080 cells was directly examined. Erastin (10 μM), glutamate (50 mM) and SAS (1 mM) abolished the Na$^+$-independent uptake of [$^{14}$C]cystine while RSL3 had no effect on this process (FIGS. 6F, 12E).

How erastin inhibits system $x_c^-$ was investigated. Analysis of affinity purification data (Yagoda et al., 2007) identified SLC7A5 (LAT1, 4F2lc, CD98lc) as the lone protein bound by an active erastin affinity analog in lysates from both HRAS-wildtype BJeH and HRAS-mutant BJeLR cells (FIG. 6G). SLC7A5 (like SLC7A11) is one of six light chains that bind SLC3A2 to form amino acid transporters of differing substrate selectivity. The SLC7A5/SLC3A2 complex (system L) transports large, neutral amino acids (Kanai and Endou, 2003) (FIG. 6B). In a profile of 123 metabolites from human Jurkat T lymphocytes treated with erastin (1 μM, 25 min) (Ramanathan and Schreiber, 2009), highly significant decreases were observed in the levels of system L substrates (Kanai and Endou, 2003), while the levels of non-system L substrates were unchanged or increased (FIG. 6H). However, unlike inhibition of system $x_c^-$ using excess glutamate (12.5 mM), inhibition of system L using excess D-phenylalanine (12.5 mM) (Kanai and Endou, 2003) did not strongly sensitize to erastin (FIG. 6I). Together, these results suggest that erastin inhibits system L-mediated amino acid uptake, but that this does not contribute directly to ferroptosis. Rather, erastin binding to SLC7A5 or the SLC7A5/SLC3A2 complex interferes with cystine uptake by the SLC3A2/SLC7A11 complex in trans.

Example 9

Figure 7:
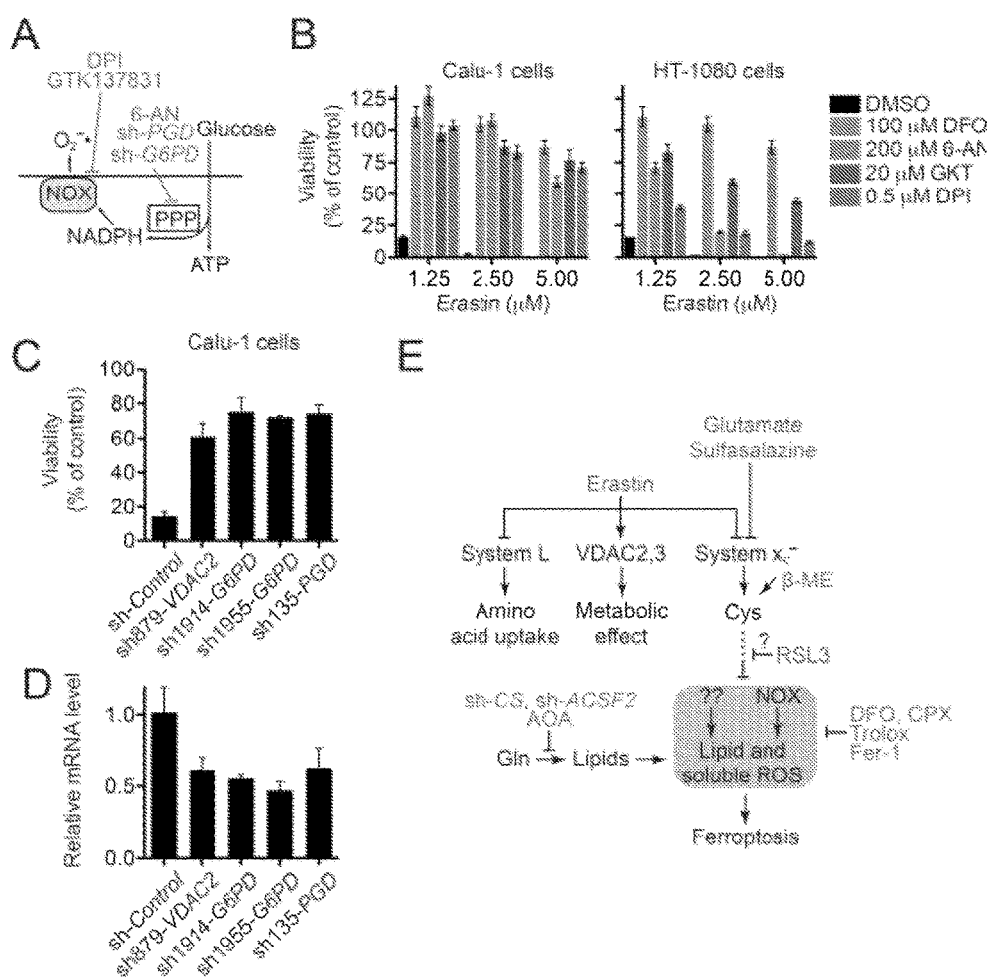
FIGS. 7A-7E show the role of NOX in erastin-induced death.
Figure 13:
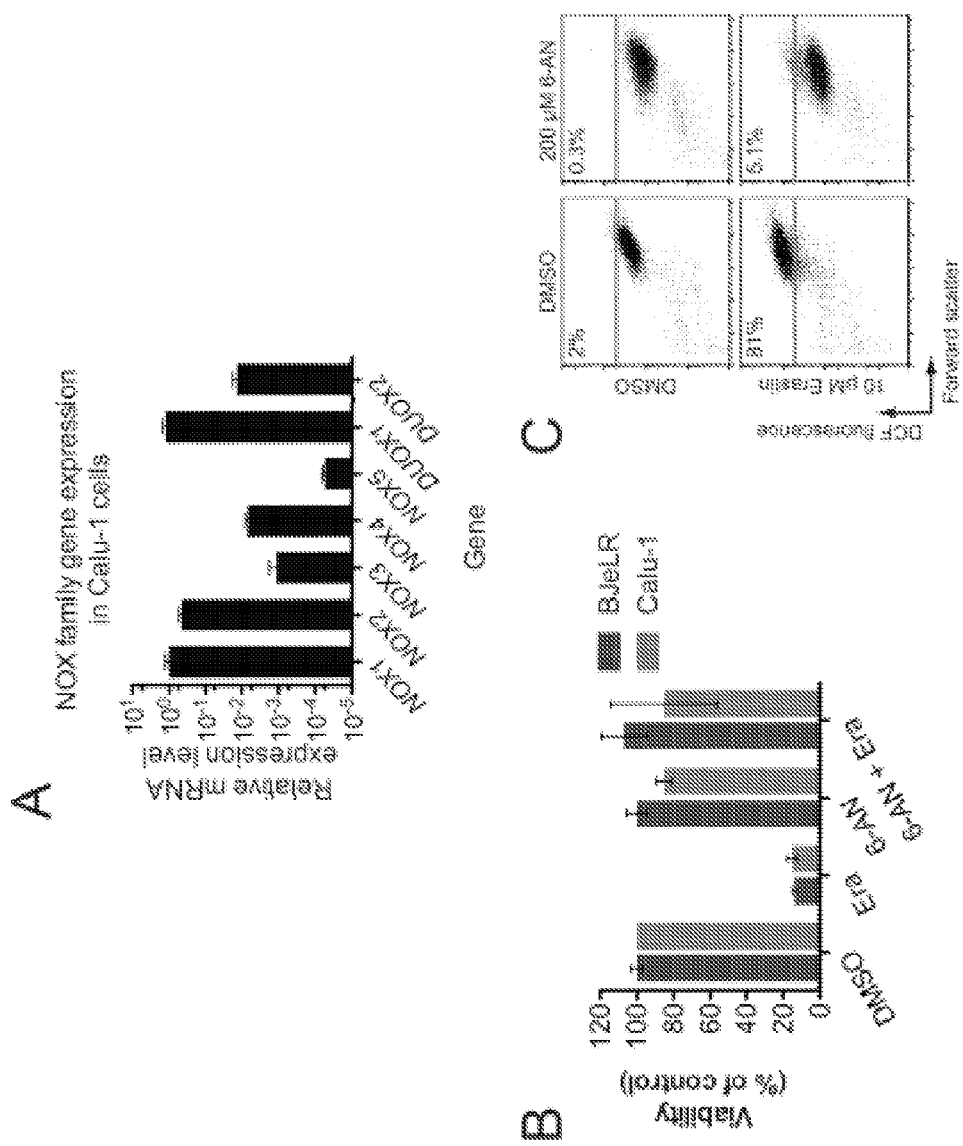
FIGS. 13A-13B show that erastin-induced death is prevented by inhibition of the PPP/NOX pathway.
FIG. 13C shows H$_2$DCFDA-reactive ROS measured in BJeLR cells that were treated for 8.5 hours, as indicated, prior to the onset of overt death in these cells. Experiments were performed at 3 times with similar results, and representative data from one experiment are shown.
Figure 14:
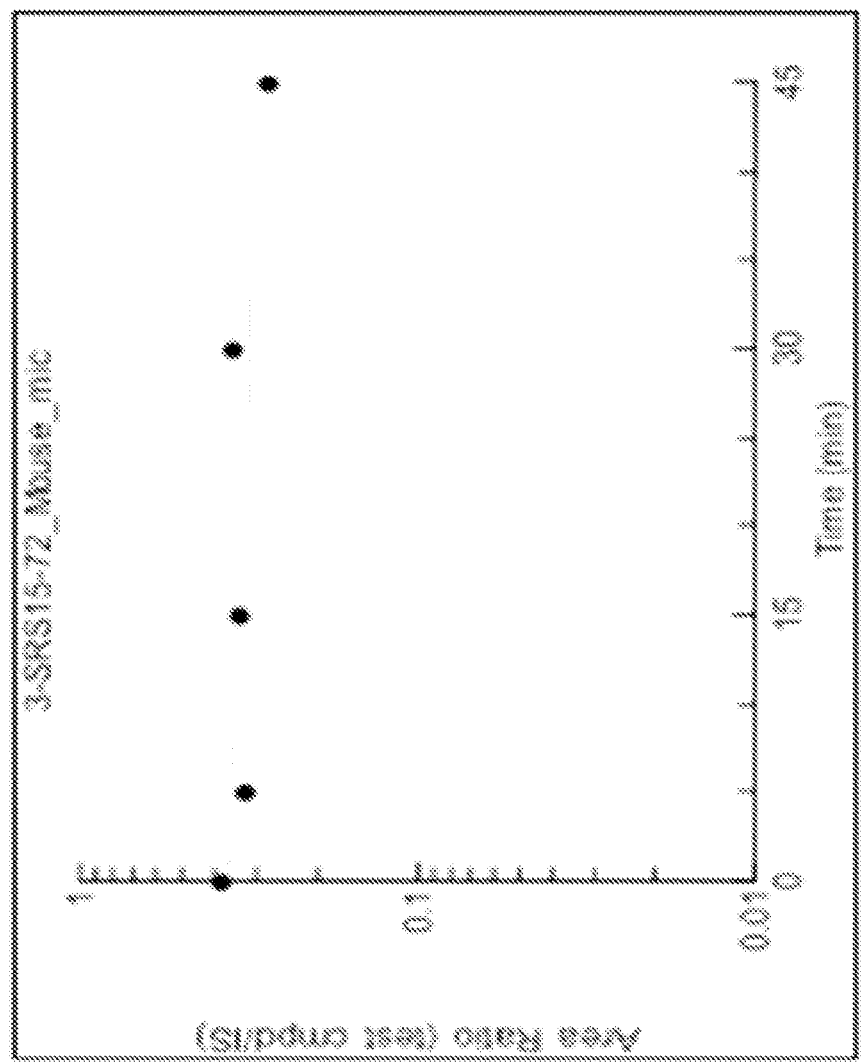
FIGS. 14A-14D show the results of mouse microsomal stability testing for certain Fer-1 analogs: SRS15-72 (FIG. 14A), SRS16-80 (FIG. 14B), SRS16-96 (FIG. 14C), and a control (FIG. 14D).
Figure 14:
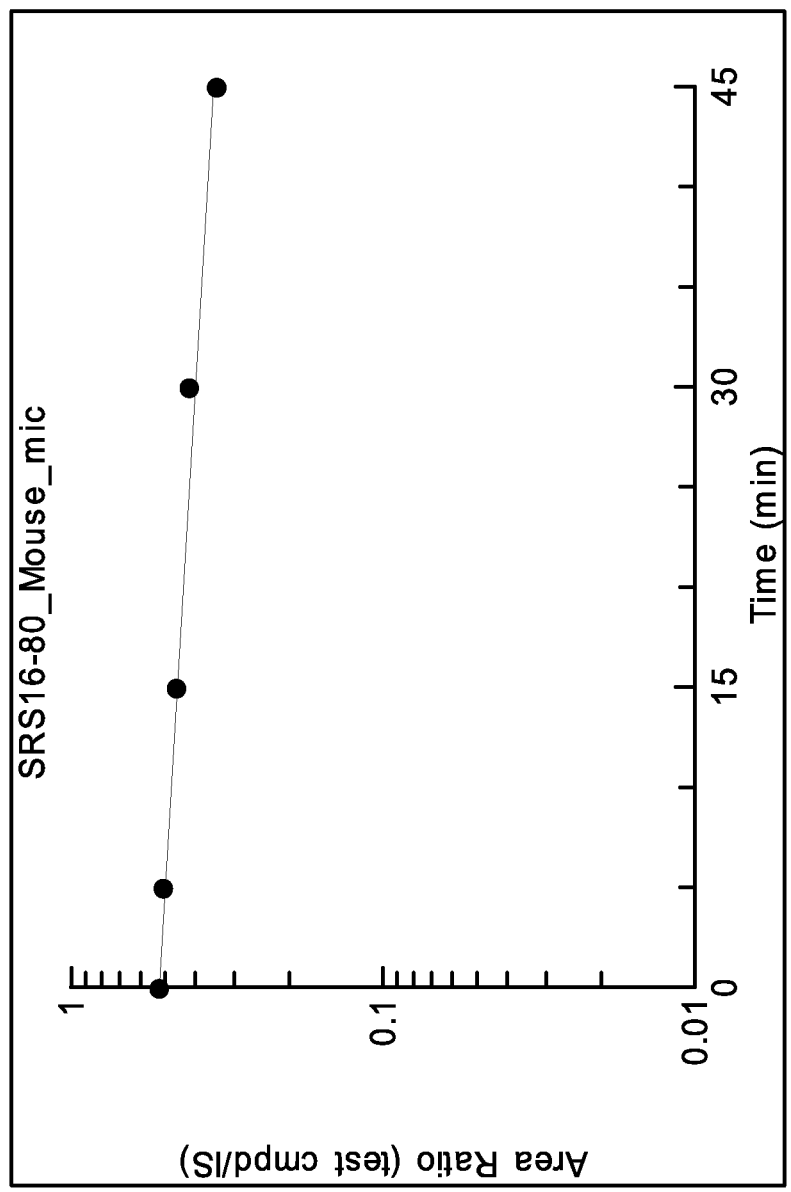
Figure 14:
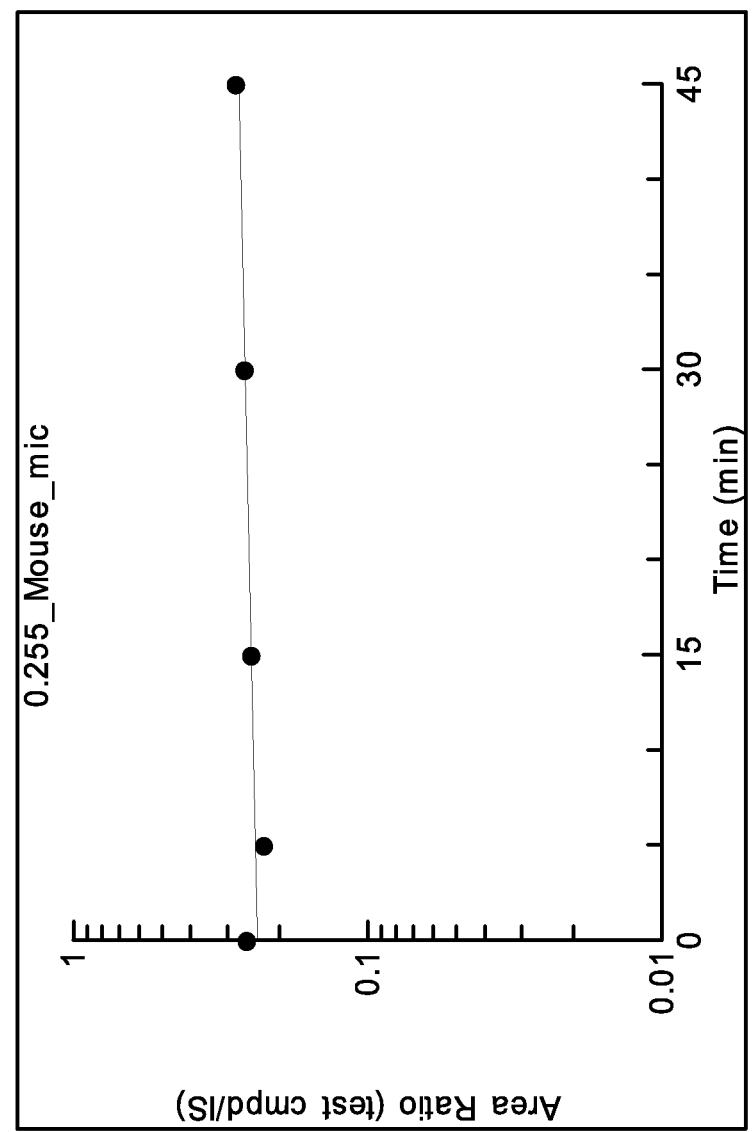
Figure 14:
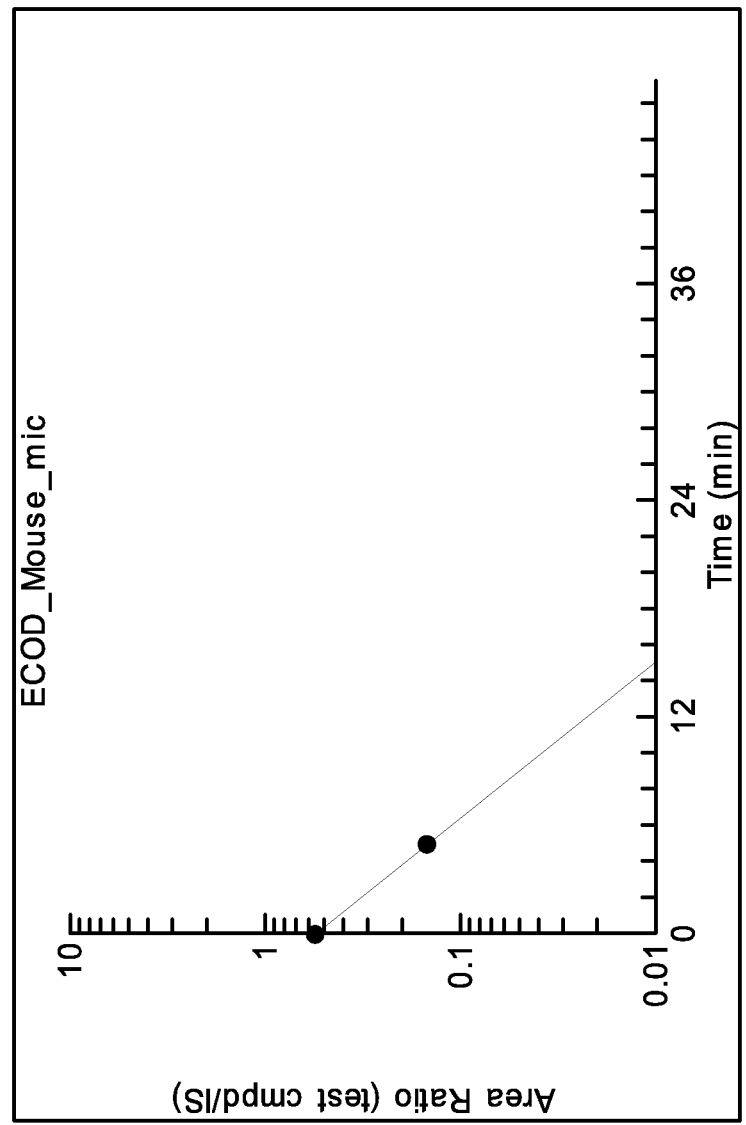

NAPDH Oxidases Provide One Source of Death-Inducing Ros in Erastin-Treated Cells Blocking system $x_c^-$ inhibits cysteine-dependent glutathione (GSH) synthesis and inhibits the trans-plasma membrane cysteine redox shuttle (Banjac et al., 2008; Ishii et al., 1981). Both effects impair cellular antioxidant defenses, thereby facilitating toxic ROS accumulation. Having ruled out the mitochondrial ETC as a source of death-inducing ROS in erastin-treated cells (FIGS. 1D-F), the role of the NADPH oxidase (NOX) family of superoxide-producing enzymes (NOX1-5, DUOX1,2), which are up-regulated in several RAS-mutant tumors (Kamata, 2009) was examined. Erastin-induced ferroptosis was strongly suppressed in Calu-1 cells by the canonical NOX inhibitor diphenylene iodonium (DPI), the NOX1/4 specific inhibitor GKT137831 (Laleu et al., 2010) and an inhibitor of the NADPH-generating pentose phosphate pathway (PPP), 6-aminonicotinamde (6-AN) (FIGS. 7A and 7B). Given that Calu-1 cells express NOX1 at much higher levels than NOX4 (FIG. 13A), NOX1 is the most likely candidate to mediate the observed NOX-dependent lethal effects in these cells. Additionally, shRNA-mediated silencing of two PPP enzymes, glucose-6-phosphate dehydrogenase (G6PD) and phosphoglycerate dehydrogenase (PGD), also prevented erastin-induced ferroptosis in Calu-1 cells to the same extent as silencing of VDAC2 (FIGS. 7C and 7D). 6-AN also prevented cell death as well as ROS production in BJeLR cells (FIGS. 13B and 13C), suggesting an important role for this pathway is these cell types. On the other hand, NOX and PPP inhibitors were only partially effective at preventing erastin-induced ferroptosis in HT-1080 cells (FIG. 7B), indicating that other pathways, in addition to the PPP/NOX pathway, can contribute to the onset of death in erastin-treated cells, once the appropriate conditions have been set by the inhibition of system $x_c^-$.

Ferroptotic death is morphologically, biochemically and genetically distinct from apoptosis, various forms of necrosis, and autophagy. This process is characterized by the overwhelming, iron-dependent accumulation of lethal lipid ROS (FIG. 7E, blue outline). Unlike other forms of apoptotic and non-apoptotic death (Christofferson and Yuan, 2010; Jacobson and Raff, 1995), this requirement for ROS accumulation appears to be universal. In at least some cells, NOX-family enzymes make important contributions to this process. Indeed, although the possibility of a death-inducing protein or protein complex activated downstream of ROS accumulation cannot be excluded, the inventors posit that the executioners of death in cancer cells undergoing ferroptosis are these ROS themselves. An important prediction of this model is that under anoxic conditions ferroptosis will be inactive. However, even here, agents such as erastin that prevent uptake of essential amino acids by system L are likely to be toxic to cells.

Using an shRNA library targeting most known genes encoding mitochondrial proteins (Pagliarini et al., 2008), specific roles for RPL8, IREB2, ATP5G3, TTC35, CS and ACSF2 in erastin-induced ferroptosis were identified. A plausible new hypothesis to emerge from these data is that CS and ACSF2 are required to synthesize a specific lipid precursor necessary for death (FIG. 7E). Just as important, the high-resolution of the arrayed approach (1 hairpin/well, minimum 5 hairpins/gene) provides confidence that the various mitochondrial genes not identified in the screen, including many implicated in apoptotic and non-apoptotic death (BID, BAK1, BAX, AIFM1, PP/F, HTRA2, ENDOG, PGAM5), are truly not required for erastin-induced ferroptosis. This screening collection will be a valuable resource for future studies of the role of the mitochondria in cell physiology.

In cancer cells, inhibition of system $x_c^-$-mediated cystine uptake by erastin, SAS or glutamate may be sufficient to initiate iron-dependent ferroptosis. Inhibition of system $x_c^-$ is, however, not necessary: RSL3 does not inhibit cystine uptake and yet triggers an otherwise similar iron and ROS-dependent ferroptototic death program. Thus, RSL3 likely modulates the activity of a target lying downstream of or in parallel to system $x_c^-$ (FIG. 7E). Importantly, this may enable RSL3 to activate ferroptosis in cells or conditions where cystine uptake via system $x_c^-$ is not limiting for survival. Lanperisone, another recently identified oncogenic RAS-selective lethal small molecule that causes non-apoptotic, iron-dependent death in mouse Kras-mutant tumor cells (Shaw et al., 2011), may also inhibit the function of system $x_c^-$ or another target in the ferroptotic pathway. Other compounds that behave as RSLs, such as PEITC, oncrasin and piperlongumine (Guo et al., 2008; Raj et al., 2011; Trachootham et al., 2006), trigger mitochondrial cytochrome C release, caspase activation and other features of apoptosis not observed in cancer cells undergoing ferroptosis. Certain tumor cells are highly resistant to apoptosis (Ni Chonghaile et al., 2011). Thus, agents such as erastin, RSL3 and lanperisone that can trigger non-apoptotic death may exhibit a unique spectrum of clinical activity.

In some brain cell populations, inhibition of system $x_c^-$ by glutamate triggers oxidative cell death dependent on iron and lipid ROS, but also $Ca^{2+}$ influx, mitochondrial damage, mitochondrial ROS production and chromatin fragmentation (Li et al., 1997; Murphy et al., 1989; Ratan et al., 1994; Tan et al., 1998; Yonezawa et al., 1996). These latter events are not required for RSL-induced ferroptosis in cancer cells, perhaps because heightened activity of NOX or other pro-oxidant enzymes, or basally altered membrane lipid composition, is sufficient to promote death in the absence of these additional features. Regardless, the oxidative death pathways triggered in cancer cells and brain cells by blockade of cystine uptake both appear to access a core iron- and ROS-dependent ferroptotic mechanism, accounting for the ability of Fer-1 and CPX to attenuate death in both cases (FIG. 7E).

The specific role of iron in ferroptosis remains unclear. Ferroptosis cannot be explained by a simple increase in $H_2O_2$-dependent, iron-catalyzed ROS production (i.e. Fenton chemistry), as $H_2O_2$-induced death is distinct from RSL-induced ferroptosis (FIGS. 1 and 2). Rather, the results are most consistent with one or more iron-dependent enzymes functioning as part of the core, oxidative lethal mechanism. The void created in the antioxidant defenses of the cell by the inhibition of cystine uptake by erastin may be required to unleash the activity of these enzymes. Thus, for better or worse, the aberrantly elevated levels of iron observed in some cancer cells (Pinnix et al., 2010) and pathological neuronal populations (Duce et al., 2010; Lei et al., 2012) may predispose to ferroptotic death in situations of cystine or cysteine limitation.

Example 10

Fer-1 and its Analogs are Able to Inhibit Death in Erastin Treated Cells

The ability of various compounds disclosed herein to inhibit death in erastin (10 μM)-treated HT-1080 cells were tested. The results are shown in Table 1 below. Cell viability was assessed by Alamar Blue. $EC_{50}$ values (nM) were computed from dose response curves.

TABLE 1

| EC50 Values | |
|---|---|
| Compound | EC50 (nM) |
| SRS8-28 (Fer-1) | 95 |
| SRS15-15 | Not active |
| SRS15-18 | 87.7 |
| SRS15-23 | 23 |
| SRS15-24 | 8.6 |
| SRS15-25 | 54.3 |
| SRS15-17 | 171.4 |
| SRS15-20_mono | 21.7 |
| SRS15-20_di | 914 |
| SRS15-21 | 23 |
| SRS15-22 | 21.1 |
| SRS15-72 | 288 |
| SRS16-41 | 16 |
| SRS16-80 | 583 |
| SRS16-86 | 367 |

Example 11

Metabolic Stability in Microsomes

Test compounds (0.5 μM) were incubated at 37° C. for up to 45 minutes in 50 mM of potassium phosphate buffer (pH 7.4) containing mouse liver microsomal protein (0.5 mg/mL) and an NADPH generating system (0.34 mg/mL β-nicotinamide adenine dinucleotide phosphate (NADP), 1.56 mg/mL glucose-6-phosphate, 1.2 units/mL glucose-6-phosphate dehydrogenase). At 0, 5, 15, 30, and 45 minute intervals, an aliquot was taken and quenched with acetonitrile (ACN) containing internal standard. No-cofactor controls at 45 minutes were prepared. Following completion of the experiment, the samples were analyzed by LC-MS/MS.

The half-life ($t_{1/2}$) was calculated using the following equation:

$$t_{1/2} = 0.693/k$$

Where, k is the elimination rate constant of test compounds obtained by fitting the data to the equation:

$$C = \text{initial} \times \exp(-k \times t)$$

Intrinsic clearance (Clint) is calculated as liver clearance from the half-life using the following equation:

$$CL\ int = \frac{rate}{min^{-1}} \times \frac{ml}{0.5\ mg} \times \frac{52.5\ mg}{g\ liver}$$

Where:
rate=k/min
0.5 mg protein/mL incubation
52.5 mg protein/g liver
The results are shown in Table 2 below. Ethoxycoumarin was used as a control.

TABLE 2

Microsomal Stability
(Mouse, Compound Conc = 0.5 µM)

| Test compound | Elimination rate constant (k) | Half life (t½) (min) | Intrinsic Clearance (CLint) (mL/min/g liver) |
|---|---|---|---|
| SRS16-80 | 0.0089 | 77.7 | 0.94 |
| SRS16-86 | <0.0048 | >90 | <0.5* |
| SRS15-72 | 0.0045 | 154.0 | 0.47 |
| SRS 16-41 | 0.3149 | 2.0 | 35.9 |
| Ethoxycoumarin | 0.2661 | 2.6 | 27.94 |

*Rate constant was negative (−0.0032 mL/min/g liver)
**: Half life more than 90 min will be reported as >90; and less than 1.4 will be reported as <1.4.
***: Rate constants for microsomes less than 0.0048 or negative will be reported as <0.0048; and more than 0.48 will be reported as >0.48.

Example 12

In Vitro Stability Study in Plasma

The assay was conducted by incubating 1 µM of test compounds with Mouse Plasma (Strain C57BL/4) for a series of incubation times (0, 15, 30, 60, 120 minutes) at various temperatures (wet ice, room temperature, or 37° C.) with 5% $CO_2$ and shaking (130 rpm). At each time point, the samples were quenched with 200 µL of stop solution containing an internal standard and kept on ice. The samples were analysed by LC-MS/MS. The results are shown in Tables 3 and 4 below.

TABLE 3

| | 37° C. | | |
|---|---|---|---|
| Compound Name | Time points (minutes) | Sum of Peak Area Ratios** | Percent Remaining* |
| SRS16-80 | 0 | 0.382 | 100.0% |
| SRS16-80 | 15 | 0.0911 | 23.8% |
| SRS16-80 | 30 | 0.0379 | 9.9% |
| SRS16-80 | 60 | 0.017 | 4.5% |
| SRS16-80 | 120 | 0.0095 | 2.5% |
| SRS16-86 | 0 | 0.9018 | 100.0% |
| SRS16-86 | 15 | 0.7414 | 82.2% |
| SRS16-86 | 30 | 0.78 | 86.5% |

TABLE 3-continued

| | 37° C. | | |
|---|---|---|---|
| Compound Name | Time points (minutes) | Sum of Peak Area Ratios** | Percent Remaining* |
| SRS16-86 | 60 | 0.7568 | 83.9% |
| SRS16-86 | 120 | 0.5758 | 63.9% |

*Percent remaining: Percentage of peak area at each time point compared to peak area at 0 min.
**Two peaks were seen for both compounds, which are believed to be the isomers. Hence, sum of the peaks were used for calculation.

TABLE 4

| | | Room Temperature | | Wet Ice | |
|---|---|---|---|---|---|
| Compound | Time points (min) | Peak Area Ratio | Percent Remaining* | Peak Area Ratio | Percent Remaining |
| SRS 15-72 | 0 | 2.0737 | 100.0% | 2.6066 | 100.0% |
| SRS 15-72 | 15 | 1.1581 | 55.8% | 2.0815 | 79.9% |
| SRS 15-72 | 30 | 0.5320 | 25.7% | 1.6279 | 62.5% |
| SRS 15-72 | 60 | 0.2502 | 12.1% | 1.4397 | 55.2% |
| SRS 15-72 | 120 | 0.0841 | 4.1% | 1.2446 | 47.7% |
| SRS 16-41 | 0 | 5.8556 | 100.0% | 6.9233 | 100.0% |
| SRS 16-41 | 15 | 0.6709 | 11.5% | 5.7631 | 83.2% |
| SRS 16-41 | 30 | 0.0885 | 1.5% | 4.7595 | 68.7% |
| SRS 16-41 | 60 | 0.0206 | 0.4% | 3.4547 | 49.9% |
| SRS 16-41 | 120 | 0.0159 | 0.3% | 1.9564 | 28.3% |

As demonstrated by Examples 10-12, the Fer-1 analogs show improved microsomal stability and solubility while maintaining good inhibition potency of ferroptosis.

Example 13

Fer-1, SRS11-92, and Analogs Thereof are Potent Inhibitors of a Variety of Clinically Relevant Oxidative Cell Death Phenotypes Fer-1 (disclosed in International Application Serial No. PCT/US/2013/035021, filed Apr. 2, 2013, which is incorporated by reference in its entirety herein) is a drug-like, easily synthesized, potent inhibitor of ferroptosis that acts via a reductive mechanism to specifically prevent the loss of unsaturated membrane lipids, whose oxidative destruction is presumably toxic to cells (see below). Fer-1 is an alkyl, diaminoaryl-type structure. The structurally related diarylamines and hindered dialkylamines are well-established antioxidants (also known as scavengers or reducing agents) used in the food industry and in the materials industry (Huang, et al., 2005). These antioxidants retard autoxidation that is caused primarily by radical chain reactions between oxygen and the substrates. There has been a tremendous interest in investigating the effect of phenols, diphenylamines and hindered alkylamines as potential antioxidants in biological and medicinal systems toward the search of novel therapeutics (Behl, et al., 1999). Most studies of amine antioxidants have been focused either on diarylamines or hindered dialkylamines. Here, a third subfamily of antioxidants, the alkyl, diaminoarenes, represented by Fer-1, is described.

Figure 15:
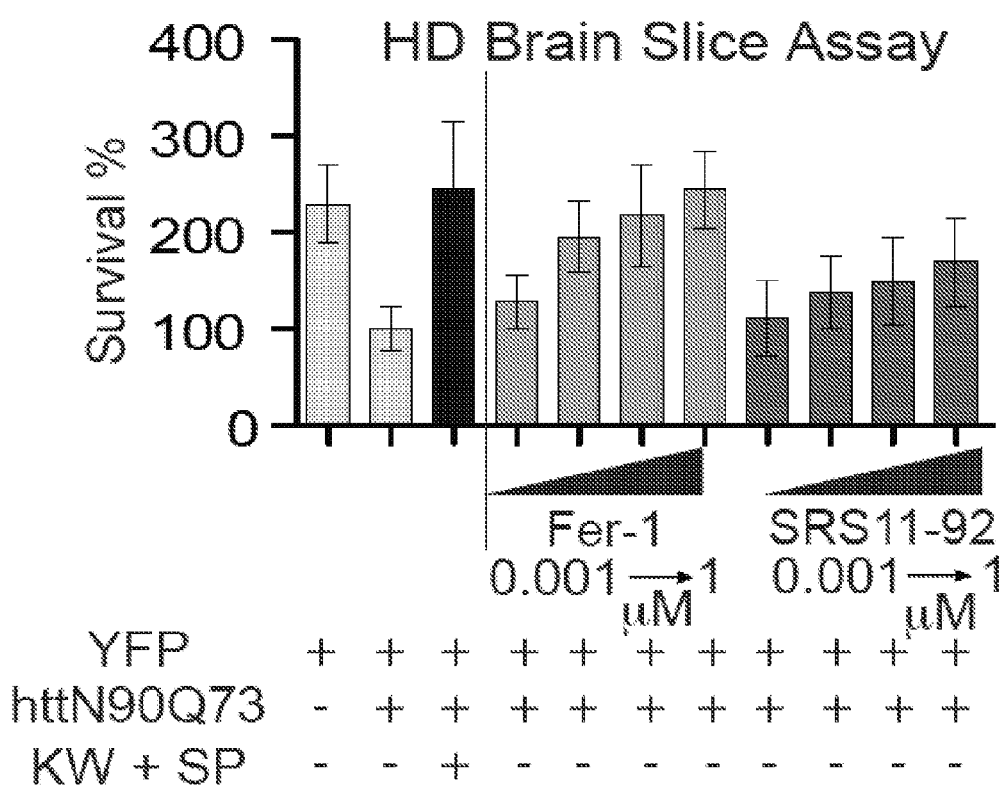
FIGS. 15A-C show the effects of ferrostatins in Huntington's disease (HD).
Figure 15:
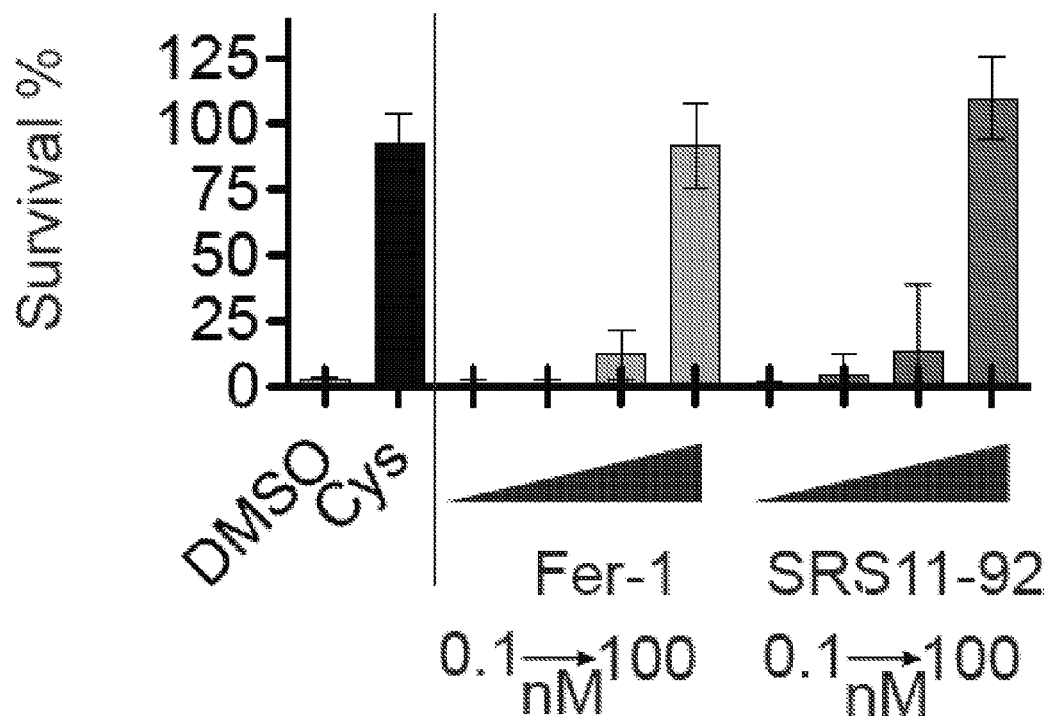
Figure 15:
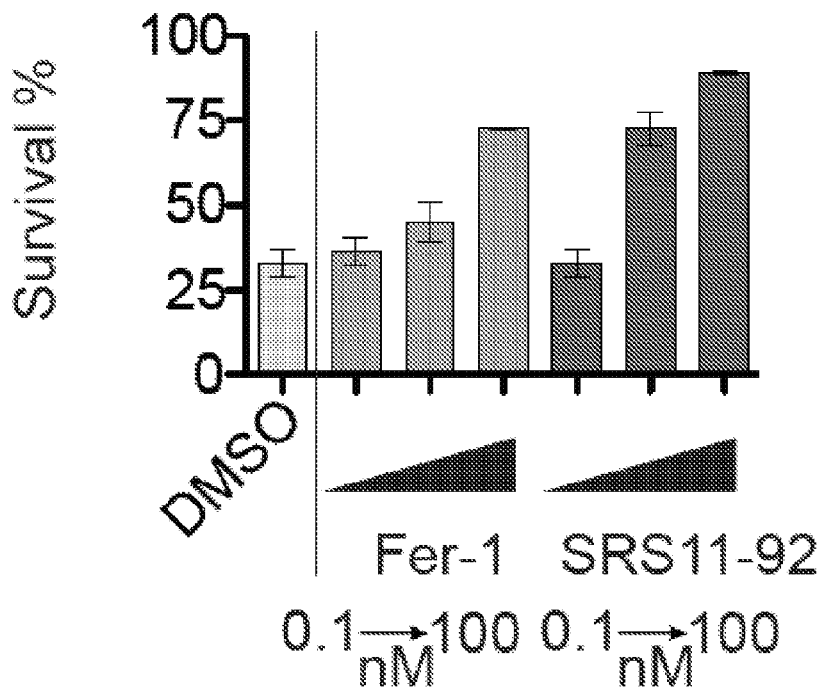

Fer-1 attenuates lipid peroxidation and ferroptosis in cancer cells treated with small molecules that block cystine import or glutathione production, as well as cell death in rat organotypic hippocampal brain slices treated with toxic concentrations of glutamate, which also blocks cystine import (Dixon, et al., 2012). Therefore, Fer-1 could be effective at preventing iron-dependent oxidative stress and/ or glutamate toxicity in other contexts. Huntington's disease (HD), like other aging-associated diseases, is reported to involve perturbation of glutamate (Petr, et al., 2013, Ribeiro, et al., 2011, Anitha, et al., 2011, Miller, et al., 2010, Estrada Sanchez, et al., 2008, Zeron, et al., 2002, Cha, et al., 1998), glutathione (Mason, et al., 2013, Ribeiro, et al., 2012, Cruz-Aguado, et al., 2000) and iron (Chen, et al., 2013, Bartzokis, et al., 1999, Morrison, et al., 1994, Chen, et al., 1993) levels, the accumulation of lipid oxidation breakdown products (Johri, et al., 2012), and non-apoptotic neuronal cell death (Turmaine, et al., 2000). In fact, Fer-1 prevents cell death in rat corticostriatal brain slices induced by the expression, via biolistic transformation, of a huntingtin (htt) exon 1 fragment with a pathogenic repeat (73Q) (mN90Q73), along with yellow fluorescent protein (YFP) to mark transfected neurons (FIG. 15A). Slices were treated with DMSO (vehicle control), a positive control death inhibitor combination of the adenosine A2R receptor antagonist KW-6002 (KW, 50 µM) and the JNK inhibitor SP600125 (SP, 30 µM), or ferrostatins (Fer-1 or SRS11-92, an effective analog, 1 nM to 1 µM). Four days later, the number of healthy medium spiny neurons (MSNs) was quantified, as previously described (Varma, et al., 2011, Hoffstrom, et al., 2010). A significant increase in the number of healthy MSNs was observed upon Fer-1 and SRS11-92 treatment at 10 nM, 100 nM and 1 µM. Moreover, with 1 µM treatment of Fer-1, the number of healthy MSNs was statistically indistinguishable from both the YFP (no htt) control and the control inhibitor combination (KW+SP) (FIG. 15A).

Fer-1 was also found to be effective in an in vitro model of periventricular leukomalacia (PVL), a syndrome afflicting premature infants that is caused primarily by the death of developing oligodendrocytes (OLs) (Desilva, et al., 2008, Follett, et al., 2004, Dommergues, et al., 1998) (FIG. 15B). It has been suggested that OL death is iron-dependent (Dommergues, et al., 1998); in autopsy studies, elevated levels of lipid ROS biomarkers are observed, potentially suggesting the involvement of ferroptosis (Desilva, et al., 2008, Follett, et al., 2004, Folkerth, et al., 2006, Haynes, et al., 2005, Haynes, et al., 2003). To trigger death, cultured OLs were exposed to cystine-free conditions, which ultimately deplete glutathione. Fer-1, SRS11-92 and Fer-1 analogs fully protected OLs from cystine deprivation when tested at 100 nM (FIG. 15B).

In addition, the efficacy of Fer-1, SRS11-92, and selected analogs was tested in a model of iron-induced cell death in freshly isolated mouse kidney proximal tubules that simulates major elements of rhabdomyolysis-induced acute kidney injury (FIG. 15C). Cell death in this model is known to involve oxidative lipid damage (Sogabe, et al., 1996, Park, et al., 2011); it was therefore believed that Fer-1 might be protective. 10 µM each of hydroxyquinoline and ferrous ammonium sulfate (HQ+Fe) were used to induce cell death, which was quantified by monitoring LDH release after 60 min. In this model, Fer-1, SRS11-92 and analogs prevented lethality (FIG. 15C). Together, the results of these assays demonstrate that Fer-1, SRS11-92 and analogs are potent inhibitors of a variety of clinically relevant oxidative cell death phenotypes. By implication, cell death in these models may involve, at least in part, the induction of lipid peroxidation and perhaps ferroptosis.

Example 14

Fer-1 is not a General Antioxidant

Figure 16:
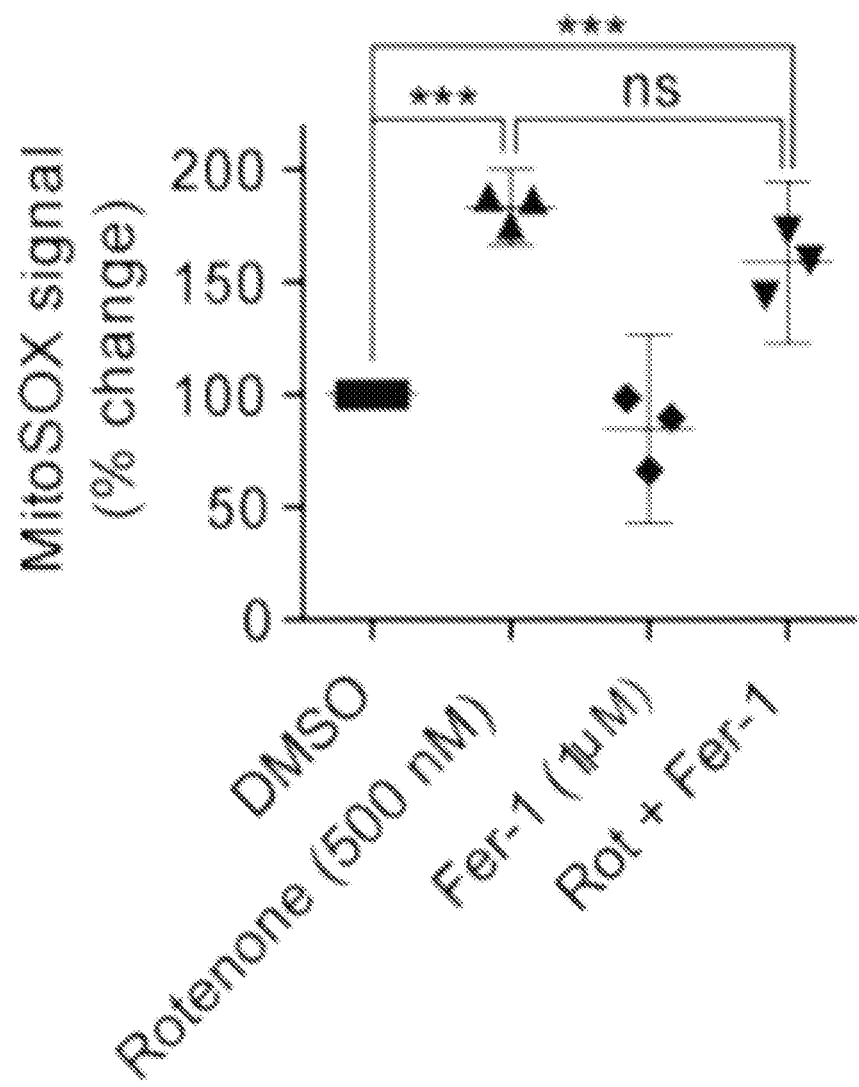
FIGS. 16A-C show that Fer-1 does not inhibit all forms of ROS production or ROS-inducted death.
Figure 16:
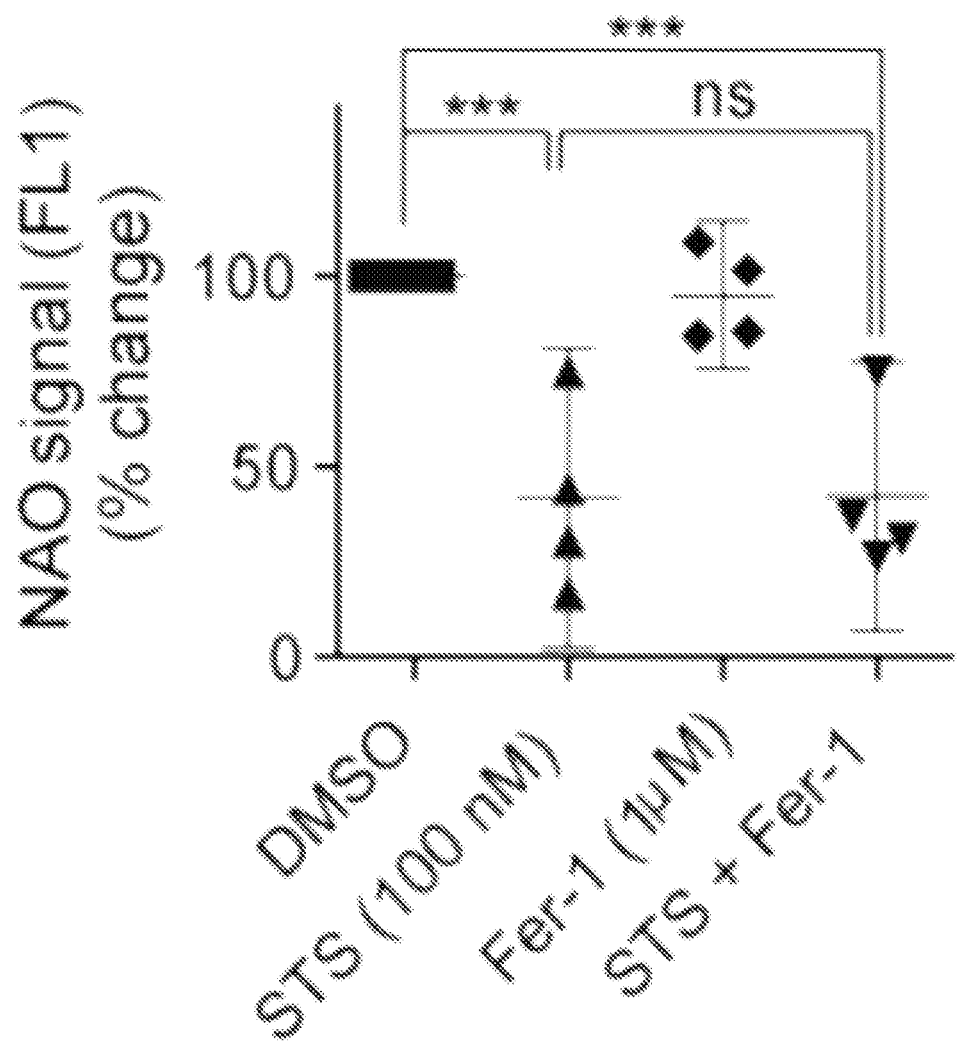
Figure 16:
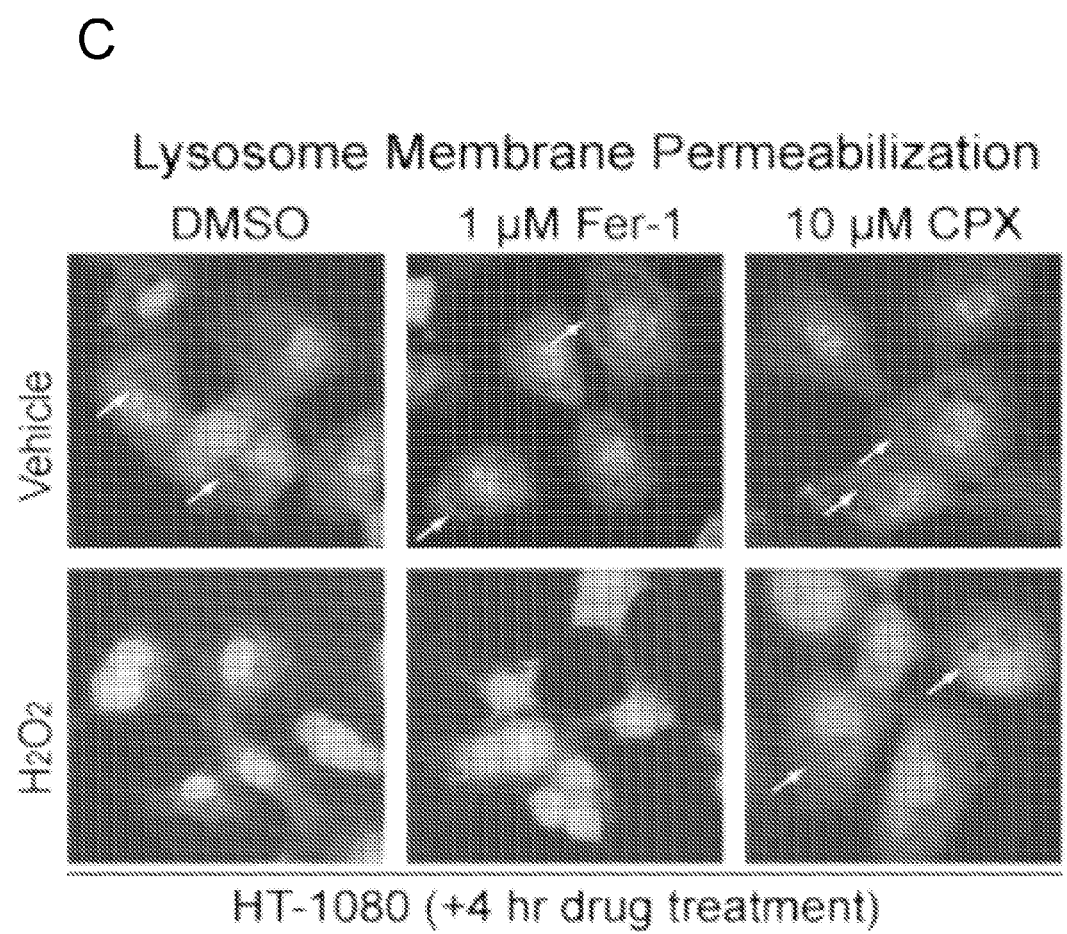

Given that ROS also play important homeostatic roles, an important consideration in the design of antioxidants is specificity: that they only inhibit pathogenic ROS. Fer-1 was found to be able to prevent specific forms of ROS accumulation. In HT-1080 cancer cells, Fer-1 did not prevent the accumulation of mitochondrial superoxide in response to the electron transport chain inhibitor rotenone (detected using the fluorescent probe MitoSOX) (FIG. 16A), mitochondrial cardiolipin oxidation in response to the apoptosis inducing agent staurosporine (detected using the fluorescent probe 10-N-nonylacridine orange) (FIG. 16B), or lysosomal membrane destruction in response to $H_2O_2$ (detected by following acridine orange re-localization) (FIG. 16C), consistent with the inability of Fer-1 to prevent cell death involving mitochondrial ROS overproduction, apoptosis or lysosome rupture in these cells. These results revealed that Fer-1 is not a general antioxidant; the effect of Fer-1 is restricted to certain ROS, membranes and/or membrane lipids.

Example 15

Ferrostatin Structure Activity Relationships and Improved Pharmacokinetic/Pharmacodynamic Properties Solvents, inorganic salts, and organic reagents were purchased from commercial sources such as Sigma and Fisher and used without further purification unless otherwise mentioned. Erastin was dissolved in DMSO to a final concentration of 73.1 mM and stored in aliquots at −20° C.

Chromatography: Merck pre-coated 0.25 mm silica plates containing a 254 nm fluorescence indicator were used for analytical thin-layer chromatography. Flash chromatography was performed on 230-400 mesh silica (SiliaFlash® P60) from Silicycle.

Spectroscopy: $^1H$, $^{13}C$ and $^{19}F$ NMR spectra were obtained on a Bruker DPX 400 MHz spectrometer. HRMS spectra were taken on double focusing sector type mass spectrometer HX-110A. Maker JEOL Ltd. Tokyo Japan (resolution of 10,000 and 10 KV accel. Volt. Ionization method; FAB (Fast Atom Bombardment) used Xe 3Kv energy. Used Matrix, NBA (m-Nitro benzyl alcohol).

Scheme 5

General Scheme: General synthetic scheme for the synthesis of Ferrostatin-1 and other ferrostatins.

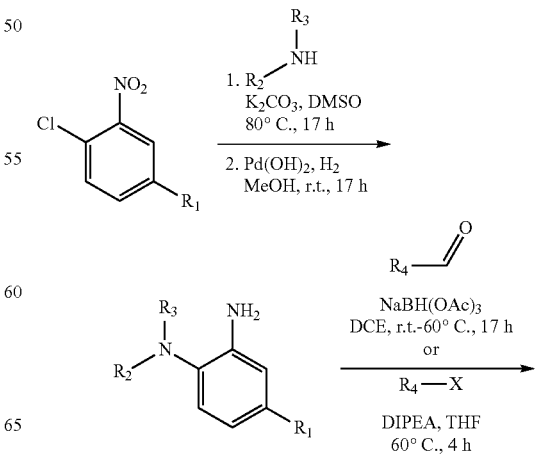

-continued

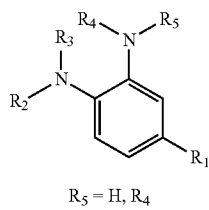

Ferrostatin-1: $R_1$ = $CO_2Et$; $R_2$ = cyclohexyl; $R_3$ = H.
$R_5$ = H, $R_4$ General Procedure A (ArS$_N$2 Reaction) (Beaulieu et al., 2003)

To the ethyl 4-chloro-3-nitrobenzoate (1 equiv., 200 mg, 0.871 mmol) in dry DMSO (2 mL) was added $K_2CO_3$ (2 equiv., 240.8 mg, 1.742 mmol) and various amines (1.2 equiv., 119.5 µL, 1.045 mmol). The mixture was stirred for 17 hours at 60° C. The solution was poured in water, and the organic layer was extracted three times with ethyl acetate. After drying with anhydrous magnesium sulfate, the solvents were removed under vacuum. The residue was purified by flash-column chromatography on silica gel to provide the desired ethyl 4-(substituted-amino)-3-nitrobenzoate derivatives.

General Procedure B (Hydrogenolysis)

The ethyl 4-(substituted-amino)-3-nitrobenzoates (130 mg, 0.445 mmol) were dissolved in MeOH (10 mL) and hydrogenated ($H_2$ gas) over 10% Pd(OH)$_2$ on charcoal (90 mg) for 17 hours at room temperature. The solution was filtered through a pad of celite, and volatiles were removed under vacuum. The residue was purified by flash-column chromatography on silica gel to provide the desired Ferrostatin-1 derivatives.

General Procedure C (Reductive Amination Reaction) (Abdel-Magid et al., 1996)

A representative example is the reductive amination of Fer-1 with benzaldehyde.

Method I: the ethyl 3-amino-4-(cyclohexylamino)benzoate (Fer-1) (100 mg, 0.382 mmol, 1 equiv) and benzaldehyde (39 µL, 0.382 mmol, 1 equiv) were heated in DCE for 1 hour at 80° C. in the presence of molecular sieve (4 Å), and then the mixture was cooled down to room temperature before addition of the NaBH(OAc)$_3$ in small portions over 3 hours. The reaction mixture was stirred at room temperature under a nitrogen atmosphere for 17 hours. The reaction mixture was quenched with aqueous saturated NaHCO$_3$, and the product was extracted with EtOAc. The EtOAc extract was dried (MgSO$_4$), and the solvent was evaporated. The residue was purified by flash-column chromatography on silica gel to provide the desired ethyl 3-(benzylamino)-4-(cyclohexylamino)benzoate.

Method II: To the ethyl 3-amino-4-(cyclohexylamino) benzoate (Fer-1) (100 mg, 0.382 mmol, 1 equiv) and benzaldehyde (39 µL, 0.382 mmol, 1 equiv) in DCE was added NaBH(OAc)$_3$ (129.5 mg, 0.611 mmol, 1.6 equiv). The reaction mixture was treated in the same way as in method I.

General Procedure D (Alkylation Reaction)

A representative example is the methylation of the SRS8-70 (Table 1, entry 18) using methyl iodide. To the ethyl 3-amino-4-(cyclooctylamino)benzoate (SRS8-70; 58 mg, 0.199 mmol) in DMF (1 mL), MeI (28 µL, 0.398 mmol) and $K_2CO_3$ (82 mg, 0.508 mmol) were added. The mixture was stirred at 40° C. for 6 hours then poured in water. The organic layer was extracted with EtOAc then dried under MgSO$_4$, and the solvent was evaporated. The residue was purified by flash-column chromatography on silica gel to provide the desired ethyl 4-(cyclooctylamino)-3-(dimethylamino)benzoate (SRS9-01).

General Procedure E (Addition of the Fer-1 to an Acylchloride, Alkyl-, Benzyl-Chloroformates)

A representative example is the addition of aniline of the Fer-1 to the benzylchloroformate. To the ethyl 3-amino-4-(cyclohexylamino)benzoate (Fer-1; SRS8-28; 22 mg, 0.084 mmol) in THF (1 mL), benzylchloroformate (24 µL, 0.168 mmol) and DIPEA (44 µL, 0.252 mmol) were added at 0° C. The mixture was stirred at room temperature for 17 hours then poured in water. The organic layer was extracted with EtOAc then dried under MgSO$_4$, and the solvent was evaporated. The residue was purified by flash-column chromatography on silica gel to provide the desired ethyl 3-(benzyloxycarbonylamino)-4-(cyclohexylamino)benzoate (SRS11-89, SI Table 5, entry 2).

A general route to ferrostatin analogs using a three-step synthesis generated 67 analogs. An SNAr reaction between the commercially available ethyl 4-chloro-3-nitrobenzoate and cyclohexylamine, followed by catalytic hydrogenolysis of the nitro group, provided the desired ferrostatin derivatives. The anilines of the latter were reacted through reductive amination with arylaldehydes in the presence of sodium triacetoxyborohydride or through straightforward alkylation with arylalkylhalides in the presence of Hunig's base (Scheme 5). Examination of the Fer-1 structure suggests a possible release of two protons and two electrons, resulting in the formation of a redox-stable compound B (Scheme 6). This mechanism could form the basis for the antioxidant scavenging ability of Fer-1; the imine analog SRS16-86 is likely reduced in cells if it acts through this mechanism.

Scheme 6: Fer-1 as a reducing agent: release of 2 protons and 2 electrons results in a formation of ethyl 4-(cyclohexylimino)-3-iminocyclohexa-1,5-dienecarboxylate intermediate B.

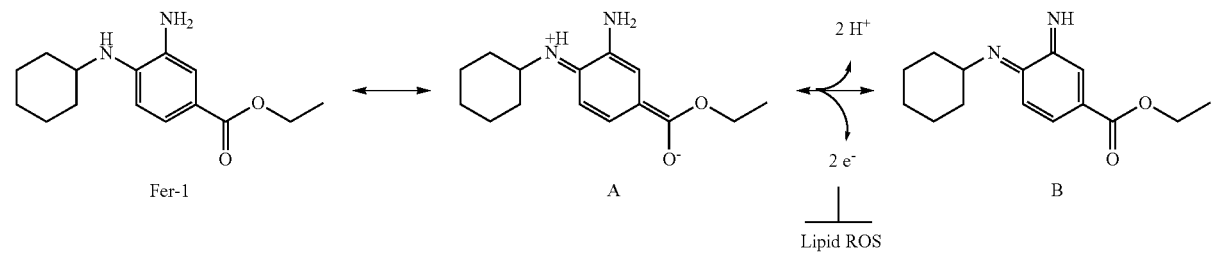

TABLE 2

SI, Synthetic scheme of Ferrostatin-1 analogs with various hydrophobic moieties. See, e.g., Dixon et al., Cell 2012, 149, 1060-1072.

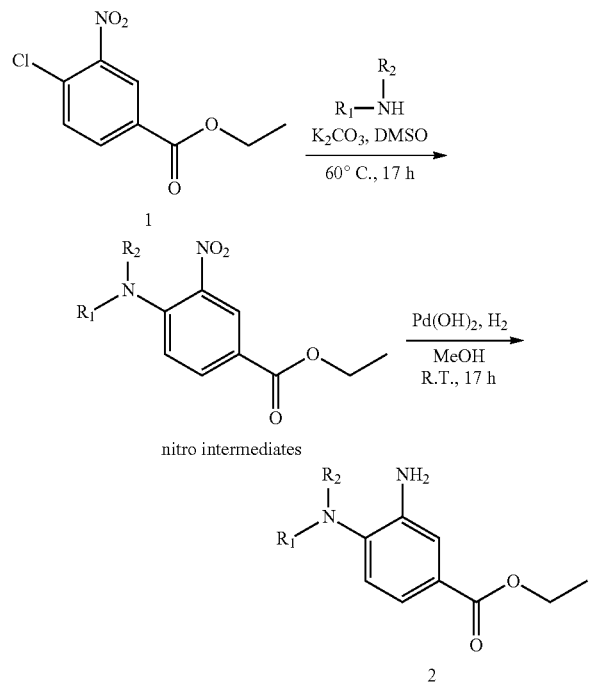

| | R₁ | R₂ | Name (Yield) | EC50 (nM) | Log P |
|---|---|---|---|---|---|
| 1 | cyclohexyl | H | Fer-1 (SRS8-28)[1] (85%) | 95 | 3.2 |
| 2 | cyclopropyl | H | SRS8-72[1] (74%) | 880 | 1.9 |
| 3 | cyclobutyl | H | SRS8-71[1] (80%) | 265 | 2.3 |
| 4 | cyclopentyl | H | SRS8-73[1] (85%) | 120 | 2.7 |
| 5 | phenyl | H | SRS8-42[1] (64%) | 200 | 2.9 |
| 6 | methylcyclohexyl | H | SRS8-48[1] (89%) (80% as mixture of isomers) | 90 | 3.5 |
| 7 | t-butylcyclohexyl | H | SRS13-10_F1_ single isomer SRS13-10_F2_ single isomer SRS13-10[1]_F1+F2_ mixture of isomers | 44 13 62 | 4.7 |
| 8 | cycloheptyl | H | SRS8-90[1] (86%) | 130 | 3.6 |

TABLE 2-continued

SI, Synthetic scheme of Ferrostatin-1 analogs with various hydrophobic moieties. See, e.g., Dixon et al., Cell 2012, 149, 1060-1072.

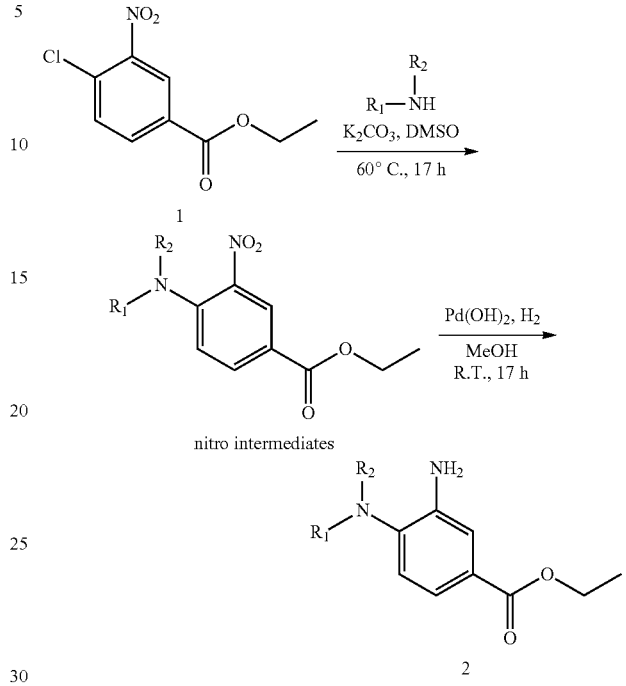

| | R₁ | R₂ | Name (Yield) | EC50 (nM) | Log P |
|---|---|---|---|---|---|
| 9 | cyclooctyl | H | SRS8-70[1] (89%) | 80 | 4.1 |
| 10 | n-heptyl | H | SRS8-94[1] (90%) | 80 | 4.3 |
| 11 | bicyclic | H | SRS9-06[1] (80%) | 70 | 5.8 |

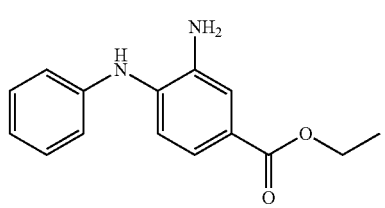 [SMILES: CCOC(=O)c1ccc(Nc2ccccc2)c(N)c1]

Synthesis of ethyl 3-amino-4-(phenylamino)benzoate (SRS8-42. SI, Table 2)

$^1$H NMR (400 MHz, CDCl$_3$) δ 7.52 (d, J=7.9 Hz, 2H), 7.30 (t, J=7.9 Hz, 2H), 7.19 (d, J=8.1 Hz, 1H), 6.97 (d, J=8.3 Hz, 3H), 5.74 (s, NH), 4.37 (q, J=7.1 Hz, 2H), 3.70 (s, NH$_2$), 1.41 (t, J=7.1 Hz, 3H); $^{13}$C NMR (126 MHz, CDCl$_3$) δ 166.8, 142.9, 137.9, 135.6, 129.4, 124.6, 121.8, 121.3, 118.4, 117.9, 60.7, 14.4.

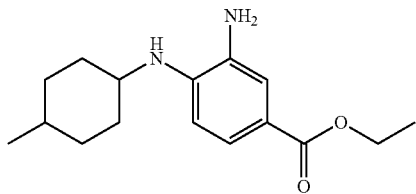 [SMILES: CCOC(=O)c1ccc(NC2CCC(C)CC2)c(N)c1]

Synthesis of ethyl 3-amino-4-(4-methylcyclohexylamino)benzoate (SRS8-48. SI, Table 2)

$^1$H NMR (CDCl$_3$, 400 MHz) δ 7.58 (d, J=8.3 Hz, 1H), 7.41 (s, 1H), 6.59 (d, J=8.4 Hz, 1H), 4.30 (d, J=7.1 Hz, 2H), 3.26 (s, 1H), 2.13 (d, J=11.2 Hz, 2H), 1.78 (d, J=12.3 Hz, 2H), 1.35 (t, J=7.0 Hz, 4H), 1.23-1.07 (m, 3H), 0.93 (d, J=6.4 Hz, 3H); $^{13}$C NMR (100 MHz, CDCl$_3$) δ 166.98, 141.15, 132.14, 124.13, 119.19, 118.69, 110.50, 60.25, 52.21, 33.91, 33.11, 32.23, 22.20, 14.46; HRMS (FAB) calculated for C$_{16}$H$_{24}$N$_2$O$_2$: 276.37; found: 276.2.

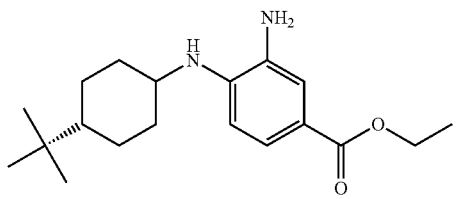

Synthesis of single isomer of ethyl 3-amino-4-(4-tert-butylcyclohexyl-amino)benzoate (SRS13-10 F1. SI, Table 2)

$^1$H NMR (CDCl$_3$, 400 MHz) δ 7.49 (d, J=8.4 Hz, 1H), 7.43 (s, 1H) 0.6.61 (d, J=8.4 Hz, 1H), 4.32 (q, J=7.1 Hz, 2H), 3.86 (b, 1H), 3.25 (b, 1H+NH$_2$), 2.26-2.13 (m, 2H), 1.95-1.81 (m, 2H), 1.43-1.33 (m, 3H), 1.22-1.12 (m, 4H), 1.10-1.04 (m, 1H), 0.89 (s, 9H); $^{13}$C NMR (100 MHz, CDCl$_3$) δ 167.0, 142.3, 131.67, 124.3, 118.6, 118.4, 109.52, 60.2, 52.0, 47.7, 33.82, 32.4, 27.6, 26.2, 14.5; HRMS (FAB) calculated for C$_{19}$H$_{30}$N$_2$O$_2$: 318.45; found: 318.24.

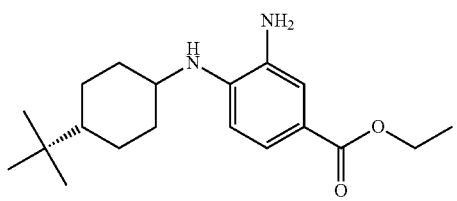

Synthesis of single isomer of ethyl 3-amino-4-(4-tert-butylcyclohexyl-amino)benzoate (SRS13-10 F2. SI, Table 2)

$^1$H NMR (CDCl$_3$, 400 MHz) δ 7.66-7.56 (m, 1H), 7.44 (s, 1H). 6.65-6.56 (m, 1H), 4.39-4.26 (m, 2H), 3.75 (s, 1H), 3.22 (B, NH$_2$), 2.10-2.96 (m, 2H), 1.70-1.52 (m, 4H), 1.43-1.34 (m, 3H), 1.30-1.20 (m, 2H), 1.13-1.05 (m, 1H), 0.88 (s, 9H); $^{13}$C NMR (100 MHz, CDCl$_3$) δ 167.1, 142.4, 131.9, 124.5, 118.7, 118.4, 109.6, 60.1, 47.8, 46.5, 32.5, 30.3, 27.4, 21.6, 14.45; HRMS (FAB) calculated for C$_{19}$H$_{30}$N$_2$O$_2$: 318.45; found: 318.24.

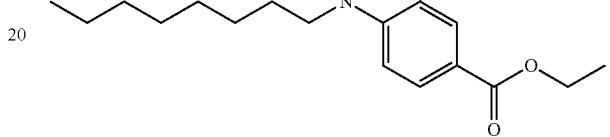

Synthesis of ethyl 3-amino-4-(octylamino)benzoate (SRS8-94. SI, Table 2)

$^1$H NMR (CDCl$_3$, 400 MHz) δ 7.61 (d, J=8.3 Hz, 1H), 7.43 (d, J=2.0 Hz, 1H), 6.60 (d, J=8.3 Hz, 1H), 4.33 (q, J=7.1 Hz, 2H), 3.17 (t, J=7.1 Hz, 2H), 1.69 (q, J=7.3 Hz, 2H), 1.52-1.23 (m, 13H), 0.91 (t, J=6.6 Hz, 3H); $^{13}$C NMR (100 MHz, CDCl$_3$) δ 167.1, 143.2, 131.9, 124.3, 118.9, 118.1, 109.2, 60.2, 43.7, 31.8, 29.4, 29.3, 27.2, 22.7, 14.5, 14.1; HRMS (FAB) calculated for C$_{17}$H$_{28}$N$_2$O$_2$: 292.42. found: 292.22.

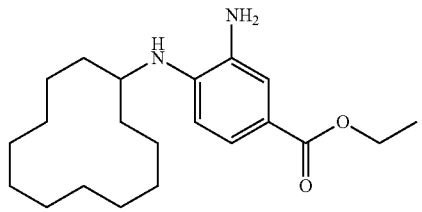 [SMILES: CCOC(=O)c1ccc(NC2CCCCCCCCCCC2)c(N)c1]

Synthesis of ethyl 3-amino-4-(cyclododecylamino)benzoate (SRS9-06. SI, Table 2)

$^1$H NMR (400 MHz, CDCl$_3$) δ 7.62 (d, J=8.4 Hz, 1H), 7.43 (s, 1H), 6.60 (d, J=9.6 Hz, 1H), 4.32 (d, J=9.6 Hz, 2H), 3.19 (s, 1H), 1.43 (d, J=26.7 Hz, 25H), 1.28 (s, 3H); $^{13}$C NMR (100 MHz, CDCl$_3$) δ 167.1, 142.6, 131.7, 124.5, 118.6, 118.16, 109.2, 60.2, 49.2, 29.6, 24.33, 24.0 23.3, 23.2, 21.22, 14.5; HRMS (FAB) calculated for O$_{21}$H$_{34}$N$_2$O$_2$: 346.51; found: 346.29.

TABLE 3

SI, EC50 and Log P of Ferrostatin-1 analogs with various cyclic amines bearing heteroatoms.

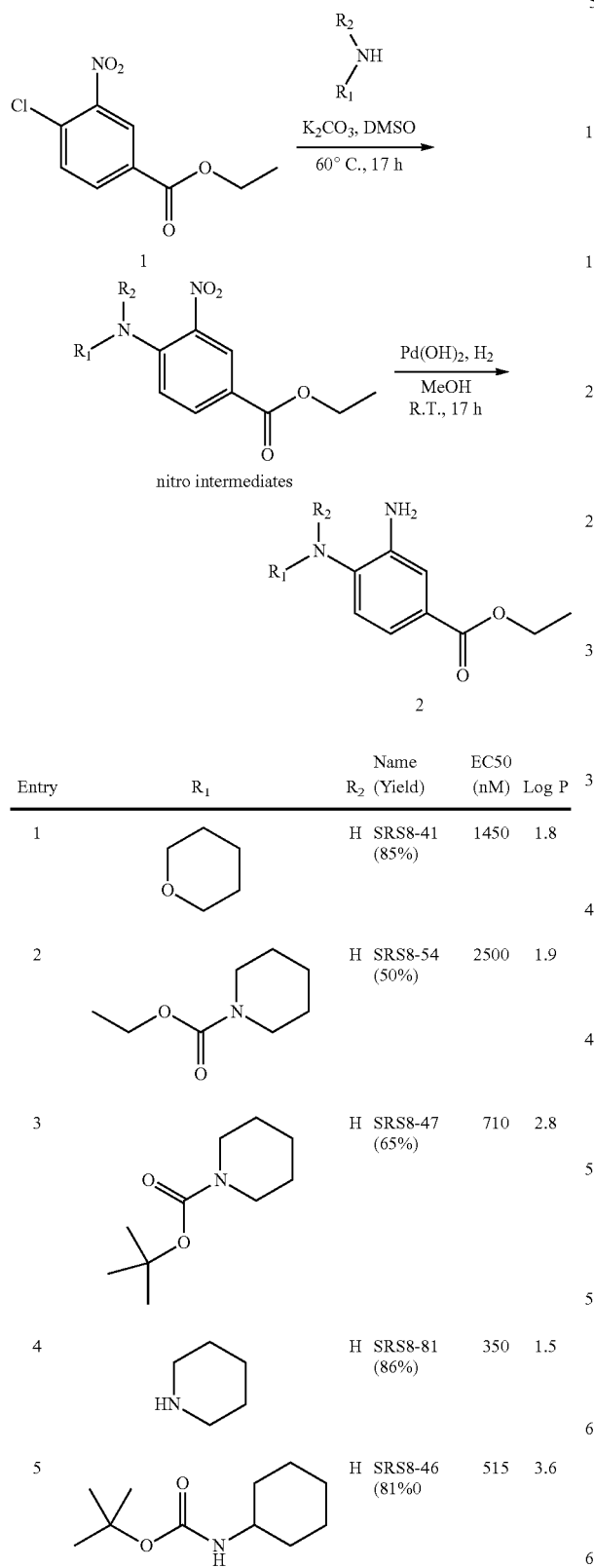

| Entry | R₁ | R₂ | Name (Yield) | EC50 (nM) | Log P |
|---|---|---|---|---|---|
| 1 | tetrahydropyran | H | SRS8-41 (85%) | 1450 | 1.8 |
| 2 | ethyl piperidine-1-carboxylate | H | SRS8-54 (50%) | 2500 | 1.9 |
| 3 | tert-butyl piperidine-1-carboxylate | H | SRS8-47 (65%) | 710 | 2.8 |
| 4 | piperidine | H | SRS8-81 (86%) | 350 | 1.5 |
| 5 | tert-butyl cyclohexylcarbamate | H | SRS8-46 (81%) | 515 | 3.6 |

TABLE 3-continued

SI, EC50 and Log P of Ferrostatin-1 analogs with various cyclic amines bearing heteroatoms.

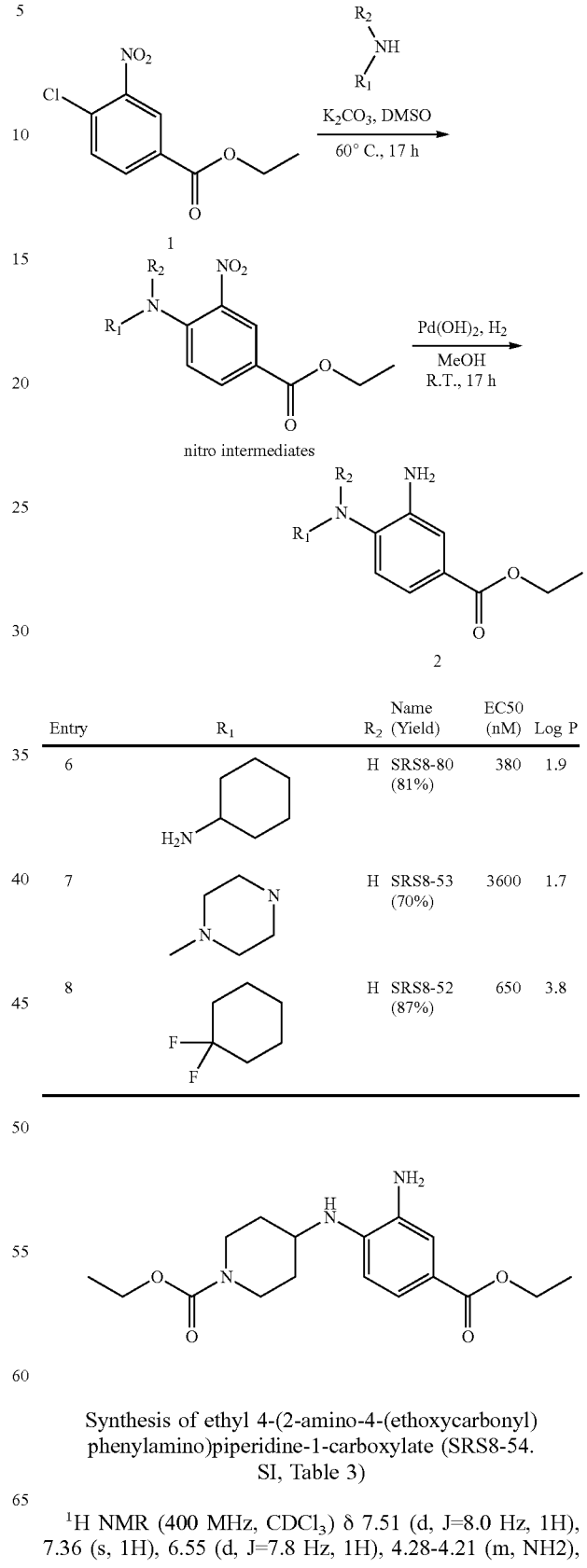

| Entry | R₁ | R₂ | Name (Yield) | EC50 (nM) | Log P |
|---|---|---|---|---|---|
| 6 | cyclohexylamine | H | SRS8-80 (81%) | 380 | 1.9 |
| 7 | 1-methylpiperazine | H | SRS8-53 (70%) | 3600 | 1.7 |
| 8 | 1,1-difluorocyclohexane | H | SRS8-52 (87%) | 650 | 3.8 |

Synthesis of ethyl 4-(2-amino-4-(ethoxycarbonyl) phenylamino)piperidine-1-carboxylate (SRS8-54. SI, Table 3)

¹H NMR (400 MHz, CDCl₃) δ 7.51 (d, J=8.0 Hz, 1H), 7.36 (s, 1H), 6.55 (d, J=7.8 Hz, 1H), 4.28-4.21 (m, NH2), 4.12-4.00 (m, 4H), 3.47 (s, 1H), 2.96 (s, 2H), 1.98 (s, 2H), 1.44-1.11 (m, 10H); $^{13}$C NMR (100 MHz, CDCl$_3$) δ 167.0, 155.5, 141.1, 132.5, 123.8, 119.0, 118.3, 109.5, 61.4, 60.2, 49.5, 42.6, 32.0, 14.7, 14.4; HRMS (FAB) calculated for C$_{17}$H$_{25}$N$_3$O$_4$: 335.40; found: 335.18.

Hz, 2H), 3.45 (s, 2H), 3.25 (s, 1H), 2.09 (d, J=26.0 Hz, 4H), 1.44 (s, 9H), 1.29 (d, J=30.4 Hz, 7H); $^{13}$C NMR (100 MHz, CDCl$_3$) δ 167.0, 155.3, 141.8, 132.0, 124.1, 118.7, 118.5, 109.4, 79.2, 60.2, 50.9, 49.2, 32.0, 31.8, 28.4, 14.5; HRMS (FAB) calculated for C$_{20}$H$_{31}$N$_3$O$_4$: 377.48. found: 377.23.

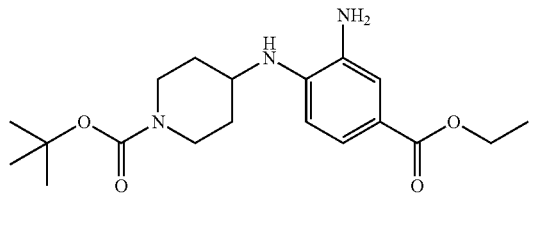 [SMILES: CCOC(=O)c1ccc(NC2CCN(C(=O)OC(C)(C)C)CC2)c(N)c1]

Synthesis of tert-butyl 4-(2-amino-4-(ethoxycarbonyl)phenylamino)-piperidine-1-carboxylate (SRS8-47. SI, Table 3)

$^1$H NMR (400 MHz, CDCl$_3$) δ 7.57 (d, J=10.1 Hz, 1H), 7.42 (s, 1H), 6.60 (d, J=8.4 Hz, 1H), 4.31 (q, J=7.1 Hz, 2H), 3.26 (s, 2H), 2.97 (t, J=11.7 Hz, 2H), 2.05 (d, J=12.6 Hz, 2H), 1.41 (d, J=45.5 Hz, 16H); $^{13}$C NMR (100 MHz, CDCl$_3$) δ 167.0, 154.7, 141.3, 132.3, 124.0, 119.0, 118.5, 109.6, 77.0, 60.2, 53.5, 49.6, 32.1, 28.4, 14.4; HRMS (FAB) calculated for C$_{19}$H$_{29}$N$_3$O$_4$: 363.45; found: 363.21.

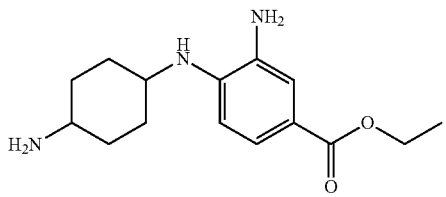

Synthesis of ethyl 3-amino-4-(4-aminocyclohexylamino)benzoate (SRS8-80. SI, Table 3)

$^1$H NMR (400 MHz, MeOD) 7.45 (d, J=8.3 Hz, 1H), 7.38 (s, 1H), 6.62 (d, J=8.4 Hz, 1H), 4.27 (d, J=7.1 Hz, 2H), 3.41 (s, 1H), 2.18 (s, 2H), 2.04 (s, 2H), 1.37 (t, J=7.1 Hz, 4H), 1.31 (s, 3H); $^{13}$C NMR (100 MHz, MeOD) δ 167.8, 141.0, 132.7, 122.8, 117.5, 116.79, 108.8, 59.9, 50.4, 49.7, 31.78, 30.82, 13.33; HRMS (FAB) calculated for C$_{15}$H$_{23}$N$_3$O$_2$: 277.36; found: 277.18.

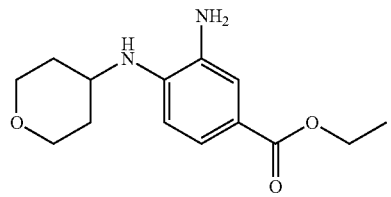 [SMILES: CCOC(=O)c1ccc(NC2CCOCC2)c(N)c1]

Synthesis of ethyl 3-amino-4-(cyclohexylamino)benzoate (SRS8-81. SI, Table 3)

$^1$H NMR (400 MHz, CDCl$_3$) δ 7.55 (d, J=8.2 Hz, 1H), 7.41 (s, 1H), 6.57 (d, J=8.2 Hz, 1H), 4.30 (d, J=6.8 Hz, 2H), 3.49 (s, 1H+NH$_2$), 3.24 (b, NH), 2.83 (s, 2H), 2.11 (s, 2H), 1.55 (d, J=9.2 Hz, 2H), 1.35 (s, 3H), 1.26 (s, 2H); $^{13}$C NMR (100 MHz, CDCl$_3$) δ 167.0, 141.4, 132.1, 124.1, 119.0, 118.6, 109.6, 60.3, 49.5, 44.9, 32.9, 29.7, 14.5; LC/MS (APCI+, M+1) 264.67

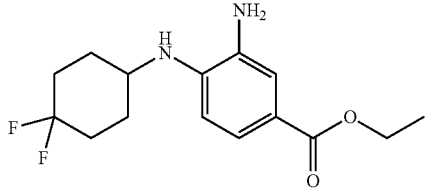

Synthesis of ethyl 3-amino-4-(4,4-difluorocyclohexylamino)benzoate (SRS8-52. SI, Table 3)

$^1$H NMR (400 MHz, CDCl$_3$) δ 7.63 (s, 1H), 7.46 (s, 1H), 6.63 (s, 1H), 4.37 (s, 2H), 3.95 (s, 1H) 3.28 (s, 1H), 2.16 (s, 4H), 1.96 (d, J=13.7 Hz, 2H), 1.68 (s, 2H), 1.37 (s, 3H); $^{13}$C NMR (100 MHz, CDCl$_3$) δ 166.8, 141.5, 132.1, 124.3, 119.6, 119.0, 109.9, 60.3, 49.2, 31.9, 30.9, 28.7, 14.4; $^{19}$F (CDCl$_3$) −94.9, −98.5; HRMS (FAB) calculated for C$_{15}$H$_{20}$F$_2$N$_2$O$_2$: 298.33; found: 298.15.

Preparation of the Nitrobenzene Bearing Various Esters (SI, Table 4, Entries 2-7) and Amide (SI, Table 4, Entry 8)

A representative example is the coupling reaction between the 4-chloro-3-nitrobenzoic acid and the 4-(2-hydroxyethyl)morpholine (SI, Scheme 1, 1c). To the 4-chloro-3-nitrobenzoic acid (500 mg, 2.487 mmol) in DCM, under nitrogen, was added the 4-(2-hydroxyethyl)morpholine (332 μL, 2.736 mmol) and DMAP (91 mg, 0.467 mmol). The mixture was cooled to 0° C. before the addition of the N,N' Dicyclohexylcarbodiimide (DCC) (615 mg, 2.985 mmol). Then the reaction mixture was left at room temperature for 17 h. The precipitate was filtered over celite and the organic solvent was evaporated. The residue was purified by flash-column chromatography on silica gel to provide the desired 2-morpholinoethyl 4-chloro-3-nitrobenzoate (SI, Scheme 1, 1c).

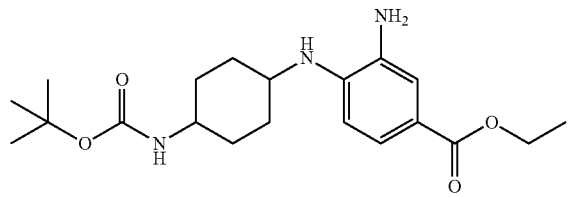 [SMILES: CCOC(=O)c1ccc(NC2CCC(NC(=O)OC(C)(C)C)CC2)c(N)c1]

Synthesis of ethyl 3-amino-4-(4-(tert-butoxycarbonylamino)cyclohexyl-amino)benzoate (SRS8-46. SI, Table 3)

$^1$H NMR (400 MHz, CDCl$_3$) δ 7.55 (d, J=8.1 Hz, 1H), 7.39 (s, 1H), 6.56-6.51 (m, 1H), 4.55 (s, 1H), 4.29 (d, J=9.9

SI, Scheme 1: Synthesis of 4-chloro-3-nitrobenzene analogs bearing various esters and amid (1a-g).

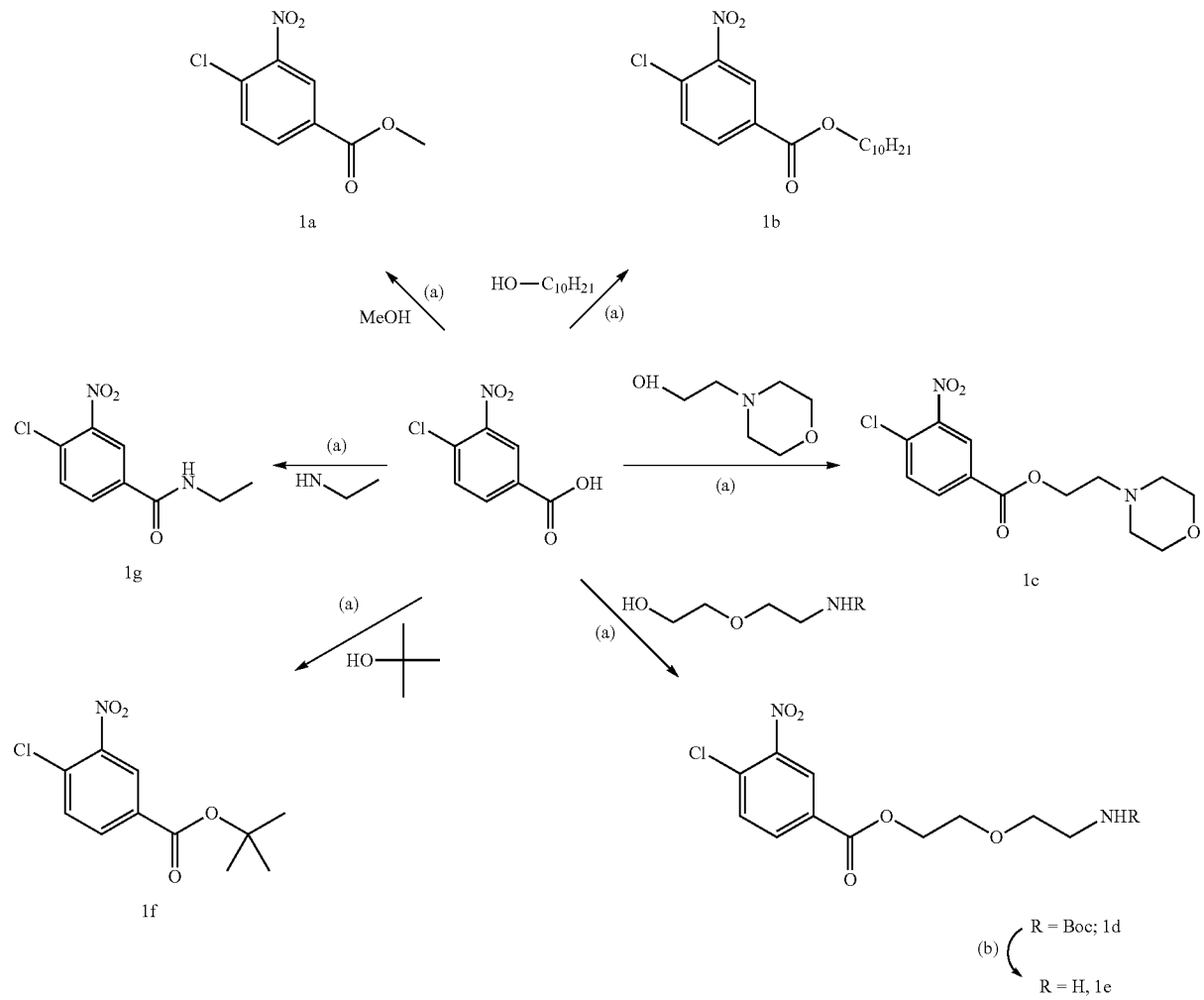

(a) DCC, DMAP, DCM, r.t., 17 h. (b) HCl in Dioxane 4.0M, r.t. 17 h.

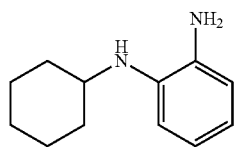 [SMILES: Nc1ccccc1NC1CCCCC1]

Synthesis of N1-cyclohexylbenzene-1,2-diamine
(SRS8-75. SI, Table 4)

$^1$H NMR (CDCl$_3$, 400 MHz) δ 6.91-6.81 (m, 1H), 6.74 (dt, J=14.4, 6.6 Hz, 3H), 3.30 (s, 1H), 2.12 (d, J=10.5 Hz, 2H), 1.83 (d, J=12.7 Hz, 2H), 1.72 (d, J=9.0 Hz, 1H), 1.53-1.37 (m, 2H), 1.36-1.19 (m, 3H); $^{13}$C NMR (100 MHz, CDCl$_3$) δ 136.9, 134.5, 120.7, 118.3, 117.0, 112.8, 51.9, 33.8, 26.2, 25.2; HRMS (FAB) calculated for C$_{12}$H$_{18}$N$_2$: 190.28; found 190.15.

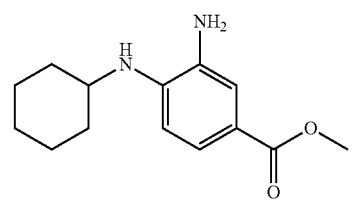 [SMILES: COC(=O)c1ccc(NC2CCCCC2)c(N)c1]

Synthesis of methyl 3-amino-4-(cyclohexylamino)benzoate (SRS8-61. SI, Table 4)

$^1$H NMR (CDCl$_3$, 400 MHz) δ 6.64-6.57 (m, 1H), 7.42 (s, 1H), 6.64-6.57 (m, 1H), 3.35 (s, 1H), 2.09 (d, J=11.4 Hz, 2H), 1.80 (d, J=12.6 Hz, 2H), 1.69 (dt, J=12.9, 4.2 Hz, 1H), 1.42 (d, J=11.5 Hz, 2H), 1.31-1.20 (m, 3H); $^{13}$C NMR (100 MHz, CDCl$_3$) δ 167.5, 142.2, 131.7, 124.4, 118.6, 118.0, 109.5, 51.6, 51.3, 33.3, 25.8, 24.9; HRMS (FAB) calculated for C$_{14}$H$_{20}$N$_2$O$_2$: 248.32; found: 248.15.

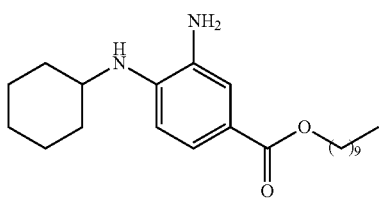

Synthesis of decyl 3-amino-4-(cyclohexylamino)benzoate (SRS12-29. SI, Table 4)

$^1$H NMR (CDCl$_3$, 400 MHz) δ 7.59 (d, J=8.4 Hz, 1H), 7.42 (s, 1H), 6.61 (d, J=8.4 Hz, 1H), 4.27-4.24 (m, 2H), 3.35 (b, 1H), 2.10-2.07 (m, 2H), 2.78-1.72 (m, 4H), 1.43-1.29 (m, 22H), 0.90-0.88 (m, 3H); $^{13}$C NMR (100 MHz, CDCl$_3$) δ 167.0, 141.2, 132.2, 124.2, 119.2, 118.7, 110.4, 64.5, 51.8, 33.1, 31.9, 29.55, 29.3, 28.9, 26.1, 25.8, 24.9, 22.7, 14.1; HRMS (FAB) calculated for C$_{23}$H$_{38}$N$_2$O$_2$: 374.56; found: 374.47.

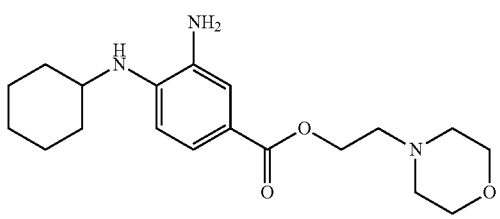 [SMILES: Nc1cc(C(=O)OCCN2CCOCC2)ccc1NC1CCCCC1]

Synthesis of 2-morpholinoethyl 3-amino-4-(cyclohexylamino)benzoate (SRS12-47. SI, Table 4)

$^1$H NMR (CDCl$_3$, 400 MHz) δ 7.56 (d, J=5.0 Hz, 1H), 7.39 (d, J=2.0 Hz, 1H), 6.59 (d, J=8.4 Hz, 1H), 4.40 (t, J=6.0 Hz, 2H), 3.90 (b, NH), 3.73-3.71 (m, 4H), 3.33 (b, 1H), 3.19 (b, NH$_2$), 2.76 (t, J=6.0 Hz, 2H), 2.59-2.56 (m, 4H), 2.09-2.04 (m, 2H), 1.82-1.17 (m, 8H); 13C NMR (100 MHz, CDCl$_3$) δ 166.8, 142.3, 131.8, 124.5, 118.6, 117.9, 109.4, 67.0, 61.8, 57.3, 53.9, 51.3, 49.1, 34.0, 33.3, 25.8, 24.9; HRMS (FAB) calculated for C$_{19}$H$_{29}$N$_3$O$_3$: 347.45; found: 348.31.

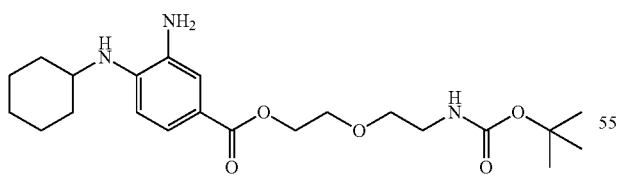

Synthesis of 2-(2-(tert-butoxycarbonylamino)ethoxy)ethyl 3-amino-4-(cyclohexylamino)benzoate (SRS8-37. SI, Table 4)

$^1$H NMR (400 MHz, CDCl$_3$) δ 7.58 (d, J=10.2 Hz, 1H), 7.42 (s, 1H), 6.59 (d, J=8.4 Hz, 1H), 4.41 (s, 2H), 3.77 (s, 2H), 3.58 (d, J=4.7 Hz, 2H), 3.33 (s, 3H), 2.07 (d, J=11.6 Hz, 2H), 1.78 (d, J=12.6 Hz, 2H), 1.73-1.64 (m, 1H), 1.44 (s, 12H), 1.24 (s, 3H); $^{13}$C NMR (100 MHz, CDCl$_3$) δ 166.9, 156.0, 142.4, 131.7, 124.6, 118.7, 117.8, 109.5, 79.3, 70.2, 69.2, 63.3, 51.3, 40.4, 33.3, 28.4, 25.9, 24.9; LC/MS (APCI+, M+1) 421.69

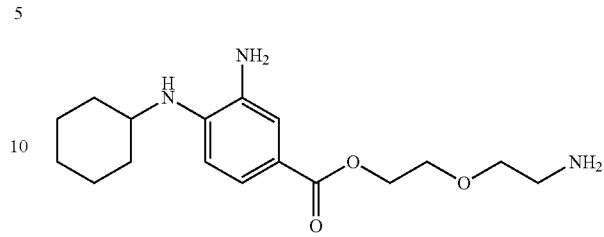

Synthesis of 2-(2-aminoethoxy)ethyl 3-amino-4-(cyclohexylamino)benzoate (SRS8-43. SI, Table 4)

$^1$H NMR (400 MHz, CDCl$_3$) δ 7.46 (d, J=8.0 Hz, 1H), 7.39 (5, 1H), 6.70 (d, J=8.0 Hz, 1H), 4.48-4.41 (m, 2H), 3.95 (5, 4H), 3.84-3.80 (m, 2H), 3.75-3.68 (m, 2H), 3.28 (5, 1H), 3.10-3.00 (m, 2H), 2.07 (d, J=11.1 Hz, 2H), 1.79 (d, J=9.5 Hz, 2H), 1.69 (d, J=8.6 Hz, 1H), 1.41 (d, J=11.7 Hz, 2H), 1.29-1.18 (m, 3H); LC/MS (APCI+, M+1) 321.69

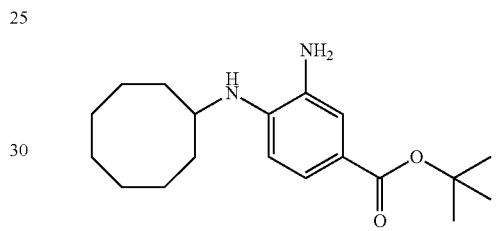

Synthesis of tert-butyl 3-amino-4-(cyclooctylamino)benzoate (SRS8-87. SI, Table 4)

$^1$H NMR (CDCl$_3$, 400 MHz) δ 7.53 (dd, J=8.3, 1.9 Hz, 1H), 7.35 (d, J=1.9 Hz, 1H), 6.51 (d, J=8.4 Hz, 1H), 3.20 (s, 1H), 1.91 (s, 2H), 1.75 (d, J=7.7 Hz, 2H), 1.56 (s, 19H); $^{13}$C NMR (100 MHz, CDCl$_3$) δ 166.4, 141.6, 132.0, 124.0, 120.0, 118.3, 109.7, 79.7, 52.3, 32.7, 28.4, 27.0, 26.0, 24.1; HRMS (FAB) calculated for C$_{19}$H$_{30}$N$_2$O$_2$: 318.45; found: 318.23.

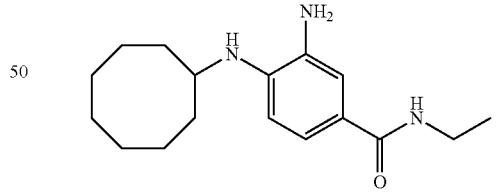

Synthesis of 3-amino-4-(cyclooctylamino)-N-ethylbenzamide (SRS9-11. SI, Table 4)

$^1$H NMR (400 MHz, CDCl$_3$) δ 7.25 (d, J=2.1 Hz, 1H), 7.20 (dd, J=8.3, 2.1 Hz, 1H), 6.52 (d, J=8.3 Hz, 1H), 5.93 (s, 1H), 3.54 (s, 1H), 3.48-3.44 (m, 2H), 1.90 (s, 2H), 1.76 (d, J=8.1 Hz, 1H), 1.60 (s, 11H), 1.23 (t, J=7.3 Hz, 3H); $^{13}$C NMR (100 MHz, CDCl$_3$) δ 167.5, 140.3, 132.9, 123.2, 119.9, 116.4, 110.2, 52.5, 34.7, 32.8, 27.0, 26.0, 24.1, 15.1; LC/MS (APCI+, M+1) 389.83

TABLE 4

SI, Synthetic scheme of Ferrostatin-1 analogs with various $R_3$ substitutions.

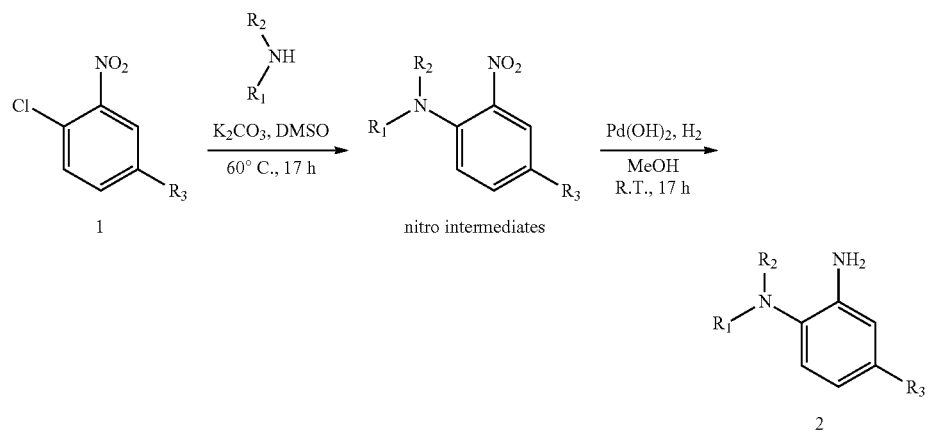

| Entry | $R_1$ | $R_2$ | $R_3$ | Name (Yield) | EC50 (nM) | Log P |
|---|---|---|---|---|---|---|
| 1 | cyclohexyl | H | H | SRS8-75 (86%) | 330 | 2.9 |
| 2 | cyclohexyl | H | –OC(O)–OCH3 (methyl carbonate) | SRS8-61 (90%) | 150 | 2.8 |
| 3 | cyclohexyl | H | –OC(O)–O–C10H21 | SRS12-29 (92%) | 75 | 5.9 |
| 4 | cyclohexyl | H | –OC(O)OCH2CH2-morpholine | SRS12-47 (81%) | 660 | 2.3 |
| 5 | cyclohexyl | H | –OC(O)OCH2CH2OCH2CH2NHBoc | SRS8-37 (98%) | 160 | 3.2 |
| 6 | cyclohexyl | H | –OC(O)OCH2CH2OCH2CH2NH2 | SRS8-43 (89%) | 420 | 1.6 |
| 7 | cyclooctyl | H | –OC(O)O-tBu | SRS8-87 (87%) | 90 | 4.9 |
| 8 | cyclooctyl | H | –NHC(O)-ethyl | SRS9-11 (66%) | 950 | 3.4 |

TABLE 5

SI, EC50 and Log P of Ferrostatin-1 analogs.

| Entry/Name (Yield) | R1 | R2 | R3 | R4 | EC50 (nM) | Log P |
|---|---|---|---|---|---|---|
| 1<br>Ferrostatin-1<br>(SRS8-28; 85%) |  | H | H | H | 88 | 3.2 |
| 2<br>SRS11-89 (88%)[1] | 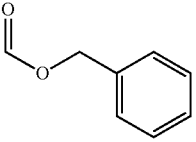 | H | H |  | >10,000 | 5.2 |
| 3<br>SRS11-97 (86%)[1] |  | H | H |  | >10,000 | 3.4 |
| 4<br>SRS11-98 (70%)[1] |  | H | H | 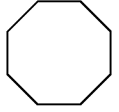 | >10,000 | 3.1 |
| 5<br>SRS8-91 (95%)[2] | 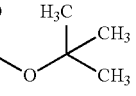 | H | H | 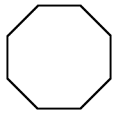 | >10,000 | 5.5 |
| 6<br>SRS8-70 (92%) | 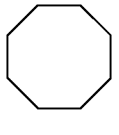 | H | H | H | 69 | 4.1 |
| 7<br>SRS9-14 (70%)[3] | 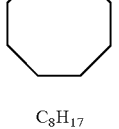 | H | H | $CH_3$ | 70 | 4.4 |
| 8<br>SRS9-01 (92%)[4] | 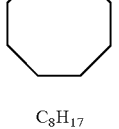 | H | $CH_3$ | $CH_3$ | 3000 | 4.6 |
| 9<br>SRS8-94 (95%) | $C_8H_{17}$ | H | H | H | 80 | 4.4 |
| 10<br>SRS12-12 (89%) | $C_8H_{17}$ | $C_8H_{17}$ | H | H | 15267 | 7.8 |

Conditions.
[1]Addition of Fer-1 to acylchloride, alkyl- or benzyl-chloroformates (1 equiv.), DIPEA, DCM, R.T., 17 h.
[2](Boc)$_2$O (1 equiv.), DMAP (cat.), THF, R.T., 17 h.
[3]using reductive amination conditions (H$_2$CO (1 equiv.), NaBH(OAc)$_3$ (1.2-1.6 equiv.), DCE, R.T., 17 h).
[4]MeI (2.2 equiv), K$_2$CO$_3$, DMF, 40° C., 17 h.

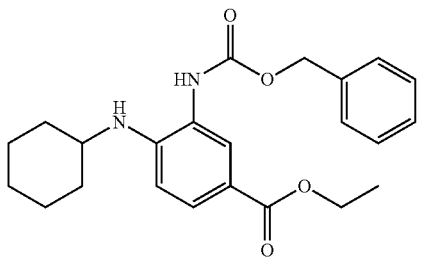 [SMILES: CCOC(=O)c1ccc(NC2CCCCC2)c(NC(=O)OCc2ccccc2)c1]

Synthesis of ethyl 3-(benzyloxycarbonylamino)-4-(cyclohexylamino)-benzoate (SRS11-89. SI, Table 5)

¹H NMR (400 MHz, CDCl₃) δ 7.83 (d, J=10.3 Hz, 2H), 7.38 (s, 5H), 6.66 (d, J=8.5 Hz, 1H), 4.34-4.11 (m, 4H), 3.32 (s, 1H), 1.99 (s, 2H), 1.74 (s, 2H), 1.64 (s, 1H), 1.36 (t, J=7.1 Hz, 5H), 1.23-1.11 (m, 3H); ¹³C NMR (100 MHz, CDCl₃) δ 166.4, 154.6, 146.7, 136.0, 130.2, 128.6, 128.4, 121.0, 117.9, 110.6, 67.5, 60.3, 51.3, 33.0, 25.7, 24.8, 14.5; HRMS (FAB) calculated for $C_{23}H_{28}N_2O_4$: 396.48; found: 396.20.

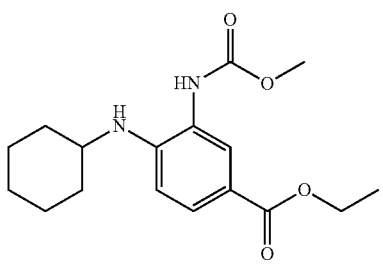 [SMILES: CCOC(=O)c1ccc(NC2CCCCC2)c(NC(=O)OC)c1]

Synthesis of ethyl 4-(cyclohexylamino)-3-(methoxycarbonylamino)benzoate (SRS11-97. SI, Table 5)

¹H NMR (400 MHz, CDCl₃) δ 7.85 (s, 2H), 6.67 (d, J=9.0 Hz, 1H), 6.04 (s, 1H), 4.32 (q, J=7.1 Hz, 2H), 3.78 (s, 2H), 3.36 (s, 1H), 2.06 (d, J=12.4 Hz, 2H), 1.79 (d, J=13.4 Hz, 2H), 1.68 (d, J=12.6 Hz, 1H), 1.37 (t, J=7.1 Hz, 5H), 1.29-1.18 (m, 3H); ¹³C NMR (100 MHz, CDCl₃) δ 166.4, 155.9, 146.7, 130.2, 129.1, 121.1, 117.9, 110.5, 60.3, 52.8, 51.3, 33.1, 25.7, 24.8, 14.5; HRMS (FAB) calculated for $C_{17}H_{24}N_2O_4$: 320.38; found: 320.17.

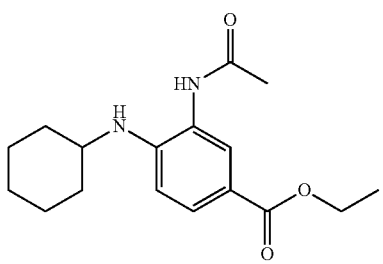 [SMILES: CCOC(=O)c1ccc(NC2CCCCC2)c(NC(C)=O)c1]

Synthesis of ethyl 4-(cyclohexylamino)-3-ethanamidobenzoate (SRS11-98. SI, Table 5)

¹H NMR (400 MHz, CDCl₃) δ 7.82 (d, J=8.6 Hz, 1H), 7.75 (s, 1H), 6.68 (d, J=8.6 Hz, 1H), 4.57-4.46 (m, 1H), 4.33 (d, J=9.8 Hz, 2H), 3.35 (s, 1H), 2.22 (s, 3H), 2.04 (d, J=12.1 Hz, 2H), 1.88 (s, 1H), 1.79 (s, 3H), 1.38 (s, 4H), 1.24 (d, J=8.6 Hz, 3H); HRMS (FAB) calculated for $C_{17}H_{24}N_2O_3$: 304.38; found: 304.18.

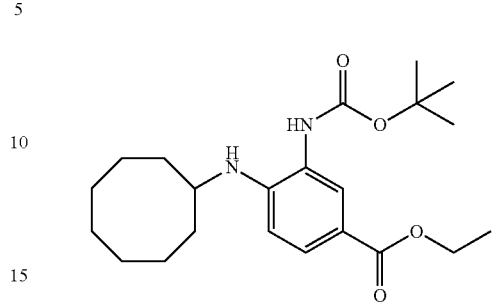

Synthesis of ethyl 3-(tert-butoxycarbonylamino)-4-(cyclooctylamino)-benzoate (SRS8-91. SI, Table 5)

¹H NMR (400 MHz, CDCl₃) δ 8.54 (d, J=1.5 Hz, 1H), 7.93 (dd, J=8.4, 1.7 Hz, 1H), 7.08 (d, J=8.4 Hz, 1H), 4.44-4.35 (m, 2H), 2.23 (q, J=10.7 Hz, 2H), 1.86 (d, J=9.0 Hz, 4H), 1.70 (s, 8H), 1.64-1.56 (m, 6H), 1.42-1.38 (m, 6H); ¹³C NMR (100 MHz, CDCl₃) δ 166.4, 150.5, 148.6, 132.0, 125.9, 123.9, 115.8, 108.6, 85.0, 61.0, 31.9, 28.1, 27.8, 27.0, 26.2, 26.0, 25.3, 14.4; HRMS (FAB) calculated for C22H34N2O4: 390.52;

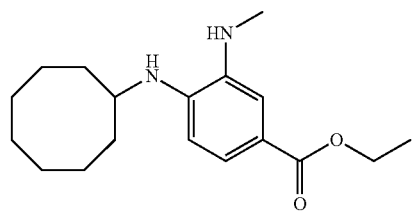 [SMILES: CCOC(=O)c1ccc(NC2CCCCCCC2)c(NC)c1]

Synthesis of ethyl 4-(cyclooctylamino)-3-(methylamino)benzoate (SRS9-14. SI, Table 5)

¹H NMR (400 MHz, CDCl₃) δ 7.60 (d, J=8.0 Hz, 1H), 7.37 (s, 1H), 6.54 (d, J=8.3 Hz, 1H), 4.34 (q, J=7.1 Hz, 2H), 3.56 (d, J=9.7 Hz, 1H), 2.90 (s, 3H), 1.94-1.86 (m, 2H), 1.80 1.72 (m, 2H), 1.67-1.53 (m, 10H), 1.38 (t, J=7.1 Hz, 3H); ¹³C NMR (100 MHz, CDCl₃) δ 167.5, 141.4, 136.3, 123.0, 119.0, 112.6, 109.2, 60.2, 52.3, 32.8, 31.4, 27.0, 26.0, 24.1, 14.5; HRMS (FAB) calculated for $C_{18}H_{28}N_2O_2$: 304.43; found: 304.21.

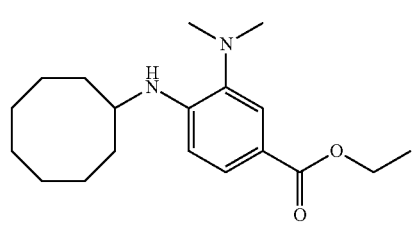 [SMILES: CCOC(=O)c1ccc(NC2CCCCCCC2)c(N(C)C)c1]

Synthesis of ethyl 4-(cyclooctylamino)-3-(dimethylamino)benzoate (SRS9-01. SI, Table 5)

$^1$H NMR (100 MHz, CDCl$_3$) δ 7.78-7.70 (m, 2H), 6.50 (d, J=8.5 Hz, 1H), 4.33 (q, J=7.1 Hz, 2H), 3.58 (s, 1H), 2.64 (s, 6H), 1.92 (s, 2H), 1.63 (d, J=23.7 Hz, 12H), 1.38 (t, J=7.1 Hz, 3H); $^{13}$C NMR (100 MHz, CDCl$_3$) δ 167.2, 146.0, 139.3, 128.0, 121.0, 117.0, 109.0, 60.1, 52.0, 44.0, 32.5, 27.2, 25.8, 24.0, 14.5; HRMS (FAB) calculated for C$_{19}$H$_{30}$N$_2$O$_2$: 318.45; found 318.23.

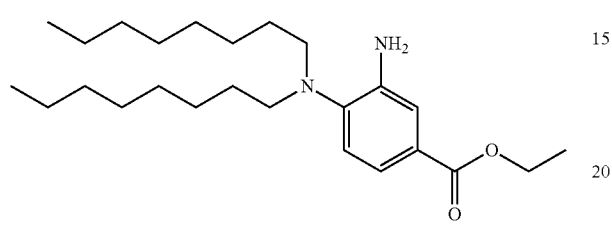

Synthesis of ethyl 3-amino-4-(dioctylamino)benzoate (SRS12-12. SI, Table 5)

$^1$H NMR (400 MHz, CDCl$_3$) δ 7.41 (s, 2H), 7.03 (d, J=8.7 Hz, 1H), 4.34 (d, J=7.1 Hz, 2H), 2.95 (s, 3H), 1.38 (d, J=7.1 Hz, 6H), 1.24 (s, 22H), 0.87 (s, 3H); $^{13}$C NMR (100 MHz, CDCl$_3$) δ 166.9, 142.8, 142.3, 126.0, 121.8, 119.7, 116.1, 60.6, 52.8, 31.8, 29.4, 29.3, 27.2, 22.6, 14.4, 14.1; LC/MS (APCI+, M−1) 403.96

TABLE 6

SI, EC50 and Log P of Ferrostatin-1 analogs.

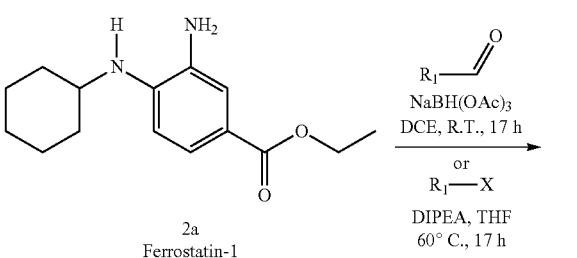

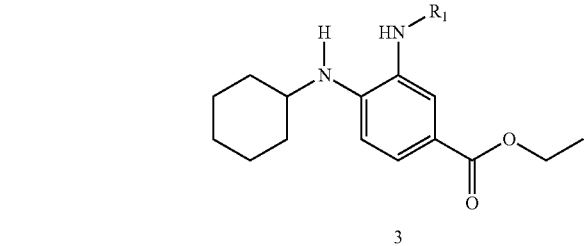

| Entry | R1 | Name (Yield) | EC50 (nM) | Log P |
|---|---|---|---|---|
| 1 | H$_2$C—Ph | SRS11-92 (98%) | 6 | 5.3 |
| 2 | H$_2$C—C$_6$H$_4$-3-Cl | SRS12-58 (90%) | 41 | 5.9 |
| 3 | H$_2$C—C$_6$H$_4$-4-Cl | SRS12-49 (91%) | 371 | 5.9 |
| 4 | H$_2$C—C$_6$H$_4$-4-Br | SRS12-35 (89%) | 44 | 6.1 |
| 5 | H$_2$C—C$_6$H$_4$-3-F | SRS12-57 (85%) | 100 | 5.5 |
| 6 | H$_2$C—C$_6$H$_4$-4-F | SRS12-33 (85%) | 50 | 5.4 |
| 7 | H$_2$C—C$_6$H$_4$-4-CF$_3$ | SRS12-48 (86%) | 46 | 6.2 |
| 8 | H$_2$C—C$_6$H$_4$-4-CN | SRS12-50 (92%) | 100 | 4.9 |
| 9 | H$_2$C—C$_6$H$_4$-2-NO$_2$ | SRS12-71 (94%) | 126 | 5.2 |

TABLE 6-continued

SI, EC50 and Log P of Ferrostatin-1 analogs.

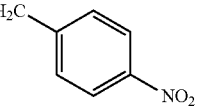

| Entry | R1 | Name (Yield) | EC50 (nM) | Log P |
|---|---|---|---|---|
| 10 | 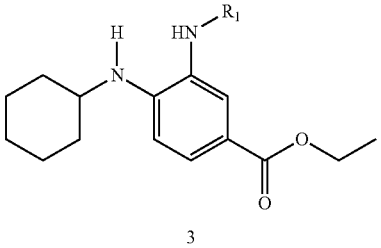 | SRS12-36 (90%) | 36 | 5.2 |
| 11 | 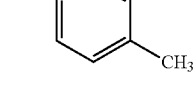 | SRS12-34 (96%) | 40 | 5.6 |
| 12 | 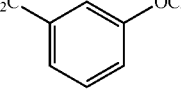 | SRS12-69 (85%) | 58 | 5.3 |
| 13 | 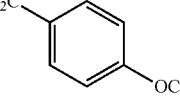 | SRS12-43 (86%) | 69 | 5.3 |

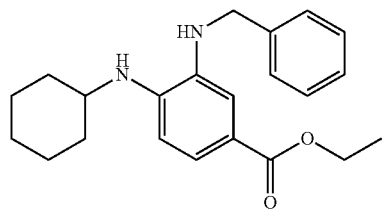 [SMILES: CCOC(=O)c1ccc(NC2CCCCC2)c(NCc2ccccc2)c1]

Synthesis of ethyl 3-(benzylamino)-4-(cyclohexylamino)benzoate (SRS11-92. SI, Table 6)

$^1$H NMR (CDCl$_3$, 400 MHz) δ 7.69-7.61 (m, 1H), 7.53-7.30 m, 6H), 6.71-6.62 (m, 1H), 4.40-4.28 (m, 4H), 3.97 (b, NH), 3.36 (b, 1H), 3.23 (m, NH), 2.17-2.03 (m, 2H), 1.87-1.76 (m, 2H), 1.75-1.66 (m, 1H), 1.47-1.34 (m, 5H), 1.32-1.19 (m, 3H); $^{13}$C NMR (100 MHz, CDCl3) δ 167.3, 142.0, 139.2, 134.8, 128.2, 127.44, 123.7, 118.8, 114.7, 109.3, 60.2, 51.4, 49.5, 33.3, 25.9, 25.0 14.5; LC/MS (APCI+, M+1) 353.06

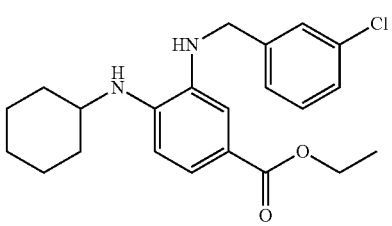 [SMILES: CCOC(=O)c1ccc(NC2CCCCC2)c(NCc2cccc(Cl)c2)c1]

Synthesis of ethyl 3-(3-chlorobenzylamino)-4-(cyclohexylamino)benzoate (SRS12-58. SI, Table 6)

$^1$H NMR (CDCl$_3$, 400 MHz) δ 7.63 (d, J=4.2 Hz, 1H), 7.43 (s, 2H), 7.30-7.28 (m, 3H), 6.65 (d, J=8.4 Hz, 1H), 4.35-4.30 (m, 4H), 3.37 (b, 1H), 2.14-2.05 (m, 2H), 1.87-1.76 (m, 2H), 1.75-1.67 (m, 1H), 1.47-1.36 (m, 5H), 1.29-1.24 (m, 3H); $^{13}$C NMR (100 MHz, CDCl$_3$) δ 167.2, 142.1, 141.3, 134.5, 134.4, 129.9, 128.1, 127.6, 126.2, 123.9, 118.9, 115.0, 110.0, 60.2, 51.5, 48.9, 33.3, 25.9, 24.9, 14.5; HRMS (FAB) calculated for C$_{22}$H$_{27}$ClN$_2$O$_2$: 386.91; found: 386.18.

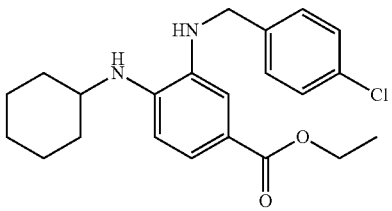 [SMILES: CCOC(=O)c1ccc(NC2CCCCC2)c(NCc2ccc(Br)cc2)c1]

Synthesis of ethyl 3-(4-chlorobenzylamino)-4-(cyclohexylamino)benzoate (SRS12-49. SI, Table 6)

$^1$H NMR (CDCl$_3$, 400 MHz) δ 7.60 (d, J=8.0 Hz, 1H), 7.41 (s, 1H), 7.34 (s, 4H), 6.64 (d, J=8.3 Hz, 1H), 4.36-4.25 (m, 4H), 3.32 (b, 1H), 2.07-2.04 (m, 2H), 1.79-1.76 (m, 2H), 1.69-1.33 (5H), 1.26-1.20 (m, 3H); $^{13}$C NMR (100 MHz, CDCl$_3$) δ 167.2, 142.0, 137.7, 134.4, 133.2, 129.4, 128.8, 123.9, 118.9, 114.9, 109.5, 60.2, 51.4, 48.7, 33.3, 25.9, 24.9 14.5; HRMS (FAB) calculated for C$_{22}$H2$_7$ClN$_2$O$_2$: 386.91; found: 386.17.

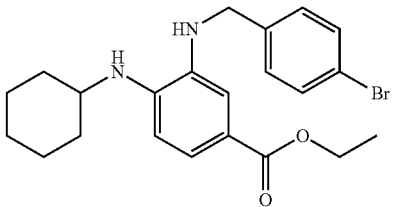

Synthesis of ethyl 3-((4-bromobenzyl)amino)-4-(cyclohexylamino)benzoate (SRS12-35. SI, Table 6)

$^1$H NMR (CDCl$_3$, 400 MHz,) δ 7.62 (d, J=8.0 Hz, 1H), 7.50 (d, J=8.4 Hz, 2H), 7.42 (s, 1H), 7.31-7.28 (m, 2H), 6.64

(d, J=8.4 Hz, 1H), 4.35-4.28 (m, 4H), 3.35 (b, 1H), 2.10-2.07 (m, 2H), 1.81-1.59 (m, 4H), 1.44-1.35 (m, 4H), 1.28-1.22 (m, 3H); $^{13}$C NMR (100 MHz, CDCl$_3$) δ 167.2, 142.0, 138.2, 134.4, 131.7, 129.74, 123.9, 121.2, 118.9, 114.4, 109.5, 60.2, 51.4, 48.8, 33.3, 25.9, 24.9, 14.5; HRMS (FAB) calculated for C$_{22}$H$_{27}$BrN$_2$O$_2$: 431.37; found: 430.13.

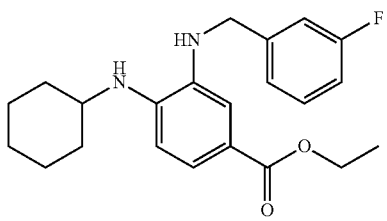 [SMILES: CCOC(=O)c1ccc(NC2CCCCC2)c(NCc2cccc(F)c2)c1]

Synthesis of ethyl 4-(cyclohexylamino)-3-(3-fluorobenzylamino)benzoate (SRS12-57. SI, Table 6)

$^1$H NMR (CDCl$_3$, 400 MHz) δ 7.62 (d, J=8.4 Hz, 1H), 7.43 (s, 1H), 7.34-7.31 (m, 1H), 7.21-7.20 (m, 1H), 7.16-7.13 (m, 1H), 7.03-6.99 (m, 1H), 6.65 (d, J=8.4 Hz, 1H), 4.35-4.30 (m, 4H), 3.94 (b, NH), 3.56 (b, 1H), 3.24 (b, NH), 2.15-2.03 (m, 2H). 1.88-1.75 (m, 2H), 1.76-1.66 (m, 1H), 1.49-1.33 (m, 5H). 1.32-1.19 (3H); $^{13}$C NMR (100 MHz, CDCl$_3$) δ 167.2, 164.3, 161.9, 142.1, 134.4, 130.1, 123.9, 123.5, 123.49, 118.9, 115.0, 114.9, 114.7, 114.4, 114.2, 109.5, 60.2, 51.4, 48.9, 33.3, 25.86, 24.9, 14.5; $^{19}$F (CDCl$_3$) δ −112.0; HRMS (FAB) calculated for C$_{22}$H$_{27}$FN$_2$O$_2$: 370.48; found: 370.20.

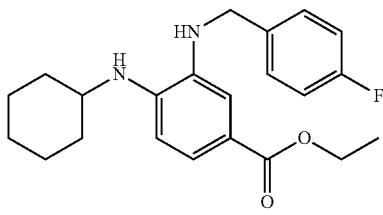 [SMILES: CCOC(=O)c1ccc(NC2CCCCC2)c(NCc2ccc(F)cc2)c1]

Synthesis of ethyl 4-(cyclohexylamino)-3-((4-fluorobenzyl)amino)benzoate (SRS12-33. SI, Table 6)

$^1$H NMR (CDCl$_3$, 400 MHz) δ 7.62 (d, J=8.4 Hz, 1H), 7.45 (s, 1H), 7.41-7.38 (m, 2H), 7.07 (d, J=8.8 Hz, 2H), 6.65 (d, J=8.0 Hz, 1H), 4.36-4.288 (m, J=4H), 3.35 (b, 1H), 2.10-2.07 (m, 2H), 1.81-1.61 (m, 4H), 1.46-1.44 (m, 4H), 1.39 (t, J=7.2 Hz, 3H); $^{13}$C NMR (100 MHz, CDCl3) δ 167.3, 163.4, 161.0, 142.0, 134.5, 129.7, 123.8, 118.8, 115.4, 114.8, 109.4, 60.2, 51.4, 48.7, 33.3, 25.9, 25.0, 14.5; $^{19}$F (CDCl$_3$) δ −114.3; HRMS (FAB) calculated for C$_{22}$H$_{27}$FN$_2$O$_2$: 370.46; found: 371.13.

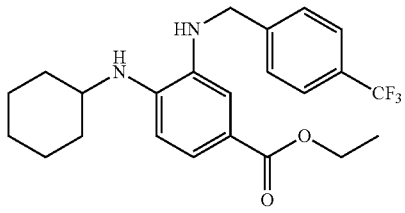 [SMILES: CCOC(=O)c1ccc(NC2CCCCC2)c(NCc2ccc(C(F)(F)F)cc2)c1]

Synthesis of ethyl 4-(cyclohexylamino)-3-(4-(trifluoromethyl)benzylamino)-benzoate (SRS12-48. SI, Table 6)

$^1$H NMR (CDCl$_3$, 400 MHz) δ 7.61 (td, J=6.2, 2.9 Hz, 3H), 7.52 (d, J=8.0 Hz, 2H), 7.40 (d, J=1.9 Hz, 1H), 6.64 (d, J=8.4 Hz, 1H), 4.38 (s, 2H), 4.30 (q, J=7.1 Hz, 2H), 3.34 (b, 1H2.11-2.03 (m, 2H), 1.84-1.74 (m, 2H). 1.70-1.66 (m, 1H), 1.43-1.32 (m, 5H). 1.2-1.17 (m, 3H); $^{13}$C NMR (100 MHz, CDCl$_3$) δ 167.2, 143.3, 142.1, 134.2, 128.2, 125.6, 124.0, 118.9, 115.0, 109.6, 60.2, 51.4, 50.8, 48.9, 33.3, 25.8, 24.9, 14.4; $^{19}$F (CDCl$_3$) δ −61.3; HRMS (FAB) calculated for C$_{23}$H$_{27}$F$_3$N$_2$O$_2$: 420.47; found: 420.22.

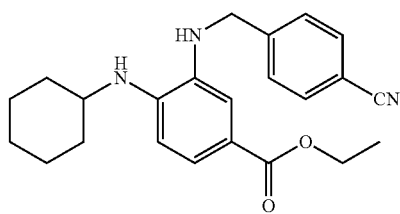 [SMILES: CCOC(=O)c1ccc(NC2CCCCC2)c(NCc2ccc(C#N)cc2)c1]

Synthesis of ethyl 3-(4-cyanobenzylamino)-4-(cyclohexylamino)benzoate (SRS12-50. SI, Table 6)

$^1$H NMR (CDCl$_3$, 400 MHz) δ 7.61 (d, J=2.0 Hz, 2H), 7.59 (d, J=1.6 Hz, 1H), 7.50 (d, J=8.4 Hz, 2H), 7.33 (d, J=1.9 Hz, 1H), 6.64 (d, J=8.4 Hz, 1H), 4.40 (s, 2H), 4.29 (q, J=7.1 Hz, 2H), 3.34 (b, 1H), 2.09-2.04 (m, 2H), 1.77-1.32 (m, 8H), 1.27-1.21 (m, 3H); $^{13}$C NMR (100 MHz, CDCl$_3$) δ 167.1, 144.8, 142.1, 133.9, 132.4, 128.4, 124.1, 119.0, 118.8, 115.0, 111.2, 110.0, 60.2, 51.4, 48.8, 33.3, 25.9, 24.9, 14.4: HRMS (FAB) calculated for C23H27N3O2: 377.48; found: 377.39.

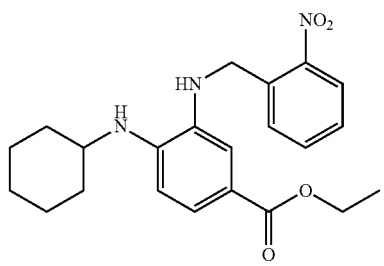 [SMILES: CCOC(=O)c1ccc(NC2CCCCC2)c(NCc2ccccc2[N+](=O)[O-])c1]

Synthesis of ethyl 4-(cyclohexylamino)-3-(2-nitrobenzylamino)benzoate (SRS12-71. SI, Table 6)

$^1$H NMR (CDCl$_3$, 400 MHz) δ 7.99 (dd, J=8.1, 1.3 Hz, 1H), 7.62-7.58 (m, 1H), 7.57-7.54 (m, 1H), 7.52 (d, J=1.5 Hz, 1H), 7.44 (ddd, J=8.1, 7.1, 1.7 Hz, 1H), 7.32 (d, J=1.9 Hz, 1H), 6.65-6.58 (m, 1H), 4.58 (s, 2H), 4.28 (q, J=7.1 Hz, 2H), 4.08 (s, NH), 3.53 (s, NH), 3.39-3.27 (m, 1H), 2.06 (dd, J=12.5, 4.0 Hz, 2H), 2.11-2.02 (m, 2H), 1.82-1.73 (m, 2H), 1.71-1.62 (m, 2H), 1.39-1.31 (m, 4H), 1.28-1.22 (m, 3H), 1.27-1.16 (m, 3H); $^{13}$C NMR (100 MHz, CDCl$_3$) δ 167.1, 149.1, 142.9, 134.5, 133.6, 133.3, 131.1, 128.4, 124.9, 124.6, 118.6, 116.6, 109.7, 60.17, 51.42, 47.0, 33.2, 25.9, 24.9, 14.4; HRMS (FAB) calculated for C$_{22}$H$_{27}$N$_3$O$_4$: 397.47; found: 397.20.

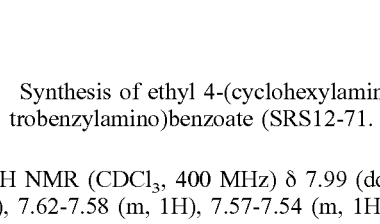

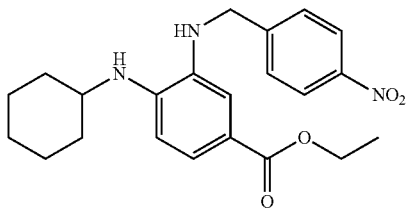 [SMILES: CCOC(=O)c1ccc(NC2CCCCC2)c(NCc2ccc([N+](=O)[O-])cc2)c1]

Synthesis of ethyl 4-(cyclohexylamino)-3-((4-nitrobenzyl)amino)benzoate (SRS12-36. SI, Table 6)

$^1$H NMR (CDCl$_3$, 400 MHz) δ 8.24 (d, J=8.4 Hz, 2H), 7.62-7.7.55 (m, 3H), 7.34-7.2 (m, 1H), 6.66 (d, 8.4 Hz, 1H), 4.45 (s, 2H), 4.32-4.27 (m, 2H), 3.37 (b, 1H), 2.10-2.03 (m, 2H), 1.82-1.67 (m, 4H), 1.44-1.33 (m, 4H), 1.29-1.24 (m, 3H); $^{13}$C NMR (100 MHz, CDCl$_3$) δ 167.1, 146.8, 142.0, 133.8, 129.5, 128.4, 124.1, 123.9, 118.9, 114.9, 109.7, 60.3, 51.5, 48.5, 33.3, 25.9, 24.9, 14.5; LC/MS (APCI+, M+1) 397.96

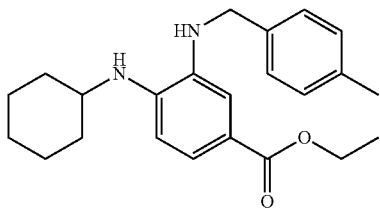 [SMILES: CCOC(=O)c1ccc(NC2CCCCC2)c(NCc2ccc(C)cc2)c1]

Synthesis of ethyl 4-(cyclohexylamino)-3-((4-methylbenzyl)amino)benzoate (SRS12-34. SI, Table 6)

$^1$H NMR (CDCl$_3$, 400 MHz) δ 7.62 (d, J=8.0 Hz, 1H), 7.49 (s, 1H), 7.33 (d, J=8.0 Hz, 2H), 7.20 (d, J=7.6 Hz, 2H), 6.66 (d, J=8.4 Hz, 1H), 4.33 (q, J=6.8 Hz, 2H), 4.27 (s, 2H), 3.35 (b, 1H), 2.39 (s, 3H), 2.13-2.0 (m, 2H), 1.84-1.74 (m, 2H), 1.73-1.64 (m, 1H), 1.41-1.36 (m, 4H), 1.28-1.21 (m, 3H); $^{13}$C NMR (100 MHz, CDCl$_3$) δ 167.3, 141.8, 137.1, 136.1, 134.8, 129.3, 128.2, 123.6, 118.9, 114.7, 109.3, 60.2, 51.5, 49.25, 33.3, 25.9, 25.0, 21.1, 14.5; HRMS (FAB) calculated for C$_{23}$H$_{30}$N$_2$O$_2$: 366.50; found: 366.23.

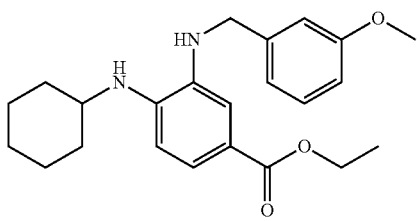 [SMILES: CCOC(=O)c1ccc(NC2CCCCC2)c(NCc2cccc(OC)c2)c1]

Synthesis of ethyl 4-(cyclohexylamino)-3-(4-(methoxycarbonyl)-benzylamino)benzoate (SRS12-69. SI, Table 6)

$^1$H NMR (CDCl$_3$, 400 MHz) δ 7.60 (ddd, J=8.4, 1.9, 1.0 Hz, 1H), 7.45 (d, J=1.8 Hz, 1H), 7.32-7.27 (m, 1H), 7.04-6.95 (m, 2H), 6.89-6.81 (m, 1H), 6.62 (dd, J=8.7, 1.3 Hz, 1H), 4.31 (tdd, J=7.2, 6.7, 1.2 Hz, 2H), 4.27 (s, 2H), 3.90 (s, NH), 3.82 (d, J=1.1 Hz, 3H), 3.33 (s, 1H), 2.09-2.02 (m, 2H), 1.82-1.73 (m, 2H), 1.71-1.63 (m, 1H), 1.45-1.32 (m, 5H), 1.26-1.17 (m, 3H); $^{13}$C NMR (100 MHz, CDCl$_3$) δ 167.3, 159.9, 141.9, 140.8, 134.7, 129.7, 123.7, 120.5, 118.9, 114.8, 113.8, 112.8, 109.4, 60.2, 55.2, 49.5, 33.3, 25.9, 25.0, 14.5; HRMS (FAB) calculated for C$_{23}$H$_{30}$N$_2$O$_3$: 382.50; found: 382.37.

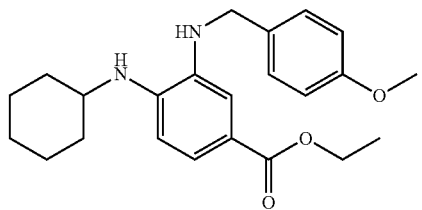 [SMILES: CCOC(=O)c1ccc(NC2CCCCC2)c(NCc2ccc(OC)cc2)c1]

Synthesis of ethyl 4-(cyclohexylamino)-3-((4-methoxybenzyl)amino)-benzoate (SRS12-43. SI, Table 6)

$^1$H NMR (CDCl$_3$, 400 MHz) δ 7.63 (d, J=8.4 Hz, 1H), 7.49 (s, 1H), 7.37 (d, J=8.4 Hz, 2H), 6.94 (d, J=8.8 Hz, 2H), 6.65 (d, J=8.4 Hz, 1H), 4.5 (q, J=7.2, 2H), 4.26 (s, 2H), 3.85 (s, 3H), 3.35 (b, 1H), 2.10-2.07 (m, 2H), 1.82-1.60 (m, 4H), 1.47-1.33 (m, 4H), 1.30-1.27 (m, 3H); LC/MS (APCI+, M+1) 282.19.

TABLE 7

SI, EC50 of Ferrostatin-1 analogs.

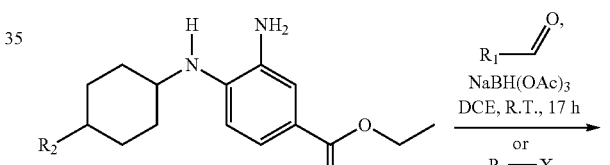

| Entry | R$_1$ | R$_2$ | Name (Yield) | EC50 (nM) | Log P |
|---|---|---|---|---|---|
| 1 | H$_2$C—Ph | H | SRS11-92 (98%) | 6 | 5.3 |
| 2 | R$_{1a}$ | tert-butyl | SRS13-29 (95%) | 83 | 6.8 |
| 3 | H$_2$C—naphthyl | H | SRS12-51 (91%) | 58 | 6.5 |

TABLE 7-continued

SI, EC50 of Ferrostatin-1 analogs.

| Entry | R₁ | R₂ | Name (Yield) | EC50 (nM) | Log P |
|---|---|---|---|---|---|
| 4 | H₂C-(2-pyridyl) | H | SRS12-46 (85%) | 33 | 4.0 |
| 5 | H₂C-(3-pyridyl) | H | SRS13-12 (87%) | 48 | 4.0 |
| 6 | H₂C-(4-pyridyl) R₁ₑ | H | SRS12-45 (90%) | 25 | 4.0 |
| 7 | R₁ₑ | tert-butyl | SRS13-30 (89%) | 114 | 5.6 |
| 8 | H₂C-(4-pyrimidinyl) R₁ᶜ | H | SRS13-35 (92%) | 27 | 2.9 |
| 9 | R₁ᶜ | tert-butyl | SRS13-37 (88%) | 15 | 4.4 |
| 10 | H₂C-(2-F,5-CN-phenyl) | H | SRS12-54 (85%) | 159 | 5.1 |
| 11 | H₂C-(3,5-difluorophenyl) | H | SRS12-59 (86%) | 96 | 5.7 |
| 12 | H₂C-(3-Br,5-F-phenyl) | H | SRS12-52 (89%) | 105 | 6.3 |
| 13 | H₂C-(3,5-dimethoxyphenyl) | H | SRS12-53 (85%) | 41 | 5.3 |
| 14 | H₂C-(4-OC(O)OCH₃-phenyl) | H | 4MO43 (85%) | 47 | 5.2 |
| 15 | H₂C-(4-C(O)OR₂-phenyl) R₁d | H | SRS12-80; R₂ = CH₃ (86%) | 33 | 5.2 |
| 16 | R₁d | H | SRS12-84; R₂ = CH₂CH₃ (88%) | 53 | 5.6 |

Synthesis of single isomer of ethyl 3-(benzylamino)-4-(4-tert-butylcyclohexylamino)benzoate (SRS13-29. SI, Table 7)

$^1$H NMR (CDCl$_3$, 400 MHz) δ 7.62 (d, J=8.3, 1H), 7.48-7.32 (m, 6H), 6.65 (d, J=8.3 Hz, 1H), 4.35-4.29 (m, 4H), 3.36 (b, 1H), 2.19 (s, 2H), 1.86 (s, 2H), 1.38 (t, J=7.1, 0.8 Hz, 3H), 1.22-1.15 (m, 4H), 1.09-1.03 (m, 1H), 0.90 (s, 9H); $^{13}$C NMR (100 MHz, CDCl$_3$) δ 167.3, 141.9, 139.2, 134.8, 128.7, 128.3, 127.5, 123.6, 118.8, 114.5, 109.3, 60.2, 52.1, 49.5, 47.6, 33.8, 32.4, 27.6, 26.2, 14.5; HRMS (FAB) calculated for C$_{26}$H$_{36}$N$_2$O$_2$: 408.58; found: 408.28.

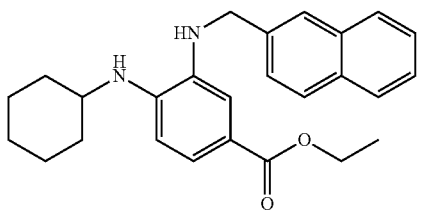 [SMILES: CCOC(=O)c1ccc(NC2CCCCC2)c(NCc2ccc3ccccc3c2)c1]

Synthesis of ethyl 4-(cyclohexylamino)-3-(naphthalen-2-ylmethylamino)-benzoate (SRS12-51. SI, Table 7)

$^1$H NMR (CDCl$_3$, 400 MHz) δ 7.87-7.82 (m, 4H), 7.63-7.60 (m, 1H), 7.55 (d, J=5.0 Hz, 1H), 7.51 (s, 1H), 7.50-7.48 (m, 2H), 6.64 (d, J=8.4 Hz, 1H), 4.46 (s, 2H), 4.31 (q, J=7.1 Hz, 2H), 3.93 (s, NH,) 3.34 (b, 1H), 3.24 (b, NH), 2.09-2.03 (m, 2H), 1.79-1.63 (m, 3H), 1.45-1.33 (m, 5H), 1.27-1.19 (m, 3H); $^{13}$C NMR (100 MHz, CDCl$_3$) δ 167.3, 142.0, 136.7, 134.8, 133.5, 132.86, 128.4, 127.8, 127.7, 126.7, 126.4, 126.2, 125.9, 123.8, 118.9, 114.8, 109.4, 60.2, 51.4, 49.7, 33.3, 25.9, 25.0, 14.5; HRMS (FAB) calculated for C$_{26}$H$_{30}$N$_2$O$_2$ 402.53; found: 402.23.

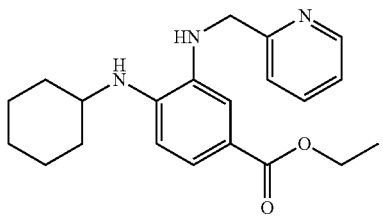 [SMILES: CCOC(=O)c1ccc(NC2CCCCC2)c(NCc2ccccn2)c1]

Synthesis of ethyl 4-(cyclohexylamino)-3-(pyridin-2-ylmethylamino)-benzoate (SRS12-46. SI, Table 7)

$^1$H NMR (CDCl$_3$, 400 MHz) δ 8.62 (d, J=4.4 Hz, 1H), 7.71-7.67 (m, 1H), 7.61-7.59 (m, 1H), 7.42 (s, 1H), 7.34 (d, J=8.0 Hz, 1H), 7.28 (s, 1H), 7.24-7.21 (m, 1H), 6.64 (d, J=8.4 Hz, 1H), 4.45 (s, 2H), 4.32 (q, J=7.2, 2H), 3.36 (b, 1H), 2.12-2.09 (m, 2H), 1.85-1.66 (m, 3H), 1.46-1.34 (m, 5H), 1.32-1.24 (m, 3H); $^{13}$C NMR (100 MHz, CDCl$_3$) δ 167.3, 158.1, 149.2, 142.1, 136.7, 134.6, 123.6, 122.3, 122.2, 118.6, 114.7, 109.2, 51.4, 50.1, 33.3, 26.1, 25.9, 25.0, 14.5; HRMS (FAB) calculated for O$_{21}$H$_{27}$N$_3$O$_2$: 353.46; found: 353.21.

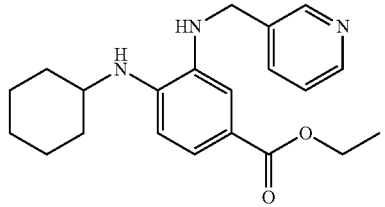 [SMILES: CCOC(=O)c1ccc(NC2CCCCC2)c(NCc2cccnc2)c1]

Synthesis of ethyl 4-(cyclohexylamino)-3-(pyridin-3-ylmethylamino)-benzoate (SRS13-12. SI, Table 7)

$^1$H NMR (CDCl$_3$, 400 MHz) δ 8.70 (d, J=2.3 Hz, 1H), 8.59-8.56 (m, 1H), 7.75 (d, J=7.6 Hz, 1H), 7.64-7.53 (m, 1H), 7.44 (s, 1H), 7.37-7.26 (m, 1H), 6.66 (d, J=8.8 Hz, 1H), 4.36-4.31 (m, 4H) 3.39-3.33 (b, 1H), 2.13-2.01 (m, 2H), 1.87-1.75 (m, 2H), 1.71-1.66 (m, 1H), 1.43-1.33 (m, 5H), 1.30-1.20 (m, 3H); $^{13}$C NMR (100 MHz, CDCl$_3$) δ 167.2, 149.3, 148.6, 136.1, 134.0, 124.18, 123.7, 115.1, 112.3, 109.6, 60.3, 51.5, 46.9, 33.29, 31.3, 25.83, 24.9, 14.5; HRMS (FAB) calculated for C$_{21}$H$_{27}$N$_3$O$_2$: 353.46; found: 354.12.

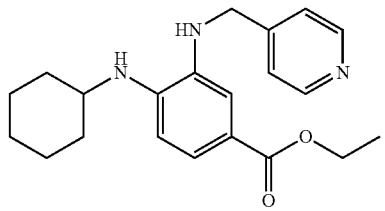 [SMILES: CCOC(=O)c1ccc(NC2CCCCC2)c(NCc2ccncc2)c1]

Synthesis of ethyl 4-(cyclohexylamino)-3-((pyridin-4-ylmethyl)amino)-benzoate (SRS12-45. SI, Table 7)

$^1$H NMR (CDCl$_3$, 400 MHz) δ 8.50 (d, J=1.2 Hz, 1H), 7.62 (d, J=7.6 Hz, 1H), 7.35 (s, 1H), 6.66 (d, J=8.4 Hz, 1H), 4.37-4.28 (m, 4H), 3.36 (b, 1H), 2.11-2.08 (m, 2H), 1.84-1.76 (m, 2H), 1.76-1.70 (m, 1H), 1.44-1.33 (m, 4H), 1.29-1.22 (m, 3H); $^{13}$C NMR (100 MHz, CDCl$_3$) δ 167.08, 150.04, 148.31, 142.06, 133.98, 124.05, 122.63, 118.98, 115.01, 109.73, 60.22, 51.44, 48.06, 33.34, 25.85, 24.91, 14.44: HRMS (FAB) calculated for O$_{21}$H$_{27}$N$_3$O$_2$: 353.46; found: 354.21.

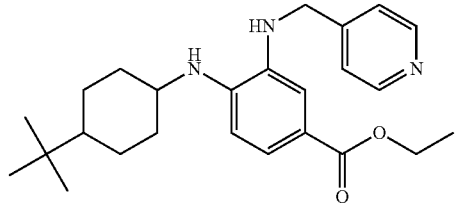 [SMILES: CCOC(=O)c1ccc(NC2CCC(C(C)(C)C)CC2)c(NCc2ccncc2)c1]

Synthesis of ethyl 4-(4-tert-butylcyclohexylamino)-3-(pyridin-4-ylmethylamino)benzoate (SRS13-30. SI, Table 7)

$^1$H NMR (CDCl$_3$, 400 MHz) δ 8.63-8.55 (m, 2H), 7.62 (dd, J=8.4, 1.9 Hz, 1H). 7.38-7.30 (m, 3H), 6.67 (d, J=8.4

Hz, 1H), 4.37 (s, 2H), 4.31 (q, J=7.1 Hz, 2H), 3.30-3.24 (m, 1H), 2.28-2.16 (m, 2H), 1.93-1.82 (m, 2H), 1.36 (t, J=7.1 Hz, 3H), 1.24-1.16 (m, 4H,), 1.11-1.05 (m, 1H), 0.91 (s, 9H); $^{13}$C NMR (100 MHz, CDCl$_3$) δ 167.1, 150.0, 148.3, 142.2, 134.0, 124.0, 122.6, 119.0, 114.9, 109.8, 60.2, 52.1, 48.1, 47.7, 33.9, 32.4, 27.6, 26.2, 14.4; HRMS (FAB) calculated for C$_{25}$H$_{35}$N$_3$O$_2$: 409.56; found: 409.27.

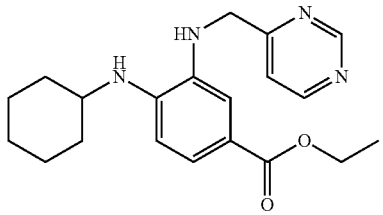 [SMILES: CCOC(=O)c1ccc(NC2CCCCC2)c(NCc2ccncn2)c1]

Synthesis of ethyl 4-(cyclohexylamino)-3-(pyrimidin-5-ylmethylamino)-benzoate (SRS13-35. SI, Table 7)

$^1$H NMR (CDCl$_3$, 400 MHz) δ 9.17 (s, 1H), 8.63 (d, J=5.1 Hz, 1H), 7.57 (d, J=8.3 Hz, 1H), 7.34-7.27 (m, 2H), 6.62 (d, J=8.4 Hz, 1H), 4.41 (s, 2H), 4.26 (q, J=7.1 Hz, 2H), 4.15 (s, 2H), 3.34 (b, 1H), 2.07 (d, J=11.8 Hz, 2H), 1.77 (d, J=13.1 Hz, 2H), 1.66 (d, J=12.1 Hz, 1H), 1.39-1.21 (m, 8H); $^{13}$C NMR (100 MHz, CDCl$_3$) δ 167.1, 158.6, 157.0, 141.9, 133.8, 123.8, 119.3, 118.7, 114.4, 109.5, 60.2, 51.4, 49.3, 33.2, 25.8, 24.9, 14.5; LC/MS (APCI+, M+1) 354.69

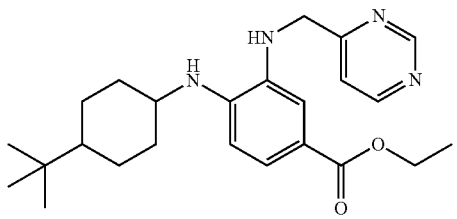 [SMILES: CCOC(=O)c1ccc(NC2CCC(C(C)(C)C)CC2)c(NCc2ccncn2)c1]

Synthesis of ethyl 4-(4-tert-butylcyclohexylamino)-3-(pyrimidin-5-ylmethylamino)benzoate (SRS13-37. SI, Table 7)

$^1$H NMR (CDCl$_3$, 400 MHz) δ 9.23 (s, 1H), 8.74-8.64 (m, 1H), 7.62 (s, 1H), 7.41-7.31 (m, 2H), 6.66 (d, J=8.4 Hz, 1H), 4.47 (s, 2H), 4.31 (d, J=10.0 Hz, 2H), 4.04 (d, J=16.2 Hz, 2H), 2.23 (s, 2H), 1.89 (s, 2H), 1.35 (t, J=7.1 Hz, 3H), 1.21 (s, 4H), 1.09 (d, J=9.0 Hz, 1H), 0.92-0.088 (s, 9H); $^{13}$C NMR (100 MHz, CDCl$_3$) δ 166.9, 158.7, 157.1, 142.1, 133.8, 123.9, 119.3, 118.8, 114.6, 109.6, 60.2, 52.1, 49.3, 47.7, 33.8, 32.4, 27.6, 26.2, 14.5; LC/MS (APCI+, M+1) 410.19

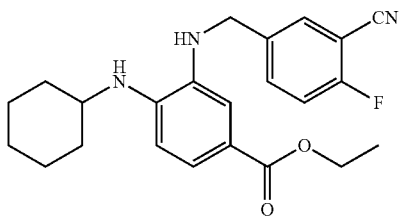 [SMILES: CCOC(=O)c1ccc(NC2CCCCC2)c(NCc2ccc(F)c(C#N)c2)c1]

Synthesis of ethyl 3-(3-cyano-4-fluorobenzylamino)-4-(cyclohexylamino)-benzoate (SRS12-54. SI, Table 7)

$^1$H NMR (CDCl$_3$, 400 MHz) δ 7.70-7.65 (m, 1H), 7.62-7.60 (m, 2H), 7.31 (s, 1H), 7.20 (t, J=8.8 Hz, 1H), 6.65 (d, J=8.4 Hz, 1H), 4.34-4.27 (m, 4H), 3.35 (b, 1H), 2.10-2.04 (m, 2H), 1.83-1.75 (m, 2H), 1.72-1.65 (m, 1H), 1.45-1.31 (m, 5H), 1.29-1.19 (m, 3H); $^{13}$C NMR (100 MHz, CDCl$_3$) δ 167.1, 163.7, 161.1, 142.1, 136.4, 134.4, 133.6, 132.5, 124.2, 118.9, 116.5, 115.0, 113.9, 109.8, 60.3, 51.5, 47.8, 33.4, 25.84, 24.9, 14.4; $^{19}$F (CDCl$_3$) δ −107.7; HRMS (FAB) calculated for C$_{23}$H$_{26}$FN$_3$O$_2$: 395.47; found: 395.08.

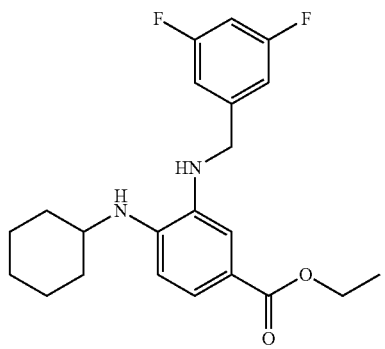 [SMILES: CCOC(=O)c1ccc(NC2CCCCC2)c(NCc2cc(F)cc(F)c2)c1]

Synthesis of ethyl 4-(cyclohexylamino)-3-(3,5-difluorobenzylamino)-benzoate (SRS12-59. SI, Table 7)

$^1$H NMR (CDCl$_3$, 400 MHz) δ 7.62 (d, J=8.0 Hz, 1H), 7.37 (s, 1H), 7.30-6.95 (d, J=6.8 Hz, 2H), 6.76-6.72 (m, 1H), 6.65 (d, J=8.4 Hz, 1H), 4.32-4.30 (m, 4H), 3.93 (b, NH), 3.36 (b, 1H), 3.28 (b, NH), 2.11-2.08 (m, 2H), 1.82-1.79 (m, 2H), 1.71-1.69 (m, 1H), 1.47-1.33 (m, 5H), 1.31-1.20 (m, 3H); $^{13}$C NMR (100 MHz, CDCl$_3$) δ 167.1, 164.5, 162.0, 143.4, 142.1, 134.0, 124.1, 118.9, 115.0, 110.5, 109.7, 102.7, 60.2, 51.4, 48.6, 33.3, 25.86, 24.9, 14.4; $^{19}$F (CDCl$_3$) δ −108.7; HRMS (FAB) calculated for C$_{22}$H$_{26}$F$_2$N$_2$O$_2$: 388.45; found: 388.00.

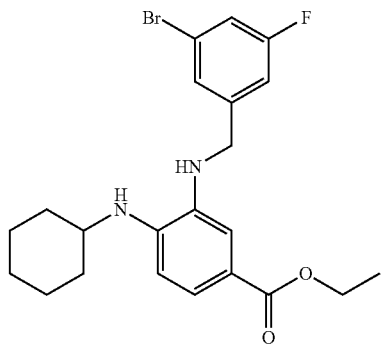 [SMILES: CCOC(=O)c1ccc(NC2CCCCC2)c(NCc2cc(F)cc(Br)c2)c1]

Synthesis of ethyl 3-(3-bromo-5-fluorobenzylamino)-4-(cyclohexylamino)-benzoate (SRS12-52. SI, Table 7)

$^1$H NMR (CDCl$_3$, 400 MHz) δ 7.60 7.61 (dd, J=8.4, 1.9 Hz, 1H), 7.35 (d, J=1.8 Hz, 2H), 7.17 (dt, J=8.1, 2.1 Hz, 1H), 7.06 (d, J=9.2 Hz, 1H), 6.64 (d, J=8.4 Hz, 1H), 4.33-4.27 (m, 4H), 3.91 (s, NH), 3.34 (b, 1H), 3.24 (s, NH), 2.12-2.03 (m, 2H), 1.84-1.75 (m, 2H), 1.72-1.65 (m, 1H), 1.45-1.32 (m, 5H), 1.29-1.21 (m, 3H); $^{13}$C NMR (100 MHz, CDCl$_3$) δ 167.1, 164.1, 161.6, 143.5, 142.1, 134.0, 126.7, 124.1, 122.7, 118.2, 115.1, 113.8, 109.7, 60.2, 51.5, 48.4, 33.3, 25.9, 24.9, 14.4; $^{19}$F (CDCl$_3$) −109.6; HRMS (FAB) calculated for C$_{22}$H$_{26}$BrFN$_2$O$_2$: 449.36; found: 450.00.

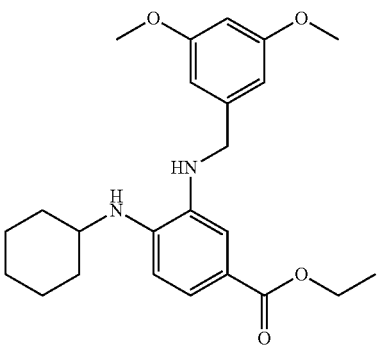 [SMILES: CCOC(=O)c1ccc(NC2CCCCC2)c(NCc2cc(OC)cc(OC)c2)c1]

Synthesis of ethyl 4-(cyclohexylamino)-3-(3,5-dimethoxybenzylamino)-benzoate (SRS12-53. SI, Table 7)

$^1$H NMR (CDCl$_3$, 400 MHz) δ 7.60 (dd, J=8.3, 1.9 Hz, 1H), 7.44 (d, J=2.0 Hz, 1H), 6.62 (d, J=8.4 Hz, 1H), 6.58 (d, J=2.3 Hz, 2H), 6.42-6.4 (m, 1H), 4.31 (q, J=7.1 Hz, 2H), 4.23 (s, 2H), 3.80 (s, 6H), 3.33 (b, 1H), 2.07-2.04 (m, 2H), 1.79-1.34 (m, 8H), 1.26-1.20 (m, 3H); LC/MS (APCI+, M+1) 412.67

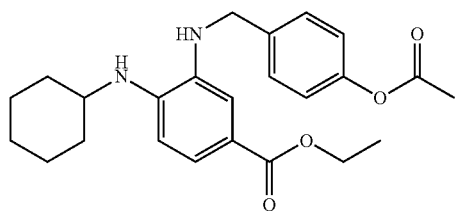 [SMILES: CCOC(=O)c1ccc(NC2CCCCC2)c(NCc2ccc(OC(C)=O)cc2)c1]

Synthesis of ethyl 4-(cyclohexylamino)-3-(4-(ethanoyloxy)benzylamino)-benzoate (4M043. SI, Table 7)

$^1$H NMR (400 MHz, CDCl$_3$) δ 7.61 (dd, J=8.3, 1.9 Hz, 1H), 7.46-7.40 (m, 3H), 7.09 (d, J=8.5 Hz, 2H), 6.63 (d, J=8.5 Hz, 1H), 4.37-4.29 (m, 2H), 4.28 (s, 2H), 3.33 (s, 1H), 2.31 (s, 3H), 2.10-2.03 (m, 2H), 1.78 (d, J=13.4 Hz, 2H), 1.67 (d, J=12.8 Hz, 1H), 1.41 (s, 1H), 1.36 (t, J=7.1 Hz, 4H), 1.27-1.19 (m, 3H); $^{13}$C NMR (126 MHz, CDCl$_3$) δ 169.6, 167.3, 150.0, 142.0, 136.8, 134.61, 129.4, 123.8, 121.8, 118.8, 114.6, 109.3, 60.2, 51.5, 48.9, 33.4, 25.9, 25.0, 21.1, 14.5; LC/MS (APCI+, M+1) 411.01

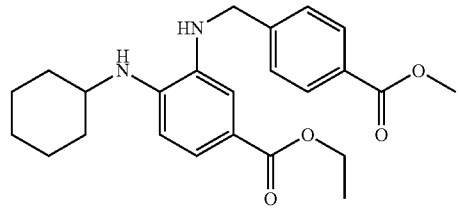 [SMILES: CCOC(=O)c1ccc(NC2CCCCC2)c(NCc2ccc(C(=O)OC)cc2)c1]

Synthesis of ethyl 4-(cyclohexylamino)-3-(4-(methoxycarbonyl)-benzylamino)benzoate (SRS12-80. SI, Table 7)

$^1$H NMR (CDCl$_3$, 400 MHz) δ 8.07-7.99 (m, 2H), 7.60 (dd, J=8.4, 1.9 Hz, 1H), 7.51-7.44 (m, 2H), 7.40 (d, J=1.9 Hz, 1H), 6.64 (d, J=8.4 Hz, 1H), 4.37 (s, 2H), 4.30 (q, J=7.1 Hz, 2H), 3.92 (d, J=0.6 Hz, 3H), 3.89 (d, J=0.7 Hz, 1H), 3.39-3.29 (m, 1H), 2.11-2.02 (m, 2H), 1.83-1.73 (m, 2H), 1.72-1.62 (m, 1H), 1.48-1.30 (m, 5H), 1.30-1.16 (m, 3H); $^{13}$C NMR (100 MHz, CDCl$_3$) δ 167.2, 166.9, 144.5, 142.0, 134.3, 130.0, 128.7, 127.8, 123.9, 118.9, 114.9, 109.5, 60.2, 52.1, 51.4, 49.0, 33.3, 25.9, 24.9, 14.5; HRMS (FAB) calculated for C$_{24}$H$_{30}$N$_2$O$_4$: 410.51; found: 410.10.

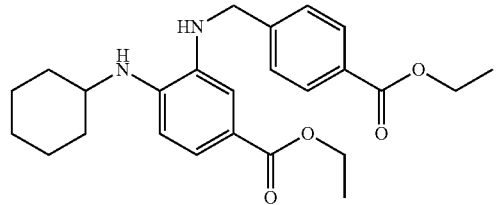 [SMILES: CCOC(=O)c1ccc(CNc2cc(C(=O)OCC)ccc2NC2CCCCC2)cc1]

Synthesis of ethyl 4-(cyclohexylamino)-3-(4-(ethoxycarbonyl)benzylamino)-benzoate (SRS12-84. SI, Table 7)

$^1$H NMR (CDCl$_3$, 400 MHz) δ 8.05 (d, J=8.3 Hz, 2H), 7.61 (dd, J=8.3, 1.9 Hz, 1H), 7.48 (d, J=8.3 Hz, 2H), 7.41 (d, J=1.8 Hz, 1H), 6.66-6.62 (m, 1H), 4.41-4.36 (m, 4H), 4.30 (t, J=7.1 Hz, 2H), 3.35 (s, 1H), 3.11 (d, J=7.5 Hz, 1H), 2.07 (d, J=12.8 Hz, 2H), 1.79 (d, J=13.4 Hz, 2H), 1.68 (d, J=13.0 Hz, 1H), 1.44-1.36 (m, 8H), 1.26 (d, J=7.9 Hz, 3H); $^{13}$C NMR (100 MHz, CDCl$_3$) δ 167.2, 166.4, 144.3, 142.0, 134.3, 129.9, 129.6, 128.7, 127.8, 123.9, 118.9, 114.9, 109.5, 60.9, 60.2, 57.8, 51.4, 49.0, 33.3, 25.9, 24.9, 14.5; HRMS (FAB) calculated for C$_{25}$H$_{32}$N$_2$O$_4$: 424.53; found: 424.12.

TABLE 8
SI, EC50 of Ferrostatin-1 analogs.
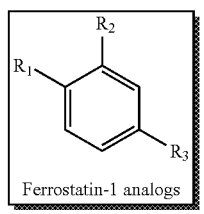
Ferrostatin-1 analogs
| Entry | R1 | R2 | R3 | Name (Yield) | EC50 (nM) | Log P |
|---|---|---|---|---|---|---|
| 1 Ferrostatin-1 | cyclohexyl-NH | NH$_2$ | O-C(=O)-O-CH$_2$CH$_3$ | SRS8-28 (85%) | 88 | 3.2 |
| 2 | cyclohexyl-NH | NO$_2$ | O-C(=O)-O-CH$_2$CH$_3$ | SRS8-24 (77%) | >10,000 | 3.8 |
| 3 | Cl | NH$_2$ | O-C(=O)-O-CH$_2$CH$_3$ | SRS8-62 (89%) | >10,000 | 2.1 |
| 4 | H | NH$_2$ | O-C(=O)-O-CH$_2$CH$_3$ | CA$_1$ | >10,000 | 1.6 |
| 5 | NH$_2$ | NH$_2$ | O-C(=O)-O-CH$_2$CH$_3$ | CA$_2$ | 6900 | 0.5 |
SI, Scheme 2. Synthesis of Ferrostation analogs SRS14-86, SRS14-91, SRS14-92, SRS14-93.
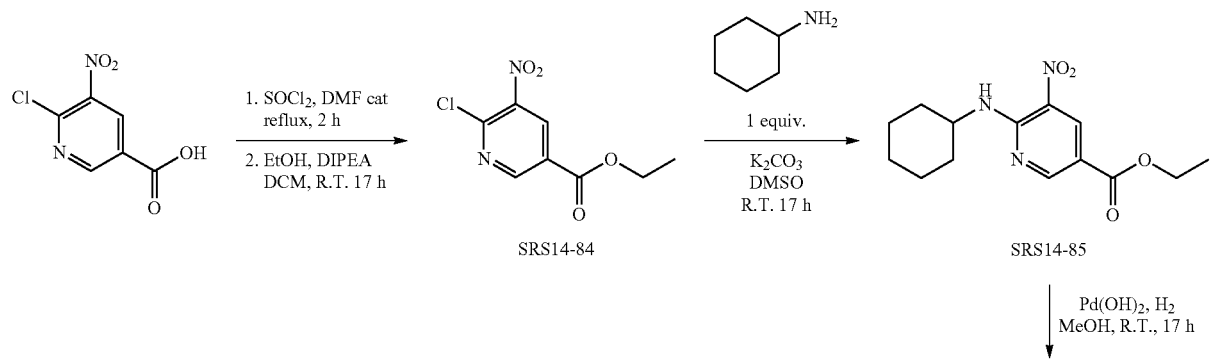

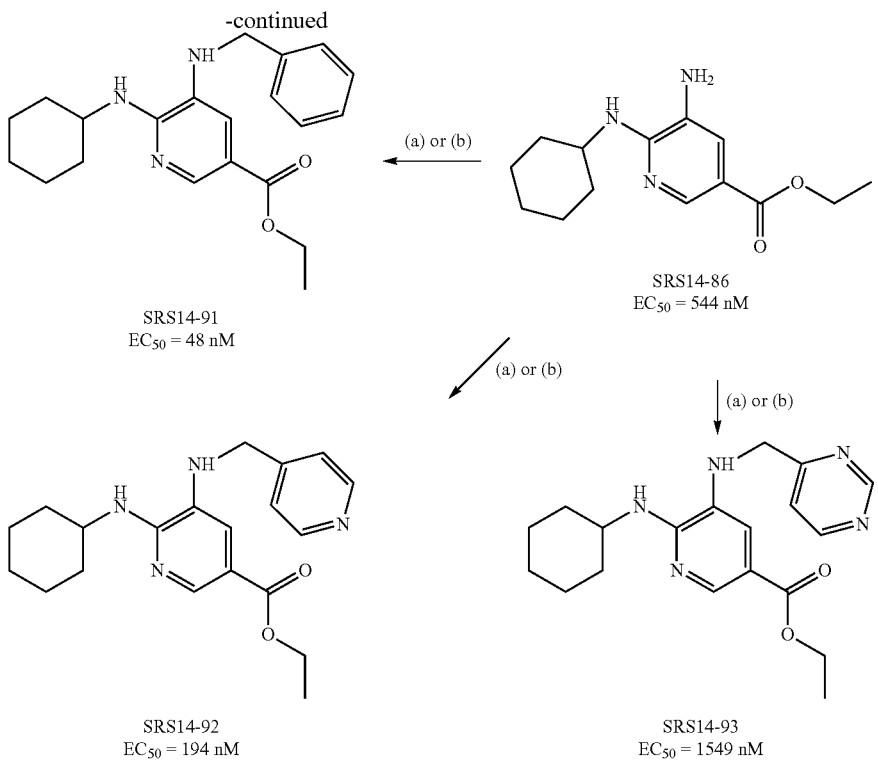

SRS14-91
EC$_{50}$ = 48 nM

SRS14-86
EC$_{50}$ = 544 nM

SRS14-92
EC$_{50}$ = 194 nM

SRS14-93
EC$_{50}$ = 1549 nM (a) alkylation reaction: arylhalide, DIPEA, THF, 60° C., 17 h. (b) reductive amination reaction: aryhaldehyde, NaBH(OAc)$_3$, molecular sieve (4Å), DCE, R.T. to 80° C., 17 h.

Synthesis of ethyl 5-amino-6-(cyclohexylamino)pyridine-3-carboxylate (SRS14-86. SI, Scheme 2)

Following the above general procedure A and B and starting from the ethyl ester (SRS14-84, SI, Scheme 2), which was prepared from the corresponding acid, the crude reaction mixture was purified by column chromatography (dichloromethane: methanol=20:1) to provide the desired ethyl 5-amino-6-(cyclohexylamino)pyridine-3-carboxylate (SRS14-86, SI, Scheme 2) (195 mg, 0.739 mmol, 85% (2 steps)). $^1$H NMR (400 MHz, CDCl$_3$) δ 8.42 (d, J=2.0 Hz, 1H), 7.36 (d, J=2.0 Hz, 1H), 4.78 (d, J=7.6 Hz, 1H), 4.30-4.21 (m, 2H), 4.08-3.92 (m, 1H), 3.36 (s, 1H), 2.07-1.56 (m, 10H), 1.42-1.24 (m, 3H); LC/MS (APCI+, M+1) 264.26.

Synthesis of ethyl 5-(benzylamino)-6-(cyclohexylamino)pyridine-3-carboxylate (SRS14-91. SI, Scheme 2)

Following the above general procedure C or D, the crude reaction mixture was purified by column chromatography (dichloromethane: methanol=40:1) to provide the desired ethyl 5-(benzylamino)-6 (cyclohexylamino)-pyridine-3-carboxylate (SRS14-91, SI, Scheme 2) (14.8 mg, 0.04 mmol, 53%). $^1$H NMR (500 MHz, CDCl$_3$) δ 8.49 (d, J=1.9 Hz, 1H), 7.40 (dd, J=34.8, 27.7 Hz, 5H), 4.59 (s, 1H), 4.47-4.25 (m, 4H), 4.08 (s, 1H), 2.11-1.51 (m, 10H), 1.38 (t, J=11.5, 4.4 Hz, 3H); LC/MS (APCI+, M+1) 354.66.

Synthesis of ethyl 6-(cyclohexylamino)-5-(pyridin-4-ylmethylamino)pyridine-3-carboxylate (SRS14-92. SI, Scheme 2)

Following the above general procedure C or D, the crude reaction mixture was purified by column chromatography (dichloromethane: methanol=20:1) to provide the desired ethyl 6-(cyclohexylamino)-5-(pyridin-4-ylmethylamino)-pyridine-3-carboxylate (SRS14-92, SI, Scheme 2) (16 mg, 0.045 mmol, 54%), $^1$H NMR (400 MHz, CDCl$_3$) δ 8.55 (d, J=50.9 Hz, 3H), 7.46-7.15 (m, 3H), 4.67 (s, 1H), 4.40-4.25 (m, 2H), 4.07 (s, 2H), 2.10-1.62 (m, 10H), 1.40-1.19 (m, 3H); LC/MS (APCI+, M+1) 355.36.

Synthesis of ethyl 6-(cyclohexylamino)-5-(pyrimidin-4 ylmethylamino)-pyridine-3-carboxylate (SRS14-93. SI, Scheme 2)

Following the above general procedure C or D, the crude reaction mixture was purified by column chromatography (dichloromethane: methanol=15:1) to provide the desired ethyl 6-(cyclohexylamino)-5-(pyrimidin-4-yl-methylamino)-pyridine-3-carboxylate (SRS14-93, SI, Scheme 2), (18 mg, 0.051 mmol, 58%).

$^1$H NMR (500 MHz, CDCl$_3$) δ 9.26 (s, 1H), 8.74 (d, J=5.1 Hz, 1H), 8.49 (d, J=1.8 Hz, 1H), 7.37 (d, J=5.1 Hz, 1H), 7.32 (d, J=1.8 Hz, 1H), 4.40 (d, J=40.5 Hz, 2H), 4.34 (dd, J=14.2, 7.1 Hz, 2H), 4.11 (s, 1H), 2.11-1.48 (m, 10H), 1.42-1.31 (m, 3H); LC/MS (APCI+, M+1) 356.26.

SI, Scheme 3. Synthesis of Ferrostatin analog SRS14-55.

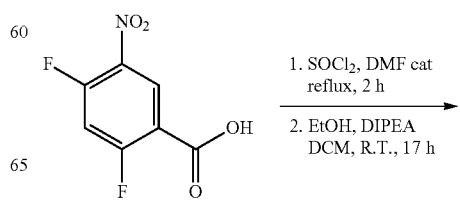

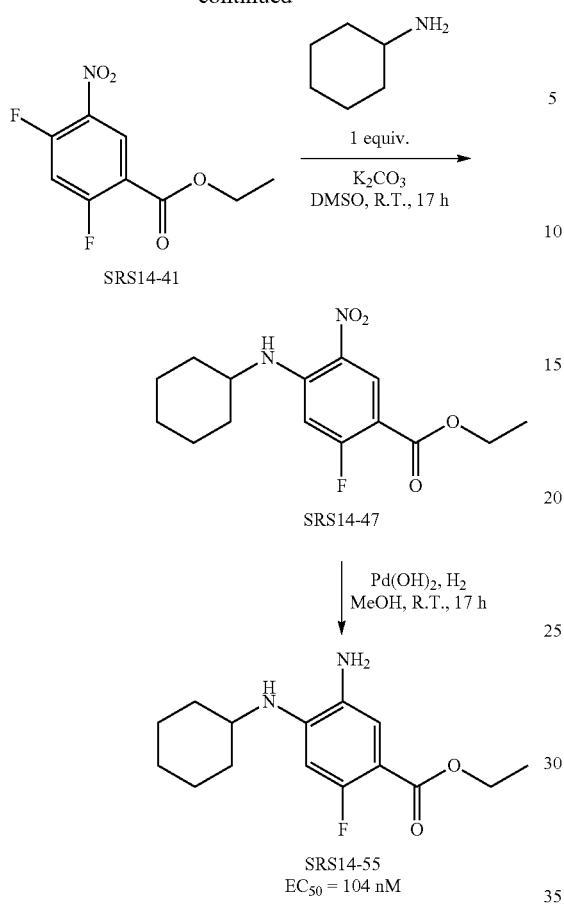

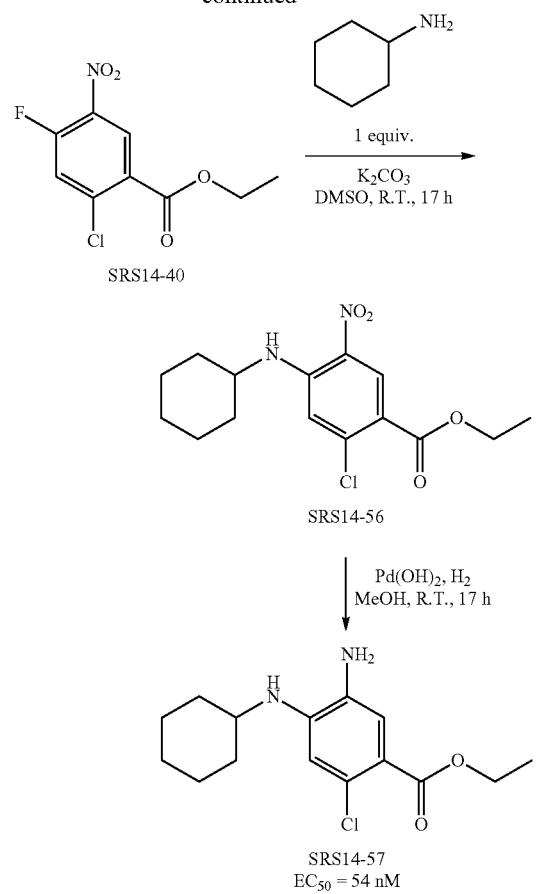

Synthesis of ethyl 5-amino-4-(cyclohexylamino)-2-fluorobenzoate (SRS14-55. SI, Scheme 3)

Following the above general procedure A and B and starting from the ethyl ester (SRS14-41, SI, Scheme 3), which was prepared from the corresponding acid, the crude reaction mixture was purified by column chromatography (dichloromethane: methanol=20:1) to provide the desired ethyl 5-amino-4-(cyclohexylamino)-2-fluorobenzoate (SRS14-55, SI, Scheme 3) (109 mg, 0.389 mmol, 90% (2 steps)). $^1$H NMR (400 MHz, CDCl$_3$) δ 7.37-7.26 (m, 1H), 6.36-6.23 (m, 1H), 4.34 (dd, J=8.9, 6.2, 1.8 Hz, 2H), 3.27 (s, 1H), 3.01 (s, 1H), 2.07 (d, J=8.6 Hz, 2H), 1.81 (d, J=8.5 Hz, 2H), 1.69 (s, 1H), 1.38 (ddd, J=8.9, 6.3, 3.1 Hz, 5H), 1.27 (s, 3H); LC/MS (APCI+, M+1) 281.36.

Synthesis of ethyl 5-amino-2-chloro-4-(cyclohexylamino)benzoate (SRS14-57. SI, Scheme 4)

Following the above general procedure A and B and starting from the ethyl ester (SRS14-40, SI, Scheme 4), which was prepared from the corresponding acid, the crude reaction mixture was purified by column chromatography (dichloromethane: methanol=20:1) to provide the desired ethyl 5-amino-2-chloro-4-(cyclohexylamino)benzoate (SRS14-57, SI, Scheme 4) (136 mg, 0.459 mmol, 75% (2 steps)). $^1$H NMR (400 MHz, CDCl$_3$) δ 7.57 (d, J=8.4 Hz, 1H), 7.42 (s, 1H), 6.59 (d, J=8.4 Hz, 1H), 4.17-4.06 (m, 2H), 3.47 (s, 1H), 3.35-3.27 (m, 1H), 1.78 (d, J=13.0 Hz, 2H), 1.67 (d, J=12.0 Hz, 1H), 1.42-1.31 (m, 5H), 1.26 (td, J=7.1, 1.6 Hz, 5H); LC/MS (APCI+, M+1) 297.47.

SI, Scheme 4. Synthesis of Ferrostatin analog SRS14-57.

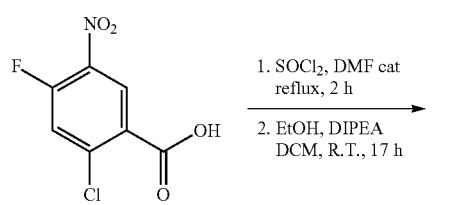

SI, Scheme 5. Synthesis of Ferrostatin analog SRS14-58.

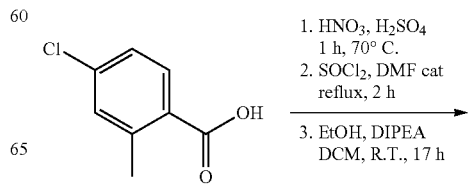

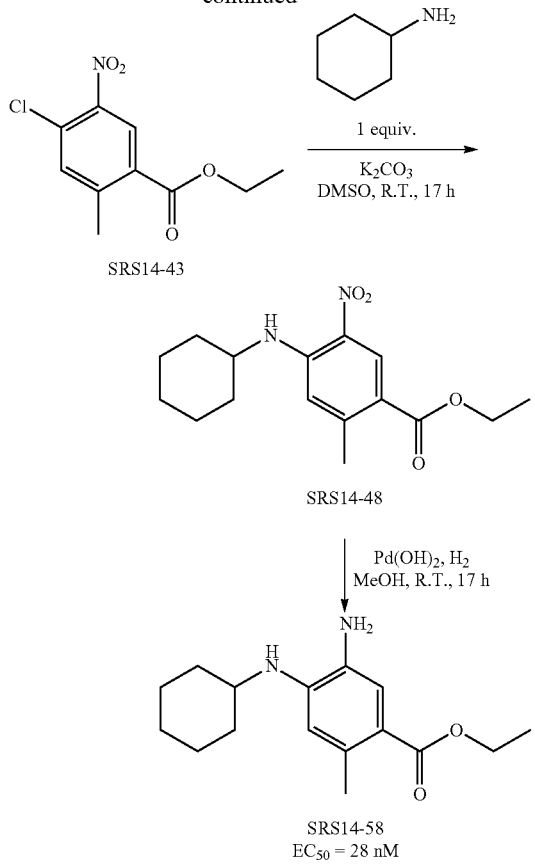

Synthesis of ethyl 5-amino-4-(cyclohexylamino)-2-methylbenzoate (SRS14-58. SI, Scheme 5)

Following the above general procedure A and B and starting from the ethyl ester (SRS14-43, SI, Scheme 5), which was prepared from the corresponding acid, the crude reaction mixture was purified by column chromatography (dichloromethane: methanol=40:1) to provide the desired ethyl 5-amino-4-(cyclohexylamino)-2-methylbenzoate (SRS14-58, SI, Scheme 5) (18 mg, 0.064 mmol, 83% (2 steps)). $^1$H NMR (400 MHz, CDCl$_3$) δ 7.43 (d, J=2.2 Hz, 1H), 6.41 (s, 1H), 4.30 (dd, J=9.5, 4.6 Hz, 2H), 3.40-3.28 (m, 2H), 2.56 (d, J=2.6 Hz, 3H), 2.09 (d, J=9.3 Hz, 2H), 1.81 (d, J=10.0 Hz, 2H), 1.70 (d, J=8.6 Hz, 1H), 1.39 (ddd, J=14.9, 9.3, 8.1 Hz, 5H), 1.29-1.16 (m, 3H); LC/MS (APCI+, M+1) 277.16.

Results

Figure 17:
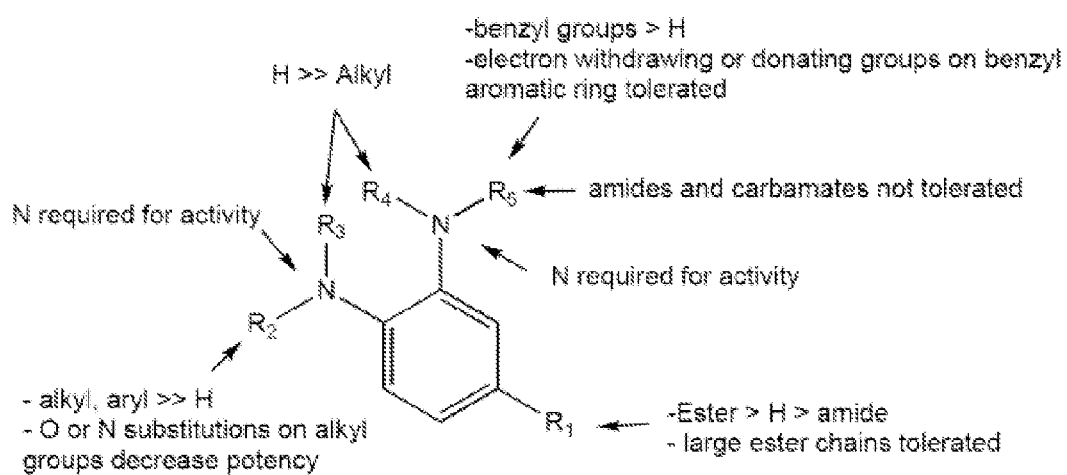
FIG. 17 shows an SAR of Fer-1 based on potency in the HT-1080 death-suppression.
Figure 18:
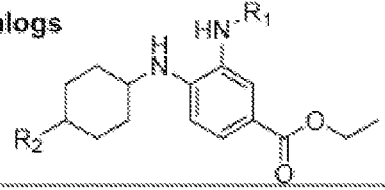
FIGS. 18A-B show an SAR study of Fer-1.
Figure 18:
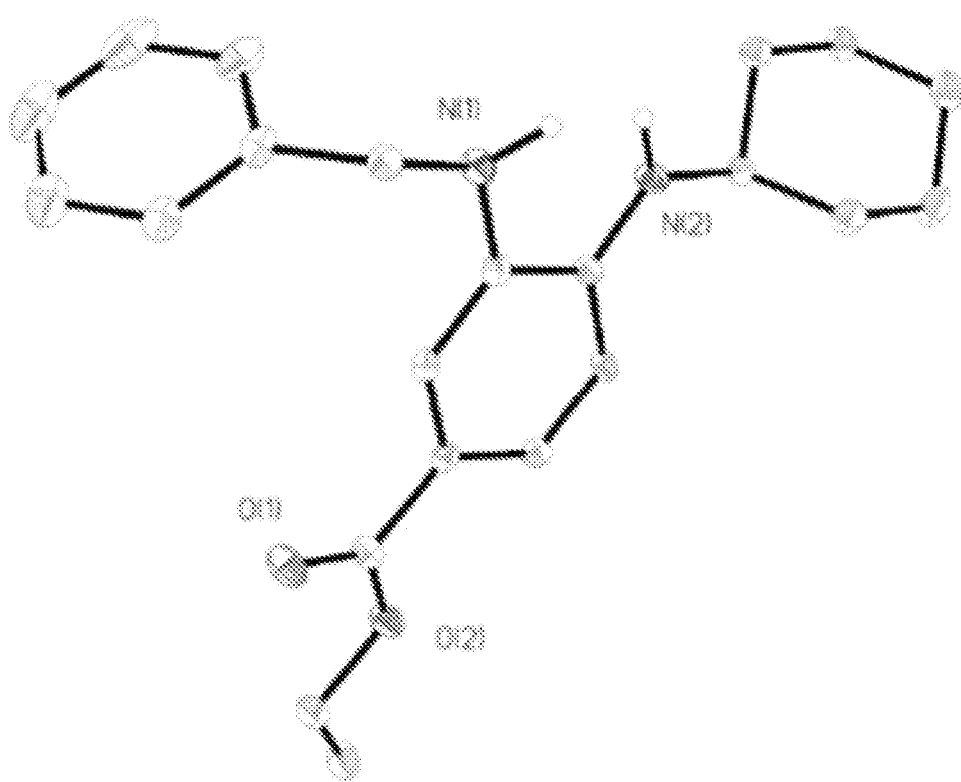

The 67 analogs were tested for cell death inhibition by treating HT-1080 fibrosarcoma cells with a lethal concentration of erastin (10 µM) in the presence of each ferrostatin analog. Based on the activity of the analogs generated in this assay, a structure activity relationship (SAR) for the Fer-1 scaffold (FIG. 17) was established. Analogs with a nitro group in place of the amine were inactive, confirming previous suggestions that this amine is essential for ferrostatin activity. In addition, analogs lacking cyclohexylamines were not active. Introduction of heteroatoms into the N-cyclohexyl moiety resulted in consistent reductions in potency, consistent with the hypothesis that the hydrophobicity of this portion of the scaffold is crucial for anchoring or concentrating within lipid membranes. Modifications of the ethyl ester, some involving substantial extensions, were generally well tolerated. Finally, both amines are essential for full activity and the amines must be mono-substituted or unsubstituted; the sole exception being the imine of SRS16-86, which can perhaps be reduced in cells. Thus, it appears that the ability to oxidize both amines is crucial for the potency of ferrostatins (Scheme 6). In addition, conversion of the amine group into methyl-, benzyl- or tert-butylcarbamates or amides was not tolerated, consistent with the mechanism proposed in Scheme 6, as these groups will interfere with the tautomerization, which will result in the inhibition of the release of 2 protons and 2 electrons. Aryl amine substituents with electron withdrawing or electron donating groups (—Cl, —Br, —F, —CN, —CF$_3$, —NO$_2$, esters or —OCH$_3$) or nitrogen in the aromatic ring did not affect potency, suggesting that these modifications did not inhibit the electronic delocalization and the release of reducing equivalents into the cell. Overall, this series of Fer-1 analogs provided insight into the Fer-1 mechanism of action and also allowed the identification of analogs with greater potency and improved properties. Indeed, a number of compounds were discovered (SRS11-92, SRS12-45, SRS13-35 and SRS13-37) that were more potent than Fer-1 (FIG. 18A; also discussed in International Application Serial No. PCT/US2013/035021, filed Apr. 2, 2013, which is incorporated by reference in full herein). For example, the SRS11-92 was 15-fold more potent than the parent Fer-1, with an EC50=6 nM (FIG. 18a, entry 3). An X-ray structure of SRS11-92 analog was obtained (FIG. 18B) to confirm its purity and the orientation of both secondary amines.

In parallel with the above cell-based assay, a 2,2-diphenyl-1-picrylhydrazyl (DPPH) assay was used to examine the ability of each analog to scavenge free radicals in a cell-free in vitro solution—a test of intrinsic antioxidant capacity. The reduction of the DPPH radical by ferrostatins resulted in a decrease in absorbance, indicating the antiradical capacity of the ferrostatins. Redox active analogs scavenged the DPPH radical by 60-90% within 30 minutes (FIG. 18a). Consistent with the notion that the lipophilic character of the N-cyclohexyl ring is essential for cell death inhibition in cells, but not intrinsic anti-oxidant activity, Fer-1 analogs bearing heteroatom substitutions such as O- or N-methyl in this moiety retained antioxidant activity in the DPPH assay (68% and 86% reduction of DPPH respectively, despite resulting in much lower potency in the HT-1080 death-suppression assay. Conversely, analogs with electron-withdrawing functional groups (i.e. carbamate and amide analogs) on the primary amine did not scavenge the DPPH radical (0-10%) and did not prevent cell death, suggesting that these groups act to prevent the delocalization and oxidation necessary for radical scavenging, as proposed in Scheme 6.

As a first step in investigating inhibition of ferroptosis in vivo, select ferrostatin analogs were tested for their stability in mouse microsomes and plasma. These compounds had half-lives (T$_{1/2}$)<12 min, where a T$_{1/2}$>30 is generally accepted as indicative of minimally acceptable in vivo PK. Interestingly, an imine analog (SRS16-80) of one of the most potent analogs, incorporating an adamantyl ring in place of the cyclohexyl moiety, showed a T$_{1/2}$ of 154 min. While the imine in SRS16-80 led to about 6-fold lower potency (EC50~300 nM), it corroborated the hypothesis that the benzylic position was the source of cytochrome P450 reactivity. Interestingly, in silico evaluation of these Fer-1 analogs' microsmal stability (Schrodinger Suite P450_SOM) was in agreement with the experimental results.

The imine was then evaluated for mouse plasma stability and found to be rapidly hydrolyzed, due to an isopropyl ester present in this compound ($T_{1/2}$<15 min). This plasma instability was prevented by replacing the isopropyl ester with a t-butyl ester, creating a compound (SRS16-86) with a $T_{1/2}$>120 min in plasma and in liver microsomes (EC50~350 nM).

Example 16

Design and Synthesis of Microsome and Plasma Stable Ferrostatin Analogs

Experimental data pointed to the benzylic position of ferrostatin analogs as the site of metabolic liability in microsomes, and the ester group as the target of plasma esterases. Therefore, analog synthesis focuses on modification of these positions with the goal of improving microsomal and plasma stability in vitro and with the ultimate goal of producing analogs with improved in vivo properties for use in animal models of disease. Because in silico evaluation of Fer-1 analogs' P450 stability using the Schrodinger Suite P450_SOM program showed agreement with the experimental results with liver microsomes, this computer program is used to guide prioritization of compound synthesis and testing of analogs proposed based on modifications known to inhibit metabolism.

One of the most useful methods of blocking metabolism at a specific site is to use a steric shield—a bulky group that hinders oxidation at the position by cytochrome P450. An efficient synthesis of Fer-1 analogs with bulky, blocking groups incorporated at the benzylic site of oxidation (FIG. 19) is shown in Scheme 7.

Scheme 7: Synthesis of Fer-1 analogs with sterically shielding amine substituents.

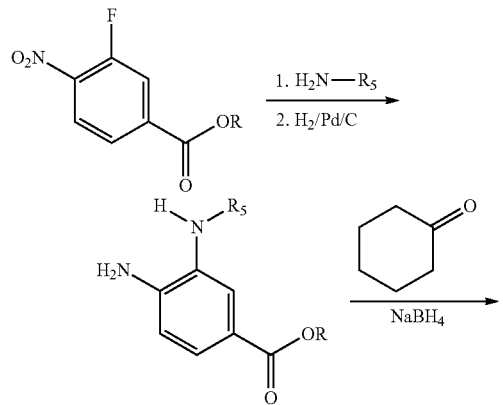

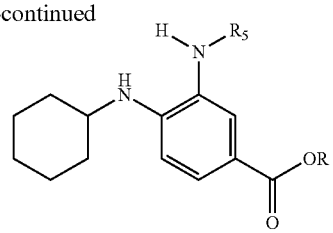

This straightforward synthetic route is a variation of the synthesis outlined in Scheme 5. Treatment of commercially available 3-fluoro-4-nitrobenzoic acid with a benzylamine containing the desired bulky substituent at the benzylic position would displace fluoride via an SNAr reaction to give the corresponding aminonitro compound (Saitoh, et al., 2009). A wide range of benzyl amines are commercially available, including the enantiomerically pure ones shown in FIG. 19. Enantiomerically pure amines are important because cytochrome P450s are known to be enantioselective in their oxidations. Benzylically disubstituted amines would increase the amount of steric shielding and have the advantage of being achiral. The 2,6-dimethylbenzyl amine illustrates another mode of shielding the benzylic position.

Figure 19:
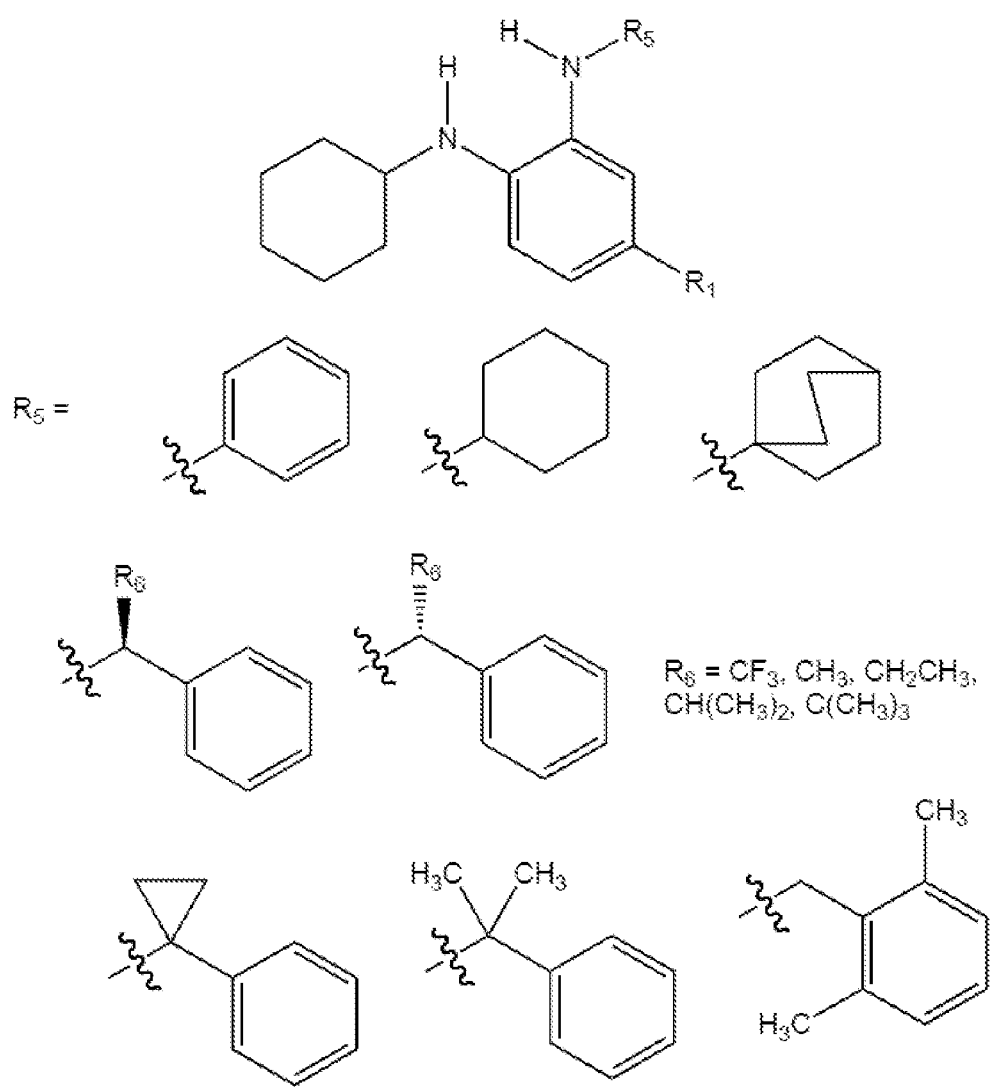
FIG. 19 shows Fer-1 analogs with sterically shielding amine substituents.

The synthetic route shown in Scheme 7 also allows ready access to other substituted amine analogs that can be explored, and that may be more resistant to metabolism, as they do not have a benzylic position to react with P450s. Thus, aniline, cyclohexylamine, and adamantly amine may be used as starting materials to give the corresponding analogs (FIG. 19).

Figure 20:
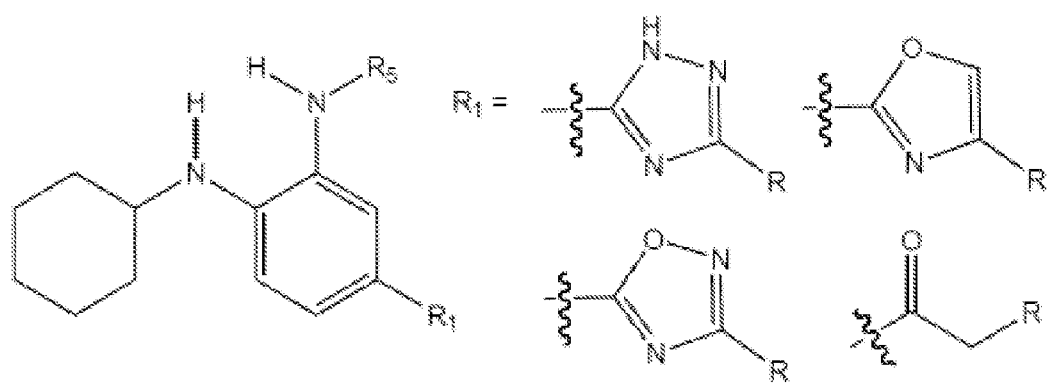
FIG. 20 shows Fer-1 analogs incorporating ester bioisosteres.

The t-butyl ester is resistant to plasma esterases; however, this group may be acid labile, and may not be resistant to the acidic conditions in the stomach upon oral dosing. Bioisosteres, functionalities that are biologically equivalent to the functional group they are replacing, are commonly used to produce active analogs with improved properties, such as resistance to metabolism (Hamada, et al., 2012). A number of ester bioisosteres have been reported in the literature and can be incorporated into analogs of Fer-1. As shown in the synthetic route in Scheme 8, the acid or ester group of 3-fluoro-4-nitrobenzoic acid can be readily converted into ester bioisosteres, such as oxazoles (Wu, et al., 2004), oxadiazoles (Pipik, et al., 2004), triazoles (Passaniti, et al., 2002), or ketones (Genna, et al., 2011). These intermediates can then be used in the synthetic route outlined in Scheme 7 to produce the desired Fer-1 analogs with ester bioisosteres that are resistant to esterases (FIG. 20).

Scheme 8: Synthesis of Fer-1 analogs containing ester bioisosters

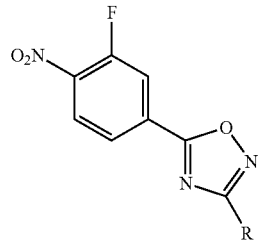

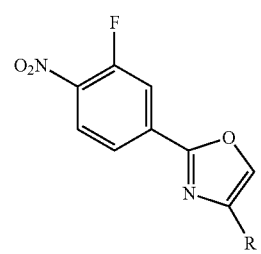

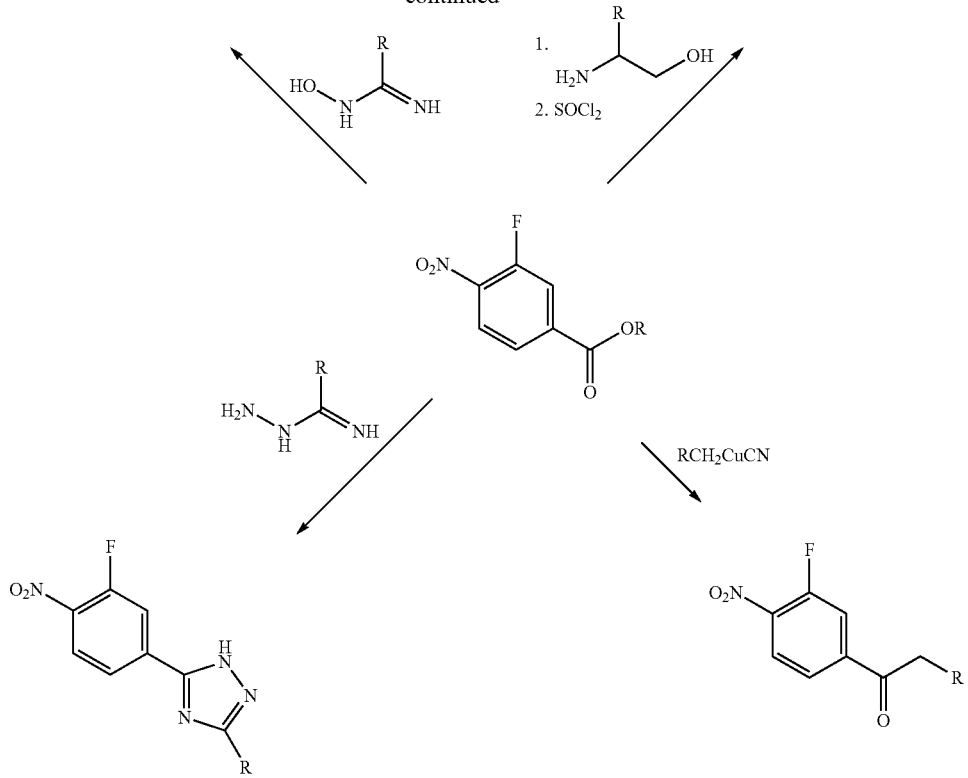

All analogs are tested in vitro for their ability to inhibit erastin-induced ferroptosis in cells. Those with an $IC_{50}$ of <50 nM are tested for metabolic stability in mouse liver microsomes and plasma. Those analogs with $T_{1/2}$>30 minutes in those assays undergo pharmacokinetic analysis in mice. Those analogs with the best in vivo PK parameters are tested in the HD mouse model (see below).

Rescue Activity of Fer-1 Analogs (Dixon, et al., 2012)

HT-1080 cells are cultured in DMEM containing 10% fetal bovine serum, 1% supplemented non-essential amino acids and 1% pen/strep mixture (Gibco) and maintained in a humidified environment at 37° C. with 5% $CO_2$ in a tissue culture incubator. 1,000 HT-1080 cells are seeded per well in duplicate 384-well plates (Corning) using a BioMek FX liquid handling robot (Beckman Coulter). The next day, the medium is replaced with 36 μL of medium containing 10 μM erastin with 4 μL of medium containing a dilution series (previously prepared) of DMSO, Fer-1 (positive control) or Fer-1 analogs. 24 hours later, 10 μL Alamar Blue (Invitrogen) cell viability solution is added to the growth media to a final concentration of 10%. Cells are incubated a further 6 hours and then the Alamar Blue fluorescence intensity recorded using a Victor 3 platereader (PerkinElmer)(ex/em 530/590). All experiments are performed at least twice and the background (no cells)-subtracted Alamar Blue values for each combination are averaged between replicates. From these data, sigmoidal dose-response viability curves and EC50 values are computed using Prism 5.0 (GraphPad).

Plasma and Metabolic Stability

Each compound (1 μM) is incubated with mouse plasma, for 4 hours at 37° C., with shaking at 100 rpm. The concentration of compound in the buffer and plasma chambers is determined using LC-MS/MS. Metabolism of each compound is predicted using Sites of Metabolism (Schrodinger Suite), which combines intrinsic reactivity analysis (Hammett-Taft) with induced fit docking against 2C9, 2D6 and 3A4. This approach identifies 90% of known metabolism sites and has a false positive rate of 17%. The in vitro metabolic stability of each compound in mouse liver microsomes is determined. Pooled mouse liver microsomes are prepared and stored at −80° C. until needed. Compound stability in liver microsomes is measured at 0, 15, 30, 45 and 60 minutes in duplicate, using LC-MS/MS analysis.

Pharmacokinetic Evaluation of Compounds in Mice

To evaluate the PK profile of compounds, IV, IP, and PO administration of each compound is used in C57BL/6J wt mice. Mice are dosed IV at 10 mg/kg and sacrificed using Nembutal and $CO_2$ euthanasia. Six week old mice (Charles River) that have been acclimated to their environment for 2 weeks are used. All animals are observed for morbidity, mortality, injury, availability of food and water twice per day. Animals in poor health are euthanized. Blood samples are collected via cardiac puncture at each time point (0, 30 minutes, 2, 4, 8, 24 h). In addition, brains are collected, and compound concentration determined at each time point using LCO2N MS/MS. Standard PK parameters are calculated for each route of administration, including T1/2, Cmax, AUC, clearance, Vd and % F.

Figure 21:
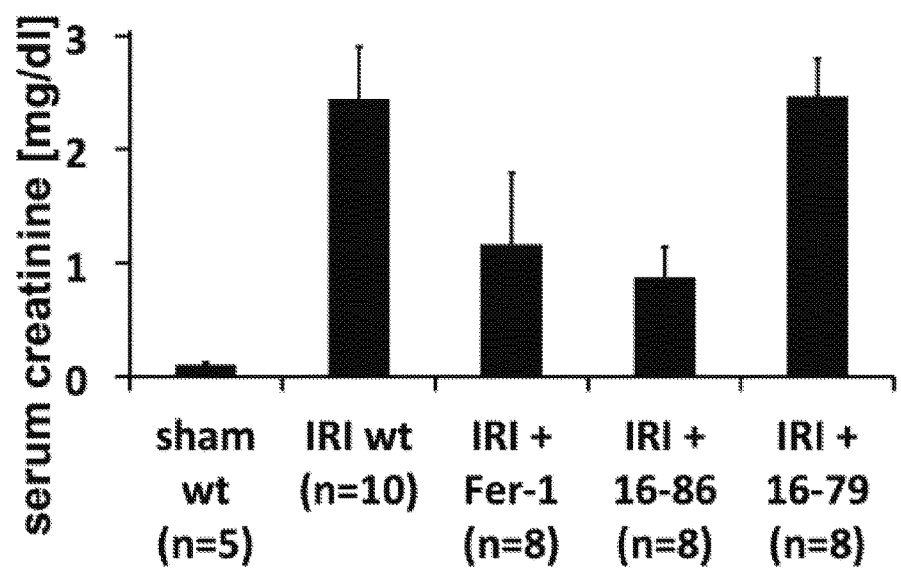
FIG. 21 shows that Fer-1 and SRS16-86 suppress cell death in an in vivo kidney ischemia reperfusion injury mode (IRI). Mice were dosed IP with 2 mg/kg Fer-1 or SRS16-86, or vehicle 30 minutes prior to surgery to induce IRI. Serum creatinine is used as a marker of kidney damage.

As an initial in vivo study, the effects of Fer-1 and SRS16-86 on serum creatinine, a marker of kidney damage, were evaluated in an ischemia reperfusion injury (IRI) model of kidney failure (FIG. 21). Mice were dosed IP with each compound 2 mg/kg or with vehicle, 30 minutes prior to induction of IRI. Both Fer-1 and SRS16-86 were effective in this simple in vivo test, which does not require substantial metabolic stability. However, more sophisticated in vivo models, such as the HD model, require optimized PK/PD parameters.

Example 17

Synchronized Renal Tubular Cell Death Involves Ferroptosis

Materials and Methods:

Mice

All WT mice (C57BL/6) reported in this study were obtained from Charles River. Eight- to 12-wk-old male C57BL/6 mice (average weight~23 g) were used for all WT experiments, unless otherwise specified. Caspase-8 fl/fl mice were kindly provided by Razquella Hakem (Department of Medical Biophysics, University of Toronto, Toronto and Ontario Cancer Institute, University Health Network, Toronto). FADD fl/fl mice were generated by and provided by Manolis Pasparakis (Institute for Genetics, University of Cologne, Cologne, Germany). Doxycyclin-inducible renal tubule-specific Pax8-rtTA; Tet-on.Cre mice have been published (Galluzzi et al., 2014) and were kindly provided by Tobias B. Huber (Renal Division, University Medical Center Freiburg, Freiburg, Germany). RIPK3-deficient mice were kindly provided by Vishva M. Dixit. All in vivo experiments were performed according to the Protection of Animals Act, after approval of the German local authorities or the Institutional Animal Care and Use Committee (IA-CUC) of the University of Michigan, and the National Institutes of Health Guide for the Care and Use of Laboratory Animals (National Research Counsel, 2011), after approval from the University of Michigan IACUC or by the Local authorities responsible for the approval at Ghent University. In all experiments, mice were carefully matched for age, sex, weight, and genetic background. Genotypes were confirmed by tail-snip PCR using the following primers: Pax8-rtTA forward, 5'-CCATGTCTAGACTGGACAAGA-3' (SEQ ID NO:8); Pax8-rtTA reverse, 5'-CTCCAGGCCACATAT-GATTAG-3' (SEQ ID NO:9); tetO-Cre forward, 5'-GCAT-TACCGGTCGATGCAACGAGTGATGAG-3' (SEQ ID NO:10); tetO-Cre reverse, 5'-GAGTGAACGAACCTG-GTCGAAATCAGTGCG-3' (SEQ ID NO:11); caspase-8 flox/flox forward, 5'-ATAATTCCCCCAAATCCTCG-CATC-3' (SEQ ID NO:12); caspase-8 flox/flox reverse, 5'-GGCTCACTCCCAGGGCTTCCT-3' (SEQ ID NO:13); FADD flox/flox forward, 5'-TCACCGTTGCTCTTTGTC-TAC-3' (SEQ ID NO:14); FADD flox/flox reverse (I), 5'-GTAATCTCTGTAGGGAGCCCT-3' (SEQ ID NO:15); and FADD flox/flox reverse (II), 5'-CTAGCGCATAGGAT-GATCAGA-3' (SEQ ID NO:16).

Histology, Immunohistochemistry, and Evaluation of Structural Organ Damage.

Organs were dissected as indicated in each experiment and infused with 4% (vol/vol) neutral-buffered formaldehyde, fixated for 48 h, dehydrated in a graded ethanol series and xylene, and finally embedded in paraffin. Stained sections were analyzed using an Axio Imager microscope (Zeiss). Kidney damage was quantified by two experienced pathologists in a double-blind manner on a scale ranging from 0 (unaffected tissue) to 10 (severe organ damage). The following parameters were chosen as indicative of morphological damage to the kidney after ischemia-reperfusion injury (IRI): brush border loss, red blood cell extravasation, tubule dilatation, tubule degeneration, tubule necrosis, and tubular cast formation. These parameters were evaluated on a scale of 0-10, which ranged from not present (0), mild (1-4), moderate (5 or 6), severe (7 or 8), to very severe (9 or 10). Each parameter was determined on at least four different animals.

Statistics.

For all experiments, differences of datasets were considered statistically significant when P values were lower than 0.05, if not otherwise specified. Statistical comparisons were performed using the two tailed Student t test. Asterisks are used in the figures to specify statistical significance (*P<0.05; P<0.02; *P<0.001). P values in survival experiments (Kaplan-Meier plots) were calculated using GraphPad Prism, ver. 5.04 software. Statistics are indicated as SD unless otherwise specified.

Cell Lines and Reagents.

Necrostatin (Nec-1) was obtained from Sigma-Aldrich. Sanglifehrin A (SfA) was provided by Novartis Pharma. The zVAD-fmk (herein referred to as zVAD) was purchased from BD Biosciences. The monoclonal anti-Fas antibody was from Immunotech. Smac mimetics (Birinapant) was from Absource Diagnostics (Selleckchem). Murine NIH 3T3 fibroblasts were originally obtained from ATCC and were cultured in Dulbecco's modified Eagle medium (DMEM) (Invitrogen) supplemented with 10% (vol/vol) FCS, 100 U/mL penicillin, and 100 µg/mL streptomycin. Human HT-1080 fibrosarcoma cells were originally obtained from ATCC and were cultured in DMEM (Invitrogen) supplemented with MEM NEAA (Invitrogen), 10% (vol/vol) FCS, 100 U/mL penicillin, and 100 µg/mL streptomycin. Murine NIH 3T3 cells were originally obtained from ATCC and were cultured in DMEM (Invitrogen) supplemented with 10% (vol/vol) FCS, 100 U/mL penicillin, and 100 µg/mL streptomycin. Jurkat cells were originally obtained from ATCC and were cultured in RPMI 1640 supplemented with 10% (vol/vol) FCS, 100 U/mL penicillin, and 100 µg/mL streptomycin. All cell lines were cultured in a humidified 5% $CO_2$ atmosphere.

Induction of Cell Death.

For induction of necroptosis, HT-29 cells were stimulated for 24 h at 37° C. with 100 ng/mL TNFα plus 1 µM Smac mimetics plus 25 µM zVAD as indicated (vehicle-treated cells served as control). For induction of ferroptosis, NIH and HT-1080 cells were each stimulated for 24 h at 37° C. with 50 µM erastin as indicated (vehicle-treated cells served as a control). For induction of apoptosis, Jurkat cells were stimulated for 4 h with 100 ng/mL monoclonal anti-Fas (clone 7C11; Immunotech). Anti-Fas-induced apoptosis of Jurkat cells was inhibited by further addition of 25 µM zVAD (vehicle-treated cells served as control).

Analysis of Cell Death.

For immunoblotting, cells were lysed in ice cold 10 mM Tris.HCl, pH7.5, 50 mM NaCl, 1% Triton X-100, 30 mM sodium pyrophosphate, 50 mM NaF, 100 µM $Na_3VO_4$, 2 µM $ZnCl_2$, and 1 mM phenylmethylsulfonyl fluoride (modified Frackelton buffer). Insoluble material was removed by centrifugation (14,000×g, 10 min, 4° C.), and protein concentration was determined using a commercial Bradford assay kit according to the manufacturer's instructions (Bio-Rad).

Equal amounts of protein (17 µg per lane) were resolved on a 12% SDS/PAGE gel and transferred to a nitrocellulose membrane (Amersham Biosciences). Western blot was performed using a polyclonal cleaved caspase-3 antibody (Asp-175 from Cell Signaling) and a corresponding secondary horseradish peroxidase linked polyclonal anti-rabbit antibody (Acris). Immune complexes were visualized by enhanced chemiluminescence (ECL; Amersham Biosciences).

Fluorescence-Activated Cell Sorting.

Phosphatidylserine exposure to the outer cell membrane of apoptotic cells or at the inner plasma membrane of necrotic cells and incorporation of 7-AAD into necrotic cells were quantified by fluorescence-activated cell sorting (FACS) analysis. The ApoAlert annexin V-FITC antibody and the 7-AAD antibody were purchased from BD Biosciences.

Isolation of Renal Tubules.

Six to 12 mice were used for each isolated tubule preparation, depending on the amount of material needed for particular experiments. For preparation of isolated tubules, mice were anesthetized with ketamine (100 mg/kg i.p.) and xylazine (10 mg/kg i.p.), and the kidneys were immediately removed. Type I collagenase was from Worthington Biochemical. Percoll was purchased from Amersham Biosciences. All other reagents and chemicals, including delipidated BSA, were of the highest grade available from Sigma-Aldrich. Immediately after removal of the kidneys, the parenchyma was injected with 0.3-0.5 cc of a cold 95% $O_2$/5% $CO_2$-gassed solution consisting of 115 mM NaCl, 2.1 mM KCl, 25 mM $NaHCO_3$, 1.2 mM $KH_2PO_4$, 2.5 mM $CaCl_2$, 1.2 mM $MgCl_2$, 1.2 mM $MgSO_4$, 25 mM mannitol, 2.5 mg/mL fatty acid-free BSA, 5 mM glucose, 4 mM sodium lactate, 1 mM alanine, and 1 mM sodium butyrate (solution A) with the addition of 1 mg/mL collagenase (type I; Worthington Biochemical). The cortices were then dissected and minced on an ice-cold tile and then resuspended in additional solution A for 8-10 min of digestion at 37° C., followed by enrichment of proximal tubules using centrifugation on self-forming Percoll gradients. For Nec-1 studies in renal tubules, renal cortices were dissected in ice-cold dissection solution (DS) [HBSS with 10 mmol/L glucose, 5 mmol/L glycine, 1 mmol/L alanine, 15 mmol/L Hepes (pH 7.4); osmolality, 325 mOsmol/L] and sliced into 1-mm pieces. The fragments were transferred to collagenase solution (DS with 0.1% (wt/vol) type 2 collagenase and 96 µg/mL soybean trypsin inhibitor) and digested for 30 min at 37° C. and 61×g. After digestion, the supernatant was sieved through two nylon sieves: first 250-µm pore size and then 100-µm pore size. The longer proximal tubule segments remaining in the 100-µm sieve were resuspended by flushing the sieve in the reverse direction with warm DS (37° C.) containing BSA 1% (wt/vol). The proximal tubule suspension was centrifuged for 5 min at 170×g, washed, and then resuspended into the appropriate amount of culture medium (1:1 DMEM/F12 without phenol red and supplemented with heat-inactivated 1% FCS, 15 mmol/L Hepes, 2 mmol/L L-glutamine, 50 nmol/L hydrocortisone, 5 µg/mL insulin, 5 µg/mL transferrin, 5 ng/mL sodium selenite, 0.55 mmol/L sodium pyruvate, 10 mL/L 100× nonessential amino acids, 100 IU/mL penicillin, and 100 µg/mL streptomycin buffered to pH 7.4 (osmolality of 325 mOsmol/kg $H_2O$). The proximal tubule fragments were seeded onto a tissue culture plate and cultured at 37° C. and 95% air/5% $CO_2$ in a standard humidified incubator.

In Vivo Microscopy on the Postischemic Cremaster Muscle.

The surgical preparation of the cremaster muscle was performed as originally described by Baez with minor modifications (Traykova-Brauch et al., 2008; Mulay et al., 2013). Mice were anesthetized using a ketamine/xylazine mixture (100 mg/kg ketamine and 10 mg/kg xylazine), administrated by i.p. injection. The left femoral artery was cannulated in a retrograde manner for administration of microspheres and drugs. The right cremaster muscle was exposed through a ventral incision of the scrotum. The muscle was opened ventrally in a relatively avascular zone, using careful electrocautery to stop any bleeding, and spread over the transparent pedestal of a custom-made microscopic stage. Epididymis and testicle were detached from the cremaster muscle and placed into the abdominal cavity. Throughout the procedure as well as after surgical preparation during in vivo microscopy, the muscle was superfused with warm-buffered saline.

The setup for in vivo microscopy was centered around equipment for stroboscopic fluorescence epiillumination microscopy. Light from a 75-W xenon source was narrowed to a near monochromatic beam of a wavelength of 700 nm by a galvanometric scanner (Polychrome II; TILL Photonics) and directed onto the specimen via an FITC filter cube equipped with dichroic and emission filters (DCLP 500, LP515; Olympus). Microscopy images were obtained with Olympus water immersion lenses (20×/numerical aperture (N.A.) 0.5 and 10×/N.A. 0.3) and recorded with an analog black-and-white charge-coupled device (CCD) video camera (Cohu 4920; Cohu) and an analog video recorder (AG-7350-E; Panasonic). Oblique illumination was obtained by positioning a mirroring surface (reflector) directly below the specimen and tilting its angle relative to the horizontal plane. The reflector consisted of a round cover glass (thickness, 0.19-0.22 mm; diameter, 11.8 mm), which was coated with aluminum vapor (Freichel) and brought into direct contact with the overlying specimen as described previously (Mulay et al., 2013). For measurement of centerline blood flow velocity, green fluorescent microspheres (2-µm diameter; Molecular Probes) were injected via the femoral artery catheter, and their passage through the vessels of interest was recorded using the FITC filter cube under appropriate stroboscopic illumination (exposure, 1 ms; cycle time, 10 ms; length of the electromagnetic wave, 488 nm), integrating video images for sufficient time (>80 ms) to allow for the recording of several images of the same bead on one frame. Beads that were flowing freely along the centerline of the vessels were used to determine blood-flow velocity.

For off-line analysis of parameters describing the sequential steps of leukocyte extravasation, Cap-Image image analysis software (Dr. Zeintl Biomedical Engineering) was used. Rolling leukocytes were defined as those moving slower than the associated blood flow and were quantified as described previously (Mulay et al., 2013). Firmly adherent cells were determined as those resting in the associated blood flow for more than 30 s and related to the luminal surface per 100-µm vessel length. Transmigrated cells were counted in regions of interest (ROI), covering 75 µm on both sides of a vessel over a 100-µm vessel length. By measuring the distance between several images of one fluorescent bead under stroboscopic illumination, centerline blood-flow velocity was determined. From measured vessel diameters and centerline bloodflow velocity, apparent wall-shear rates were calculated, assuming a parabolic flow-velocity profile over the vessel cross-section.

Animals were treated with ferrostatin-1 (2 mg/kg i.p.) or vehicle 30 min before the experiment. For the analysis of postischemic leukocyte responses, three postcapillary vessel segments in a central area of the spread-out cremaster muscle were randomly chosen. After having obtained baseline recordings of leukocyte rolling, firm adhesion, and transmigration in all three vessel segments, ischemia was induced by clamping all supplying vessels at the base of the cremaster muscle using a vascular clamp (Martin). After 30 min of ischemia, the vascular clamp was removed, and reperfusion was restored for 160 min. Measurements were repeated at 60 min and 120 min after onset of reperfusion. Subsequently, FITC dextran was infused intraarterial (i.a.) for the analysis of microvascular permeability. After in vivo microscopy, blood samples were collected by cardiac puncture for the determination of systemic leukocyte counts using a Coulter AcT Counter (Coulter). Anesthetized animals were then euthanized by exsanguination.

Analysis of microvascular permeability was performed as described previously (Linkerman et al., 2012). Briefly, the macromolecule FITC-dextran (5 mg in 0.1 mL saline, Mr 150,000; Sigma-Aldrich) was infused intraarterially after determination of centerline blood-flow velocity. Five post-capillary vessel segments, as well as the surrounding perivascular tissue, were excited at 488 nm, and emission >515 nm was recorded by a CCD camera (Sensicam; PCO) 30 min after injection of FITC-dextran using an appropriate emission filter (LP 515). Mean gray values of fluorescence intensity were measured by digital image analysis (TILLvisION 4.0; TILL Photonics) in six randomly selected ROIs (50×50 µm2), localized 50 µm distant from the postcapillary venule under investigation. The average of mean gray values was calculated.

Acute Oxalate Nephropathy Model.

Mice were divided into two groups. One group received vehicle injections and another group received Ferrostatin-1 (10 mg/kg i.p.). Then, 15 min later, both groups were given a single i.p. injection of 100 mg/kg sodium oxalate and 3% sodium oxalate in drinking water. Blood samples and kidneys were harvested after 24 h. Kidneys were kept at −80° C. for protein isolation and at −20° C. for RNA isolation. One part of the kidney was also kept in formalin to be embedded in paraffin for histological analysis. Kidney sections (2 µm) were stained with periodic acid-Schiff (PAS) reagent. Tubular injury was scored by assessing the percentage of necrotic tubules. Ly6B.2+ neutrophils were identified by immunostaining (clone 7/4; Serotec). Pizzolato stain was used to visualize CaOx crystals, and crystal deposit formation in the kidney was evaluated as described previously (Mulay et al., 2013), using the following point values: 0, no deposits; 1, crystals in papillary tip; 2, crystals in cortical medullary junction; 3, crystals in cortex. When crystals were observed in multiple areas, points were combined. Serum creatinine and blood urea nitrogen were measured using Creatinine FS kit and Urea FS kit (both from DiaSys Diagnostic Systems) according to the manufacturer's protocol. Neutrophil infiltrates were counted in 15 high-power fields (hpfs) per section. For real-time quantitative RT-PCR, total RNA was isolated from kidneys using a Qiagen RNA extraction kit following the manufacturer's instructions. After quantification, RNA quality was assessed using agarose gels. From isolated RNA, cDNA was prepared using reverse transcriptase (Superscript II; Invitrogen). Real-time quantitative RT-PCR (TaqMan) was performed using SYBR-Green PCR master mix and analyzed with a Light Cycler 480 (Roche). All gene expression values were normalized using 18S RNA as a housekeeping gene. All primers used for amplification were from Metabion. The expression of KIM-1, IL-6, CXCL-2, and NF-κB p65 was analyzed using the following primers: Kim-1 forward, 5'-TCAGCTCGGGAATGCACA-3' (SEQ ID NO:17); Kim-1 reverse, 5'-TGGTTGCCTTCCGTGTCT-3' (SEQ ID NO:18); IL-6 forward, 5'-TGATGCACTTGCAGAAAACA-3' (SEQ ID NO:19); IL-6 reverse, 5'-ACCAGAGGAAATTTTCAATAG-3' (SEQ ID NO:20); CXCL-2 forward, 5'-TCCAGGTCAGTTAGCCTTGC-3' (SEQ ID NO:21); CXCL-2 reverse, 5'-CGGTCAAAAAGTTTGCCTTG-3' (SEQ ID NO:22); NF-κB p65 forward, 5'-CGCTTCTCTTCAATCCGGT-3' (SEQ ID NO:23); NF-κB p65 reverse, 5'-GAGTCTCCATGCAGCTACGG-3' (SEQ ID NO:24).

Kidney Model of Ischemia-Reperfusion Injury.

Induction of kidney IRI was performed via a midline abdominal incision and a bilateral renal pedicle clamping for either 40 min (severe IRI, or "lethal-to-WT" IRI) or 50 min (ultra-severe IRI) using microaneurysm clamps (Aesculab). Throughout the surgical procedure, the body temperature was maintained between 36° C. and 37° C. by continuous monitoring using a temperature-controlled self-regulated heating system (Fine Science Tools). After removal of the clamps, reperfusion of the kidneys was confirmed visually. The abdomen was closed in two layers using standard 6-0 sutures. Sham-operated mice underwent the identical surgical procedures, except that microaneurysm clamps were not applied. To maintain fluid balance, all of the mice were supplemented with 1 mL of prewarmed PBS administered intraperitoneally directly after surgery. All mice were killed 48 h after reperfusion for each experiment. For assays investigating combination therapy with [Nec-1+SfA], mice received a total volume of 150 µL of Clinoleic with 10 mg of SfA per kg of body weight and 1.65 mg of Nec-1 per kg body weight 60 min before ischemia. Then, 2 mg of SRS16-86 or SRS16-79 per kg body weight were dissolved in 2% DMSO and were applied intraperitoneally as a total volume of 400 µL 15 min before the onset of surgery in all experiments. All ischemic-reperfusion experiments were performed in a double-blinded manner.

Model of Cerulein-Induced Pancreatitis.

Cerulein-induced pancreatitis (CIP) has been described elsewhere in detail (3). Briefly, male C57BL/6 WT mice (n=7) and male RIPK3-ko mice (n=7) received i.p. injections of 50 µg cerulein/kg body weight once every hour for 10 h (in each case, 200 µL of total volume supplemented with PBS). Animals were euthanized 24 h after the first injection, and samples of blood and tissues were rapidly harvested. Quantification of pancreas injury was performed by measuring serum amylase and lipase activity.

LPS-Induced Lethal Shock.

Mice were injected intraperitoneally (i.p.) with 15 mg/kg *Escherichia coli* 0111:B4 LPS (Sigma-Aldrich). Mice were pretreated by an i.p. injection of 5 mg/kg ethyl 3-amino-4-(cyclohexylamino)benzoate (Fer-1; Matrix Scientific), 10 mg/kg [5-((7-Cl-1H-indol-3-yl)methyl)-3-methylimidazolidine2,4-dione] (Nec-1s; synthesized in house), a combination of Fer-1 and Nec-1s, or vehicle (1% DMSO in PBS) 30 min before the LPS challenge. Rectal body temperature and survival rates were monitored daily up to 96 h. Experiments were approved by the animal ethics committee of Ghent University.

Results:

Conditional Deletion of FADD or Caspase-8 does not Induce Cell Death in Renal Tubular Epithelia.

Figure 22:
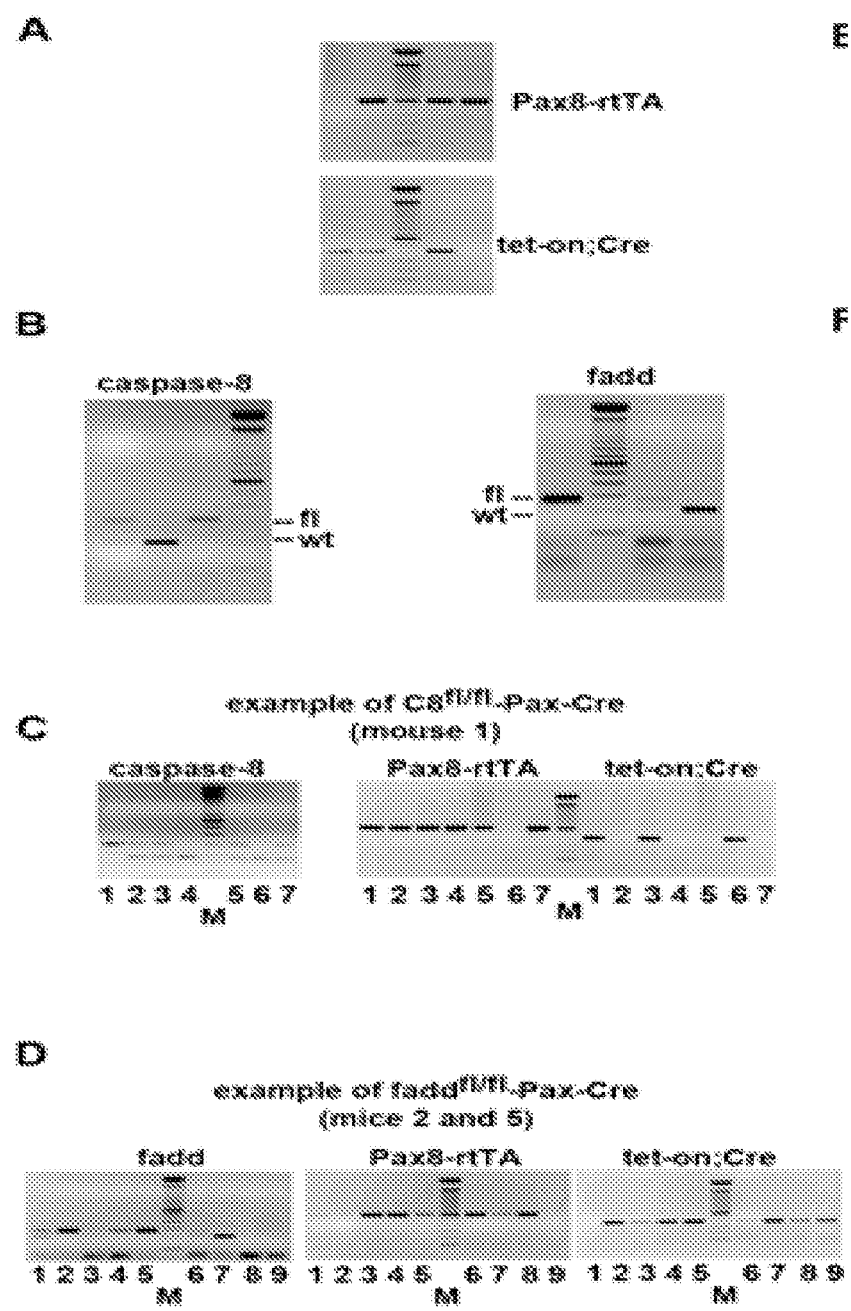
FIG. 22 shows the generation of doxycyclin-inducible kidney tubular specific conditional FADD- and caspase-8 knockout mice. (A-D) Representative genotyping of either FADD-inducible or caspase-8 doxycyclin-inducible kidney tubular-specific conditional knockout mice. (E) Indistinguishability of fl/wt and fl/fl mice after doxycyclin treatment for 3 wk via the drinking water (see Materials and Methods for details). (F) Mice of the indicated genotypes were treated for 0 wk, 1 wk, 2 wk, or 3 wk with doxycyclin before detection of serum lipase (Upper) and serum urea (Lower) levels (n=3-8 per group for all blood values).
Figure 22:
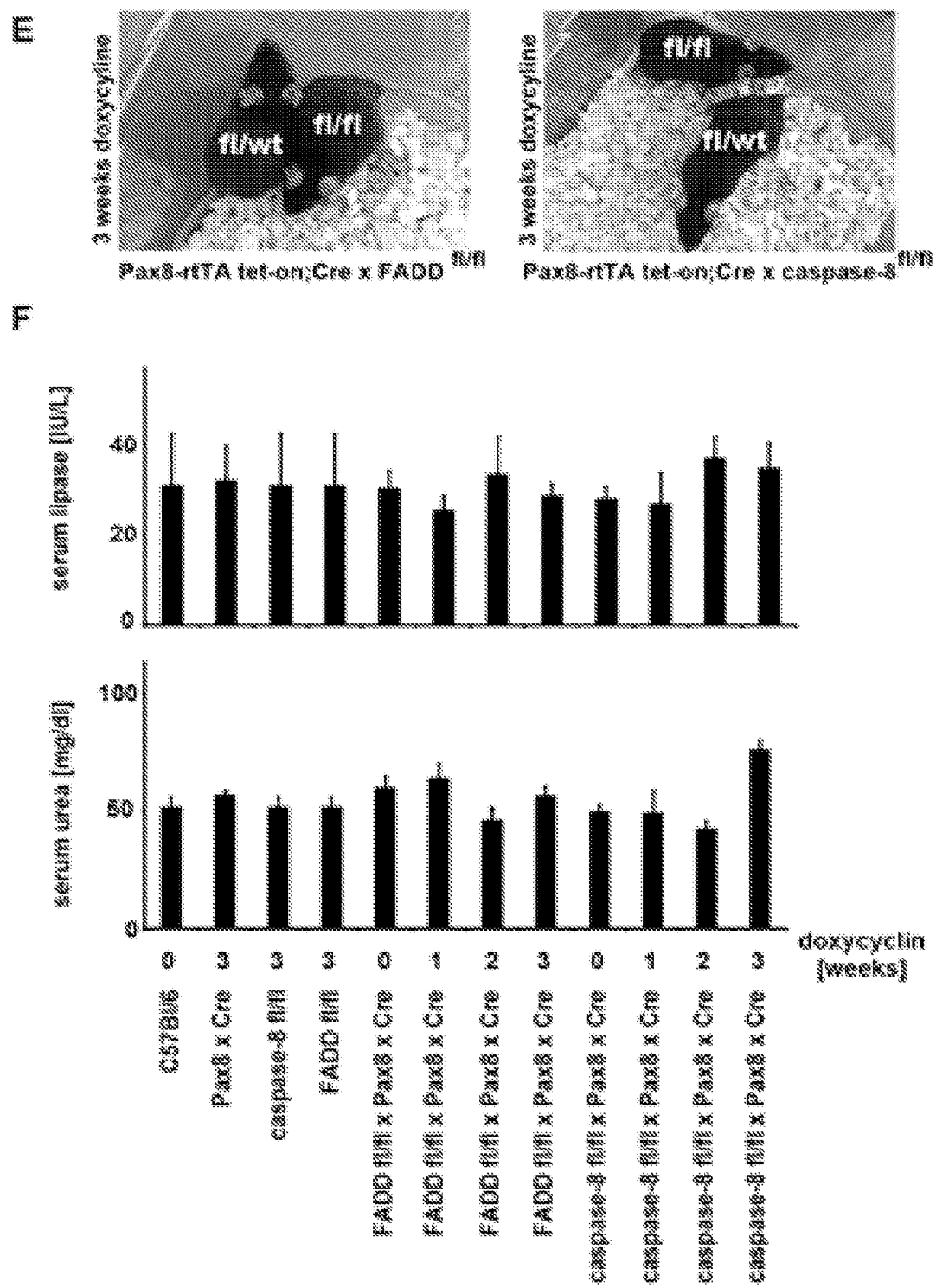
Figure 23:
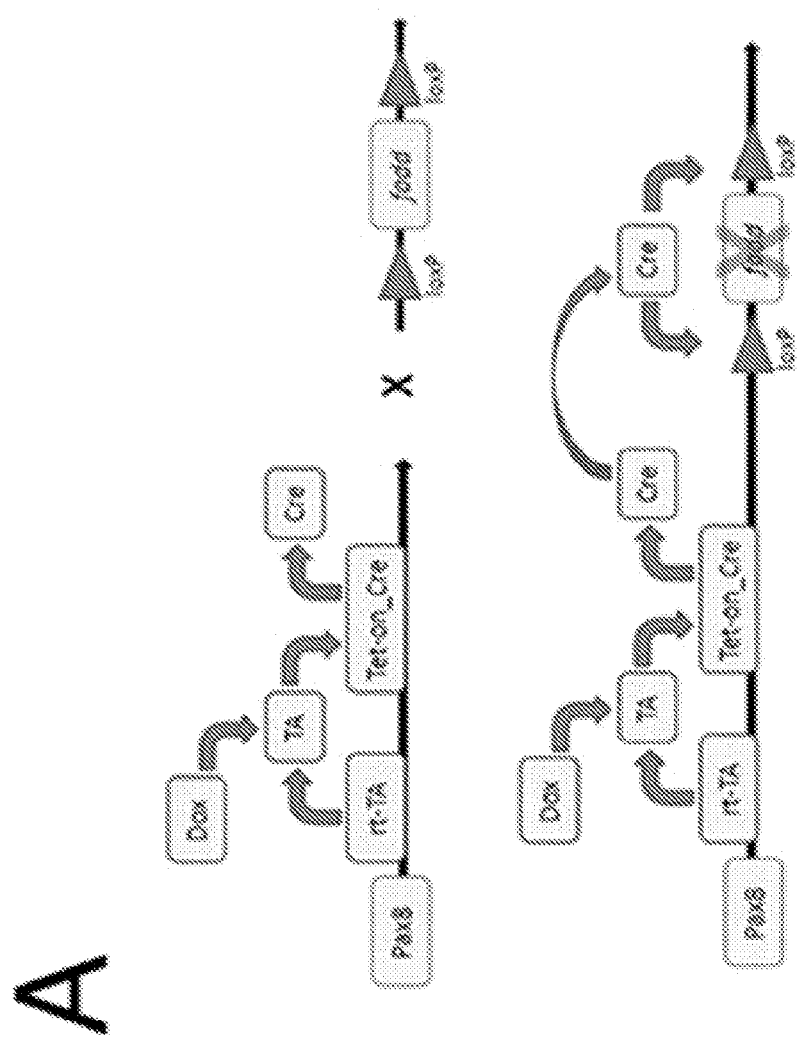
FIG. 23 shows that conditional deletion of FADD or caspase-8 does not sensitize renal tubules to necroptosis. (A) Scheme of the doxycyclin-inducible conditional tubular knockout. (B) After 3 weeks of doxycycline treatment, no detection of the FADD protein in freshly isolated renal tubules was possible; L929 cells serve as a positive control. (C) Periodic acid-Schiff (PAS) staining of normal renal morphology in Pax8-rtA; Tet-on.CrexFADD fl/fl mice after 3-wk treatment with doxycyclin via the drinking water. (D-F) Similarly, caspase-8 was inducibly depleted from tubules. Note that the anti-mouse monoclonal antibody against caspase-8 cross-reacts with a nonspecific protein just below the band of caspase-8. Mouse embryonic fibroblasts (MEFs) from caspase-8/RIPK3-dko mice serve as a negative control, MEFs from cyclophilin D-deficient ppif-ko mice serve as a positive control, as do the C57BL/6 WT mice. (G) Serum creatinine levels remain in the normal range in all mice investigated as indicated. (H) Doxycyclin-induced conditional FADD-deficient or caspase-8-deficient mice react to 20 mg/kg body weight cisplatin-induced acute kidney injury similarly to nonstimulated mice. (I) Necrostatin-1 (Nec-1; 50 μM) does not influence the amount of LDH released from hypoxic renal tubules, either in the presence (Left) or absence (Right) of glycine (glc) (n=8-10 per group).
Figure 23:
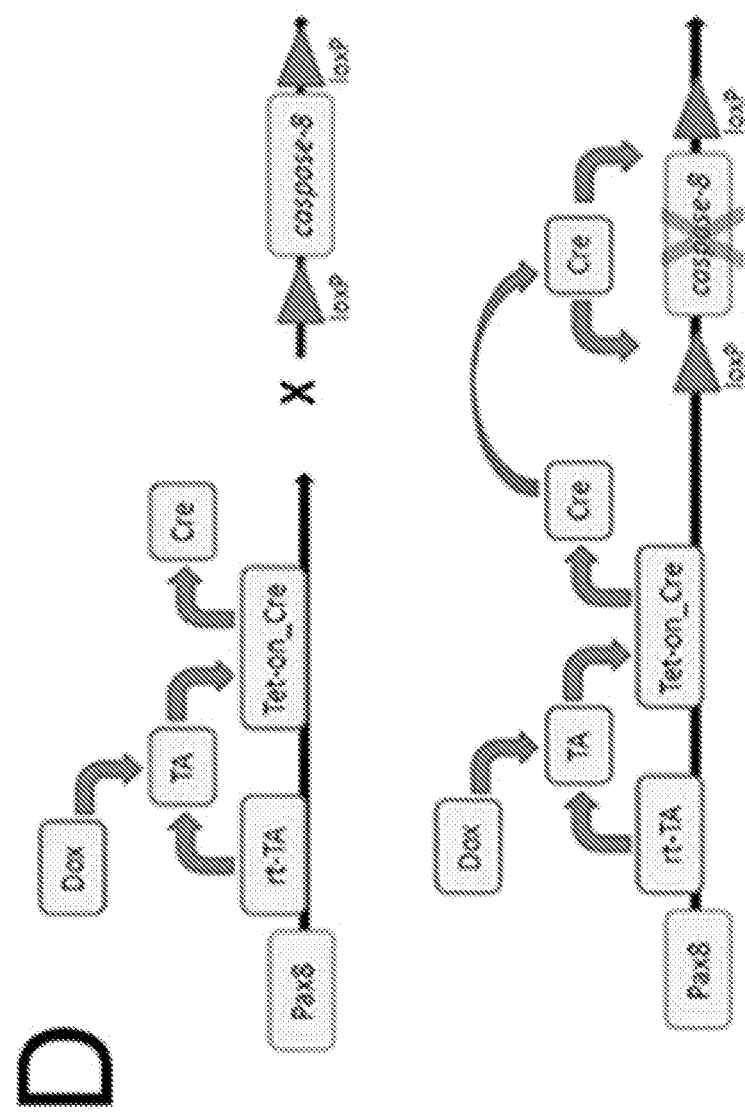
Figure 23:
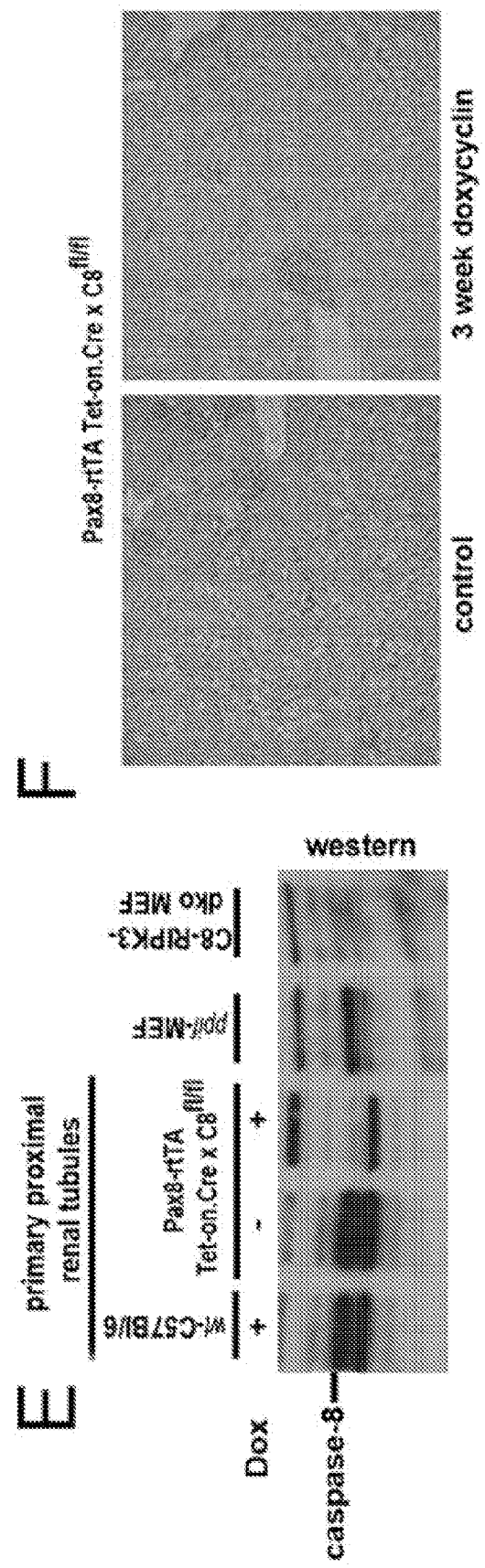
Figure 23:
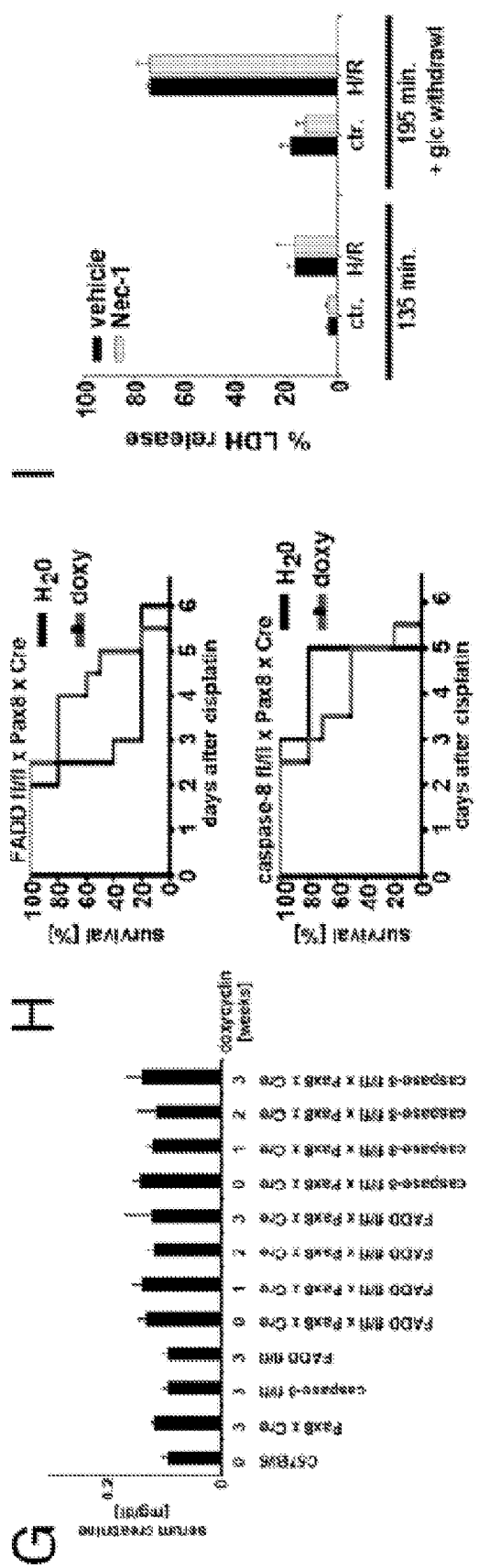
Figure 24:
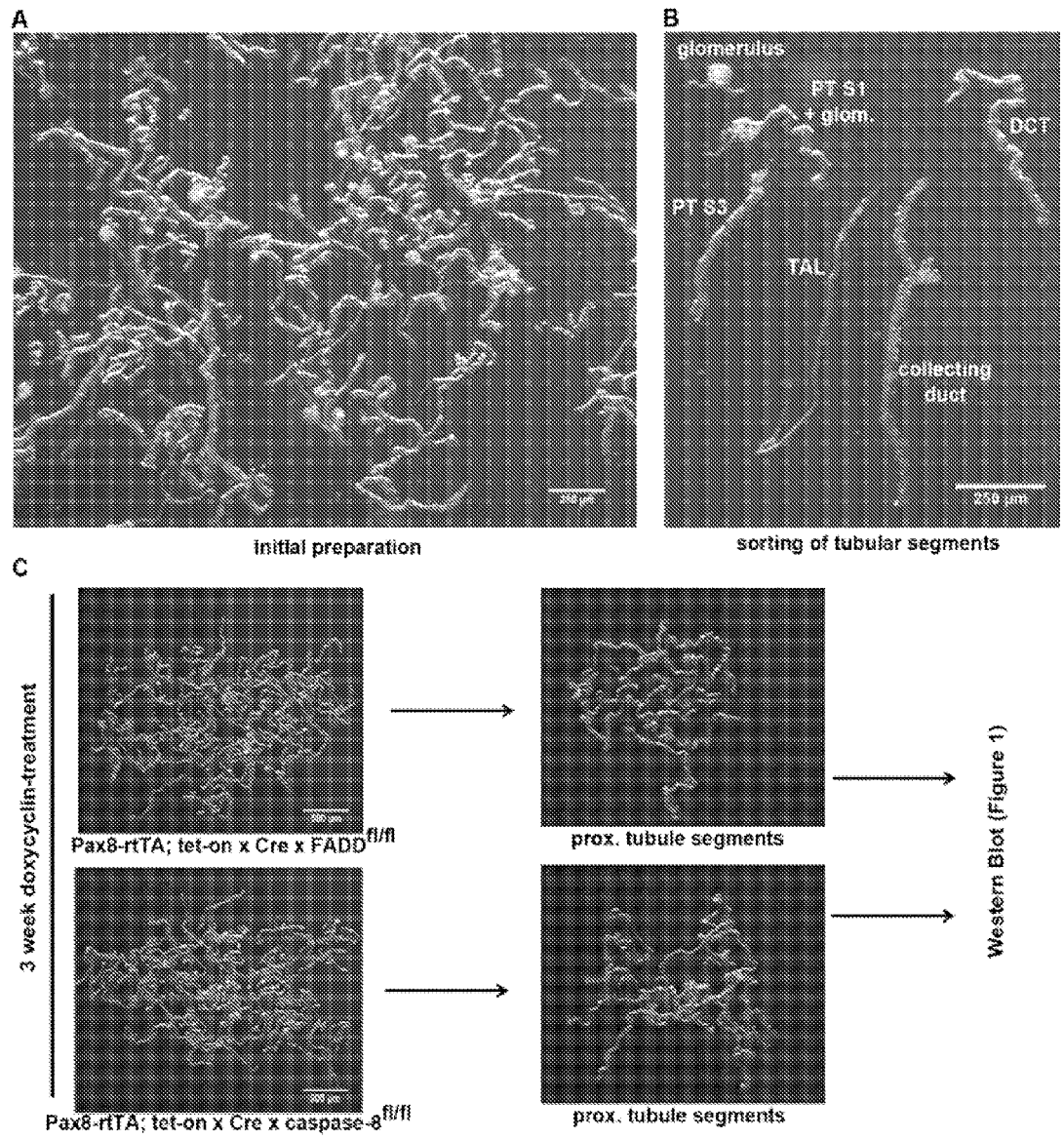
FIG. 24 shows preparation of murine renal tubules for Western blot analysis. (A) Classical appearance after performance of the initial enzymatic preparation steps (see Example 17; Materials and Methods for details). (B) Overview of hand-picked tubular segments. For Western blot analysis, proximal tubules were collected due to the very high susceptibility to undergo necrosis in acute kidney injury. (C) Doxycyclin-fed mice were killed after 3 wk of transactivator induction, and renal tubules were collected. Proximal tubular segments were subsequently pooled and loaded onto gels for Western blotting in FIG. 23. DCT, distal convoluted tubule; TAL, thick ascending limb.

The mode of cell death of tubular cells in acute kidney injury (AKI) has been a matter of intense discussion (Linkerman et al., 2012; Linkerman et a., 2013A) Because RIPK3-deficient mice have been shown to be partially protected from IRI-induced tubular necrosis (Linkerman et al., 2013B; Luedde et al., 2014) and because Nec-1 phenocopies this effect (Linkerman et al., 2012; Degterev et al., 2005; Smith et al., 2007), it was hypothesized that necroptosis might be the mode of cell death that drives parenchymal cells into necrosis. However, it was not ruled out that tubular cell death might have occurred secondary to some changes outside the tubular compartment: e.g., in RIPK3-dependent organ perfusion, which might be altered also upon Nec-1 treatment if the necroptotic pathway was involved. In fact, a discrepancy between the strong in vivo protection and the marginal protective effect of RIPK3-deficient freshly isolated tubules would be consistent with this hypothesis (Linkerman et al., 2013B). A powerful approach to definitively study the involvement of cell-specific necroptosis is to delete components of the necroptosis-suppressing complex, which consists of FADD, caspase-8, RIPK1, and FLIP (Dillon et al., 2012; Dillon et al., 2014), and to analyze spontaneously occurring necroptosis. Therefore, tubular cell-specific inducible conditional mice (Pax8-rtTA Tet-on.Cre) (Traykova-Brauch et al., 2008) were crossed to FADD or capase-8 floxed mice (FIG. 22 A-E) and confirmed the deficiency of the protein of interest by Western blotting from freshly isolated renal tubules (FIGS. 23 A and B and D and E), which were carefully confirmed to be devoid of any other cells (FIG. 24). Unlike in all other tissues reported so far, inducible deletion of FADD or caspase-8 in Pax8-rtTA; Tet-on.Cre×FADD fl/fl and Pax8-rtTA; Tet-on.Cre×caspase-8 fl/fl mice did not affect serum markers of renal function (FIG. 23G and FIG. 22F), histological appearance (FIGS. 23 C and F), or organ function for the entire observation period of 3 wk after addition of doxycycline into the drinking water (FIG. 23G and FIG. 22F). After the 3-wk period of doxycyclin feeding, mice were morphologically indistinguishable from nondoxy-fed littermates (FIG. 22E). In addition, induction of acute kidney injury by application of the nephrotoxin cisplatin (20 mg/kg body weight) led to similar survival kinetics as in WT mice (FIG. 23H). In freshly isolated renal tubules treated with 50 µM Nec-1, no protection was detected both in the presence or in the absence of glycine (FIG. 23I). This result is in line with our previous observation of low levels of RIPK3 in tubular cell lines (Linkerman et al., 2012) and marginal sensitivity for necroptosis compared with a glomerular endothelial cell line and L929 fibrosarcoma cells (Linkerman et aL, 2012). Taken together, these data strongly argue against necroptosis as the primary mode of regulated cell death in renal tubules and suggest that the effects in RIPK3-ko and Nec-1-treated mice are due to extratubular effects.

RIPK3-Deficient Mice Exhibit Increased Renal Perfusion and Fail to Gain Normal Body Weight.

Figure 25:
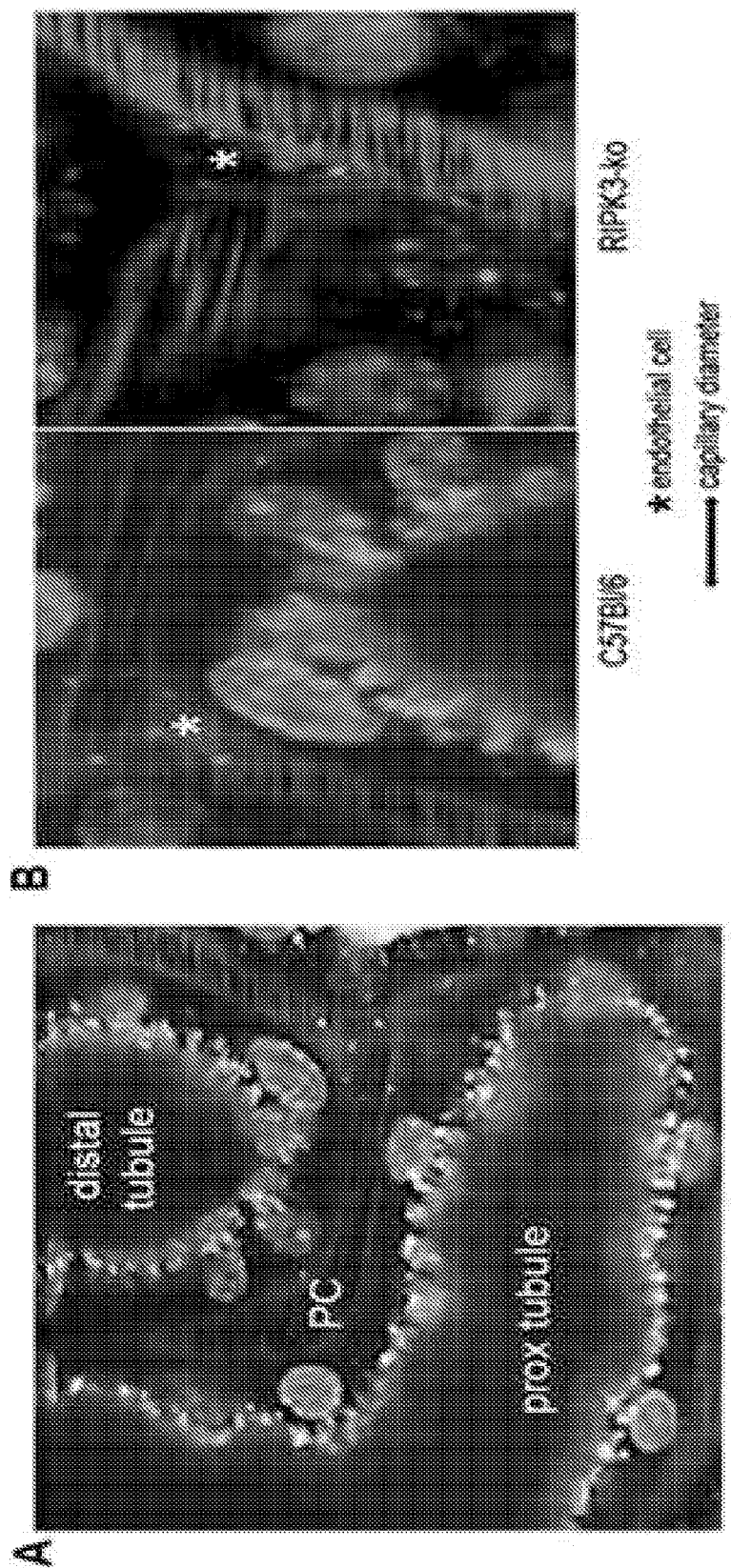
FIG. 25 shows the phenotype of RIPK3-deficient mice. (A) Example of high-resolution intravital microscopy. Green, autofluorescence of the kidney tubules; red, 70 kDa rhodamine dextran (applied via a jugular catheter); yellow, Texas Red (2 kDa) dye, which is freely filtered in the glomerular and reabsorbed in the proximal tubule, counterstaining the endolysosomal compartment; PC, peritubular capillary. (B and C) Intravital microscopy reveals significantly increased peritubular diameters in untreated RIPK3-deficient mice compared with WT littermates. Data in C were generated by counting the diameters of peritubular capillaries at a number of at least 1.115 per group. (D) Based on the data presented in B, the increase in peritubular diameters is associated with 125.7% overall organ perfusion in RIPK3-deficient mice. (E) Model of cerulein-induced pancreatitis (CIP) in WT and RIPK3-deficient mice. No significant protection from increased serum concentrations of serum lipase or serum amylase was detected in RIPK3-deficient mice compared with WT mice (n=7 mice per group). (F and G) Failure to gain overall body weight in both female (Left) and male (Right) RIPK3-deficient mice compared with corresponding littermates, followed for 30 wk after an age of 4 wk (n=8-21 per group).
Figure 25:
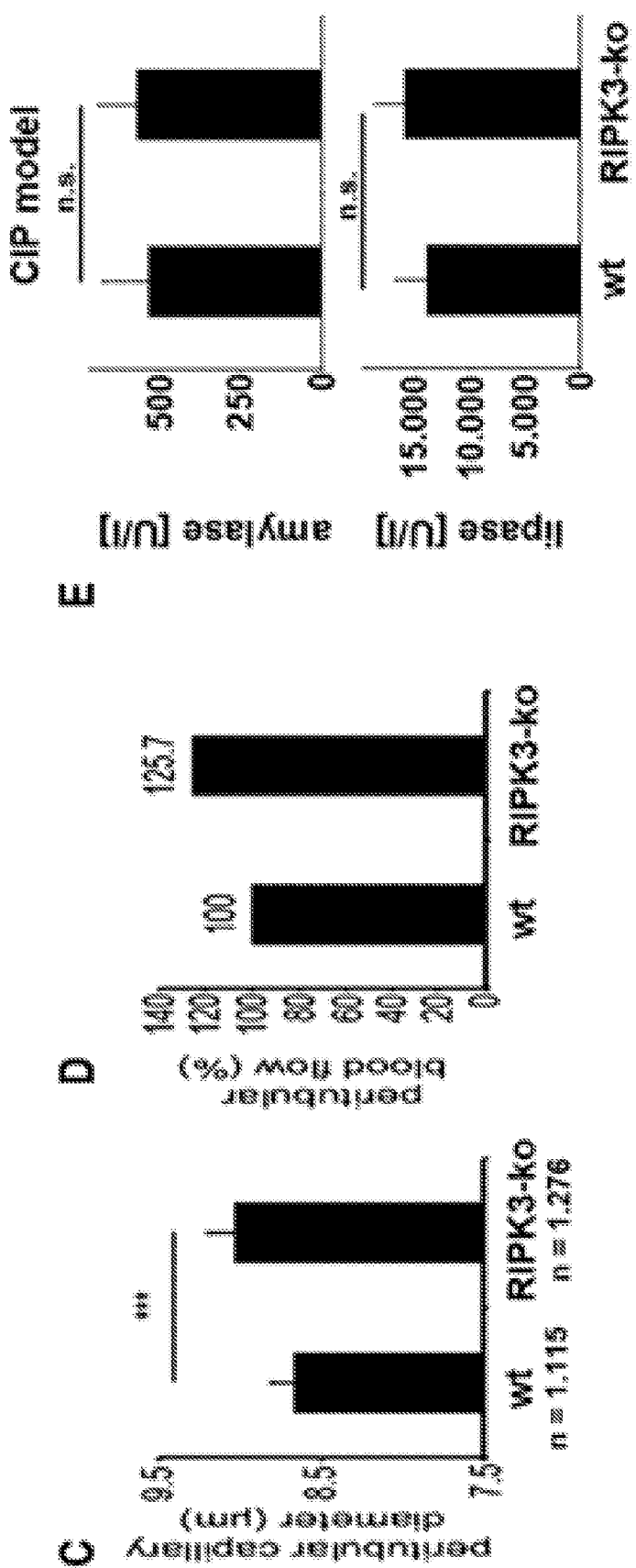
Figure 25:
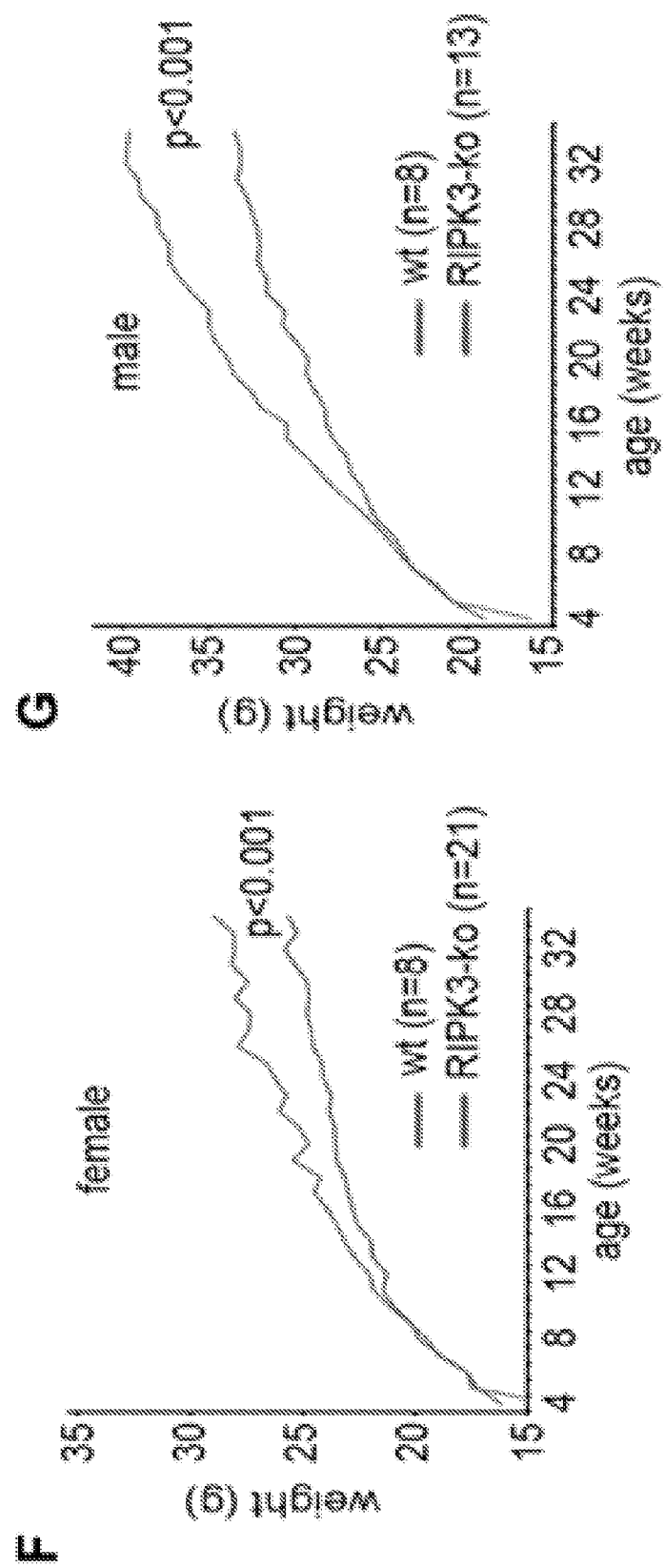

Using low-resolution intravital microscopy, the effects of Nec-1 on the diameter of peritubular capillaries were previously investigated (Linkerman et aL, 2013A). Using a similar approach with higher resolution (FIG. 25A), RIPK3-ko mice were analyzed and statistically significant increases in peritubular diameters were detected (FIGS. 25 B and C), which would account for 25.7% increase in blood flow (FIG. 25D) according to the law of Hagen Poiseuille and could help maintain peritubular perfusion after ischemia when it is known to be compromised. Taking into consideration that, in all renal cells investigated, the highest RIPK3 expression was found in endothelial cells, vascular effects cannot be ruled out, and endothelial cell-specific conditional RIPK3 depletion should be investigated in IRI models. In this respect, it is noteworthy that, in another model of necrotic parenchymal damage that does not rely on ischemia-reperfusion injury, the cerulein-induced pancreatitis, in our hands, RIPK3-deficient mice are not protected from the increase in serum levels of amylase and lipase (FIG. 25E). In addition, RIPK3-ko mice fail to gain normal body weight in comparison with WT littermates in both males and females (FIGS. 25 F and G).

Morphological Changes of Synchronized Tubular Cell Death are Prevented by Ferrostatins.

If apoptosis and necroptosis account for only minor damage of acute tubular necrosis, then what pathway of regulated necrosis might be causative of synchronized tubular death that was identified in an improved ex vivo model of freshly isolated murine renal tubules upon depletion of fatty acids (FIG. 26A). It was confirmed that such tubules are functional before the onset of the fatty-acid depletion for maximal control purposes. Importantly, such synchronized tubular (cell) death very much resembles the appearance of casts found in urine sediments of patients with acute kidney injury. The dynamics of the tubular necrosis suggest a direct cell-to-cell communication to deliver the deadly signal. Because a beneficial effect of the second generation ferrostatin 11-92 (Skouta et al., 2014) in a model of acute injury of freshly isolated renal tubules was previously reported, the morphology of such tubules in the presence of erastin, a well-described inducer of ferroptosis, a necrotic type cell death that largely depends on lipid peroxidation (Dixon et al., 2012, Yagoda et al., 2014), over time (FIG. 26B). Whereas the faint plasma membrane of untreated tubules did not change in SRS16-86-treated tubules (a novel third-generation ferrostatin was looked for (FIG. 27)), vehicle-treated and especially erastin-treated tubules showed membrane protrusions and obvious signs of deformation and functional insufficiency (FIG. 26B). When erastin was applied into the tubule, a similar type of cell death occurred even without fatty-acid depletion. In another well established lactate dehydrogenase (LDH) release-based assay of ex vivo tubulotoxicity (Skouta et al., 2014), hydroxyquinoline-iron-induced cell death, Fer-1 and the Nox-inhibitor GKT were found to be protective whereas Nec-1 did not show any protection (FIG. 26C).

Ferroptosis Mediates IRI-Mediated Immune-Cell Infiltration of the Cremaster Muscle.

Figure 26:
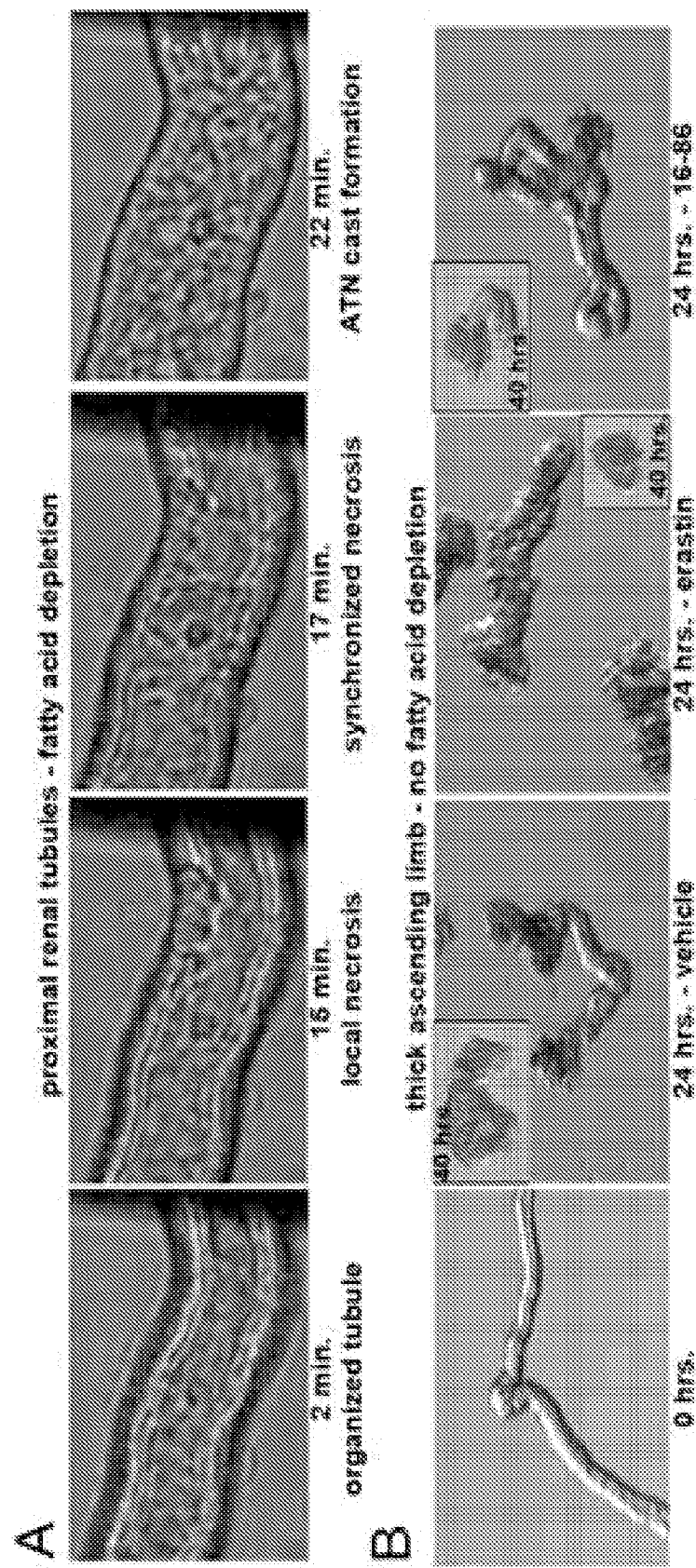
FIG. 26 shows that ferroptosis mediates synchronized tubular necrosis and contributes to immune-cell extravasation into ischemic tissue. (A) Snapshots of functional freshly isolated proximal renal tubule segments undergoing rapid synchronized necrosis upon fatty-acid depletion. (B) In the presence of fatty acids, addition of erastin accelerated, whereas SRS16-86 (a third-generation ferrostatin; see FIG. 27) prevented, tubular necrosis. (C) During the time course of hydroxyquinoline/Fe-induced tubular necrosis, Fer-1 and the Nox-inhibitor GKT prevented LDH release whereas Nec-1 did not show protection. (D) Reflected light oblique transillumination imaging of leukocyte passages through postcapillary venules in IRI of the cremaster muscle in the presence of vehicle or Fer-1. (E) FITC dextran leakage in the same model. (F) Leukocyte rolling is affected by Fer-1 within the first hour after reperfusion. (G) Significantly reduced leukocyte transmigration in the presence of Fer-1.
Figure 26:
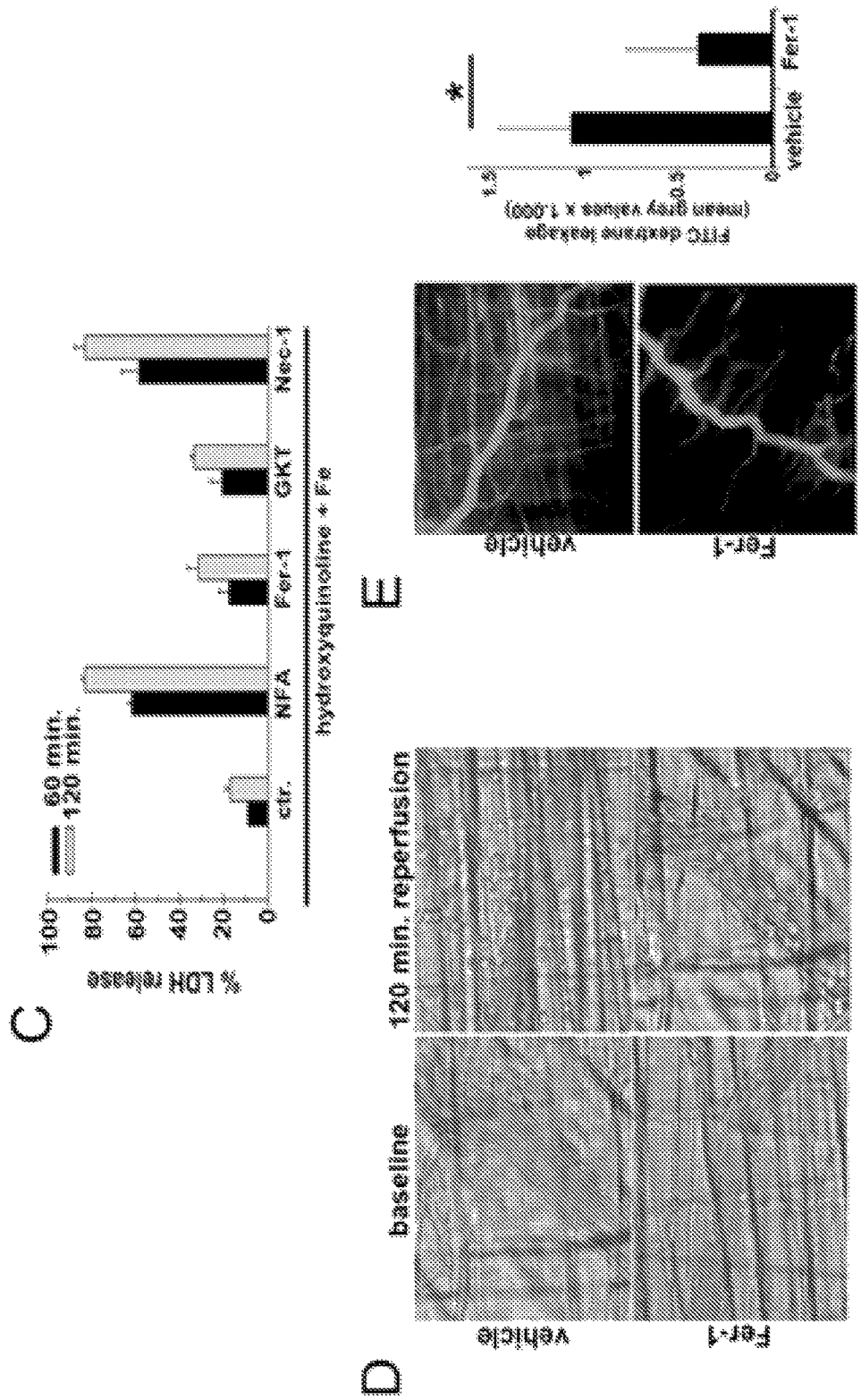
Figure 26:
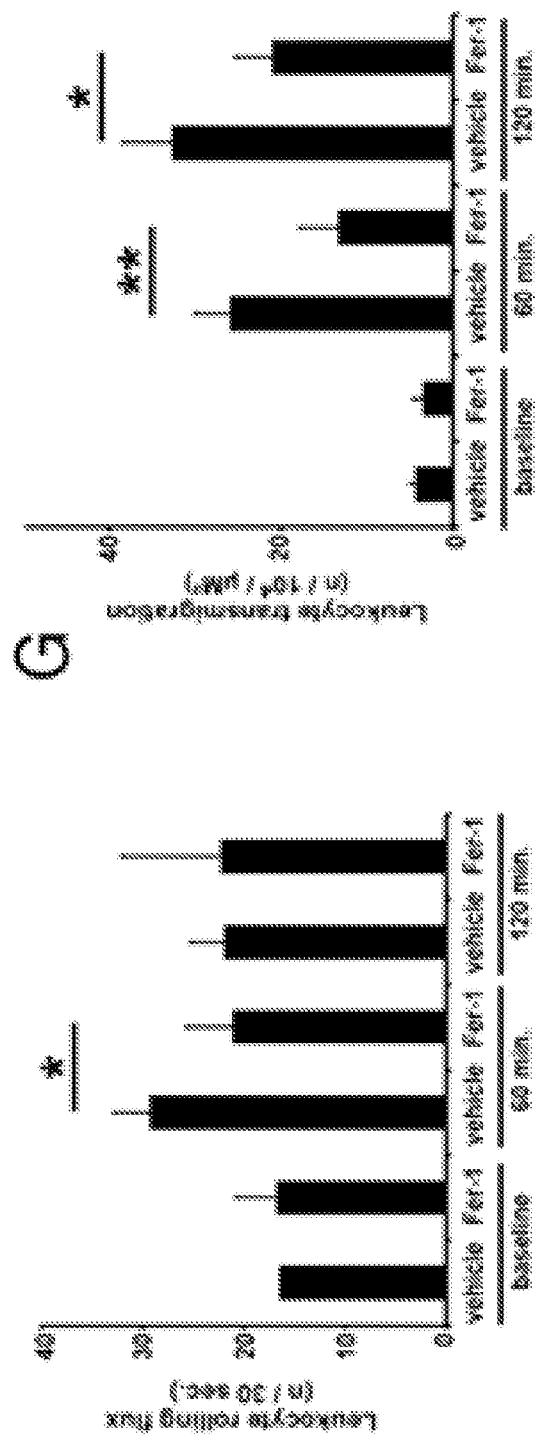
Figure 27:
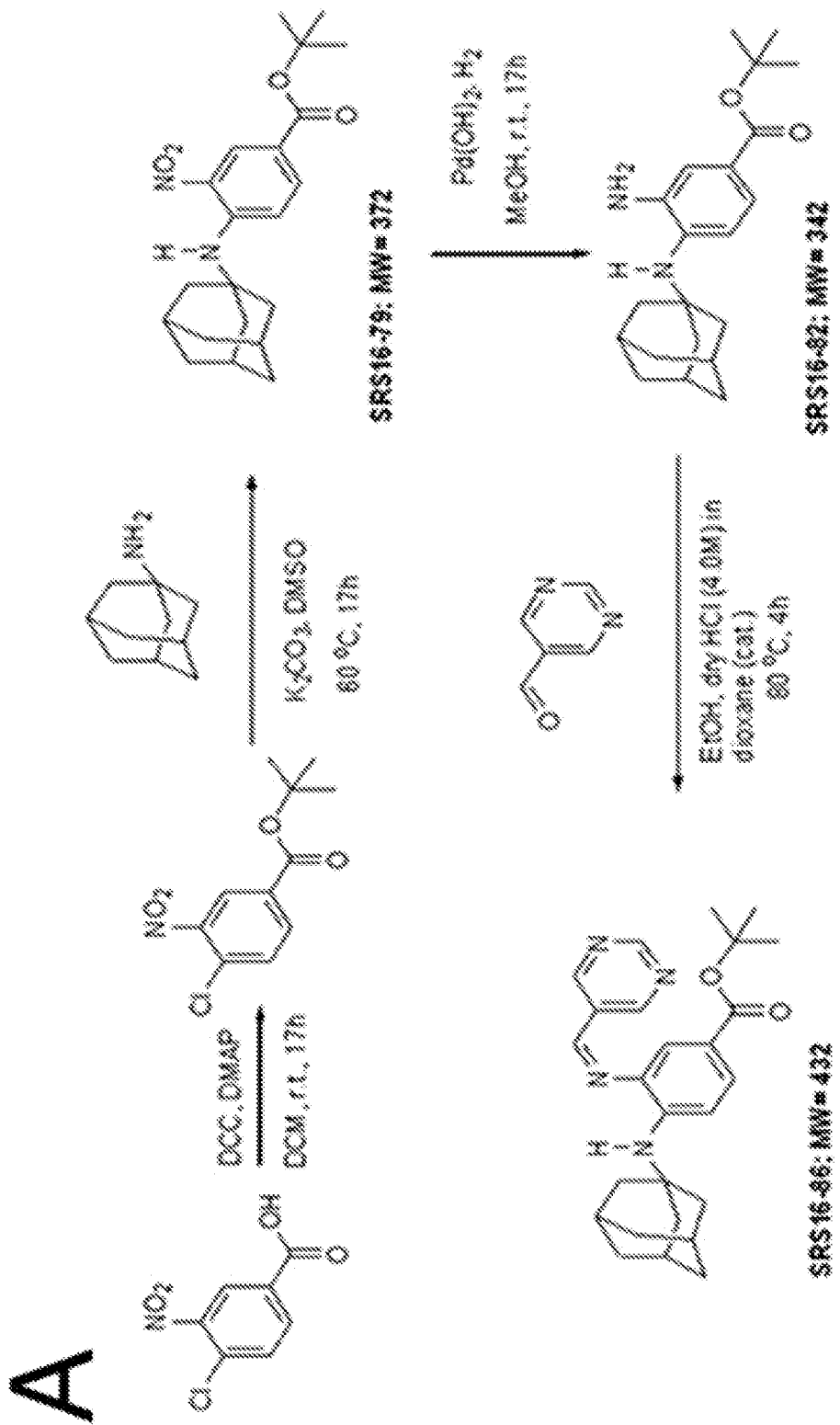
FIG. 27 shows generation and in vitro testing of a ferrostatin derivative for in vivo applications. (A) Synthetic route of the most microsomal and plasma stable ferrostatin analog (SRS16-86). (B) Model structure of the two novel ferrostatin derivates SRS16-79 (inactive compound) and SRS16-86 (active compound). (C) FACS analysis for the necrotic marker 7AAD and phosphatidylserine accessibility (annexin V) in HT1080 and NIH 3T3 cells treated with either vehicle or 50 µM erastin in the presence or absence of 1 µM Fer-1, SRS16-86, or SRS16-79. (D) Absence of cleaved caspase-3 in necroptosis and ferroptosis. Western blot of cleaved caspase-3 in lysates from 100 ng/mL TNFα plus 1 µM Smac mimetics plus 25 µM zVAD-treated HT-29 cells, 50 µM erastin-treated NIH 3T3 cells, and 50 µM erastin-treated HT1080 cells for 24 h. Monoclonal anti-Fas-treated Jurkat cells (100 ng/mL) served as positive control. TSZ, TNFα/SMAC-mimetic/zVAD.
Figure 27:
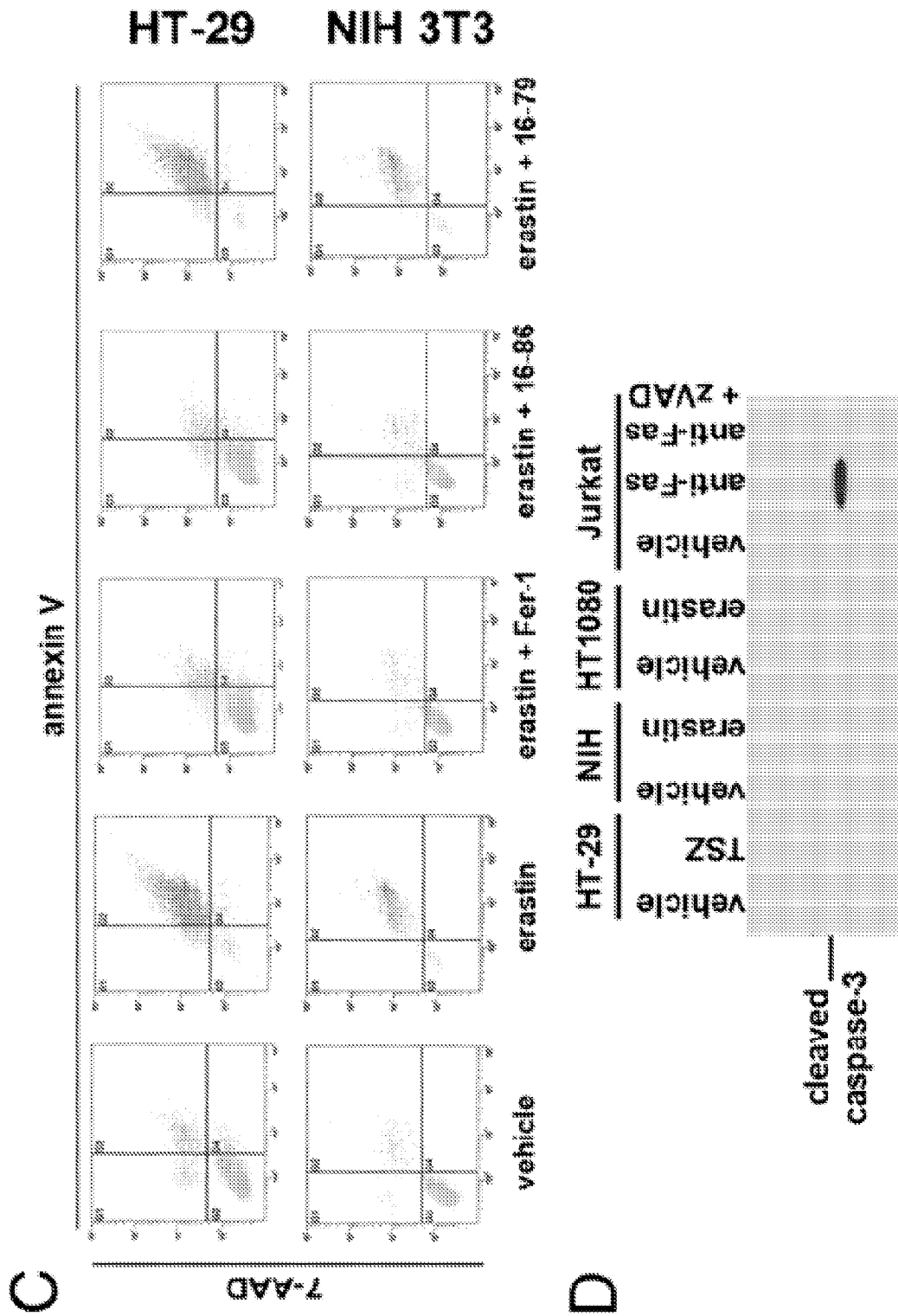
Figure 28:
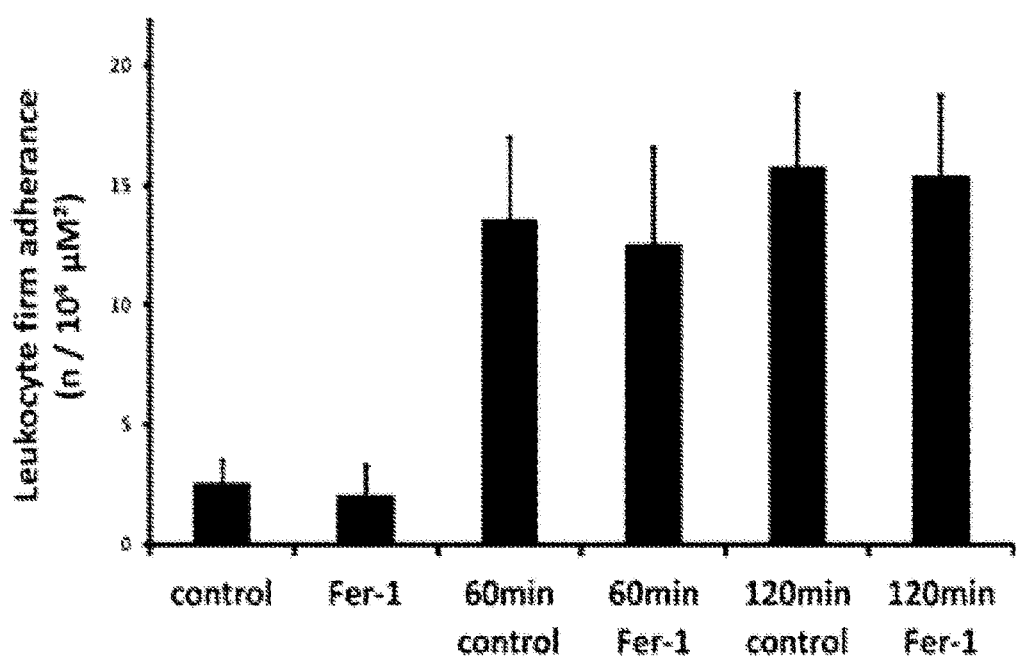
FIG. 28 shows that leukocyte adherence remains unchanged in IRI of the cremaster muscle upon addition of Fer-1. Intravital evaluation of intravascular firm adhesion of leukocytes in postcapillary venules following 1 h and 2 h after onset of reperfusion.

The concept of immunogenic necrotic cell death proposes to trigger an autoamplification loop, which is triggered by a necroinflammatory microenvironment. To understand how ferroptosis attracts immune cells during hypoxia/reperfusion situations, *musculus* cremaster IRI assays and read out the immune-cell infiltration by intravital microscopy (FIG. 26 D-F) and quantified rolling, adherent, and transmigrated cells in the presence and absence of ferrostatins were performed (FIGS. 26 F and G and FIG. 28). Less immune-cell infiltration into the postischemic area suggested either that Fer-1 directly inhibits leukocyte transmigration or that the local proinflammatory microenvironment was less chemoattractive, presumably by less damage-associated molecular pattern (DAMP) release due to less ferroptotic cell death.

Table 5 shows the results of a measurement of microhemodynamic parameters and systemic leukocyte counts, as indicated, based on intravital microscopy in the presence and absence of Fer-1.

TABLE 5

| Leukocyte adherence upon addition of Fer-1 | | |
|---|---|---|
| | Vehicle | Ferrostatin |
| Inner diameter (µm) | 27.6 ± 2.2 | 25.9 ± 1.6 |
| Vmean (mm$^{-1}$ s$^{-1}$) | 0.8 ± 0.1 | 0.8 ± 0.2 |
| Shear rate (s$^{-1}$) | 1208.8 ± 257.4 | 1272.0 ± 167.3 |
| SLC (n × 10$^{-8}$/µl) | 3.1 ± 3.6 | 1.6 ± 1.5 |

Ferroptosis Mediates Tubule Necrosis in Oxalate Nephropathy, but not in an LPS-Induced Septic Shock Model.

Figure 29:
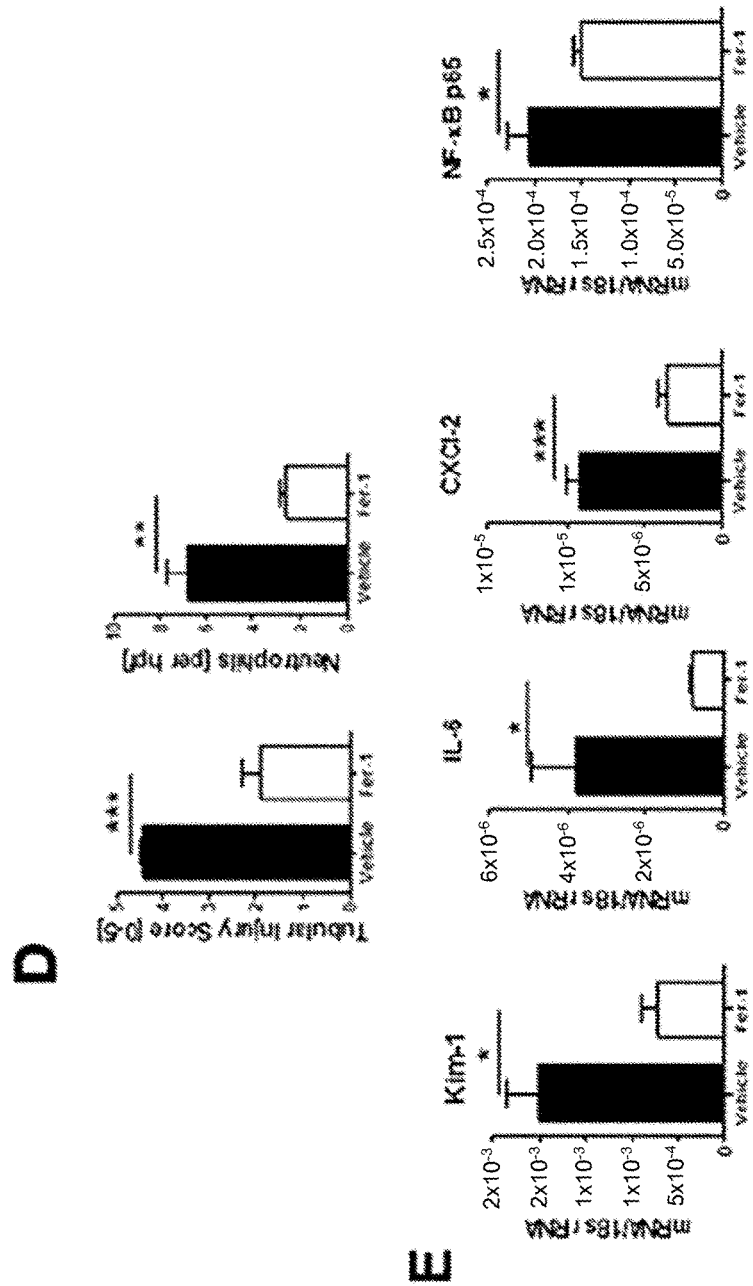
FIG. 29 shows that ferroptosis contributes to crystal-induced acute kidney injury, but not to the LPS-induced shock model. (A) PAS and Pizzolato staining of mice treated with CaOx and Fer-1. (B) CaOx deposition is not different between the two groups. (C) Evaluation of functional markers of acute kidney injury in mice that underwent CaOx-induced nephropathy. (D) Fer-1 significantly reduces the ultrastructural damage in CaOx nephropathy. (E) Significant reduction of expression of Kim-1 (TIM-1), IL-6, $CXCL_2$, and p65 in the Fer-1-treated Ca-Ox model (*P=0.05-0.02, P=0.02-0.001, *P≤0.001; n=8-10 per group). (F and G) In the model of LPS-induced septic shock, 12 mice per group were injected intraperitoneally with LPS as described in Example 17, Materials and Methods. (F) Temperature drop and (G) overall survival rates following 96 h after LPS injection (n=12 per group, error bars indicate SEM).
Figure 29:
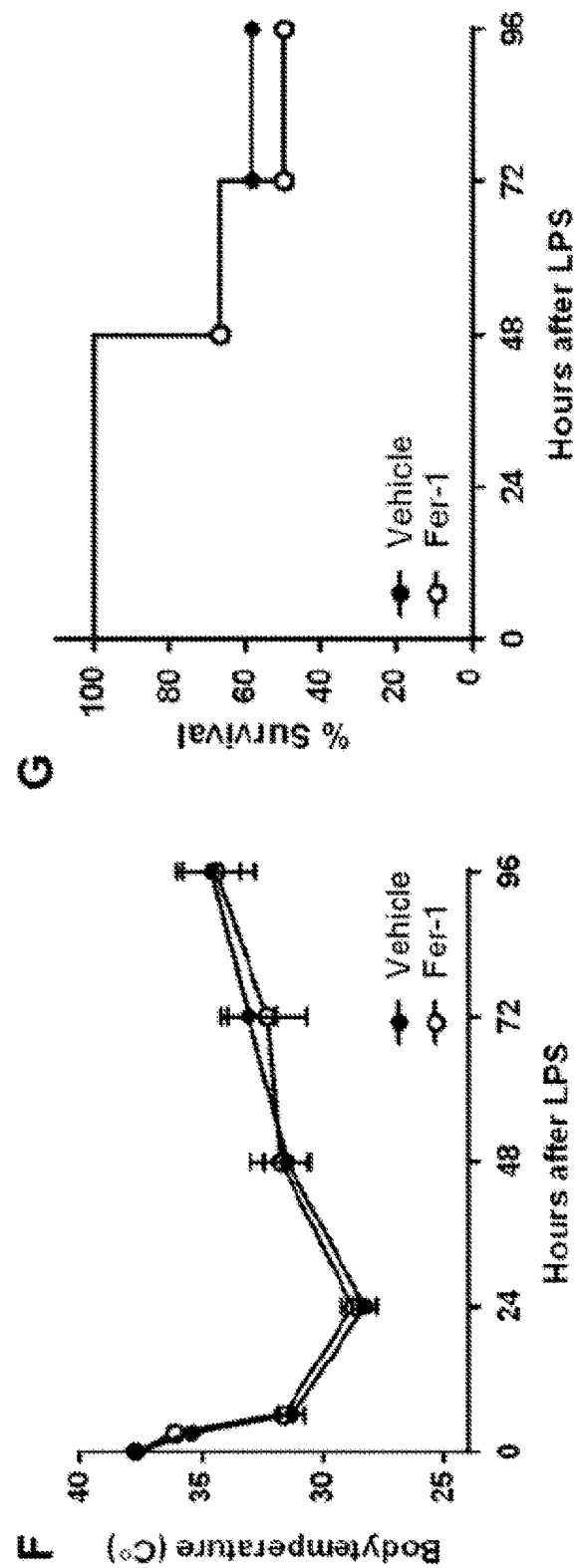

Having identified ferroptosis to be of relevance in acute postischemic injury, another model of acute renal failure, oxalate nephropathy, which has recently been established was investigated (Mulay et al., 2013). Intrarenal CaOx crystal deposition was identical in all groups (FIGS. 29 A and B). However, neutrophil infiltration and expression levels of proinflammatory cytokines (CXCL-2, IL-6), kidney injury molecule 1 (KIM-1), and the p65 subunit of NF-κB were statistically significantly reduced upon a once daily i.p. application of Fer-1 (FIG. 29E). Importantly, Fer-1 also significantly reduced the tubular injury score (FIG. 29D) and the functional serum markers of kidney injury creatinine and urea (FIG. 29C). Because RIPK3-deficient mice have been demonstrated to be resistant to sepsis models, Fer-1 in the model of LPS-induced shock was also investigated (FIG. 29F), but no difference compared with vehicle-treated mice was evident. Therefore, ferroptosis seems to be a valuable target for both postischemic and toxic acute kidney injury. However, given the poor plasma stability of Fer-1, a more stable compound for the in vivo applications was developed.

Ferroptosis Mediates Necrotic Tubular Cell Death in Renal Ischemia—Reperfusion Injury.

For in vivo experiments, SRS16-86 was used in comparison with SRS16-79, an inactive derivative (FIG. 27B). The ferroptosis-inhibiting ability of SRS16-86 and SRS16-79 was confirmed in vitro by FACS analysis of erastin-treated HT1080 cells and in NIH 3T3 cells (FIG. 27C). In both necroptosis and ferroptosis, cleaved caspase 3 was not detected (FIG. 27D).

Active (SRS16-86) and inactive (SRS16-79) compounds were applied to a model of severe ischemia-reperfusion injury (IRI), which was described previously (Linkerman et al., 2013B). Upon 40 min of ischemia before reperfusion, it is known that all WT mice die between 48 h and 72 h, which can be anticipated from the 48-h serum creatinine values above 2.0 mg/dL. As demonstrated in FIG. 30 A-D, creatinine levels of all vehicle-treated C57BL/6 mice exceeded 2.0 mg/dL and showed strong morphologic damage and high serum urea levels whereas Fer-1-treated and, to a greater extent, SRS16-86-treated mice were protected from functional acute renal failure (FIGS. 30 C and D) and structural organ damage (FIGS. 30 A and B) after IRI. Mice treated with SRS16-79 in a similar manner did not show any differences compared with the vehicle-treated controls. Side effects from treatment with the same dose of SRS16-86 4 wk after application were not observed. The effect of SRS16-86 exceeded that of any single compound previously experienced to be protective from renal IRI.

Ferrostatins Further Increase the Protective Effect of Necrostatin-1/Sanglifehrin A Combination Therapy in Renal IRI.

Figure 30:
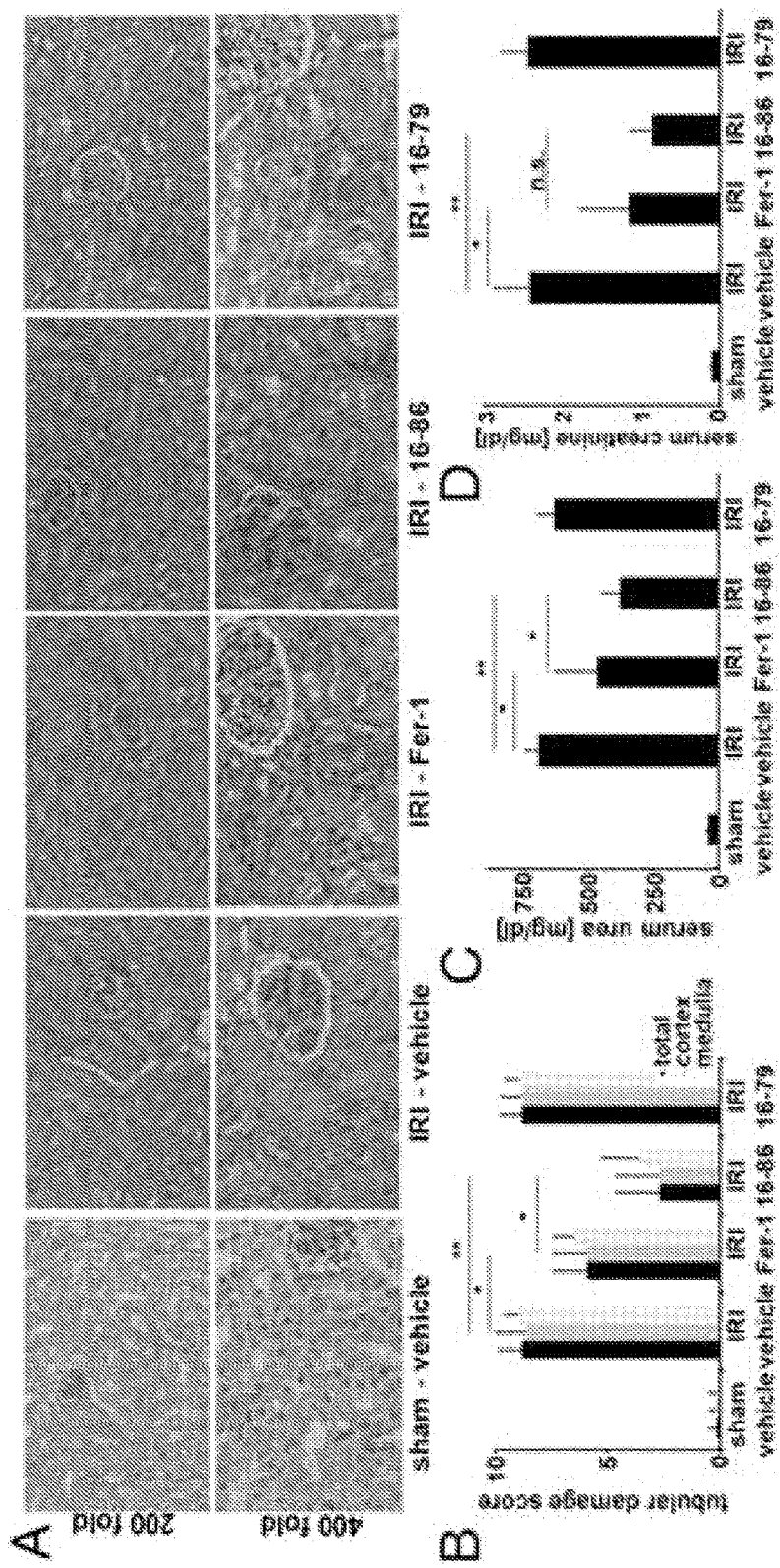
FIG. 30 shows that ferroptosis significantly contributes to renal ischemia-reperfusion injury. (A and B) Representative PAS stainings and quantification of renal damage from mice treated with severe ischemic durations before reperfusion. Mice were killed 48 h after reperfusion. (C and D) Functional markers of acute kidney injury after severe IRI (as in A and B). (E and F) Histologic PAS staining and quantification of sham operation or ultrasevere IRI (50 min of ischemia before reperfusion) in WT mice treated with (Nec-1+SfA) combination therapy together with either SRS16-79 or SRS16-86. (G and H) C57BL/6 were treated as in E, and functional markers of acute kidney injury were measured 48 h after the onset of reperfusion. n.s., not significant; *P=0.05-0.02, P=0.02-0.001, *P≤0.001; n=10 per group in all experiments).
Figure 30:
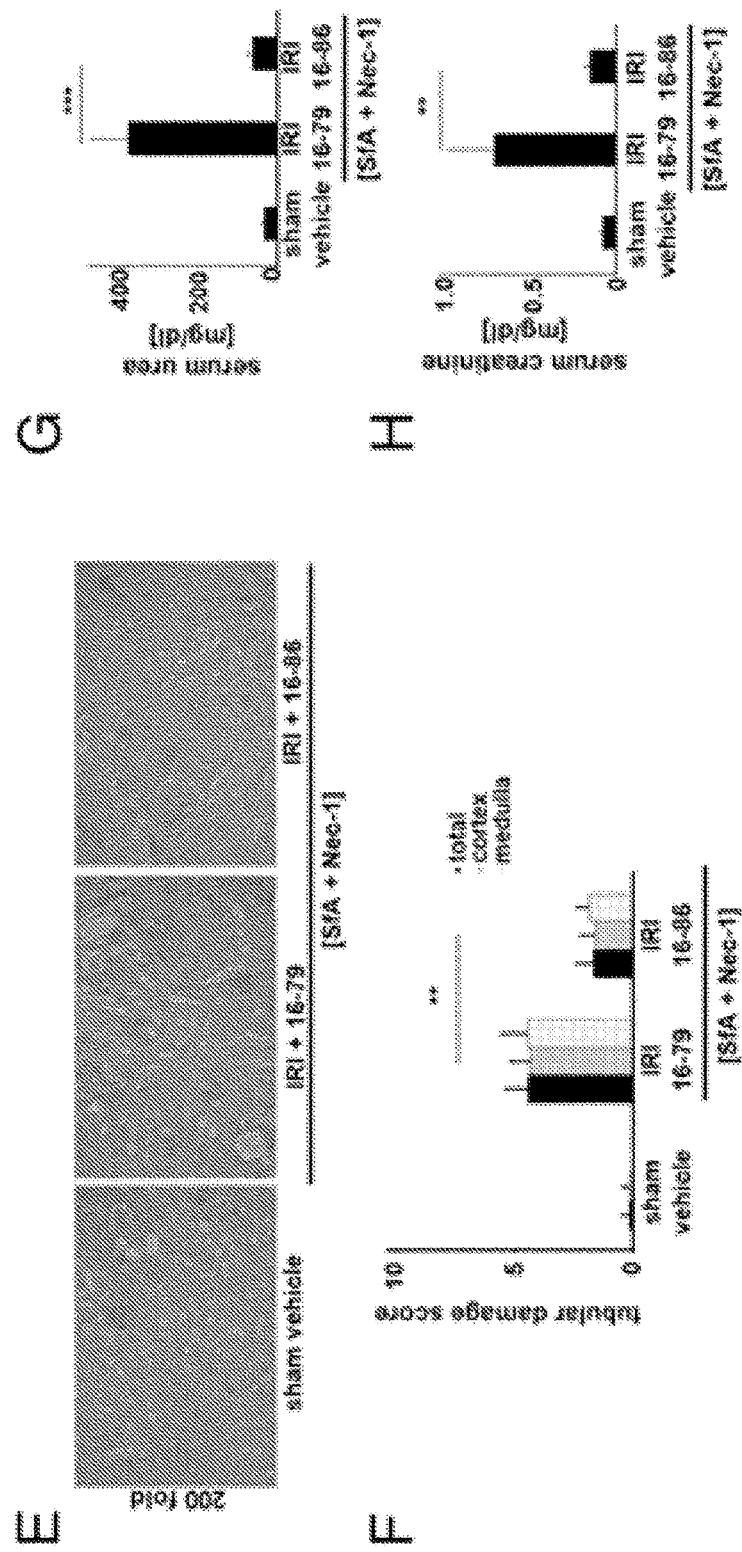

Given that Nec-1 protects from renal IRI to a lesser extent than SRS16-86, and given that interference with mitochondrial permeability transition (MPT)-induced regulated necrosis (MPT-RN) by the compound sanglifehrin A (SfA) also mildly protects from IRI, with marked additive protective effects in combination therapy with Nec-1 (Linkerman et al., 2013B; Linkerman et al., 2014A), the influence of SRS16-86 and SRS16-79 in Nec-1+SfA-treated mice was investigated. Because the effect of the Nec-1+SfA treatment could be investigated only in a severe ischemia model and additive protective effects by SRS16-86 were under investigation, the ischemic duration was increased to create a model of ultrasevere IRI (see Materials and Methods for details). In such settings, even the combination therapy with Nec-1+SfA did not fully rescue creatinine values and organ damage (FIG. 30 E-H). Addition of SRS16-86, but not SRS16-79, reduced plasma levels of serum urea and serum creatinine, suggesting that a triple combination therapy with Nec-1+SfA plus SRS16-86 is superior in the prevention of renal IRI compared with the double-combination therapy with Nec-1+SfA. In addition, this result indicates either that at least three independent pathways of regulated necrosis may be involved in IR-mediated organ damage or that inhibition of overlapping elements with SfA and Nec-1 are incomplete.

Discussion

Parenchymal cell necrosis, but not apoptosis, which seems to be minimally involved in the pathogenesis of acute kidney injury (Linkerman et al., 2014), triggers the release of DAMPs, some of which can trigger regulated necrosis and therefore initiate a necroinflammatory feedback loop. In clinical routine, immunosuppression is a standard procedure, but an anti-cell death therapy does not exist apart from cyclosporine (Linkerman et al., 2014A). Therefore, defining the precise mechanisms that trigger regulated necrosis is essential for the development of new drugs. Our data indicate that alternative interpretations apart from "pure" necroptosis exist and suggest that ferroptosis is of importance in renal tubules, which, other than the skin, the gastrointestinal tract, or immune cells, do not depend on a necroptosis-inhibiting complex, at least not of FADD and caspase-8. To date, it cannot be ruled out that previously described protection against ischemia—reperfusion injury in diverse organs is mediated by increased perfusion rather than direct protection from parenchymal necroptosis. Our results regarding the cerulein-induced pancreatitis are in line with this hypothesis and are in contrast to previously published data (He et al., 2007; Zhang et al., 2009). Several unanswered questions remain: Why are RIPK3-deficient mice protected in several models of IRI if the parenchymal cells do not undergo necroptosis? Why do necrostatins protect such tissues from organ failure if necroptosis is not the predominant mechanism of parenchymal cell death? Endothelial cell-specific deletion of RIPK3 will help to answer these open questions.

DOCUMENTS

ABDEL-MAGID, A. F.; Carson, K. G.; Harris, B. D.; Maryanoff, C. A.; Shah, R. D. J. Org. Chem. 1996, 61, 3849-3862.

ANITHA, M., Nandhu, M. S., Anju, T. R., Jes, P. & Paulose, C. S. Targeting glutamate mediated excitotoxicity in Huntington's disease: neural progenitors and partial glutamate antagonist-memantine. Medical hypotheses 76, 138-140, doi:10.1016/j.mehy.2010.09.003 (2011).

BANJAC, A., Perisic, T., Sato, H., Seiler, A., Bannai, S., Weiss, N., Kolle, P., Tschoep, K., Issels, R. D., Daniel, P. T., et al. (2008). The cystine/cysteine cycle: a redox cycle regulating susceptibility versus resistance to cell death. Oncogene 27, 1618-1628.

BARTZOKIS, G., Cummings, J., Perlman, S., Hance, D. B. & Mintz, J. Increased basal ganglia iron levels in Huntington disease. Arch Neurol 56, 569-574 (1999).

BEAULIEU, P. L.; Hache, B.; Von Moos, E. Synthesis, 2003, 11, 1683-1692.

BEHL, C. Alzheimer's disease and oxidative stress: implications for novel therapeutic approaches. Prog Neurobiol 57, 301-323 (1999).

BERGSBAKEN, T., Fink, S. L., and Cookson, B. T. (2009). Pyroptosis: host cell death and inflammation. Nat Rev Microbiol 7, 99-109.

BLOIS, M. S. (1958). Antioxidant determinations by the use of a stable free radical. Nature 181, 1199-1200.

CATER, H. L., Gitterman, D., Davis, S. M., Benham, C. D., Morrison, B., 3rd, and Sundstrom, L. E. (2007). Stretch-induced injury in organotypic hippocampal slice cultures reproduces in vivo post-traumatic neurodegeneration: role of glutamate receptors and voltage-dependent calcium channels. J Neurochem 101, 434-447.

CATER, H. L., Gitterman, D., Davis, S. M., Benham, C. D., Morrison, B., 3rd, and Sundstrom, L. E. (2007). Stretch-induced injury in organotypic hippocampal slice cultures reproduces in vivo post-traumatic neurodegeneration: role of glutamate receptors and voltage-dependent calcium channels. J Neurochem 101, 434-447.

CHA, J. H. et al. Altered brain neurotransmitter receptors in transgenic mice expressing a portion of an abnormal human huntington disease gene. Proc Natl Acad Sci USA 95, 6480-6485. (1998).

CHEAH, J. H., Kim, S. F., Hester, L. D., Clancy, K. W., Patterson, S. E., 3rd, Papadopoulos, V., and Snyder, S. H. (2006). NMDA receptor-nitric oxide transmission mediates neuronal iron homeostasis via the GTPase Dexras1. Neuron 51, 431-440.

CHEN, J. C. et al. MR of human postmortem brain tissue: correlative study between T2 and assays of iron and ferritin in Parkinson and Huntington disease. AJNR. American journal of neuroradiology 14, 275-281 (1993).

CHEN, J. et al. Iron accumulates in Huntington's disease neurons: protection by deferoxamine. PLoS One 8, e77023, doi:10.1371/journal.pone.0077023 (2013).

CHOI, D. W. (1988). Glutamate neurotoxicity and diseases of the nervous system. Neuron 1, 623-634.

CHRISTOFFERSON, D. E., and Yuan, J. (2010). Necroptosis as an alternative form of programmed cell death. Current Opinion in Cell Biology 22, 263-268.

CHUNG, N., Zhang, X. D., Kreamer, A., Locco, L., Kuan, P. F., Bartz, S., Linsley, P. S., Ferrer, M., and Strulovici, B. (2008). Median absolute deviation to improve hit selection for genome-scale RNAi screens. J Biomol Screen 13, 149-158.

CRUZ-AGUADO, R., Turner, L. F., Diaz, C. M. & Pinero, J. Nerve growth factor and striatal glutathione metabolism in a rat model of Huntington's disease. Restorative neurology and neuroscience 17, 217-221 (2000).

DEGTEREV A, et al. (2005) Chemical inhibitor of nonapoptotic cell death with therapeutic potential for ischemic brain injury. Nat Chem Biol 1(2):112-119.

DESILVA, T. M. et al. Glutamate transporter EAAT2 expression is up-regulated in reactive astrocytes in human periventricular leukomalacia. J Comp Neurol 508, 238-248, doi:10.1002/cne.21667 (2008).

DILLON C P, et al. (2012) Survival function of the FADD-CASPASE-8-cFLIP(L) complex. Cell Reports 1(5):401-407.

DILLON C P, et al. (2014) RIPK1 blocks early postnatal lethality mediated by caspase-8 and RIPK3. Cell 157(5): 1189-1202.

DIXON, D. J. et al., (2012) Ferroptosis: An Iron-Dependent Form of Nonapoptotic Cell Death. Cell, Vol. 149, Issue 5, pp. 1060-1072.

DOLMA, S., Lessnick, S. L., Hahn, W. C., and Stockwell, B. R. (2003). Identification of genotype-selective antitumor agents using synthetic lethal chemical screening in engineered human tumor cells. Cancer Cell 3, 285-296.

DOMMERGUES, M. A., Gallego, J., Evrard, P. & Gressens, P. Iron supplementation aggravates periventricular cystic white matter lesions in newborn mice. European journal of paediatric neurology: EJPN: official journal of the European Paediatric Neurology Society 2, 313-318 (1998).

DUCE, J. A., Tsatsanis, A., Cater, M. A., James, S. A., Robb, E., Wikhe, K., Leong, S. L., Perez, K., Johanssen, T., Greenough, M. A., et al. (2010). Iron-export ferroxidase activity of beta-amyloid precursor protein is inhibited by zinc in Alzheimer's disease. Cell 142, 857-867.

ESTRADA SANCHEZ, A. M., Mejia-Toiber, J. & Massieu, L. Excitotoxic neuronal death and the pathogenesis of Huntington's disease. Archives of medical research 39, 265-276, doi:10.1016/j.arcmed.2007.11.011 (2008).

FOLKERTH, R. D. Periventricular leukomalacia: overview and recent findings. Pediatric and developmental pathology: the official journal of the Society for Pediatric Pathology and the Paediatric Pathology Society 9, 3-13, doi:10.2350/06-01-0024.1 (2006).

FOLLETT, P. L. et al. Glutamate receptor-mediated oligodendrocyte toxicity in periventricular leukomalacia: a protective role for topiramate. J Neurosci 24, 4412-4420, doi:10.1523/JNEUROSCI.0477-04.2004 (2004).

FUCHS, Y., and Steller, H. (2011). Programmed cell death in animal development and disease. Cell 147, 742-758.

GALLUZZI L, Kepp O, Krautwald S, Kroemer G, Linkermann A (2014) Molecular mechanisms of regulated necrosis. Semin Cell Dev Biol 35C:24-32.

GENNA, D. T. & Posner, G. H. Cyanocuprates convert carboxylic acids directly into ketones. Org Lett 13, 5358-5361, doi:10.1021/ol202237j (2011).

GOUT, P. W., Buckley, A. R., Simms, C. R., and Bruchovsky, N. (2001). Sulfasalazine, a potent suppressor of lymphoma growth by inhibition of the x(c)-cystine transporter: a new action for an old drug. Leukemia 15, 1633-1640.

GUO, W., Wu, S., Liu, J., and Fang, B. (2008). Identification of a small molecule with synthetic lethality for K-ras and protein kinase C iota. Cancer Res 68, 7403-7408.

HAMADA, Y. & Kiso, Y. The application of bioisosteres in drug design for novel drug discovery: focusing on acid protease inhibitors. Expert opinion on drug discovery 7, 903-922, doi:10.1517/17460441.2012.712513 (2012).

HAYNES, R. L. et al. Oxidative and nitrative injury in periventricular leukomalacia: a review. Brain pathology 15, 225-233 (2005).

HAYNES, R. L. et al. Nitrosative and oxidative injury to premyelinating oligodendrocytes in periventricular leukomalacia. Journal of neuropathology and experimental neurology 62, 441-450 (2003).

HE S, et al. (2009) Receptor interacting protein kinase-3 determines cellular necrotic response to TNF-alpha. Cell 137(6):1100-1111.

HOFFSTROM, B. G. et al. Inhibitors of protein disulfide isomerase suppress apoptosis induced by misfolded proteins. Nat Chem Biol 6, 900-906, doi:10.1038/nchembio.467 (2010).

HUANG, D., Ou, B. & Prior, R. L. The chemistry behind antioxidant capacity assays. J Agric Food Chem 53, 1841-1856, doi:10.1021/jf030723c (2005).

ISHIDA, T., Suzuki, T., Hirashima, S., Mizutani, K., Yoshida, A., Ando, I., Ikeda, S., Adachi, T., and Hashimoto, H. (2006). Benzimidazole inhibitors of hepatitis C virus NS5B polymerase: identification of 2-[(4-diarylmethoxy)phenyl]-benzimidazole. Bioorg Med Chem Lett 16, 1859-1863.

ISHII, T., Bannai, S., and Sugita, Y. (1981). Mechanism of growth stimulation of L1210 cells by 2-mercaptoethanol in vitro. Role of the mixed disulfide of 2-mercaptoethanol and cysteine. The Journal of biological chemistry 256, 12387-12392.

JACOBSON, M. D., and Raff, M. G. (1995). Programmed cell death and Bcl-2 protection in very low oxygen. Nature 374, 814-816.

JOHRI, A. & Beal, M. F. Antioxidants in Huntington's disease. Biochim Biophys Acta 1822, 664-674, doi: 10.1016/j.bbadis.2011.11.014 (2012).

KAMATA, T. (2009). Roles of Nox1 and other Nox isoforms in cancer development. Cancer Sci 100, 1382-1388.

KANAI, Y., and Endou, H. (2003). Functional properties of multispecific amino acid transporters and their implications to transporter-mediated toxicity. J Toxicol Sci 28, 1-17.

LALEU, B., Gaggini, F., Orchard, M., Fioraso-Cartier, L., Gagnon, L., Houngninou-Molango, S., Gradia, A., Duboux, G., Merlot, C., Heitz, F., et al. (2010). First in class, potent, and orally bioavailable NADPH oxidase isoform 4 (Nox4) inhibitors for the treatment of idiopathic pulmonary fibrosis. Journal of medicinal chemistry 53, 7715-7730.

LEI, P., Ayton, S., Finkelstein, D. I., Spoerri, L., Ciccotosto, G. D., Wright, D. K., Wong, B. X., Adlard, P. A., Cherny, R. A., Lam, L. Q., et al. (2012). Tau deficiency induces parkinsonism with dementia by impairing APP-mediated iron export. Nature medicine 18, 291-295.

LI, Y., Maher, P., and Schubert, D. (1997). A role for 12-lipoxygenase in nerve cell death caused by glutathione depletion. Neuron 19, 453-463.

LINKERMANN A, et al. (2012) Rip1 (receptor-interacting protein kinase 1) mediates necroptosis and contributes to renal ischemia/reperfusion injury. Kidney Int 81(8):751-761.

LINKERMANN A, et al. (2013A) The RIP1-kinase inhibitor necrostatin-1 prevents osmotic nephrosis and contrast-induced AKI in mice. J Am Soc Nephrol 24(10):1545-1557.

LINKERMANN A, et al. (2013B) Two independent pathways of regulated necrosis mediate ischemia-reperfusion injury. Proc Natl Acad Sci USA 110(29):12024-12029.

LINKERMANN A, Green D R (2014A) Necroptosis. N Engl J Med 370(5):455-465.

LINKERMANN A, et al. (2014B) Regulated Cell Death in AKI. J Am Soc Nephrol, ASN.2014030262.

LIPINSKI, C. A., Lombardo, F., Dominy, B. W., and Feeney, P. J. (2001). Experimental and computational approaches to estimate solubility and permeability in drug discovery and development settings. Advanced drug delivery reviews 46, 3-26.

LO, M., Ling, V., Wang, Y. Z., and Gout, P. W. (2008). The xc-cystine/glutamate antiporter: a mediator of pancreatic cancer growth with a role in drug resistance. British journal of cancer 99, 464-472.

LOSSI, L., Alasia, S., Salio, C., and Merighi, A. (2009). Cell death and proliferation in acute slices and organotypic cultures of mammalian CNS. Prog Neurobiol 88, 221-245.

LUEDDE M, et al. (2014) RIP3, a kinase promoting necroptotic cell death, mediates adverse remodelling after myocardial infarction. Cardiovasc Res 103(2):206-216.

MACARRON, R., Banks, M. N., Bojanic, D., Burns, D. J., Cirovic, D. A., Garyantes, T., Green, D. V., Hertzberg, R. P., Janzen, W. P., Paslay, J. W., et al. (2011). Impact of high-throughput screening in biomedical research. Nature reviews Drug discovery 10, 188-195.

MASON, R. P. et al. Glutathione peroxidase activity is neuroprotective in models of Huntington's disease. Nat Genet 45, 1249-1254, doi:10.1038/ng.2732 (2013).

MILLER, B. R. & Bezprozvanny, I. Corticostriatal circuit dysfunction in Huntington's disease: intersection of glutamate, dopamine and calcium. Future neurology 5, 735-756, doi:10.2217/fnl.10.41 (2010).

MOFFAT, J., Grueneberg, D. A., Yang, X., Kim, S. Y., Kloepfer, A. M., Hinkle, G., Piqani, B., Eisenhaure, T. M., Luo, B., Grenier, J. K., et al. (2006). A lentiviral RNAi library for human and mouse genes applied to an arrayed viral high-content screen. Cell 124, 1283-1298.

MORRISON, P. J. & Nevin, N. C. Serum iron, total iron binding capacity and ferritin in early Huntington disease patients. Irish journal of medical science 163, 236-237 (1994).

MORRISON, B., 3rd, Pringle, A. K., McManus, T., Ellard, J., Bradley, M., Signorelli, F., Iannotti, F., and Sundstrom, L. E. (2002). L-arginyl-3,4-spermidine is neuroprotective in several in vitro models of neurodegeneration and in vivo ischaemia without suppressing synaptic transmission. Br J Pharmacol 137, 1255-1268.

MULAY S R, et al. (2013) Calcium oxalate crystals induce renal inflammation by NLRP3-mediated IL-1$\beta$ secretion. J Clin Invest 123(1):236-246.

MULLEN, A. R., Wheaton, W. W., Jin, E. S., Chen, P. H., Sullivan, L. B., Cheng, T., Yang, Y., Linehan, W. M., Chandel, N. S., and Deberardinis, R. J. (2011). Reductive carboxylation supports growth in tumour cells with defective mitochondria. Nature.

MURPHY, T. H., Miyamoto, M., Sastre, A., Schnaar, R. L., and Coyle, J. T. (1989). Glutamate toxicity in a neuronal cell line involves inhibition of cystine transport leading to oxidative stress. Neuron 2, 1547-1558.

NATIONAL RESEARCH COUNCIL (2011) Guide for the Care and Use of Laboratory Animals (National Academies Press, Washington, D.C.), 8th Ed.

NI CHONGHAILE, T., Sarosiek, K. A., Vo, T. T., Ryan, J. A., Tammareddi, A., Moore Vdel, G., Deng, J., Anderson, K. C., Richardson, P., Tai, Y. T., et al. (2011). Pretreatment mitochondrial priming correlates with clinical response to cytotoxic chemotherapy. Science 334, 1129-1133.

NORABERG, J., Poulsen, F. R., Blaabjerg, M., Kristensen, B. W., Bonde, C., Montero, M., Meyer, M., Gramsbergen, J. B., and Zimmer, J. (2005). Organotypic hippocampal slice cultures for studies of brain damage, neuroprotection and neurorepair. Curr Drug Targets CNS Neurol Disord 4, 435-452.

PAGLIARINI, D. J., Calvo, S. E., Chang, B., Sheth, S. A., Vafai, S. B., Ong, S. E., Walford, G. A., Sugiana, C., Boneh, A., Chen, W. K., et al. (2008). A mitochondrial protein compendium elucidates complex I disease biology. Cell 134, 112-123.

PARK, J. S., Pasupulati, R., Feldkamp, T., Roeser, N. F. & Weinberg, J. M. Cyclophilin D and the mitochondrial permeability transition in kidney proximal tubules after hypoxic and ischemic injury. American journal of physiology. Renal physiology 301, F134-150, doi:10.1152/ajprenal.00033.2011 (2011).

PASSANITI, P. et al. Synthesis, spectroscopic and electrochemical properties of mononuclear and dinuclear bis (bipy)ruthenium(II) complexes containing dimethoxyphenyl(pyridin-2-yl)-1,2,4-triazole ligands J. Chem. Soc., Dalton Transactions 8, 1740-1746 (2002).

PETR, G. T. et al. Glutamate transporter expression and function in a striatal neuronal model of Huntington's disease. Neurochem Int 62, 973-981, doi:10.1016/j.neuint.2013.02.026 (2013).

PINNIX, Z. K., Miller, L. D., Wang, W., D'Agostino, R., Jr., Kute, T., Willingham, M. C., Hatcher, H., Tesfay, L., Sui, G., Di, X., et al. (2010). Ferroportin and iron regulation in breast cancer progression and prognosis. Sci Transl Med 2, 43ra56.

PIPIK, B., Ho, G. J., Williams, J. M. & Conlon, D. A. A preferred synthesis of 1,2,4-oxadiazoles. Synthetic Communications 34, 1863-1870 (2004).

RAJ, L., Ide, T., Gurkar, A. U., Foley, M., Schenone, M., Li, X., Tolliday, N. J., Golub, T. R., Carr, S. A., Shamji, A. F., et al. (2011). Selective killing of cancer cells by a small molecule targeting the stress response to ROS. Nature 475, 231-234.

RAMANA, Kota V. et al., "Lipid Peroxidation Products in Human Health and Disease," Oxidative Medicine and Cellular Longevity, vol. 2013, Article ID 583438, 3 pages, 2013. doi:10.1155/2013/583438.

RAMANATHAN, A., and Schreiber, S. L. (2009). Direct control of mitochondrial function by mTOR. Proc Natl Acad Sci USA 106, 22229-22232.

RATAN, R. R., Murphy, T. H., and Baraban, J. M. (1994). Oxidative stress induces apoptosis in embryonic cortical neurons. J Neurochem 62, 376-379.

RIBEIRO, F. M., Pires, R. G. & Ferguson, S. S. Huntington's disease and Group I metabotropic glutamate receptors. Molecular neurobiology 43, 1-11, doi:10.1007/s12035-010-8153-1 (2011).

RIBEIRO, M. et al. Glutathione redox cycle dysregulation in Huntington's disease knock-in striatal cells. Free Radic Biol Med 53, 1857-1867, doi:10.1016/j.freeradbiomed.2012.09.004 (2012).

SAITOH, M. et al. Design, synthesis and structure-activity relationships of 1,3,4-oxadiazole derivatives as novel inhibitors of glycogen synthase kinase-3beta. Bioorg Med Chem 17, 2017-2029, doi:10.1016/j.bmc.2009.01.019 (2009).

SALAHUDEEN, A. A., Thompson, J. W., Ruiz, J. C., Ma, H. W., Kinch, L. N., Li, Q., Grishin, N. V., and Bruick, R. K. (2009). An E3 ligase possessing an iron-responsive hemerythrin domain is a regulator of iron homeostasis. Science 326, 722-726.

SANCHEZ, M., Galy, B., Schwanhaeusser, B., Blake, J., Bahr-Ivacevic, T., Benes, V., Selbach, M., Muckenthaler, M. U., and Hentze, M. W. (2011). Iron regulatory protein-1 and -2: transcriptome-wide definition of binding mRNAs and shaping of the cellular proteome by iron regulatory proteins. Blood 118, e168-179.

SATO, H., Tamba, M., Ishii, T., and Bannai, S. (1999). Cloning and expression of a plasma membrane cystine/glutamate exchange transporter composed of two distinct proteins. The Journal of biological chemistry 274, 11455-11458.

SHAW, A. T., Winslow, M. M., Magendantz, M., Ouyang, C., Dowdle, J., Subramanian, A., Lewis, T. A., Maglathin, R. L., Tolliday, N., and Jacks, T. (2011). Selective killing of K-ras mutant cancer cells by small molecule inducers of oxidative stress. Proc Natl Acad Sci USA.

SKOUTA R, et al. (2014) Ferrostatins inhibit oxidative lipid damage and cell death in diverse disease models. J Am Chem Soc 136(12):4551-4556.

SMITH C C, et al. (2007) Necrostatin: A potentially novel cardioprotective agent? Cardiovasc Drugs Ther 21(4): 227-233.

SOGABE, K., Roeser, N. F., Venkatachalam, M. A. & Weinberg, J. M. Differential cytoprotection by glycine against oxidant damage to proximal tubule cells. Kidney international 50, 845-854 (1996).

SUNDSTROM, L., Morrison, B., 3rd, Bradley, M., and Pringle, A. (2005). Organotypic cultures as tools for functional screening in the CNS. Drug discovery today 10, 993-1000.

TAN, S., Sagara, Y., Liu, Y., Maher, P., and Schubert, D. (1998). The regulation of reactive oxygen species production during programmed cell death. The Journal of Cell Biology 141, 1423-1432.

THOMPSON, C. B. (1995). Apoptosis in the pathogenesis and treatment of disease. Science 267, 1456-1462.

TRACHOOTHAM, D., Zhou, Y., Zhang, H., Demizu, Y., Chen, Z., Pelicano, H., Chiao, P. J., Achanta, G., Arlinghaus, R. B., Liu, J., et al. (2006). Selective killing of oncogenically transformed cells through a ROS-mediated mechanism by beta-phenylethyl isothiocyanate. Cancer Cell 10, 241-252.

TRAYKOVA-BRAUCH M, et al. (2008) An efficient and versatile system for acute and chronic modulation of renal tubular function in transgenic mice. Nat Med 14(9): 979-984.

TURMAINE, M. et al. Nonapoptotic neurodegeneration in a transgenic mouse model of Huntington's disease. Proc Natl Acad Sci USA 97, 8093-8097. (2000).

VARMA, H., Lo, D. C. & Stockwell, B. R. in Neurobiology of Huntington's Disease: Applications to Drug Discovery Frontiers in Neuroscience (eds D. C. Lo & R. E. Hughes) (2011).

VASHISHT, A. A., Zumbrennen, K. B., Huang, X., Powers, D. N., Durazo, A., Sun, D., Bhaskaran, N., Persson, A., Uhlen, M., Sangfelt, O., et al. (2009). Control of iron homeostasis by an iron-regulated ubiquitin ligase. Science 326, 718-721.

VIGIL, D., Cherfils, J., Rossman, K. L., and Der, C. J. (2010). Ras superfamily GEFs and GAPs: validated and tractable targets for cancer therapy? Nat Rev Cancer 10, 842-857.

WANG, Y., Dawson, V. L., and Dawson, T. M. (2009). Poly(ADP-ribose) signals to mitochondrial AIF: a key event in parthanatos. Exp Neurol 218, 193-202.

WATKINS, P. A., Maiguel, D., Jia, Z., and Pevsner, J. (2007). Evidence for 26 distinct acyl-coenzyme A synthetase genes in the human genome. J Lipid Res 48, 2736-2750.

WISE, D. R., DeBerardinis, R. J., Mancuso, A., Sayed, N., Zhang, X. Y., Pfeiffer, H. K., Nissim, I., Daikhin, E., Yudkoff, M., McMahon, S. B., et al. (2008). Myc regulates a transcriptional program that stimulates mitochondrial glutaminolysis and leads to glutamine addiction. Proceedings of the National Academy of Sciences of the United States of America 105, 18782-18787.

WOLPAW, A. J., Shimada, K., Skouta, R., Welsch, M. E., Akavia, U. D., Pe'er, D., Shaik, F., Bulinski, J. C., and Stockwell, B. R. (2011). Modulatory profiling identifies mechanisms of small molecule-induced cell death. Proceedings of the National Academy of Sciences of the United States of America.

WU, C. et al. Discovery, modeling, and human pharmacokinetics of N-(2-acetyl-4,6-dimethylphenyl)-3-(3,4-dimethylisoxazol-5-ylsulfamoyl)thiophene-2-carboxamide (TBC3711), a second generation, ETA selective, and orally bioavailable endothelin antagonist. J Med Chem 47, 1969-1986, doi:10.1021/jm030528p (2004).

YAGODA, N., von Rechenberg, M., Zaganjor, E., Bauer, A. J., Yang, W. S., Fridman, D. J., Wolpaw, A. J., Smukste, I., Peltier, J. M., Boniface, J. J., et al. (2007). RAS-RAF-MEK-dependent oxidative cell death involving voltage-dependent anion channels. Nature 447, 864-868.

YANG, W. S., and Stockwell, B. R. (2008). Synthetic lethal screening identifies compounds activating iron-dependent, nonapoptotic cell death in oncogenic-RAS-harboring cancer cells. Chemistry & biology 15, 234-245.

YONEZAWA, M., Back, S. A., Gan, X., Rosenberg, P. A., and Volpe, J. J. (1996). Cystine deprivation induces oligodendroglial death: rescue by free radical scavengers and by a diffusible glial factor. J Neurochem 67, 566-573.

ZERON, M. M. et al. Increased sensitivity to N-methyl-D-aspartate receptor-mediated excitotoxicity in a mouse model of Huntington's disease. Neuron 33, 849-860. (2002).

ZHANG D W, et al. (2009) RIP3, an energy metabolism regulator that switches TNFinduced cell death from apoptosis to necrosis. Science 325(5938):332-336.

All documents cited in this application are hereby incorporated by reference as if recited in full herein.

Although illustrative embodiments of the present invention have been described herein, it should be understood that the invention is not limited to those described, and that various other changes or modifications may be made by one skilled in the art without departing from the scope or spirit of the invention.

What is claimed is:

1. A compound according to formula (I):

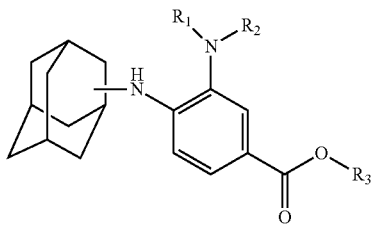

wherein:

$R_1$ and $R_2$, are independently selected from the group consisting of no atom, H, D, =O, —O⁻, halo, $C_{1-6}$alkyl, $C_{1-6}$alkyl-aryl, $C_{1-6}$alkyl-heteroaryl, $C_{2-6}$alkenyl, $C_{2-6}$alkenyl-aryl, and $C_{2-6}$alkenyl-heteroaryl, wherein the $C_{1-6}$alkyl, $C_{1-6}$alkyl-aryl, $C_{1-6}$alkyl-heteroaryl, $C_{2-6}$alkenyl, $C_{2-6}$alkenyl-aryl, and $C_{2-6}$alkenyl-heteroaryl may be optionally substituted with an atom or a group selected from the group consisting of halo, deuterium, $C_{1-4}$alkyl, $CF_3$, and combinations thereof; and $R_3$ is independently selected from the group consisting of H, $C_{1-12}$aliphatic, $C_{1-6}$-alkyl-aryl and $C_{1-6}$-alkyl-heteroaryl;

or an N-oxide, hydrate, or pharmaceutically acceptable salt thereof, with the proviso that:

when $R_3$ is ethyl, $R_1$ and $R_2$ cannot be both H, =O, —O⁻, or

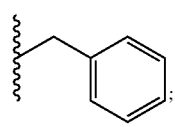

and when $R_3$ is ethyl and at least one of $R_1$ or $R_2$ is H, then the other of $R_1$ or $R_2$ cannot be

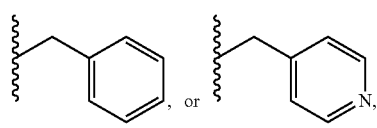

$R_1$ and $R_2$ are not both "no atom"; and when $R_3$ is H, then at least one of $R_1$ and $R_2$ is not H.

2. A compound having the structure of formula (II):

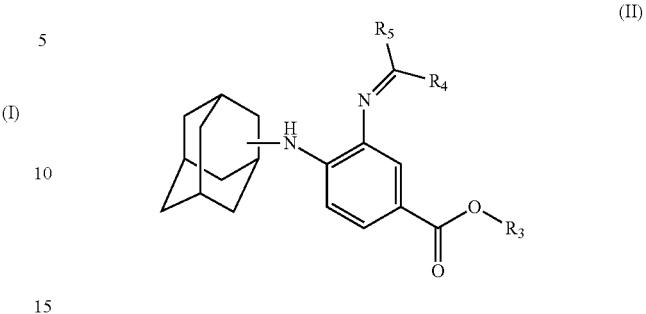

wherein:

$R_3$ is independently selected from the group consisting of H, $C_{1-12}$aliphatic, $C_{1-6}$-alkyl-aryl and $C_{1-6}$-alkyl-heteroaryl;

$R_4$ and $R_5$ are independently selected from the group consisting of no atom, H, D, =O, —O⁻, halo, aryl, heteroaryl, $C_{1-6}$alkyl, $C_{1-6}$alkyl-aryl, and $C_{1-6}$alkyl-heteroaryl; and --- is an optional bond, or an N-oxide, hydrate, or pharmaceutically acceptable salt thereof.

3. A compound having the structure of formula (III):

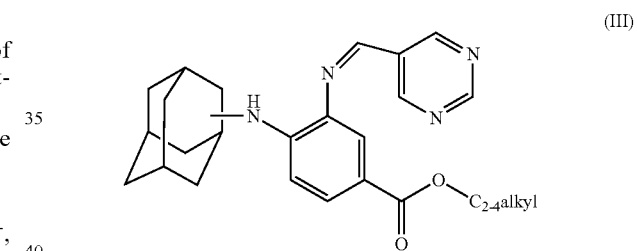

wherein the $C_{2-4}$ alkyl is selected from the group consisting of ethyl, isopropyl, n-propyl, butyl, and t-butyl, or an N-oxide, hydrate, or pharmaceutically acceptable salt thereof.

4. A compound selected from the group consisting of:

SRS15-72

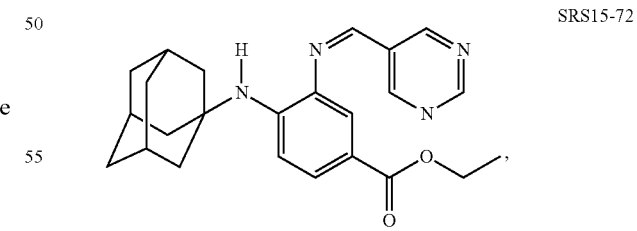

SRS16-41

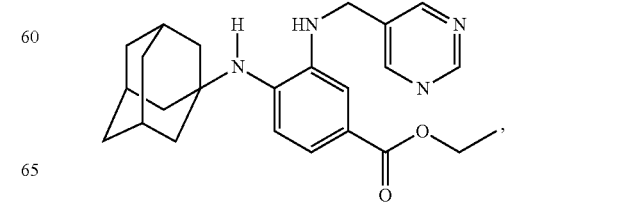

| | |
|---|---|
| SRS16-80 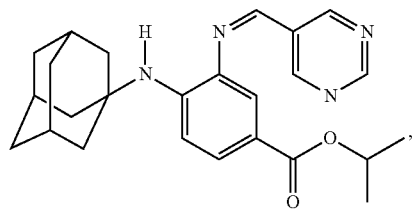 | Fer2_SRS04 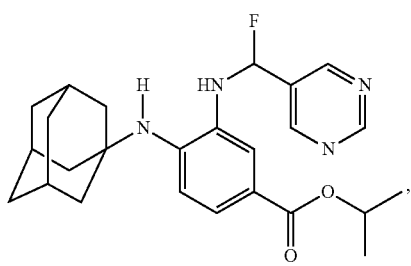 |
| SRS16-86 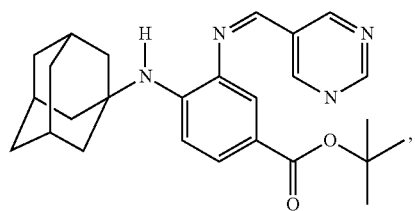 | Fer2_SRS05 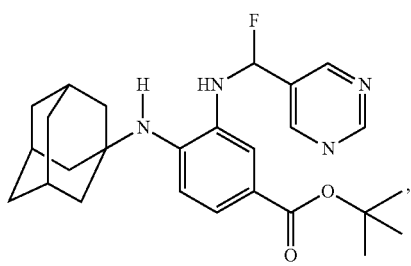 |
| SRS16-78 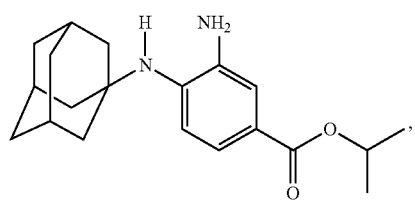 | Fer2_SRS06 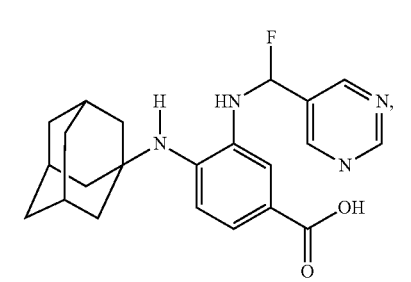 |
| SRS16-82 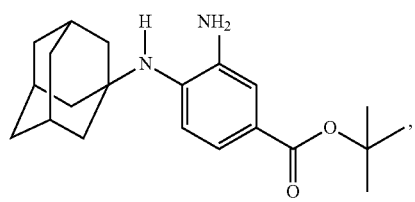 | Fer2_SRS07 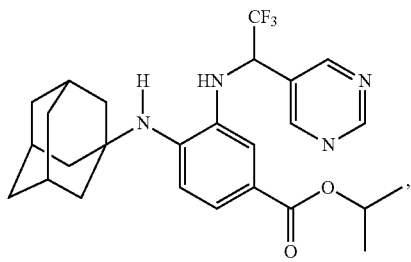 |
| Fer2_SRS01 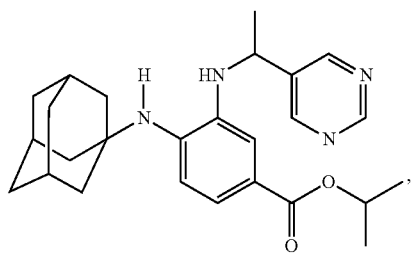 | Fer2_SRS08 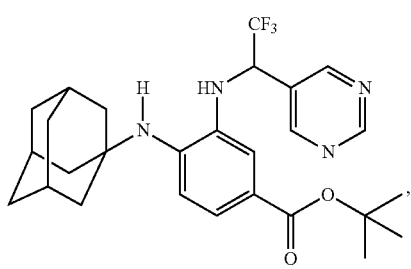 |
| Fer2_SRS02 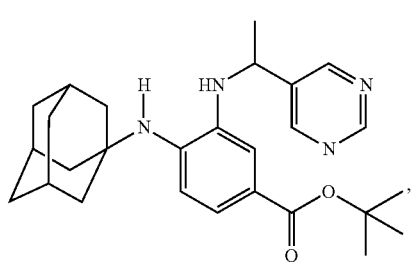 | Fer2_SRS09 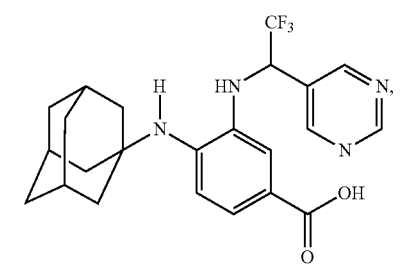 |
| Fer2_SRS03 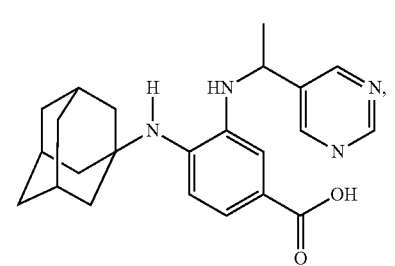 | |

-continued

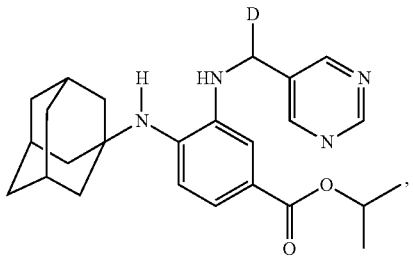

Fer2_SRS10

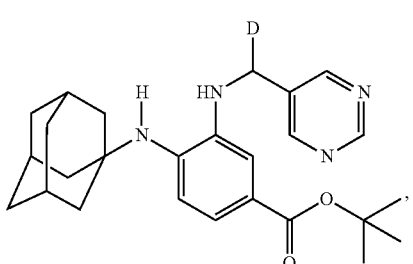

Fer2_SRS11

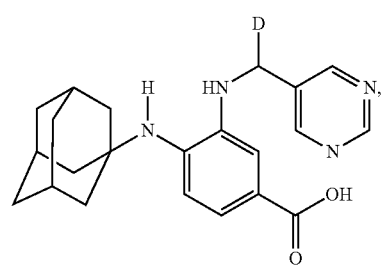

Fer2_SRS12 or an N-oxide, hydrate, or pharmaceutically acceptable salt thereof.

5. A compound according to claim 3, which is selected from the group consisting of:

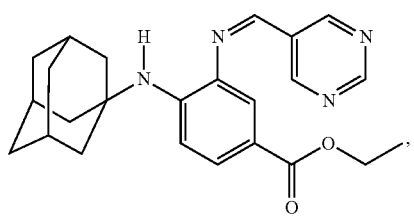

SRS15-72

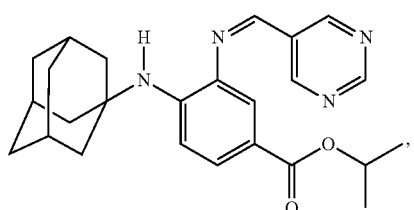

SRS16-80

-continued

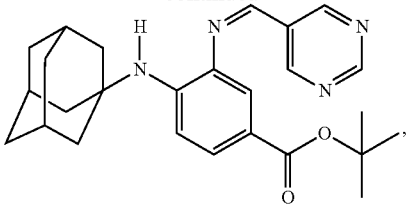

SRS16-86 and combinations thereof, or an N-oxide, hydrate, or pharmaceutically acceptable salt thereof.

6. A pharmaceutical composition comprising a pharmaceutically acceptable carrier or diluent and a compound according to formula (I):

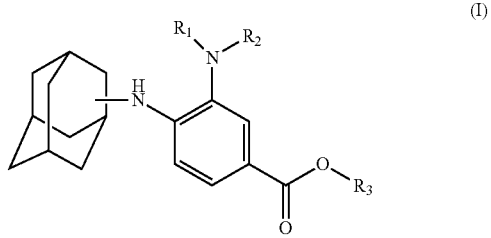

(I)

wherein:
R$_1$ and R$_2$, are independently selected from the group consisting of no atom, H, D, =O, —O$^-$, halo, C$_{1-6}$alkyl, C$_{1-6}$alkyl-aryl, C$_{1-6}$alkyl-heteroaryl, C$_{2-6}$alkenyl, C$_{2-6}$alkenyl-aryl, and C$_{2-6}$alkenyl-heteroaryl, wherein the C$_{1-6}$alkyl-aryl, C$_{1-6}$alkyl-heteroaryl, C$_{2-6}$alkenyl, C$_{2-6}$alkenyl-aryl, and C$_{2-6}$alkenyl-heteroaryl may be optionally substituted with an atom or a group selected from the group consisting of halo, deuterium, C$_{1-4}$alkyl, CF$_3$, and combinations thereof; and R$_3$ is independently selected from the group consisting of H, C$_{1-12}$aliphatic, C$_{1-6}$-alkyl-aryl and C$_{1-6}$-alkyl-heteroaryl;

or an N-oxide, hydrate, or pharmaceutically acceptable salt thereof, with the proviso that:

when R$_3$ is ethyl, R$_1$ and R$_2$ cannot be both H, =O, —O$^-$,or

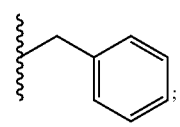

and when R$_3$ is ethyl and at least one of R$_1$ or R$_2$ is H, then the other of R$_1$ or R$_2$ cannot be

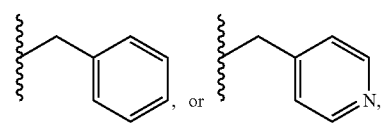

R₁ and R₂ are not both "no atom"; and
when R₃ is H, then at least one of R₁ and R₂ is not H.

7. A pharmaceutical composition comprising a pharmaceutically acceptable carrier or diluent and a compound according to formula (II):

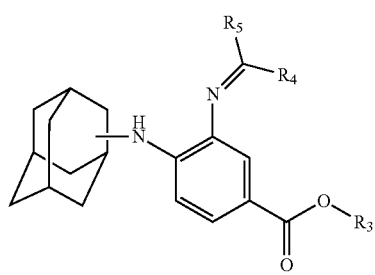

(II)

wherein:
R₃ is independently selected from the group consisting of H, C₁₋₁₂aliphatic, C₁₋₆-alkyl-aryl and C₁₋₆-alkyl-heteroaryl;
R₄ and R₅ are independently selected from the group consisting of no atom, H, D, =O, —O⁻, halo, aryl, heteroaryl, C₁₋₆alkyl, C₁₋₆alkyl-aryl, and C₁₋₆alkyl-heteroaryl; and
--- is an optional bond,
or an N-oxide, hydrate, or pharmaceutically acceptable salt thereof.

8. A pharmaceutical composition comprising a pharmaceutically acceptable carrier or diluent and a compound according to formula (III):

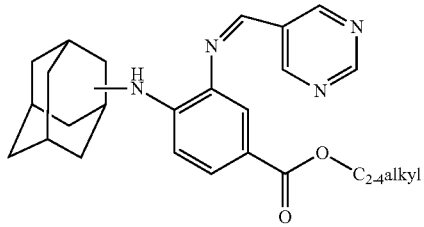

(III)

wherein the C₂₋₄ alkyl is selected from the group consisting of ethyl, isopropyl, n-propyl, butyl, and t-butyl,
or an N-oxide, hydrate, or pharmaceutically acceptable salt thereof.

9. A pharmaceutical composition comprising a pharmaceutically acceptable carrier or diluent and a compound having a structure that is selected from the group consisting of:

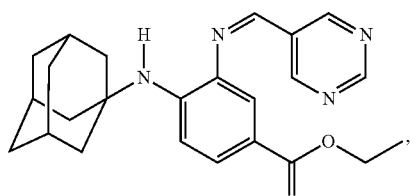

SRS15-72

-continued

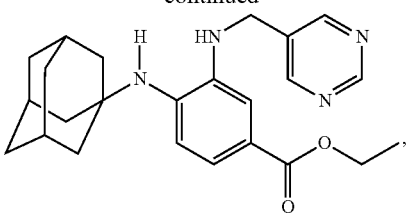

SRS16-41

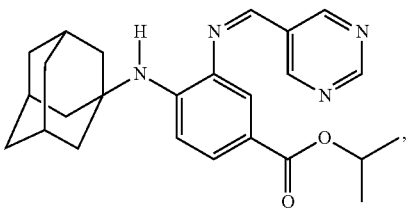

SRS16-80

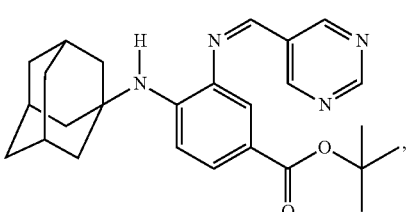

SRS16-86

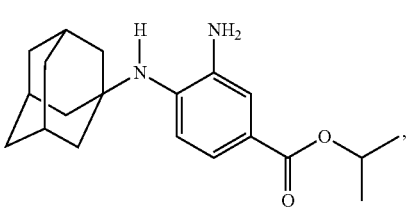

SRS16-78

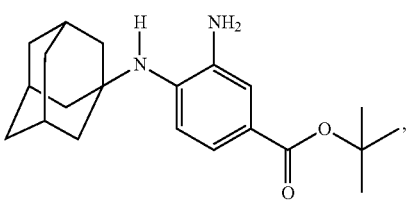

SRS16-82

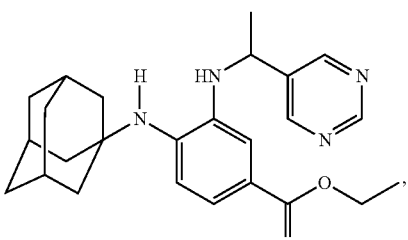

Fer2_SRS01

-continued
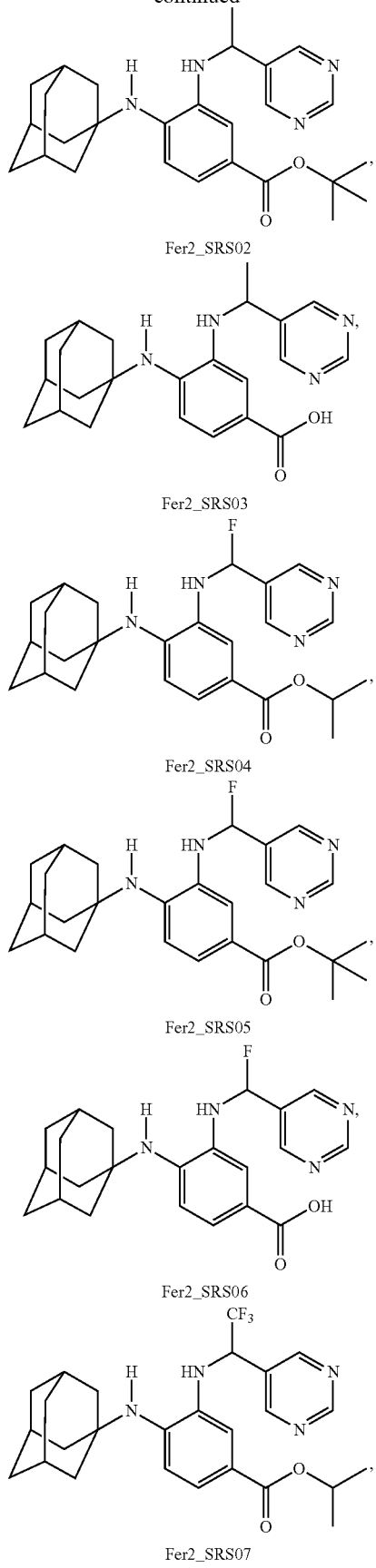
Fer2_SRS02
Fer2_SRS03
Fer2_SRS04
Fer2_SRS05
Fer2_SRS06
Fer2_SRS07
-continued
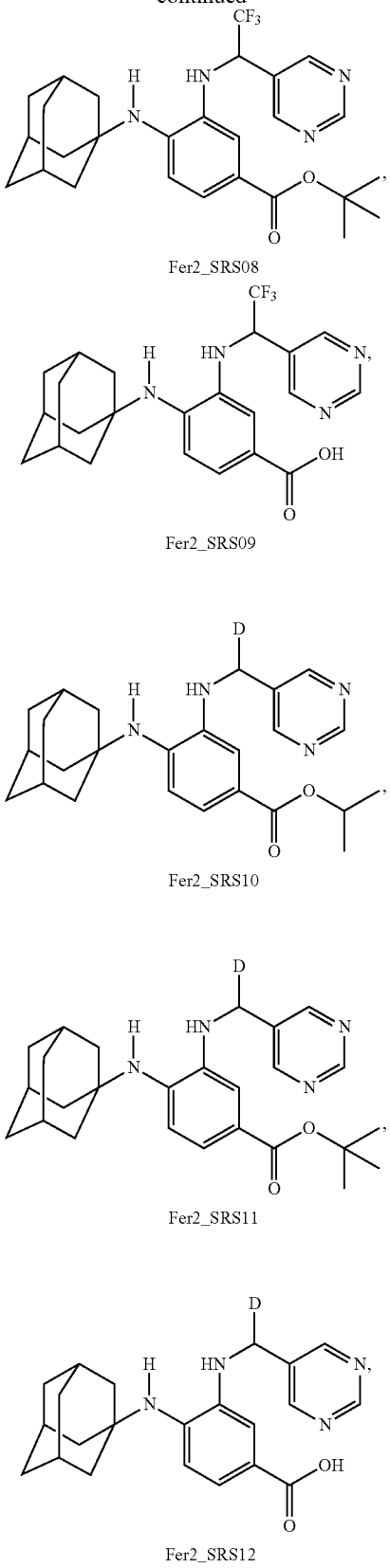
Fer2_SRS08
Fer2_SRS09
Fer2_SRS10
Fer2_SRS11
Fer2_SRS12
and combinations thereof, or an N-oxide, hydrate, or pharmaceutically acceptable salt thereof.

10. A pharmaceutical composition according to claim 8, wherein the compound has a structure that is selected from the group consisting of:

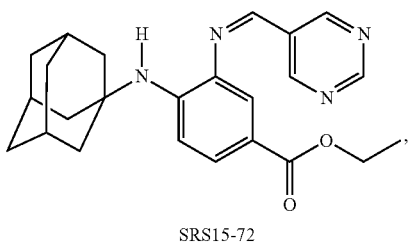

SRS15-72

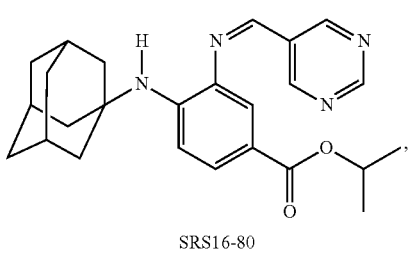

SRS16-80

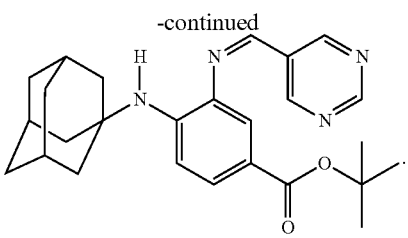

SRS16-86 and combinations thereof or an N-oxide, hydrate, or pharmaceutically acceptable salt thereof.

11. A kit comprising a compound according to claim 3 together with instructions for the use of the compound.

12. A kit comprising a pharmaceutical composition according to claim 8 together with instructions for the use of the pharmaceutical composition.

13. A compound having the formula:

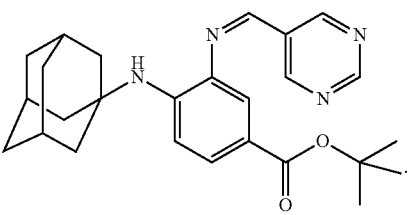

SRS16-86

* * * * *

UNITED STATES PATENT AND TRADEMARK OFFICE
CERTIFICATE OF CORRECTION

| | |
|---|---|
| PATENT NO. | : 10,259,775 B2 |
| APPLICATION NO. | : 15/100967 |
| DATED | : April 16, 2019 |
| INVENTOR(S) | : Brent R. Stockwell, Rachid Skouta and Scott Dixon |

Page 1 of 1

It is certified that error appears in the above-identified patent and that said Letters Patent is hereby corrected as shown below:

In the Claims

In Column 166, Line 35, immediately after "wherein the", please insert -- $C_{1-6}$alkyl, --

Signed and Sealed this
Sixteenth Day of August, 2022

*Katherine Kelly Vidal*
Katherine Kelly Vidal
*Director of the United States Patent and Trademark Office*